United States Patent
Dai et al.

(10) Patent No.: US 9,909,152 B2
(45) Date of Patent: Mar. 6, 2018

(54) **ENHANCED ITACONIC ACID PRODUCTION IN *ASPERGILLUS* WITH INCREASED *LAEA* EXPRESSION**

(71) Applicant: Battelle Memorial Institute, Richland, WA (US)

(72) Inventors: Ziyu Dai, Richland, WA (US); Scott E. Baker, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 102 days.

(21) Appl. No.: 14/928,511

(22) Filed: Oct. 30, 2015

(65) Prior Publication Data

US 2016/0046967 A1 Feb. 18, 2016

Related U.S. Application Data

(63) Continuation-in-part of application No. 14/703,499, filed on May 4, 2015, now Pat. No. 9,206,450, which is a continuation-in-part of application No. 13/691,396, filed on Nov. 30, 2012, now Pat. No. 9,023,637.

(60) Provisional application No. 61/565,018, filed on Nov. 30, 2011.

(51) Int. Cl.
| | |
|---|---|
| *C12P 7/46* | (2006.01) |
| *C12P 7/44* | (2006.01) |
| *C12N 1/15* | (2006.01) |
| *C12N 1/14* | (2006.01) |
| *C12P 7/48* | (2006.01) |
| *C07K 14/38* | (2006.01) |
| *C12N 9/10* | (2006.01) |

(52) U.S. Cl.
CPC .............. *C12P 7/44* (2013.01); *C07K 14/38* (2013.01); *C12N 1/14* (2013.01); *C12N 9/1051* (2013.01); *C12P 7/48* (2013.01); *C12Y 204/01258* (2013.01)

(58) Field of Classification Search
CPC ... C12P 7/44; C12P 7/48; C07K 14/38; C12Y 204/01258; C12N 9/1051; C12N 1/14
See application file for complete search history.

(56) References Cited

U.S. PATENT DOCUMENTS

| | | | |
|---|---|---|---|
| 5,532,148 A | 7/1996 | Datta et al. | |
| 9,023,637 B2 | 5/2015 | Dai et al. | |
| 2004/0058872 A1 | 3/2004 | Keller et al. | |
| 2009/0124014 A1* | 5/2009 | Berg | C12N 15/815 |
| | | | 435/471 |
| 2010/0062485 A1 | 3/2010 | Kang et al. | |
| 2013/0137150 A1 | 5/2013 | Dai et al. | |
| 2015/0232892 A1 | 8/2015 | Dai et al. | |

OTHER PUBLICATIONS

Sadowski et al., Current Opinion in Structural Biology 19:357-362, 2009.*
Kubodera et al., Biosci. Biotechnol. Biochem. 66(2):404-406, 2002.*
Bentley and Thiessen, "Biosynthesis of Itaconic Acid in Aspergillus Terreus," *J Biol Chem* 226:703-720, 1957.
Aebi et al., "Cloning and Characterization of the ALG3 Gene of *Saccharomyces cerevisiae,*" *Glycobiol.* 6:439-444, 1996.
Andersen et al., "Comparative Genomics of Citric-Acid-Producing *Aspergillus niger* ATCC 1015 Versus Enzyme-Producing CBS 513.88," *Genome Res.* 21:885-897, 2011.
Apweiler et al., "On the Frequency of Protein Glycosylation, as Deduced from Analysis of the Swiss-PROT Database," *Biochim. Biophys. Acta* 1473:4-8, 1999.
Baba et al., "Identification and Characterization of *Penicillium citrinum* VeA and LaeA as Global Regulators for ML-236B Production," *Curr. Genet.* 58:1-11, 2012.
Bayram et al., "VelB/VeA/LaeA Complex Coordinates Light Signal with Fungal Development and Secondary Metabolism," *Science* 320:1504-1506, 2008.
Bayram et al., "LaeA Control of Velvet Family Regulatory Proteins for Light-Dependent Development and Fungal Cell-Type Specificity," *PLoS Genet.* 6:e1001226, 2010.
Bok and Keller, "LaeA, a Regulator of Secondary Metabolism in *Aspergillus* spp.," *Eukaryot. Cell* 3:527-535, 2004.
Bok et al., "Secondary Metabolic Gene Cluster Silencing in *Aspergillus nidulans,*" *Mol. Microbiol.* 61:1636-1645, 2006.
Bok et al., "Chromatin-Level Regulation of Biosynthetic Gene Clusters," *Nat. Chem. Biol.* 5:462-464, 2009.
Bouhired et al., "Accurate Prediction of the *Aspergillus nidulans* Terrequinone Gene Cluster Boundaries Using the Transcriptional Regulator LaeA," *Fungal Genet. Biol.* 44:1134-1145, 2007.
Bowman et al., "Mutational Analysis of the Glycosylphosphatidylinositol (GPI) Anchor Pathway Demonstrates that GPI-Anchored Proteins Are Required for Cell Wall Biogenesis and Normal Hyphal Growth in *Neurospora crassa,*" *Eukaryot. Cell* 5:587-600, 2006.
Branden et al., "Introduction to Protein Structure," Garland Publishing Inc., New York, p. 247, 1991.
Butchko et al., "Lae1 Regulates Expression of Multiple Secondary Metabolite Gene Clusters in *Fusarium verticillioides,*" *Fungal Genet. Biol.* 49:602-612, 2012.

(Continued)

*Primary Examiner* — Delia M Ramirez
(74) *Attorney, Agent, or Firm* — Klarquist Sparkman, LLP

(57) ABSTRACT

Fungi, such as *Aspergillus niger*, having a dolichyl-P-Man:Man(5)GlcNAc(2)-PP-dolichyl mannosyltransferase (Alg3) gene genetic inactivation, increased expression of a loss of aflR expression A (LaeA), or both, are described. In some examples, such mutants have several phenotypes, including an increased production of citric acid relative to the parental strain. Methods of using the disclosed fungi to make citric acid are also described, as are compositions and kits including the disclosed fungi. Further described are *Aspergillus terreus* fungi overexpressing the LaeA gene and the use of such fungi for the production of itaconic acid.

16 Claims, 27 Drawing Sheets

(56) References Cited

OTHER PUBLICATIONS

Calvo, "The VeA Regulatory System and its Role in Morphological and Chemical Development in Fungi," *Fungal Genet. Biol.* 45:1053-1061, 2008.

Dai et al., "The Galphal Protein Regulates *Aspergillus niger* Growth and Development and the Citric Acid Production in Response to Nitrogen Sources," Abstracts of the General Meeting of the American Society for Microbiology, vol. 108, Jun. 5, 2008, pp. 0-024, US ISSN: 1060-2011.

Davidson et al., "Functional Analysis of the ALG3 Gene Encoding the Dol-P-Man: $Man_5GlcNAc_2$-PP-Dol Mannosyltransferase Enzyme of *P. pastoris*," *Glycobiology* 14:399-407, 2004.

Dellaporta et al., "A Plant DNA Minipreparation: Version II," *Plant Mol. Biol. Rep.* 1:19-21, 1983.

Denecke et al., "Congenital Disorder of Glycosylation Type Id: Clinical Phenotype, Molecular Analysis, Prenatal Diagnosis, and Glycosylation of Fetal Proteins," *Pediatr. Res.* 58:248-253, 2005.

de Oliveira and de Graaff, "Proteomics of Industrial Fungi: Trends and Insights for Biotechnology," *Appl. Microbiol. Biotechnol.* 89:225-237, 2011.

Deshpande et al., "Protein Glycosylation Pathways in Filamentous Fungi," *Glycobiology* 18:626-637, 2008.

Georgianna et al., "Beyond Aflatoxin: Four Distinct Expression Patterns and Functional Roles Associated with *Aspergillus flavus* Secondary Metabolism Gene Clusters," *Mol. Plant Pathol.* 11:213-226, 2010.

Gerngross, "Advances in the Production of Human Therapeutic Proteins in Yeasts and Filamentous Fungi," *Nat. Biotechnol.* 22:1409-1414, 2004.

Geysens et al., "Genomics of Protein Folding in the Endoplasmic Reticulum, Secretion Stress and Glycosylation in the Aspergilli," *Fungal Genet. Biol.* 46:S121-S140, 2009.

Haltiwanger and Lowe, "Role of Glycosylation in Development," *Ann. Rev. Biochem.* 73:491-537, 2004.

Huang et al., Improving itaconic acid production through genetic engineering of an industrial Aspergillus terreus strain, *Microb Cell Fact* 13:119, 2014.

Jacobs et al., "Effective Lead Selection for Improved Protein Production in *Aspergillus niger* Based on Integrated Genomics," *Fungal Genet. Biol.* 46:S141-S152, 2009.

Kainz et al., "N-Glycan Modification in *Aspergillus* Species," *Appl. Environ. Microbiol.* 74:1076-1086, 2008.

Kale et al., "Requirement of LaeA for Secondary Metabolism and Sclerotial Production in *Aspergillus flavus*," *Fungal Genet. Biol.* 45:1422-1429, 2008.

Kajiura et al., "*Arabidopsis thaliana* ALG3 Mutant Synthesizes Immature Oligosaccharides in the ER and Accumulates Unique N-Glycans," *Glycobiology* 20:736-751, 2010.

Keller et al., "LaeA, A Global Regulator of *Aspergillus* Toxins," *Med. Mycol.* 44:S83-S85, 2006.

Kim et al., "Centralized Modularity of N-Linked Glycosylation Pathways in Mammalian Cells," *PLoS One* 4:e7317, 2009.

Körner et al., "Carbohydrate Deficient Glycoprotein Syndrome Type IV: Deficiency of Dolichyl-P-Man:$Man_5GlcNAc_2$-PP-dolichyl Mannosyltransferase," *EMBO J.* 18:6816-6822, 1999.

Kornfeld and Kornfeld, "Assembly of Asparagine-Linked Oligosaccharides," *Annu. Rev. Biochem.* 54:631-664, 1985.

Kotz et al., "Approaching the Secrets of N-Glycosylation in *Aspergillus fumigatus*: Characterization of the AfOch1 Protein," *PLoS One* 5:e15729, 2010.

Kozak, "Initiation of translation in prokaryotes and eukaryotes," *Gene* 234:187-208, 1999.

Kranz et al., "CDG-Id in Two Siblings With Partially Different Phenotypes," *Am. J. Med. Genet.* 143A:1414-1420, 2007.

Kukuruzinska et al., "Protein Glycosylation in Yeast," *Annu. Rev. Biochem.* 56:915-944, 1987.

Maddi and Free, "α-1,6-Mannosylation of N-Linked Oligosaccharide Present on Cell Wall Proteins is Required for Their Incorporation into the Cell Wall in the Filamentous Fungus *Neurospora crassa*," *Eukaryot. Cell* 9:1766-1775, 2010.

Magnuson and Lasure, "Organic Acid Production by Filamentous Fungi," in *Advances in Fungal Biotechnology for Industry, Agriculture, and Medicine*, Lange and Lange (eds.), pp. 307-340, Kluwer Academic/Plenum Publishers, 2004.

Manthri et al., "Deletion of the TbALG3 Gene Demonstrates Site-Specific NGlycosylation and N-Glycan Processing in *Trypanosoma brucei*," *Glycobiology* 18:367-383, 2008.

Maras et al., "Molecular Cloning and Enzymatic Characterization of a *Trichoderma reesei* 1,2-α-D-mannosidase," *J. Biotechnol.* 77:255-263, 2000.

Nam et al., "The Effects of Culture Conditions on the Glycosylation of Secreted Human Placental Alkaline Phosphatase Produced in Chinese Hamster Ovary Cells," *Biotech. Bioeng.* 100:1178-1192, 2008.

Nevalainen et al., "Heterologous Protein Expression in Filamentous Fungi," *Trends Biotechnol.* 23:468-474, 2005.

Oda et al., "*Aspergillus oryzae laeA* Regulates Kojic Acid Synthesis Genes," *Biosci. Biotechnol. Biochem.* 75:1832-1834, 2011.

Pang et al., "Human Sperm Binding is Mediated by the Sialyl-Lewis$^x$ Oligosaccharide on the Zona Pellucida," *Science* 333:1761-1764, 2011.

Pel et al., "Genome Sequencing and Analysis of the Versatile Cell Factory *Aspergillus niger* CBS 513.88," *Nature Biotechnol.* 25:221-231, 2007.

Punt et al., "Filamentous Fungi as Cell Factories for Heterologous Protein Production," *Trends Biotechnol.* 20:200-206, 2002.

Ramamoorthy et al., "veA-Dependent RNA-pol II Transcription Elongation Factor-Like Protein, RtfA, is Associated with Secondary Metabolism and Morphological Development in *Aspergillus nidulans*," *Mol. Microbiol.* 85:795-814, 2012.

Reyes-Dominguez et al., "Heterochromatic Marks are Associated with the Repression of Secondary Metabolism Clusters in *Aspergillus nidulans*," *Mol. Microbiol.* 76:1376-1386, 2010.

Roze et al., "Volatile Profiling Reveals Intracellular Metabolic Changes in *Aspergillus parasiticus* : *veA* Regulates Branched Chain Amino Acid and Ethanol Metabolism," *BMC Biochem.* 11:33, 2010.

Sakai et al., "Heterologous Expression System in *Aspergillus oryzae* for Fungal Biosynthetic Gene Clusters of Secondary Metabolites," *Appl. Microbiol. Biotechnol.* 93:2011-2022, 2012.

Sauer et al., "Microbial Production of Organic Acids: Expanding the Markets," *Trends Biotechnol.* 26:100-108, 2008.

Schollen et al., "CDG-Id Caused by Homozygosity for an ALG3 Mutation Due to Segmental Maternal Isodisomy UPD3(q21.3-qter)," *Eur. J. Med. Genet.* 48:153-158, 2005.

Schuster et al., "On the Safety of *Aspergillus niger*—A Review," *Appl. Microbiol. Biotechnol.* 59:426-435, 2002.

Seffernick et al., "Melamine Deaminase and Atrazine Chlorohydrolase: 98 Percent Indentical but Functionally Different," *J Bacteriol* 183(8):2405-2410, 2001.

Silberstein and Gilmore, "Biochemistry, Molecular Biology, and Genetics of the Oligosaccharyltransferase," *FASEB J.* 10:849-858, 1996.

Soukup et al., "Overexpression of the *Aspergillus nidulans* Histone 4 Acetyltransferase EsaA Increases Activation of Secondary Metabolite Production," *Mol. Microbiol.* 86:314-330, 2012.

Sousa et al., "The ARO4 gene of *Candida albicans* encodes a tyrosine-sensitive DAHP synthase: evolution, functional conservation and phenotype of Aro3p-, Aro4p-deficient mutants," *Microbiology* 148(Pt5):1291-1303, 2002.

Stibler et al., "Carbohydrate-Deficient Glycoprotein Syndrome—A Fourth Subtype," *Neuropediatrics* 26: 235-237, 1995.

Sun et al., "Congenital Disorder of Glycosylation Id Presenting with Hyperinsulinemic Hypoglycemia and Islet Cell Hyperplasia," *J. Clin. Endocrinol. Metab.* 90:4371-4375, 2005.

Trombetta and Parodi, "Quality Control and Protein Folding in the Secretory Pathway," *Ann. Rev. Cell Dev. Biol.* 19:649-676, 2003.

Tsang et al., "Analytical and Computational Approaches to Define the *Aspergillus niger* Secretome," *Fungal Genet. Biol.* 46:S153-S160, 2009.

Uniprot ALG3_ASPNC [online] Nov. 2, 2010 [retrieved Jan. 9, 2013], available on the internet <URL: www.uniprot.org/uniprot/A2RA94.txt?version=27>.

(56) References Cited

OTHER PUBLICATIONS

Witkowski et al., "Conversion of a β-Ketoacyl Synthase to a Malonyl Decarboxylase by Replacement of the Active-Site Cysteine with Glutamine," *Biochemistry* 38:11643-11650, 1999.

Xing et al., "Molecular Cloning and Characterization of the Global Regulator LaeA in *Penicillium citrinum*," *Biotechnol. Lett.* 32:1733-1737, 2010.

Yan and Lennarz, "Unraveling the Mechanism of Protein N-glycosylation," *J. Biol. Chem.* 280:3121-3124, 2005.

Yu et al., "Conservation of Structure and Function of the Aflatoxin Regulatory Gene aflR from *Aspergillus nidulans* and *A. flavus*" *Curr. Genet.* 29:549-555, 1996.

Zhou et al., "Global analysis of gene transcription regulation in prokaryotes," *Cell Mol Life Sci* 63(19-20):2260-2290, 2006.

\* cited by examiner

FIG. 6A  *11414kusA*   *Alg3Δ*
8 hrs after inoculation
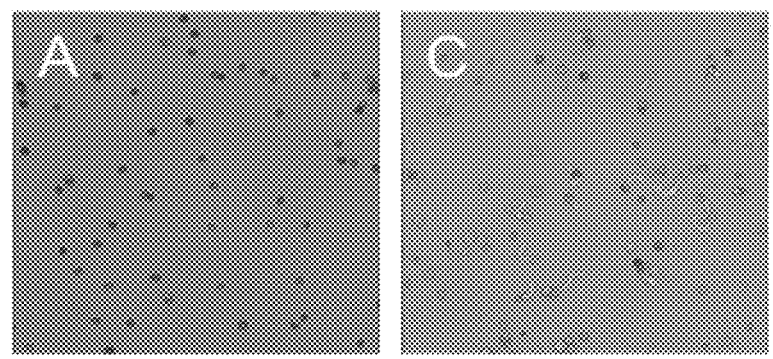
15 hrs after inoculation
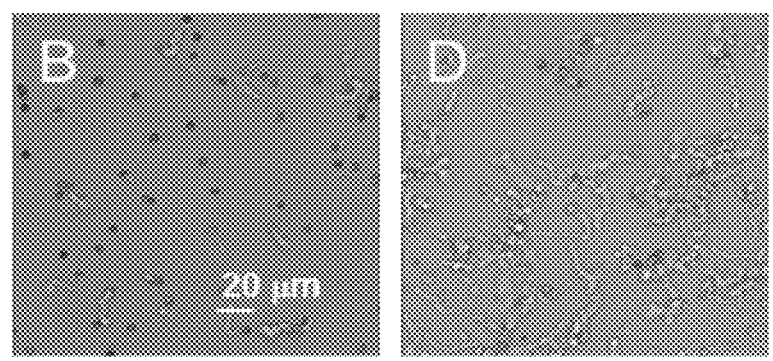
FIG. 6B
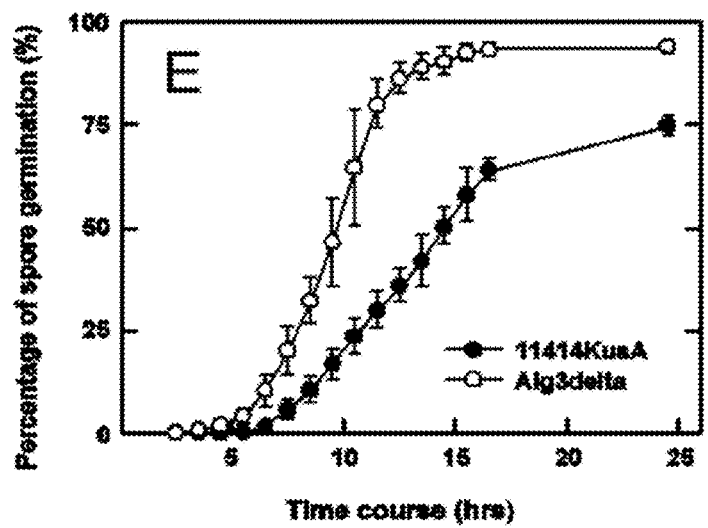

FIG. 9

<u>GENE ID: 5996303 AOR_1_556094</u> | dolichyl-P-Man:Man(5)GlcNAc(2)-PP-dolichyl mannosyltransferase [Aspergillus oryzae RIB40] (10 or fewer PubMed links)

Score = 137 bits (74), Expect = 2e-28
Identities = 400/553 (72%), Gaps = 40/553 (7%)
Strand=Plus/Plus

```
Query  801   CAGGTTTTACTCGCGATACCGTTCCTACAAAACAACCCGGCGGGGTATC-TCTCGCGGGC  859
             ||||||  |||| |||||  || |||||| |  |||||    |||||  ||  |||||||
Sbjct  643   CAGGTTCTACTAGCGATTCCCTTCCTACAGGGTAACCCCATACGATA-CGTCGCGCGGGC  701

Query  860   GTTCGAGCTAACCAGACAGTTCATGTTTAAATGGACAGTCAATTGGAGATTTGTTGGCGA  919
             || | | |  |||||||||||  ||||| ||||||| || |||||||| |||||||  ||
Sbjct  702   CTTTGAGTTGACTAGACAGTTTATGTTCAAATGGACTGTCAATTGGAGGTTTGTGGGTGA  761

Query  920   AGAAGTATTCTIAT-CTAAGAGCTTTTCCCTGGCATTGCT-GGCCGTCCACATTGTGCTG  977
             |||  | ||| ||| | ||  | |||||  ||  || ||  |  ||| | | || | |||
Sbjct  762   AGACTTGTTCCTATCCAAACAG-TTTTCTCTAGCCTTACTAGG-TTTGCATATTTTCTG  819

Query  978   CTAGGCG-CT-TTTGCCGTCACTGGTTGGCTGA-GATAC-TCCAGG-TCTAGCTTGCCTG  1032
             || || | |   ||||   ||| |||  |||   | ||| |  ||||  |   || ||||
Sbjct  820   CT-GG-GATTATTTGTTACCACAGGCTGG-TTACG-GCCGT-CAGGATCTAACGTCCCTG  874

Query  1033  -CGTTCATTCGGAATCTGCTAGC-GGGTCGACATCGCACAGT-GTCCCTCCCCAAACCCT  1089
              | ||| | |||  || |||| |  ||| || |  ||||| | ||  ||  |  |||  |
Sbjct  875   AC-TTCCTCGGAGCCTACT-CCAAGGACGCCAACGCACCGTGGT-GCTTTCTAAGTCTT  931

Query  1090  ACATCATGAGCGTGATGCTCTCGTCTCTGACAG-TTGGCTTGTTGTGCGCAAGGTCCCTT  1148
             || || ||||||| || | |||||| | |   | | || |  |  |||||||||||||||
Sbjct  932   TCATAATGACCGTGATGTTGACATCGCTGGC-GATCGGGTTGTTGTGCGCAAGGTCCCTT  990

Query  1149  CATTACCAATTCTTCGCCTACCTCTCCTGGGCGACACCCTT-CCTCCTCTGGCGCGCAGG  1207
             ||||||||||||| |||||| ||||||||||| ||| ||   ||| | | ||||| || |
Sbjct  991   CATTACCAATTCTTTGCCTATCTCTCCTGGGCTACGCC-TTGCCTTCTCTGGCGGCTCG  1049

Query  1208  GTTCATCCAATC-TTGCTGTAC-CTTATCTGGGCTA-TGCAAGAGTGGGCTTGGAACA-  1263
             | | |||||| |  |||||| |  |||| ||||||| ||  ||  ||||||||||| |
Sbjct  1050  GCTCCATCGATCCTTA-TATATGCG-ATCTGGGC-ACTACAGGAGTGGGCTTGGAATGT  1106

Query  1264  CATTCCCCAGCACCAAC-CTCAGTTCCATCATT-GTTGTCCTCTCACTTGCTACCCAGAG  1321
             | | ||| ||||||||| | |||||  | |||| ||||||| ||||||||||| |   |
Sbjct  1107  C-TACCCAAGCACCAATGC-CAGTTCT-TCGTCGTTGTCTTCTCACTTGCTGTTCAG-G  1162

Query  1322  TTT-CGGCGTCCT     1333
             ||| ||| |||||
Sbjct  1163  TTTTCGGTGTCCT     1175
```

FIG. 10A

```
                        +. ...  .........  ..  * .   ..  ..  ....+..+..+...*  +.*....+..*.**+.*
Aspergillus niger     1) MD---------------WM------RLIRDLCFNPRHTKWMAPLLVLGDAFLCALIIWKV
Aspergillus nid.      1) MA-----------------L-----TDLVSGLCSNPKHTKWIAPILNIADGLLCAFIIWKV
Fusarium oxy.         1) --------MPESASGTLSQGVRFLRNVLNGRHAL-----SKLIPIALWLVDALGCGLIIWKI
Neurospora cra.       1) MAAPSS-RPESNPPLYKQALDFALDVANGRHAL-----SKLIPPALFLVDALLCGLIIWKV
Saccharomyces cer.    1) MAGGKK-KSSTAPSRFQKTL-SSIWQDKHTVLFKPEYTLLVTAVLWFLEIAINIWVIQKV
Arabidopsis tha.      1) MA-GAS-SPASLRASRSRRL---GKETNRSDLFKKP---AVPFAFALILADAILVALIIAYV
Homo sap.             1) RKRGRSgSAAQAEGLCKQWL-QRAWQERRLLLREPRYTLLVAACLCLAEVGITFWVIHRV +****.+.**+.+++*++**+.++*+********+++*.*+.+*++*+*.*.+*..+
Aspergillus niger    40) PYTEIDWATYMQQISLYLSGERDYTLIRGSTGPLVYPAAHVYSYTALYHLTDEGRDIFFG
Aserpgillus nid.     40) PYTEIDWTTYMQQVKLYLSGERDYTLIKGSTGPLVYPAAHVYSYSLFHHLTDEGRDIVFG
Fusarium oxy.        50) PYTEIDWVAYMQQISQFVSGERDYTKMEGDTGPLVYPAAHVYTYTGLYYITDKGTNILLA
Neurospora cra.      56) PYTEIDWAAYMEQVSQILSGERDYTKVRGGTGPLVYPAAHVYIYTGLYHLTDEGRNILLA
Saccharomyces cer.   59) SYTEIDWKAYMDEVEGVINGTYDYTQLKGDTGPLVYPAGFVYIFTGLYYLTDHGHNIRLG
Arabidopsis tha.     55) PYTKIDWDAYMSQVSGFLGGERDYGNLKGDTGPLVYPAGFLYVSAVQNLT--GGEVYPA
Homo sap.            60) AYTEIDWKAYMAEVEGVINGTYDYTQLQGDTGPLVYPAGFVYIFMGLYYATSRGTDIRMA

*.+*+.+*+++*.+*+ +*.+...+***..+.++++*+*+*+*+*+****.+*...+*.
Aspergillus niger   100) QILFAVLYLITLVVVLCCYRQSG-APPY-LLPLLVLSKRLHSVYVLRLFNDGLAALAMWV
Aspergillus nid.    100) QIIFAFLYLICLTVVMACYRRVG-APPY-LFPLLVLSKRLHSVYMLRLFNDGLAALAMWG
Fusarium oxy.       110) QQIFAVLYMATLAVVMLCYWKAK-VPPY-MFIFLIASKRLHSLFVLRCFNDCFAVFFLWL
Neurospora cra.     116) QQLFAGLYMVTLAVVMGCYWQAK-APPY-LFPLLTLSKRLHSIFVLRCFNDCFAVLFLWL
Saccharomyces cer.  119) QYVFAVSYLINLLLVMRIYHRTKKVPPYVFFFICCASYRIHSIFILRLFNDPVAMMLCFG
Arabidopsis tha.    113) QILFGVLYIVNLGIVLIIYVKTD-VPWW-ALSLLCLSKRIHSIFVLRLFNDCFAMTLLHA
Homo sap.           120) QNIFAVLYLATLLLVFLIYHQTCKVPPFVFFFMCCASYRVHSIFVLRLFNDPVAMVLLFL ++ +*..++*. +..+*+.++*+*++**..*++.+++....+ + ..+........+*+
Aspergillus nig.    158) AILLFMNRKWTAAVAVWSTGVAIKMTLLLLAPAIAVVTVLSLS-LGPSVGLGVLAVLVQV
Aspergillus nid.    158) SIWLFINRKWTPAVVLWSLGLGVKMTLILLVPAVMVVLALSLD-IGRCIRLAGLALGIQI
Fusarium oxy.       168) TIFLFQRRQWTVGSLVYSWGLGIKMSLLLVLPAIGVILFLGRG-LWPSLRLAWLMAQIQF
Neurospora cra.     174) AIFFFQRRNWQAGALLYTLGLGVKMTLLLSLPAVGIVLFLGSGsFVTTLQLVATMGLVQI
Saccharomyces cer.  179) AINLFLDGRWTLGCALYSLAVSVKMNVLLFAPGLLFLLLCEFG-LWKTLPRLALCAVIQL
Arabidopsis tha.    171) SMALFLYRKWHLCMLVFSGAVSVKMNVLLYAPTLLLLLLKAMN-IIGVVSALAGAALVQI
Homo sap.           180) SINLLLAQRWGWGCCFFSLAVSVKMNVLLFAPGLLFLLLTQFG-FRGALPKLGICAGLQV +++*+***..+*.+*.+*++++*.*+********+*.+*+*+*.*.+.**..+.+*..
Aspergillus niger   217) LLAIPFLQNNPAGYLSRAFELTRQFMFKWTVNWRFVGEEVFLSKSFSLALLAVHIVLLGA
Aspergillus nid.    217) LLAIPFLKTNPSGYFERAFEFGRQFMFKWTVNWRFVGEDIFLSKGFWAGLIVLHLLILVV
Fusarium oxy.       227) AIGLPFITKNPRGYAARAFELSRQFQFKWTVNWRMLGEEVFLSKYFALSLLACHILVLLI
Neurospora cra.     234) LIGVPFLAHYPTEYLSRAFELSRQFFFKWTVNWRFVGEEIFLSKGFALTLLALHVLVLGI
Saccharomyces cer.  238) VLGLPFLLVNPVGYVSRAFDLGRQFLFKWTVNWRFLPEDVFLNRYFHLALLLAHITTLLL
Arabidopsis tha.    230) LVGLPFLITYPVSYIANAFDLGRVFIHFWSVNFKFVPERVFVSKEFAVCLLIAHLFLLVA
Homo sap.           239) VLGLPFLLENPSCYLSRSFDLGRQFLFHWTVNWRFLPEALFLHRAFHLALLTAHLTLLLL

*....*....+.++ .++.. .   .........  ..  .... +.+.++++.++++*.
Aspergillus niger   277) FAVTGWLRYSKSSLPAFIRNLL--------AGRHR-----------TVSLPKPYIMSVMLSSLT
Aspergillus nid.    277) LGFTCFLNPSGTSLPDFAGRFL--------TGQHR-----------GIALHPSFIMSALLTSLS
Fusarium oxy.       287) FISKRWIQPTGRSLYDLIPSFLrikSPFTMQEQ--------LRISHYVTPEYAMTIMLTANL
Neurospora cra.     294) FITTRWIKPARKSLVQLISPVL-----LAGKPPLTVPEhRAAARDVTPRYIMTTILSANA
Saccharomyces cer.  298) FALKRW-KRSGSSIWTILKDPS----------ER-------KETAHKVNADQMVLILFTSNF
Arabidopsis tha.    290) FANYKWCKHEG-GIIGFMRSRH---FFLTLPSSLSFSD-VSASRIITKEHVVTAMFVGNF
Homo sap.           299) FALCRW-HRTGESILSLLRDPS---------KRKV--PP------QPLTPNQIVSTLFTSNF
```

FIG. 10B

```
                      **+-+**********+*+.*+*+*****+....++...*..+++...*++**+-***..**.
Aspergillus niger  322) VGLLCARSLHYQFFAYLSWATPFLLWRAGFHPI---LLYLIWAMQEWAWNTFPSTNLSSI
Aspergillus nid.   322) VGLLCARSLHYQFFAYLSWATPFLLWQAGYHPI----LVYALWLVQEWAWNVYPSTNLSSA
Fusarium oxy.      341) IGLLFARSLHYQFYAYLAWAIPYLLWRATEDPV---IVAIIWAAQEWAWNVYPSTDLSST
Neurospora cra.    349) VGLLFARSLHYQFYAYVAWSTPFLLWRAGLHPV---LVYLLWAVHEWAWNVFPSTPASSA
Saccharomyces cer. 342) IGMCFSRSLHYQFYVWYFHTLPYLLWSGGVKKLARLLRVLILGLIELSWNTYPSTNYSSL
Arabidopsis tha.   345) IGIVFARSLHYQFYSWYFYSLPYLLWRTPF-PT--WLRLIMFLGIELCWNVYPSTPSSSG
Homo sap.          343) IGICFSRSLHYQFYVWYFHTLPYLLWAMPARWLTHLLRLLVLGLIELSWNTYPSTSCSSA .+. ........++.+....  .......+.+.+ ..-
Aspergillus niger  379) IVVLSLATQSFGVLANSASA-FYTMRSNPSGKEHNQ--
Aspergillus nid.   379) AVVLLLCAQVLGVLVNRDRA-FPSSPPTPKAKQHVQ--
Fusarium oxy.      398) IAVNTMLATVVLVYLGTARR-AVPAPAAQVGNVDDKNk
Neurospora cra.    406) VVVGVLGVTVAGVWFGAREEwEPGMKSSSKKEEAAMR-
Saccharomyces cer. 402) SLHVCHLIILLCLWLNPNPA-SPSHRSENKAKSH----
Arabidopsis tha.   402) LLLCLHLIILVGLWLAPSVD-PYQLKEHPKSQIHKKA-
Homo sap.          403) ALHICHAVILLQLWLGPQPF---PKSTQHSK-KAH----
```

FIG. 11

```
Score =  279 bits (713),  Expect = 2e-87, Method: Compositional matrix adjust.
 Identities = 159/405 (39%), Positives = 239/405 (59%), Gaps = 6/405 (1%)

Query   12   FNPRHTKWMAPLLVLGDAFLCALIIWKVFYTEIDWATYMQQISLYLSGERDYTLIRGSTG   71
             F P +T + +L  +  + +I KV YTEIDW  YM ++  ++G DYT ++G TG
Sbjct   31   FKPEYTLLVTAVLWFLEIAINIWVIQKVSYTEIDWKAYMDEVEGVINGTYDYTQLKGDTG   90

Query   72   PLVYPAAHVYSYTALYHLTDEGRDIFFGQILFAVLYLITLVVVLCCY-RQSGAPPYLLPL   130
             PLVYPA  VY +T LY+LTD G +I   GQ +FAV YLI L++V+   Y R    PPY+
Sbjct   91   PLVYPAGFVYIFTGLYYLTDHGHNIRLGQYVFAVSYLINLLLVMRIYHRTKKVPPYVFFF   150

Query   131  LVL-SKRLHSVYVLRLFNDGLAALAMWVAILLFMNRKWTAAVAVWSTGVAIKMTLLLLAP   189
             +   S R+HS+++LRLFND +A + + AI LF++ +WT   A++S V++KM +LL AP
Sbjct   151  ICCASYRIHSIFILRLFNDPVAMMLCFCAINLFLDGRWTLGCALYSLAVSVKMNVLLFAP   210

Query   190  AIAVVTVLSLSLGPSVGLGVLAVLVQVLLAIPFLQNNPAGYLSRAFELTRQFMFKWTVNW   249
             +  + +    L  ++   L  ++Q++L  +PFL  NP GY+SRAF+L RQF+FKWTVNW
Sbjct   211  GLLFLLLCEFGLWKTLPRLALCAVIQLVLGLPFLLVNPVGYVSRAFDLGRQFLFKWTVNW   270

Query   250  RFVGEEVFLSKSFSLALLAVHIVLLGAFAVTGWLRYSRSSLPAFIRNLLAGRHRTVSLPK   309
             RF+ E+VFL++  F LALL  HI  L  FA+  W R S SS+   +++   +    +
Sbjct   271  RFLPEDVFLNRYFHLALLLAHITTLLLFALKRWKR-SGSSIWTILKDPSERKETAHKVNA   329

Query   310  PYIMSVMLSSLTVGLLCARSLHYQFFAYLSWATPFLLWRAGFHP---ILLYLIWAMQEWA   366
             ++ ++ +S  +G+ +RSLHYQF+ +    P+LLW  G    +L LI + E +
Sbjct   330  DQMVLILFTSNFIGMCFSRSLHYQFYVWYFHTLPYLLWSGGVKKLARLLRVLILGLIELS   389

Query   367  WNTFPSTNLSSIIVVLSLATQSFGVLANSASAFYTMRSNPSGKEH   411
             WNT+PSTN SS+ + +    + N  A + RS   K H
Sbjct   390  WNTYPSTNYSSLSLHVCHLIILLCLWLNPNPASPSHRSENKAKSH   434
```

FIG. 12

A. nidulans

```
Query    1   MTSPAHNHYSYHSPTSSDRGRSRQNSDAMDIQSITEREPATR--------YAVAGGPAPWN   53
             M SP  N+YSY   S D GRSRQNSDAMDI  IT +EP         Y  GGPA  +
Sbjct   14   MASPNRNNYSYQGIESYDSGRSRQNSDAMDIHVITAQEPPREPPDNNDPYDGHGGPAGTS   73
```

A. niger

```
Query   54   RNGSPSMSPINSERNQFHEENGRTYHGFRRGMYFLPCDEQEQDRLDIFHKLFTVARVSES   113
                   P       R  F+EENGRTYHG+RRG+Y LPCDEQEQDRLDIFHKLFTVAR+SES
Sbjct   74   HYSKPP-------NRWLFYEENGRTYHGYRRGVYPLPCDEQEQDRLDIFHKLFTVARMSES   127

Query  114   LIYAPHPTNGRFLDLGCGTGIWAIEVANKYPDAFVAGVDLAPIQPPNHPKNCEFYAPFDF   173
             LIYAPHP NGRFLDLGCGTGIWAI+VA+KYP+AFVAGVDLAPIQPPNHP NCEFYAPFDF
Sbjct  128   LIYAPHPPNGRFLDLGCGTGIWAIDVAHKYPNAFVAGVDLAPIQPPNHPDNCEFYAPFDF   187

Query  174   EAPWAMGEDSWDLIHLQMGCGSVMGWPNLYRRIFAHLRPGAWFEQVEIDFEPRCDDRSLD   233
             EAPW +GE+SWDLIHLQMGCGSV+GW NLY+RI  HL+PGAWFEQVEIDFEPRCDDRSL+
Sbjct  188   EAPWTLGENSWDLIHLQMGCGSVLGWQNLYKRILRHLQPGAWFEQVEIDFEPRCDDRSLN   247

Query  234   GTALRHWYDCLKQATAETMRPIAHSSRDTIKDLQDAGFTEIDHQIVGLPLNPWHQDEHER   293
             G ALR WY  LKQAT +TMRPIAHSSRDTI+ L++AGFT IDHQ+VGLPLNPWH+DEHE+
Sbjct  248   GLALREWYQYLKQATQDTMRPIAHSSRDTIRHLEEAGFTQIDHQMVGLPLNPWHRDEHEQ   307

Query  294   KVARWYNLAVSESIENLSLAPFSRVYRWPLERIQQLAADVKSEAFNKEIHAYNILHIYQA   353
             KVARWYNLA+SESIE LSLAPFSR++ W L+RI+Q+ A+VKS+AFNKEIHAYNILHIYQA
Sbjct  308   KVARWYNLAISESIETLSLAPFSRIFHWDLDRIRQITAEVKSQAFNKEIHAYNILHIYQA   367

Query  354   RKP   356
             RKP
Sbjct  368   RKP   370
```

FIG. 15A. Oligo primers:PTR5F/PTR3R
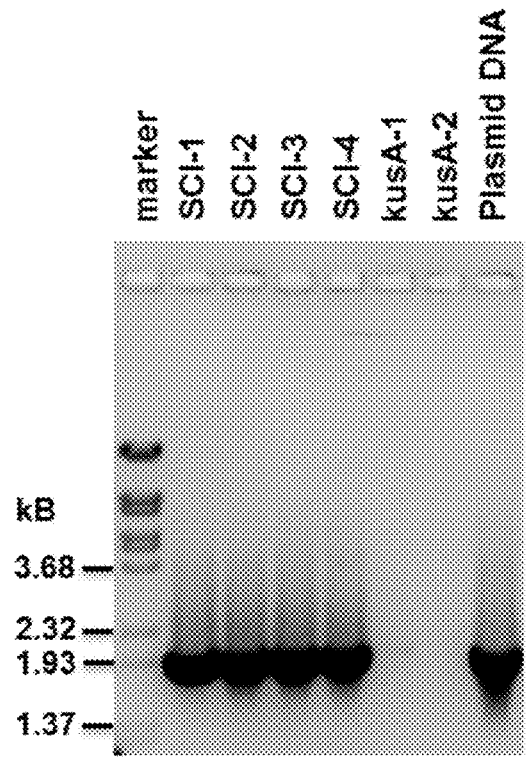
FIG. 15B. Oligo primers:LaeA5F/TRP3R
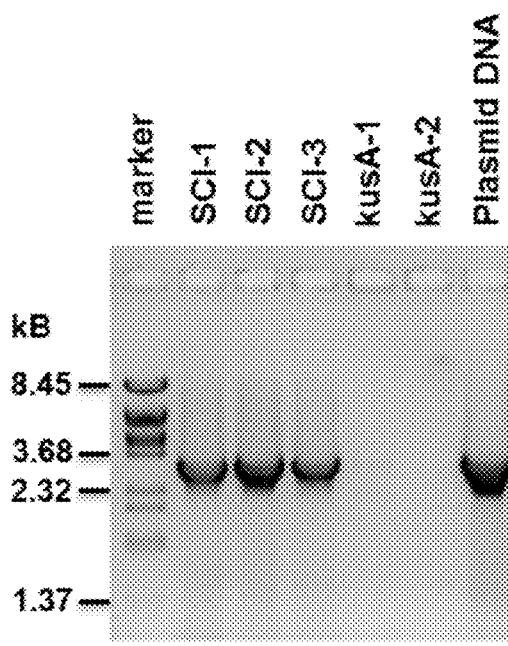

laeA deletion construct:

laeA complementation construct:

ENHANCED ITACONIC ACID PRODUCTION IN *ASPERGILLUS* WITH INCREASED *LAEA* EXPRESSION

CROSS-REFERENCE TO RELATED APPLICATIONS

This is a continuation-in-part of U.S. patent application Ser. No. 14/703,499, filed May 4, 2015, issued as U.S. Pat. No. 9,206,450 on Dec. 8, 2015, which is a continuation-in-part of U.S. application Ser. No. 13/691,396, filed Nov. 30, 2012, issued as U.S. Pat. No. 9,023,637 on May 5, 2015, which claims the benefit of U.S. Provisional Application No. 61/565,018, filed Nov. 30, 2011. The above-referenced applications are herein incorporated by reference in their entirety.

ACKNOWLEDGMENT OF GOVERNMENT SUPPORT

This invention was made with government support under contract number DE-AC05-76RL01830 awarded by the U.S. Department of Energy. The government has certain rights in the invention.

FIELD

This disclosure concerns recombinant *Aspergillus terreus* fungi that are genetically enhanced to increase the expression levels of the loss of aflR expression A (LaeA) gene, which results in a significant increase in itaconic acid production. This disclosure further concerns methods of using these fungi to produce itaconic acid.

BACKGROUND

Filamentous fungi, such as *Aspergillus niger*, are well known for their industrial applications in protein and chemical productions. They are used to produce a wide variety of products ranging from human therapeutics, glycosyl hydrolases to specialty chemicals (Punt et al., *Trends Biotechnol* 20(5):200-206, 2002; Schuster et al., *Appl Microbiol Biotechnol* 59(4-5):426-435, 2002; Gerngross, *Nat Biotechnol* 22(11):1409-1414, 2004; Nevalainen et al., *Trends Biotechnol* 23(9):468-474, 2005; Sauer et al., *Trends Biotechnol.* 26(2):100-8, 2008; Magnuson and Lasure (2004). "Organic acid production by filamentous fungi." *Advances in fungal biotechnology for industry, agriculture, and medicine*, pages 307-340). Some of industrial *A. niger* strains are capable of growing on solutions of glucose or sucrose in excess of 20% (w/v) and converting approximately 90% of the supplied carbohydrate to citric acid. These remarkable properties are the reason that *A. niger* has been used to produce citric acid for more 80 years and is currently the primary source of commercial citric acid production (Magnuson and Lasure (2004). "Organic acid production by filamentous fungi." *Advances in fungal biotechnology for industry, agriculture, and medicine*, pages 307-340).

The maximum product output in fermentation processes is the result of optimal metabolic pathways and cellular formation, which are influenced by endogenous and exogenous factors. Cellular metabolisms are tightly controlled and highly interconnected, and are regulated spatially and temporally at different levels, such as transcription, post-transcription, translation, and post-translation. Therefore, different approaches have been explored to understand the regulatory mechanisms of metabolic processes and cellular formation for maximizing the product output in filamentous fungi. For example, comparative genomics was used to examine citric-acid-producing versus enzyme-producing *A. niger* strains (Andersen et al., *Genome Res.* 21(6): 885-97, 2011), proteomics was used to examine filamentous fungi related to enzymes or organic acid production (de Oliveira and de Graaff, *Appl. Microbiol. Biotechnol.* 89(2): 225-37, 2011), or combination of both genomics and proteomics were used to examine enzyme production (Jacobs et al., *Fungal Genetics and Biology* 46(1, Supplement):S141-S152, 2009). Although these studies examined the potential involvement of selected genes and proteins in optimizing production of organic acids or proteins in filamentous fungi, methods for altering the complex post-translation modifications (such as N-glycosylation of cellular proteins) for signal transduction, cellular formation and metabolism at different growth and development stages, which may affect product output, have not been examined.

Protein glycosylation is a ubiquitous and structurally diverse form of post translation modification, which occurs at all domains of life. More than two-thirds of eukaryotic proteins are predicted to be glycosylated (Apweiler et al., *Biochim Biophys Acta* 1473(1):4-8, 1999). N- and O-linked protein glycosylation are common types of protein glycosylation, occurring mainly on the asparagine (N) and serine/threonine (S/T) residues, respectively. N-linked glycosylation has been implicated in many biochemical and cellular processes, including protein secretion, stability and translocation, maintenance of cell structure, receptor-ligand interactions and cell signaling, cell-cell recognition, pathogen infection, and host defense in various organisms (Haltiwanger and Lowe, Ann. Rev. Biochem.73(1):491-537, 2004; Dellaporta et al., *Plant Mol. Biol. Reporter* 1(4):19-21, 1983; Nam et al., *Biotech. Bioengineer.* 100(6): 1178-1192, 2008; Trombetta and Parodi, *Ann. Rev. Cell Dev. Biol.* 19(1):649-676, 2003; Tsang et al., *Fungal Genetics and Biology* 46(1): S153-S160, 2009; Pang et al., *Science*, 333(6050):1761-4, 2011).

N-glycosylation is highly complex and has been extensively studied in mammalian systems (Yan and Lennarz, *J. Biol. Chem.* 280(5):3121, 2005; Silberstein and Gilmore, FASEB J. 10(8): 849, 1996; Kornfeld and Kornfeld, *Annu. Rev. Biochem.* 54:631-664, 2005; Kim et al., *PLoS ONE* 4(10): e7317, 2009, 2009) and yeast (Kukuruzinska et al., *Annu. Rev. Biochem.* 56(1):915-944, 1987). The protein N-glycosylation pathways in filamentous fungi have also been identified (Deshpande et al., *Glycobiology* 18(8):626-637, 2008; Geysens et al., *Fungal Genetics and Biology* 46(1, Supplement): S121-S140, 2009) on the basis of the known genomic sequences. Several genes involved in N-glycosylation have been studied in filamentous fungi (Kotz et al., *PLoS ONE* 5(12):e15729, 2010; Kainz et al., *Appl Environ Microbiol* 74(4):1076-86, 2008; Maras et al., *J. Biotechnol.* 77(2-3):255-63, 2000; Maddi and Free, *Eukaryot Cell* 9(11):1766-75, 2010; Bowman et al., *Eukaryotic Cell* 5(3):587-600, 2006). In these studies, the effects of gene deletion on N-linked glycan patterns formation, the cell wall formation, overall protein secretion and/or the phenotypic changes were demonstrated.

Alg3 is localized in the ER and catalyzes the initial transfer of a mannose residue from dolichol pyrophosphate-mannose to lipid-linked Man5GlcNAc2-PP-Dol on the ER luminal side. It is involved in the early N-glycan synthesis in eukaryotes for the assembly of a Glc3Man9GlcNAc2 core oligosaccharide that is linked to the lipid carrier dolichol pyrophosphate. The Alg3 gene and its functions have been identified and studied in *S. cerevisiae, P. pastoris, T. brucei,*

A. thaliana, and human (Aebi et al., Glycobiol. 6(4):439-444, 1996; Korner et al., EMBO J. 18(23): 6816-6822, 1999; Davidson et al., Glycobiology 14(5):399-407, 2004; Manthri et al., Glycobiol. 18(5):367-83, 2008; Kajiura et al., Glycobiol. 20(6):736-51, 2010). In these studies, the Alg3 mutants exhibited a unique structural profile in the glycoproteins, such as Man3GlcNAc2, Man4GlcNAc2, Man5GlcNAc2, GlcMan5GlcNAc2, and Glc3Man5GlcNAc2, which affected the overall N-glycosylation by incomplete utilization of N-linked glycosites in glycoproteins. No obvious growth phenotype was observed in those Alg3Δ mutants of S. cerevisiae, P. pastoris, T. brucei, and plant except that the Alg3 defect in human caused severe diseases such as profound psychomotor delay, optic atrophy, acquired microcephaly, iris olobomas and hypsarrhythmia (Stibler et al., Neuropediatrics 26(5): 235-7, 1995; Sun et al., J. Clin. Endocrinol. Metab. 90(7):4371-5, 2005; Schollen et al., Eur. J. Med. Genet. 48(2):153-158, 2005, Kranz et al., Am. J. Med. Genet. 143A(13):1414-20, 2007; Denecke et al., Pediatr. Res. 58(2):248-53, 2005).

LaeA, a global regulator gene for the secondary metabolism, was first identified in A. nidulans through complementing the aflR deficient mutants (Bok and Keller, Eukaryot Cell 3:527-535, 2004). Deletion of LaeA gene inhibits the expression of secondary metabolic gene clusters, such as sterigmatocystin, penicillin, and lovastin, but has no effect on spore production in A. nidulans. The LaeA that was confirmed as a nuclear protein and a putative methyltransferase does not involve in gene clusters for nutrient utilization (Bok et al., Mol Microbiol 61:1636-45, 2006). Furthermore, the role of LaeA in secondary metabolism was confirmed in Aspergillus flavus and Aspergillus oryzae (Kale et al., Fungal Genet. Biol. 45:1422-9, 2008; Oda et al., Biosci Biotechnol Biochem 75:1832-4, 2011). Evidence indicates that LaeA reverses gene repression at the level of the heterochromatin state (Reyes-Dominguez et al., Molecular Microbiology 76:1376-86, 2010). LaeA is a component of the heterotrimeric VeA/VelB/LaeA protein complex (Bayram et al., Science Signalling 320:1504, 2008), which involves in the acetylation signal transduction for secondary metabolite production in A. nidulans (Soukup et al., Mol. Microbiol., 86(2):314-30, 2012). The veA/VelB/LaeA complex may coordinately respond to environmental cues (Ramamoorthy et al., Mol. Microbiol., 85(4):795-814, 2012) and has a role in fungal morphology (Calvo, Fungal Genetics and Biology 45:1053-61, 2008). LaeA may direct the formation of the VelB-VosA and VelB-VelA-LaeA complexes, control veA modification and protein levels, and be involved in light regulation of growth and development (Bayram et al., PLoS genetics 6: e1001226, 2010).

SUMMARY

Provided herein are isolated Aspergillus terreus fungi transformed with a heterologous nucleic acid molecule comprising an Aspergillus species gene. Also provided is a method of making itaconic acid by culturing an isolated A. terreus fungus transformed with a heterologous nucleic acid molecule comprising an Aspergillus species LaeA gene under conditions that permit the fungus to make itaconic acid. In some embodiments, the heterologous nucleic acid construct includes a heterologous LaeA gene, a heterologous promoter, a heterologous transcription terminator, and/or a heterologous selective marker gene. In non-limiting examples, the heterologous Aspergillus species LaeA gene is an A. fumigatus laeA gene, an A. nidulans laeA gene, an A. niger LaeA gene, or an A. oryzae laeA gene.

Although the current commercial conversion rate of carbohydrate to citric acid in A. niger is more than eighty to ninety percent, further improvement in production of citric acid and other metabolites is desirable. This disclosure describes the role of the dolichyl-P-Man:Man(5)GlcNAc(2)-PP-dolichyl mannosyltransferase gene (α-1,3-mannosyltransferase, Alg3) on the spore germination, filamentous growth, sporulation, and production of citric acid in Aspergillus niger. In addition, the role of LaeA in citric acid production by its over-expression is shown, alone or in combination with an Alg3Δ mutant background.

Based on these observations, provided herein are isolated fungi (such as filamentous fungi) having a gene inactivation (also referred to herein as a gene deletion) of a dolichyl-P-Man:Man(5)GlcNAc(2)-PP-dolichyl mannosyltransferase (Alg3) gene (referred to herein as Alg3Δ strains), a gene enhancement (e.g., overexpression) of a LaeA gene (referred to herein as upregulated LaeA strains), or both. Any strain of fungi can be used, such as a filamentous fungi, for example Aspergillus niger (A. niger) or particular strains thereof (for example A. niger strain 11414 or 11414KusA). In particular examples, an Alg3Δ strain exhibits one or more of the following characteristics: slower growth on citric acid production (CAP) medium, complete medium (CM) or potato dextrose agar (PDA) medium; earlier spore germination and a higher germination rate in CAP medium; delayed spore germination in CM or PDA medium; reduced sporulation on complete medium; or combinations thereof. In some examples, such increases or decreases are relative to A. niger strain 11414KusA grown under the same conditions. The combination of Alg3Δ and over-expression of LaeA resulted in some improvement of sporulation on CM.

In particular examples, such Alg3Δ strains, up-regulated LaeA strains, or Alg3Δ-upregulated LaeA strains, produce more citric acid when grown in CAP medium, such as at least 20%, at least 50%, or at least 70% more than A. niger strain 11414KusA under identical growing conditions after at least 4 days, at least 5 days or at least 10 days. Thus, one strategy to increase citric acid production is to reduce the carbohydrate consumption for protein glycosylation and cellular formation, as altering protein glycosylation can augment the carbohydrate flux into citric acid production in A. niger.

Also provided herein are compositions (such as fermentation broth) and kits that include a fungal Alg3Δ strain, up-regulated LaeA strain, or Alg3Δ-upregulated LaeA strain.

Also provided herein are methods of making citric acid using the disclosed fungal Alg3Δ strains, up-regulated LaeA strains, and Alg3Δ-upregulated LaeA strains. For example, such a method can include culturing an isolated Alg3Δ fungus, up-regulated LaeA fungus, or Alg3Δ-upregulated LaeA fungus, under conditions that permit the fungus to make citric acid, thereby making citric acid. For example, the Alg3Δ fungus, up-regulated LaeA fungus, or Alg3Δ-upregulated LaeA fungus, can be cultured in CAP medium. In some examples, the method further includes isolating the citric acid produced.

The foregoing and other objects and features of the disclosure will become more apparent from the following detailed description, which proceeds with reference to the accompanying figures.

BRIEF DESCRIPTION OF THE DRAWINGS

FIGS. 6A and 6B show spore germination of parent 11414kusA and Alg3Δ strains in citric acid production (CAP) liquid medium. (FIG. 6A, top left and bottom left panel) Inverted microscopic images for parent 11414kusA strain. (FIG. 6A, top right and bottom right panel) Inverted microscopic images for Alg3Δ strain. (FIG. 6A, top panels) Strains grown in CAP liquid culture at 30° C. for 8 hours. (FIG. 6A, bottom panels) Strains grown in CAP liquid culture at 30° C. for 15 hours. (FIG. 6B) Time course of the spore germination rate (%) of parent and Alg3Δ strains grown in CAP liquid culture. The solid cycle for parent 11414kusA strain and open cycle for the Alg3Δ strain.

FIG. 9 shows an alignment of Alg3 nucleic acid sequences from *A. niger* (top strand, nucleotides 1986-2518 of SEQ ID NO: 1) and *A. oryzae* (bottom strand, nucleotides 643-1175 of SEQ ID NO: 3).

FIGS. 10A and 10B show an alignment of Alg3 protein sequences from *A. niger* (SEQ ID NO: 2), *A. nidulans* (SEQ ID NO: 31), *Fusarium oxysporum* (SEQ ID NO: 32), *Neurospora crassa* (SEQ ID NO: 33), *S. cerevisiae* (SEQ ID NO: 34), *Arabidopsis thaliana* (SEQ ID NO: 35), and *Homo sapiens* (SEQ ID NO: 36). The signs at the top of the alignment show: '−' the average weight of column pair exchanges is less than weight matrix mean value; '.' is less than mean value plus one SD; '+' is less than mean value plus two SD; and '*' is more than mean value plus two SD.

FIG. 11 shows an alignment of Alg3 protein sequences from *A. niger* (top strand, amino acids 12-411 of SEQ ID NO: 2) and *S. cerevisiae* (bottom strand, amino acids 31-434 of SEQ ID NO: 34).

FIG. 12 shows an alignment of LaeA protein sequences from *A. nidulans* (top strand, amino acids 14-372 of SEQ ID NO: 41) and *A. niger* (bottom strand, amino acids 14-370 of SEQ ID NO: 59).

FIGS. 15A and 15B show the results of polymerase chain reaction (PCR) analysis of LaeA gene insertion in the transgenic *A. niger* genome of heterologous expression of *A. nidulans* LaeA gene. (FIG. 15A) PCR products of *A. oryzae* ptrA gene detected in selected single spore colony isolate (SCI) of LaeA gene transgenic mutants and parent kusA and Alg3Δ are control strains. (FIG. 15B) PCR products of transgene expression DNA fragment including the gpdA promoter, LaeA coding region and trpC gene transcriptional terminator. The SCI-1 to SCI-4 is the individual single spore colony of LaeA gene transgenic mutants and parent kusA and Alg3Δ are control strains. Lambda DNA marker is the restriction fragment of BstEII restriction enzyme.

SEQUENCE LISTING

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Oct. 19, 2015, 157 KB, which is incorporated by reference herein. In the accompanying sequence listing:

SEQ ID NOS: 1 and 2 are exemplary Alg3 nucleic acid and protein sequences, respectively, from A. niger.

SEQ ID NOS: 3 and 4 are exemplary Alg3 nucleic acid and protein sequences, respectively, from A. oryzae.

SEQ ID NOS: 5-30 show exemplary primer sequences.

SEQ ID NOS: 31-36 are exemplary Alg3 protein sequences from A. nidulans, Fusarium oxysporum, Arabidopsis thaliana, Neurospora crassa, S. cerevisiae, and Homo sapiens, respectively.

SEQ ID NO: 37 is an exemplary Aspergillus nidulans glyceraldehyde 3-phosphate dehydrogenase (gpdA) promoter sequence.

SEQ ID NOS: 38 and 39 are exemplary forward and reverse primers, respectively, that can be used to isolate or amplify an A. nidulans gpdA promoter.

SEQ ID NOS: 40 and 41 are exemplary Aspergillus nidulans methyltransferase (LaeA) coding and protein sequences, respectively.

SEQ ID NOS: 42 and 43 are exemplary forward and reverse primers, respectively, that can be used to isolate or amplify an A. nidulans LaeA sequence.

Figure 13:
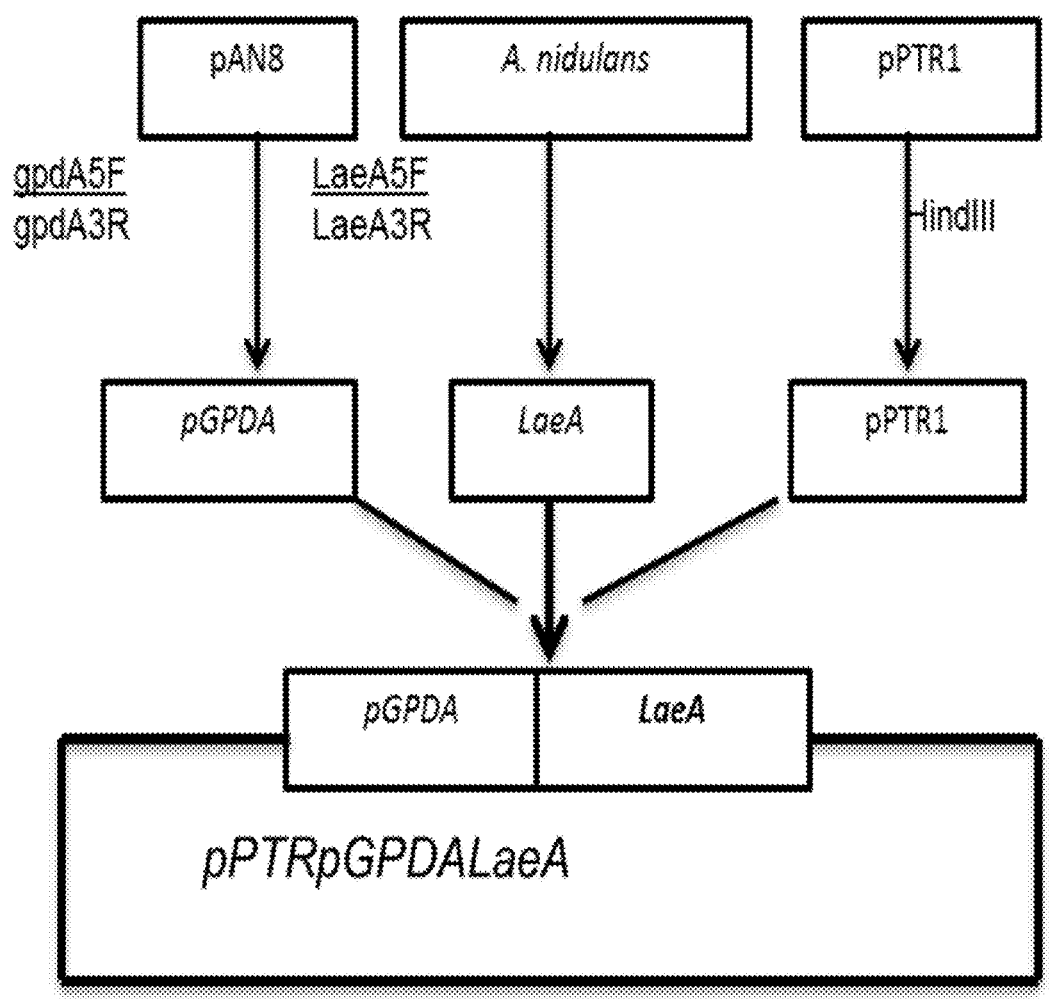
FIG. 13 is a schematic diagram showing the construction of pPTRpGPDALaeA plasmid vector. Both the glyceraldehyde 3-phosphate dehydrogenase (gpdA) promoter and LaeA (loss of aflR expression A) gene coding sequence of genomic DNA were isolated by overlap PCR from pAN7-1 plasmid vector and *A. nidulans* with additions of HindIII restriction enzyme sites at 5'-end of gpdA promoter and 3'-end of LaeA gene, confirmed by DNA sequence, and ligated into pPTR1 plasmid vector at HindIII restriction enzyme site.

SEQ ID NO: 44 is the nucleic acid sequence of the pGPDA-LaeA fragment described in FIG. 13 and Example 5.

SEQ ID NO: 45 is the upstream region of A. niger pyrG gene.

SEQ ID NO: 46 is the trpC transcriptional terminator of A. nidulans.

SEQ ID NO: 47 is the pyrithiamine resistance gene (ptrA) of Aspergillus oryzae.

SEQ ID NO: 48 is the downstream region of A. niger pyrG gene.

SEQ ID NOS: 49 and 50 are exemplary forward and reverse primers, respectively, that can be used to isolate or amplify an upstream region of A. niger pyrG.

SEQ ID NOS: 51 and 52 are exemplary forward and reverse primers, respectively, that can be used to isolate or amplify the trpC transcriptional terminator of *A. nidulans*.

SEQ ID NOS: 53 and 54 are exemplary forward and reverse primers, respectively, that can be used to isolate or amplify ptrA of *Aspergillus oryzae*.

SEQ ID NOS: 55 and 56 are exemplary forward and reverse primers, respectively, that can be used to isolate or a downstream region of *A. niger* pyrG.

SEQ ID NO: 57 is the nucleic acid sequence of the transgene fragment described in FIG. 13 and Example 6.

SEQ ID NOS: 58 and 59 are exemplary *Aspergillus niger* LaeA coding and protein sequences, respectively.

SEQ ID NO: 60 is the nucleic acid sequence of the transgene fragment used to complement the alg3Δ mutant with the original alg3 gene at pyrG locus.

SEQ ID NO: 61 is the nucleic acid sequence of the 5' end of the *A. niger* LaeA gene.

SEQ ID NO: 62 is the nucleic acid sequence of the 3' end of the *A. niger* LaeA gene.

SEQ ID NO: 63 is the nucleic acid sequence of the hph expression cassette.

SEQ ID NO: 64 is the nucleic acid sequence of the *A. niger* LaeA gene.

SEQ ID NO: 65 is the nucleic acid sequence of the LaeA deletion cassette.

SEQ ID NO: 66 is the nucleic acid sequence of the LaeA complementation construct.

SEQ ID NOs: 67-100 are oligonucleotide primers.

SEQ ID NO: 101 is the nucleotide sequence of the 1546/1548 fragment.

SEQ ID NO: 102 is the nucleotide sequence of the 1549/1550 fragment.

SEQ ID NO: 103 is the nucleotide sequence of the 1551/1553 fragment.

SEQ ID NO: 104 is the nucleotide sequence of the 1547/1552 fragment.

SEQ ID NO: 105 is the nucleotide sequence of the 1554/1555 fragment.

SEQ ID NO: 106 is the nucleotide sequence of the 1556/1557 fragment.

SEQ ID NO: 107 is the nucleotide sequence of the 1558/1559 fragment.

SEQ ID NO: 108 is the nucleotide sequence of the 1561/1562 fragment.

SEQ ID NO: 109 is the nucleotide sequence of the 1563/1564 fragment.

SEQ ID NO: 110 is the nucleotide sequence of the 1565/1566 fragment.

DETAILED DESCRIPTION

Unless otherwise explained, all technical and scientific terms used herein have the same meaning as commonly understood by one of ordinary skill in the art to which this disclosure belongs. Definitions of common terms in molecular biology may be found in Benjamin Lewin, Genes V, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All references and GENBANK™ Accession numbers mentioned herein are incorporated by reference (the sequence available on Nov. 30, 2011). The materials, methods, and examples are illustrative only and not intended to be limiting.

In order to facilitate review of the various embodiments of the disclosure, the following explanations of specific terms are provided:

Alg3 (dolichyl-P-Man:Man(5)GlcNAc(2)-PP-dolichyl mannosyltransferase): Also known as asparagine-linked glycosylation 3 and α-1,3-mannosyltransferase. Alg3 encodes an enzyme which catalyzes the addition of the first dol-p-man derived mannose in an α-1,3 linkage to Man5GlcNAc2-PP-Dol. The term Alg3 (or Alg3) includes any Alg3 gene (such as a fungal Alg3 sequence), cDNA, mRNA, or protein, that is an Alg3 involved in catalyzing the addition of the first dol-p-man derived mannose in an α-1,3 linkage to Man5GlcNAc2-PP-Dol, and when genetically inactivated results in a fungus that has an ability to produce more citric acid than the parent strain (such as at least 20%, at least 30%, at least 50%, at least 60%, or at least 70% more than a parent strain under the same growing conditions).

Alg3 sequences are publicly available for many species of *Aspergillus*. For example, GENBANK™ Accession Nos: XM_001823992.2 and XP_001824044 disclose *Aspergillus oryzae* RIB40 Alg3 nucleic acid and protein sequences, respectively; GENBANK™ Accession Nos: XM_001398659.2 and XP_001398696.2 disclose *Aspergillus niger* CBS 513.88 Alg3 nucleic acid and protein sequences, respectively (SEQ ID NOS: 1 and 2); and GENBANK™ Accession Nos: XM_748359.1 and XP_753452 disclose *Aspergillus fumigatus* Af293 Alg3 nucleic acid and protein sequences, respectively. Additional exemplary Alg3 sequences are provided in SEQ ID NOS: 1-4 and 31-36. However, one skilled in the art will appreciate that in some examples, an Alg3 sequence can include variant sequences (such as allelic variants and homologs) that retain Alg3 activity but when genetically inactivated in *Aspergillus* results in a fungus that has an ability to produce more citric acid than the parent strain (such as at least 20%, at least 30%, at least 50%, at least 60%, or at least 70% more under the same growing conditions).

*Aspergillus terreus*: A fungus found in soil and vegetation. *A. terreus* is found worldwide, but is more prevalent in warmer climates, such as tropical and subtropical regions. This fungus is commonly used in industry to produce important organic acids, such as itaconic acid and cis-aconitic acid, and was the initial source for the drug mevinolin (lovastatin), a drug for lowering serum cholesterol (Bennett, "An Overview of the Genus *Aspergillus*," pages 1-17, *Aspergillus Molecular Biology and Genomics*, edited by Masayuki Machida and Katsuyi Gomi, Caister, Academic Press, 2010).

Detectable: Capable of having an existence or presence ascertained. For example, production of citric acid is detectable if the signal generated is strong enough to be measurable.

Genetic enhancement or up-regulation: When used in reference to the expression of a nucleic acid molecule, such as a gene, refers to any process which results in an increase in production of a gene product. A gene product can be RNA (such as mRNA, rRNA, tRNA, and structural RNA) or protein. Examples of processes that increase transcription include those that facilitate formation of a transcription initiation complex, those that increase transcription initiation rate, those that increase transcription elongation rate, those that increase processivity of transcription and those that relieve transcriptional repression (for example by blocking the binding of a transcriptional repressor). Gene up-regulation can include inhibition of repression as well as stimulation of expression above an existing level. Examples of processes that increase translation include those that increase translational initiation, those that increase translational elongation and those that increase mRNA stability. In one example, additional copies of genes are introduced into a cell in order to increase expression of that gene in the resulting transgenic cell.

Gene up-regulation includes any detectable increase in the production of a gene product. In certain examples, production of a gene product increases by at least 1.5-fold, at least 2-fold, or at least 5-fold), such as LaeA. For example, a genetic enhancement of a LaeA gene in *Aspergillus* (e.g., *A. niger* or *A. terreus*) results in an *Aspergillus* strain having increased levels of the LaeA protein relative to the parent strain, which can increase the ability of the fungus to produce more citric acid or itaconic acid. Genetic enhancement is also referred to herein as "enhancing or increasing expression."

Genetic inactivation or down-regulation: When used in reference to the expression of a nucleic acid molecule, such as a gene, refers to any process which results in a decrease in production of a gene product. A gene product can be RNA (such as mRNA, rRNA, tRNA, and structural RNA) or protein. Therefore, gene down-regulation or deactivation includes processes that decrease transcription of a gene or translation of mRNA.

For example, a mutation, such as a substitution, partial or complete deletion, insertion, or other variation, can be made to a gene sequence that significantly reduces (and in some cases eliminates) production of the gene product or renders the gene product substantially or completely non-functional. For example, a genetic inactivation of an Alg3 gene in *Aspergillus* (e.g., *A. niger*) results in *Aspergillus* having a non-functional or non-existent Alg3 protein, which results in an ability of the fungus to produce more citric acid. Genetic inactivation is also referred to herein as "functional deletion".

Heterologous: Derived from separate genetic sources or species. For example, an LaeA gene that is heterologous to *A. terreus* is an LaeA gene from a species other than *A. terreus*.

Isolated: To be significantly separated from other agents. An "isolated" biological component (such as a nucleic acid molecule or protein) has been substantially separated, produced apart from, or purified away from other biological components in the cell of the organism in which the component occurs, for example, other chromosomal and extra-chromosomal DNA and RNA, and proteins. Nucleic acid molecules and proteins which have been "isolated" include nucleic acid molecules and proteins purified by standard purification methods. The term also embraces nucleic acid molecules and proteins prepared by recombinant expression in a host cell as well as chemically synthesized proteins and nucleic acids. Samples of isolated biological components include samples of the biological component wherein the biological component represents greater than 90% (for example, greater than 95%, such as greater than 98%) of the sample.

An "isolated" microorganism (such as an Alg3Δ strain of *Aspergillus*) has been substantially separated or purified away from microorganisms of different types, strains, or species. Microorganisms can be isolated by a variety of techniques, including serial dilution and culturing and resistance to certain chemicals.

Itaconic acid: An unsaturated dicarbonic acid; also known as 2-methylidenebutanedioic acid. Itaconic acid can be produced by the fermentation of carbohydrates using *Aspergillus terreus*. Itaconic acid can be used as a monomer for the production of a number of different products, including resins, plastics, acrylate latexes, paints and synthetic fibers.

Itaconic acid production medium: Media containing in grams per liter (g/l): glucose, 100; ammonium sulfate, 2.36; potassium phosphate dibase, 0.11; magnesium sulfate heptahydrate, 2.08; calcium chloride dihydrate, 0.13; sodium chloride, 0.074; copper sulfate pentahydrate $2 \times 10^{-4}$; ferrous sulfate heptahydrate, $5.5 \times 10^{-3}$; manganese chloride tetrahydrate, $7 \times 10^{-4}$; and zinc sulfate heptahydrate, $1.3 \times 10^{-3}$.

LaeA (loss of afiR expression A): LaeA encodes a protein which regulates secondary metabolite production in *Aspergillus*. The term LaeA (or LaeA) includes any LaeA gene (such as a fungal LaeA sequence), cDNA, mRNA, or protein, that is an LaeA involved in secondary metabolite production. In some embodiments, when LaeA expression is increased, for example in combination with a genetically inactivated Alg3 gene, it results in a fungus that has an ability to produce more citric acid than the parent strain (such as at least 20%, at least 30%, at least 40%, 50%, at least 60%, or at least 70% more than a parent strain under the same growing conditions). In some embodiments, when LaeA expression is increased, for example in *A. terreus*, it results in a fungus that has an ability to produce more itaconic acid than the parent strain (such as at least 20%, at least 30%, at least 40%, 50%, at least 60%, or at least 70% more than a parent strain under the same growing conditions).

LaeA sequences are publicly available for many species of *Aspergillus*. For example, GENBANK™ Accession Nos: AB267276 and BAF74528.1 disclose *Aspergillus oryzae* LaeA nucleic acid and protein sequences, respectively; GENBANK™ Accession No. EHA27020.1 discloses an exemplary *Aspergillus niger* ATCC1015 LaeA protein sequence, a parent strain of 11414kusA (other exemplary sequences are provided in SEQ ID NOS: 58 and 59); GENBANK™ Accession No: CBF88745 discloses an *Aspergillus nidulans* LaeA protein sequence; and GENBANK™ Accession Nos: AY422723 and AAR01218 disclose *Aspergillus fumigatus* LaeA nucleic acid and protein sequences, respectively. Additional exemplary LaeA sequences are provided in SEQ ID NOS: 40-41 and 58-59. However, one skilled in the art will appreciate that in some examples, an LaeA sequence can include variant sequences (such as allelic variants and homologs) that retain LaeA activity and when genetically up-regulated in *Aspergillus* (for example with addition of copy or in combination with Alg3Δ) results in a fungus that has an ability to produce more citric acid than the parent strain (such as at least 20%, at least 30%, at least 40%, at least 50%, at least 60%, or at least 70% more under the same growing conditions).

Mutation: A change in a nucleic acid sequence (such as a gene sequence) or amino acid sequence, for example as compared to a nucleic acid or amino acid sequence present in a wild-type or native organism. In particular examples, a mutation is introduced into an Alg3 gene in *Aspergillus*. Mutations can occur spontaneously, or can be introduced, for example using molecular biology methods. In particular examples, a mutation includes one or more nucleotide substitutions, deletions, insertions, or combinations thereof. In particular examples, the presence of one or more mutations in a gene can significantly inactivate that gene.

Operably linked: A first nucleic acid sequence is operably linked to a second nucleic acid sequence where the first nucleic acid sequence is joined in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Promoter: An array of nucleic acid sequences that governs transcription of a nucleic acid. A promoter includes necessary nucleic acid sequences to initiate gene transcription. A promoter also optionally includes distal enhancer or repressor elements which can be located as much as several thousand base pairs from the start site of transcription.

Recombinant: A recombinant nucleic acid molecule or protein is one that has a sequence that is not naturally occurring or has a sequence that is made by an artificial combination of two otherwise separated segments of sequence. In particular examples, this artificial combination is accomplished by chemical synthesis or by the artificial manipulation of isolated segments of nucleic acids, for example, by genetic engineering techniques such as those described in Sambrook et al. (ed.), Molecular Cloning: A Laboratory Manual, 3d ed., vol. 1-3, Cold Spring Harbor Laboratory Press, Cold Spring Harbor, N.Y., 2001. The term recombinant includes nucleic acid molecules that have been altered solely by addition, substitution, or deletion of a portion of the nucleic acid molecule.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, Gene, 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215:403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

BLASTN is used to compare nucleic acid sequences, while BLASTP is used to compare amino acid sequences. To compare two nucleic acid sequences, the options can be set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to -1; -r is set to 2; and all other options are left at their default setting. For example, the following command can be used to generate an output file containing a comparison between two sequences: C:\B12seq -i c:\seq1.txt -j c:\seq2.txt -p blastn -o c:\output.txt -q -1 -r 2.

To compare two amino acid sequences, the options of B12seq can be set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\B12seq -i c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (e.g., 100 consecutive nucleotides or amino acid residues from a sequence set forth in an identified sequence), followed by multiplying the resulting value by 100. For example, a nucleic acid sequence that has 1166 matches when aligned with a test sequence having 1554 nucleotides is 75.0 percent identical to the test sequence (i.e., 1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (i.e., 15÷20*100=75).

For comparisons of amino acid sequences of greater than about 30 amino acids, the Blast 2 sequences function is employed using the default BLOSUM62 matrix set to default parameters, (gap existence cost of 11, and a per residue gap cost of 1). Homologs are typically characterized by possession of at least 70% sequence identity counted over the full-length alignment with an amino acid sequence using the NCBI Basic Blast 2.0, gapped blastp with databases such as the nr or swissprot database. Queries searched with the blastn program are filtered with DUST (Hancock and Armstrong, 1994, *Comput. Appl. Biosci.* 10:67-70). Other programs use SEG. In addition, a manual alignment can be performed. Proteins with even greater similarity will show increasing percentage identities when assessed by this method, such as at least 75%, 80%, 85%, 90%, 95%, or 99% sequence identity.

Nucleic acid sequences that do not show a high degree of identity may nevertheless encode identical or similar (conserved) amino acid sequences, due to the degeneracy of the genetic code. Changes in a nucleic acid sequence can be made using this degeneracy to produce multiple nucleic acid molecules that all encode substantially the same protein. Such homologous nucleic acid sequences can, for example, possess at least 60%, 70%, 80%, 90%, 95%, 98%, or 99% sequence identity determined by this method.

One of skill in the art will appreciate that these sequence identity ranges are provided for guidance only; it is possible that strongly significant homologs could be obtained that fall outside the ranges provided.

Transformed: A cell, such as a fungal cell, into which a nucleic acid molecule has been introduced, for example by molecular biology methods known in the art. As used herein, the term transformation encompasses all techniques by which a nucleic acid molecule might be introduced into such a cell, including, but not limited to transfection with viral vectors, conjugation, transformation with plasmid vectors, and introduction of naked DNA by chemical-mediated, electroporation, lipofection, and biolistic particle delivery.

Overview

Disclosed herein is the finding that overexpression of the LaeA gene in *A. terreus* results in a significant increase in production of itaconic acid. In particular, *A. terreus* transformed with a nucleic acid construct comprising an *Aspergillus* species LaeA gene produces significantly more itaconic acid relative to *A. terreus* that is not transformed with the construct.

Providing herein are isolated *A. terreus* fungi transformed with a heterologous nucleic acid construct comprising an *Aspergillus* species LaeA (loss of aflR expression A) gene. Expression of LaeA is increased in the transformed fungus compared to an *A. terreus* fungus that is not transformed with the heterologous nucleic acid construct.

In some embodiments, the heterologous nucleic acid construct comprises a heterologous LaeA gene, a heterologous promoter, a heterologous transcription terminator, a heterologous selective marker gene, or any combination thereof.

In some embodiments, the *Aspergillus* species LaeA gene is a homologous LaeA gene (i.e. an *A. terreus* LaeA gene). In other embodiments, the LaeA gene is a heterologous LaeA gene, such as an LaeA gene from *A. nidulans, A. niger, A. oryzae, A. fumigatus* or another *Aspergillus* species. In some examples, the *A. nidulans* LaeA gene encodes a protein having at least 80%, at least 85%, at least 90%, at least 95%, at least 96%, at least 97%, at least 98% or at least 99% sequence identity to the amino acid sequence of SEQ ID NO: 41. In non-limiting examples, the *A. nidulans* LaeA gene encodes a protein comprising the amino acid sequence of SEQ ID NO: 41. In some examples, the *A. niger* LaeA gene encodes a protein having at least 80%, at least 85%, at least 90%, at least 95%, at least 96%, at least 97%, at least 98% or at least 99% identity to the amino acid sequence of SEQ ID NO: 59. In non-limiting examples, the *A. niger* LaeA gene encodes a protein comprising the amino acid sequence of SEQ ID NO: 59.

In some embodiments, the heterologous nucleic acid molecule comprises a promoter operably linked to an *Aspergillus* species LaeA gene, a transcription terminator and/or a selective marker gene. In particular examples, the promoter is a heterologous promoter, such as, but not limited to, the *A. nidulans* gpdA promoter, or any other promoter that is functional in *Aspergillus* (e.g., the actA, ubi4, Arsa-7, A-37, Brsa-109, gpdA, pyrG or tefl α promoters from *A. niger*). In other particular examples, the *Aspergillus* species LaeA gene is a heterologous LaeA gene, such as, but not limited to, an *A. nidulans, A. niger, A. oryzae,* or *A. fumigatus* LaeA gene. In other particular examples, the transcription terminator is a heterologous transcription terminator, such as, but not limited to, the *A. nidulans* TrpC transcription terminator. As an alternative to trpC, other transcriptional terminators can be used, such as promoters which include a transcriptional terminator (e.g., actA, ArsA7, Arsa-37, gpdA, pyrG, tefl α or ubi4). In yet other particular examples, the selective marker is a heterologous selective marker gene, such as a heterologous antibiotic resistance gene. In specific examples, selective marker gene is an *A. oryzae* pyrithiamine resistance (ptrA) gene. Other selective marker genes include, for example, the hygromycin B phosphotransferase (hph) gene, the bar gene (which confers glufosinate resistance), or bleomycin resistance gene (ble), or auxotrophic markers, such as pyrG.

In specific non-limiting examples, the heterologous nucleic acid molecule comprises the nucleotide sequence of SEQ ID NO: 109.

Further provided herein is a method of making itaconic acid. In some embodiments, the includes culturing an isolated *A. terreus* fungus transformed with a heterologous nucleic acid molecule comprising an *Aspergillus* species LaeA gene under conditions that permit the fungus to make itaconic acid. Expression of LaeA is increased in the transformed fungus compared to an *A. terreus* fungus that is not transformed with the heterologous nucleic acid construct. In some embodiments, the fungus is cultured in itaconic acid production medium, which contains grams per liter (g/l): glucose, 100; ammonium sulfate, 2.36; potassium phosphate dibase, 0.11; magnesium sulfate heptahydrate, 2.08; calcium chloride dihydrate, 0.13; sodium chloride, 0.074; copper sulfate pentahydrate $2 \times 10^{-4}$; ferrous sulfate heptahydrate, $5.5 \times 10^{-3}$; manganese chloride tetrahydrate, $7 \times 10^{-4}$; and zinc sulfate heptahydrate, $1.3 \times 10^{-3}$.

In some embodiments of the methods of making itaconic acid, the heterologous nucleic acid construct comprises a heterologous LaeA gene, a heterologous promoter, a heterologous transcription terminator, a heterologous selective marker gene, or any combination thereof.

In some embodiments of the methods, the *Aspergillus* species LaeA gene is a homologous LaeA gene (i.e. an *A. terreus* LaeA gene). In other embodiments, the LaeA gene is a heterologous LaeA gene, such as an LaeA gene from *A. nidulans, A. niger, A. oryzae, A. fumigatus* or another *Aspergillus* species. In some examples, the *A. nidulans* LaeA gene encodes a protein having at least 80%, at least 85%, at least 90%, at least 95%, at least 96%, at least 97%, at least 98% or at least 99% sequence identity to the amino acid sequence of SEQ ID NO: 41. In non-limiting examples, the *A. nidulans* LaeA gene encodes a protein comprising the amino acid sequence of SEQ ID NO: 41. In some examples, the *A. niger* LaeA gene encodes a protein having at least 80%, at least 85%, at least 90%, at least 95%, at least 96%, at least 97%, at least 98% or at least 99% identity to the amino acid sequence of SEQ ID NO: 59. In non-limiting examples, the *A. niger* LaeA gene encodes a protein comprising the amino acid sequence of SEQ ID NO: 59.

In some embodiments of the method, the heterologous nucleic acid molecule comprises a promoter operably linked to an *Aspergillus* species LaeA gene, a transcription terminator and/or a selective marker gene. In particular examples, the promoter is a heterologous promoter, such as, but not limited to, the *A. nidulans* gpdA promoter. In other particular examples, the *Aspergillus* species LaeA gene is a heterologous LaeA gene, such as, but not limited to, an *A. nidulans*, *A. niger*, *A. oryzae*, or *A. fumigatus* LaeA gene. In other particular examples, the transcription terminator is a heterologous transcription terminator, such as, but not limited to, the *A. nidulans* TrpC transcription terminator. In yet other particular examples, the selective marker is a heterologous selective marker gene, such as a heterologous antibiotic resistance gene. In specific examples, the selective marker gene is an *A. oryzae* pyrithiamine resistance (ptrA) gene. In specific non-limiting examples, the heterologous nucleic acid molecule comprises the nucleotide sequence of SEQ ID NO: 109.

Also provided by the present disclosure are compositions that include isolated *A. terreus* fungi transformed with a heterologous nucleic acid construct. The compositions may further include growth medium. Further provided by the present disclosure are kits that include isolated *A. terreus* fungi transformed with a heterologous nucleic acid construct, such as a kit that includes a medium for culturing, storing, or growing the fungus, and/or antibiotics (for selection).

This disclosure also provides the first demonstration that genetic inactivation of Alg3, a gene involved in protein N-linked glycosylation, can result in substantial improvement of citric acid production in *A. niger*, while the total biomass is similar to the parent strain. The core oligosaccharide Glc3Man9GlcNAc2 is synthesized by a series of membrane-bound glycosyltransferases, which begins on the cytoplasmic side of the membrane of the endoplasmic reticulum (ER) and flips into the luminal side of the ER membrane to complete its synthesis. The lipid-linked core Glc3Man9GlcNAc2 is subsequently transferred to a nascent protein in the ER, where the glycoproteins are folded and then shuttled to the Golgi for additional, but divergent processing. The Alg3 gene encodes the enzyme α-1,3-mannosyltransferase that converts Man5GlcNAc2-Dol-PP to Man6GlcNAc2-Dol-PP on the ER membrane of the luminal side. Provided herein is a homolog of *Saccharomyces cerevisiae* Alg3 identified from *Aspergillus niger* (e.g., see SEQ ID NOS: 1 and 2).

It is shown herein that genetic inactivation of Alg3 in *A. niger* resulted in a significant reduction of growth on complete medium (CM) and potato dextrose agar medium (PDA), but no effect on minimal medium (MM). The Alg3 deletion also caused the substantial reduction in spore production of *A. niger* on CM, but no significant change on the PDA. When the spores were germinated in CM or PDA liquid culture medium, the Alg3Δ strain showed pronounced delay in spore germination. This growth phenotype is similar to the mutants with defects in signal transduction pathways observed in *A. nidulans* and *A. niger* (Fillinger et al., *Mol. Microbiol.* 44(4):1001-16, 2002; Saudohar et al., *Microbiol.* 148(8):2635-45, 2002; Xue et al., *Eukaryot Cell* 3(2):557-60, 2004). Deletion of pkaA, cycaA or schA/pkaA in *A. nidulans* substantially reduces its growth on CM medium plates and spore germination rate in MM liquid culture medium (Fillinger et al., *Mol. Microbiol.* 44(4):1001-1016, 2002) and similar growth phenotypes were observed in the strains with the deletion of pkaR, pkaC or double deletion of pkaR/pkaC in *A. niger* (Saudohar et al., *Microbiol.* 148(8): 2635-2645, 2002). However, functional deletion of the MAP kinase SakA in *A. fumigatus* delays the spore germination in liquid CM, but stimulates spore germination in MM liquid medium (Xue et al., *Eukaryot Cell* 3(2): 557-560, 2004).

Figure 8A:
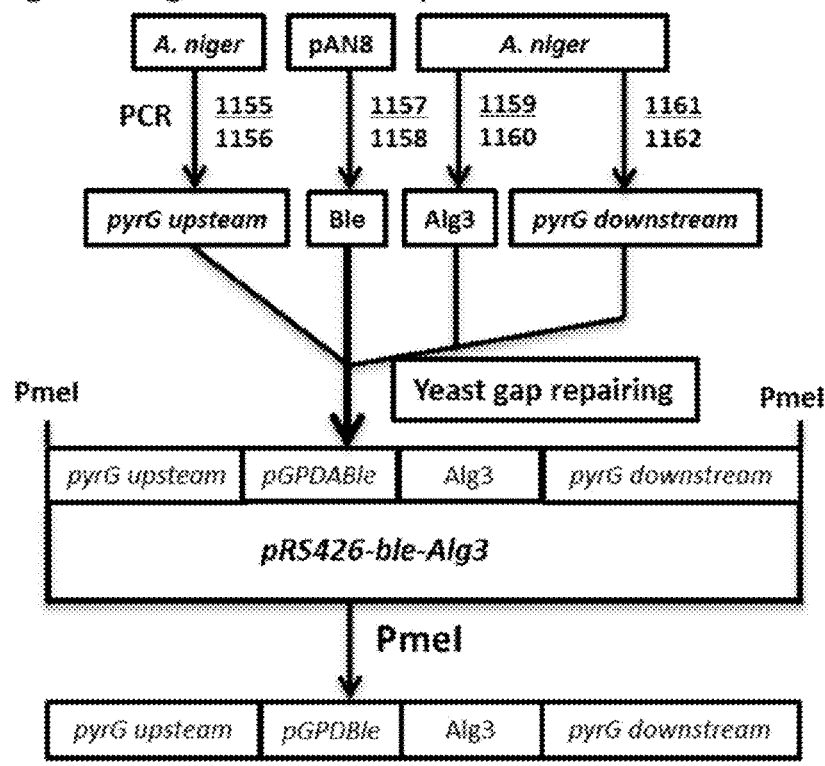
FIGS. 8A and 8B show (FIG. 8A) a schematic diagram showing the construction of the transgene used to complement the Alg3Δ mutant, and (FIG. 8B) a is a graph showing the citric acid production by parent strain 11414kusA (kusA), Alg3Δ mutant (Alg3) and Alg3Δ mutant complemented with Alg3 gene (cAlg3) after growth at 30° C., 200 rpm for 12 days
Figure 8B:
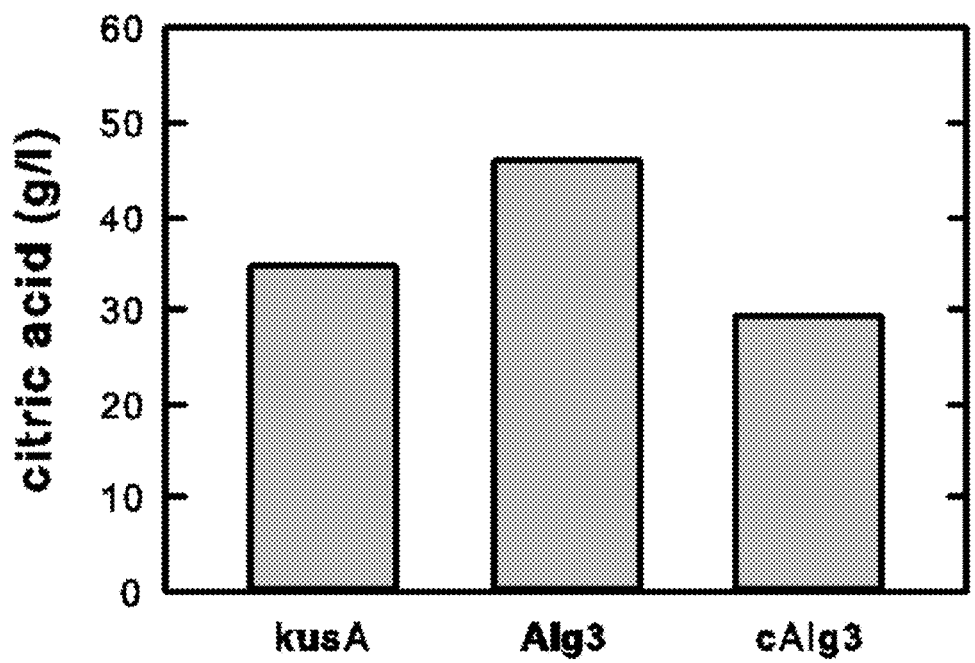

Furthermore, the Alg3 deletion reduced the overall growth on citric acid production (CAP) medium plates at different pHs. In contrast, the Alg3 deletion triggered early spore germination and substantially improved spore germination rate in CAP liquid culture medium. Citric acid production in CAP liquid culture medium was significantly improved in *A. niger*. When the alg3Δ mutant was complemented with the original alg3 gene at pyrG locus (FIG. 8A; SEQ ID NO: 60), its transcription levels was similar to parent strain with the cycle threshold (Ct) values about 23, while the Ct value for alg3Δ mutant was 30.8 in CAP liquid culture conditions, which was determined by real-time reverse-transcription PCR. Consequently, the citric acid production in the resulted complemented mutant strains was similar to the parent strain as shown in FIG. 8B. The results shown herein demonstrate the involvement of Alg3 on the growth and development and citric acid production in *A. niger*.

It is proposed that inactivation of Alg3 influences the N-glycosylation of those proteins involving in signal transduction pathways. The N-glycosylation consensus sequence (N-glycosite) for N-glycosylation in those proteins from the signal transduction pathways was observed. Most of those proteins contained 1 to 7 N-glycosites, such as, 6 N-glycosites found in sskB (map kinase kinase), 7 in Ste11/SteC, 5 in acyA, 5 in rgsA, 6 in rgsC, 4 in gprA, 4 in pkaC2, 4 in flbA and 3 in Gβ. Comparison of these results with previous studies indicates that the effects of the Alg3 deletion on spore germination and growth may be regulated by altering the N-glycosylation in those proteins involved in signal transduction pathways in *A. niger*.

When the Alg3Δ strain was grown on CM medium, spore production of Alg3Δ mutants was dramatically reduced as compared to the parent strain, while maintaining a similar level when grown on PDA medium. This phenotype of sporulation production may be influenced by both endogenous and exogenous factors. For example, protein glycosylation was greatly influenced by culture conditions in filamentous fungi, such as fully glycosylated Cel7A only isolated from MM culture medium (Stals et al., *Glycobiology* 14(8):725-737, 2004). In addition, higher amounts of proteases were secreted by the Alg3Δ strain than the parent in liquid MM culture supplemented 1 g/l yeast extract, which further influenced nutrient uptakes, cellular formation and overall N-glycosylation. This would alter the yield and N-glycosylation in G protein system in *A. niger*, where G protein signaling is crucial for detection of major environmental stimuli for food acquisition, asexual sporulation, and spore germination (Chang et al., *Genetics* 167(3):305, 2004; Li et al., *Annu. Rev. Microbiol.* 61:423-452, 2007).

The spores of parent strain germinated more slowly and had a lower germination rate than the Alg3Δ strain in CAP liquid culture medium, which contains limited nitrogen source (3.1 g/l of $NH_4NO_3$), similar to MM. A similar phenotype was observed when the stress activating kinase, a MAP kinase, was deleted in *A. fumigatus* (SakAΔ strain) and grown in MM liquid culture medium (Xue et al., *Eukaryot Cell* 3(2): 557-560, 2004). The spore germination of SakAΔ strain was dramatically influenced by nitrogen sources. For example, similar rates of spore germination between parent and SakAΔ strains were observed on MM containing 10 mM $NH_4Cl$ or 10 mM Pro, while the spore germination rates of SakAΔ strain was much higher than the parent strain in the MM culture medium containing 10 mM $NaNO_3$, $NaNO_2$, or Phe. In addition, the CAP medium contains high level of glucose and low pH, which contributes additional stresses to *A. niger* growth. Although the Alg3Δ strain had earlier and higher germination in CAP medium, its biomass formation was less than the parent strain at early stages. The dried biomass yields for both parent and Alg3Δ strains were similar after growth in CAP medium for four and half days. However, more citric acid was produced by the Alg3Δ strain than the parent strain. This indicates more glucose was directly converted to citric acid by influence citric acid metabolism and reduction of glucose consumption for complex N-glycan formation and sequentially for other cellular metabolisms.

This disclosure also provides the first demonstration that genetic inactivation of Alg3, in combination with an increase in expression of the loss of aflR expression A (LaeA) gene, can result in substantial improvement of citric acid production in *A. niger*. It is proposed that increased expression of LaeA can also improve citric acid production in *A. niger* or other filamentous fungi. To increase expression of LaeA in fungal cells, a transgene was generated and expressed in *A. niger* as follows. The LaeA gene of *A. nidulans* was operably controlled by glyceraldehyde 3-phosphate dehydrogenase (gpdA) promoter and trpC transcriptional terminator (TtrpC) of *A. nidulans*. This chimeric gene was flanked with the upstream of *A. niger* pyrG gene, the pyrithiamine resistance (ptrA) gene of *A. oryzae* and the downstream of *A. niger* pyrG gene. The transgene expression fragment containing the chimeric gene was used to transform the protoplasts of alg3Δ mutants of *A. niger*.

The present disclosure also describes the generation of an *A. niger* strain having a deletion of the LaeA gene (LaeAΔ), as well as an *A. niger* LaeAΔ strain complemented with a transgene encoding LaeA (c1LaeAΔ) at the pyrG locus. These strains were used to evaluate the role of LaeA expression on citric acid production in *Aspergillus*. The data disclosed herein demonstrates that deletion of the LaeA gene in *A. niger* (LaeAΔ) results in a loss of citric acid production in culture. When the original *A. niger* LaeA gene was used for complementation in the LaeAΔ mutant (cLaeAΔ) at the pyrG locus, citric acid production was partially recovered, which indicates the importance of the chromosomal location of LaeA gene. When *A. nidulans* LaeA was over-expressed in the *A. niger* parent strain, citric acid production was higher than the parent strain. These results indicate that LaeA enhances citric acid production in *A. niger*.

In summary, the deletion of Alg3, increasing expression of LaeA, or both, can be used to increase citric acid production in fungi (such as filamentous fungi, e.g., *A. niger*). In addition, deletion of Alg3 alters the overall N-glycosylation and further influences the spore germination, filamentous growth, sporulation and other organic acid production in *A. niger*.

Alg3Δ Fungi

The present disclosure provides isolated fungi having its Alg3 gene inactivated, wherein such inactivation results in increased citric acid production by the fungi. Such fungi are referred to herein as Alg3Δ fungi. It is disclosed herein that genetic inactivation of Alg3 results in *Aspergillus* fungi that can increase citric acid production as compared to *Aspergillus* having a native Alg3 sequence.

Contemplated herein are isolated fungi containing a genetic inactivation of a dolichyl-P-Man:Man(5)GlcNAc (2)-PP-dolichyl mannosyltransferase gene (Alg3). Any fungus can be used, such as any genus or variety of *Aspergillus*. In particular examples, the disclosed *Aspergillus* fungus is *A. niger*, such as *Aspergillus niger* strain 11414 (American Type Culture Collection (ATCC) No. 11414; NRRL 2270); 1015 (ATCC No. 1015; NRRL 328, CBS 113.46); NRRL 3 (ATCC No. 9029, CBS 120.49, N400); NRRL 3122 (ATCC No. 22343); or 11414KusA-. In other specific examples, the *Aspergillus* is *A. aculeatus, A. awamori, A. carbonarius, A. wentii, A. foetidus, A. oryzae, A. terreus*, or *A. fumigatus*.

In addition, any method for genetic inactivation can be used, as long as the expression of the gene is significantly reduced or eliminated, or the function of the expressed protein is significantly reduced or eliminated. In particular examples, the Alg3 gene is genetically inactivated by complete or partial deletion mutation or by insertional mutation. In some examples genetic inactivation need not be 100% genetic inactivation. In some embodiments, genetic inactivation refers to at least 50%, at least 60%, at least 70%, at least 80%, at least 90%, or at least 95% gene or protein inactivation. The term "reduced" or "decreased" as used herein with respect to a cell and a particular gene or protein activity refers to a lower level of activity than that measured in a comparable cell of the same species. For example, a particular fungi lacking Alg3 activity has reduced Alg3 activity if a comparable fungi not having an Alg3 genetic inactivation has detectable Alg3 activity.

Alg3 sequences are disclosed herein and others are publicly available, for example from GENBANK™ or EMBL. In some examples, the Alg3 gene functionally deleted encodes a protein having at least 80%, at least 90%, at least 95%, at least 97%, or at least 98% sequence identity to SEQ ID NO: 2, 4, 31, 32, 33, 34, 35, or 36. In some examples, the Alg3 gene functionally deleted comprises at least 80%, at least 90%, at least 95%, at least 97%, or at least 98% sequence identity to SEQ ID NO: 1 or 3 or nucleotides 1186-2582 of SEQ ID NO: 1.

The inactivation of Alg3 results in many phenotypes in the fungi. For example, Alg3Δ mutants can have one or more of the following phenotypes: slower growth on citric acid production (CAP) medium, earlier spore germination in CAP medium (for example germination in at least 3 hours, at least 4 hours, or at least 5 hours after inoculation, such as within 3 hours of inoculation), increased spore germination rate in CAP medium, increased citric acid production in CAP medium, slower growth on complete medium (CM) or potato dextrose (PDA) medium, delay initiation of spore germination in CM or PDA medium, reduced sporulation on CM, or combinations thereof.

Such changes (such as increases or decreases) can be relative to a fungi having a wild-type Alg3 gene, such as a parental strain (e.g., *A. niger* strain 11414KusA), grown under the same conditions as the Alg3Δ mutant. In some examples, an increased germination rate is germination of at least 20%, at least 25%, or at least 30% of the spores from an Alg3Δ fungus have germinated 8 hours after inoculation in CAP medium (such as 20% to 35%, such as 32%), as compared to no more than 20%, no more than 15%, or no more than 10% (such as 5 to 15%, or 10%) for *A. niger* strain 11414KusA. In some examples, an increased germination rate is germination of at least 80%, at least 85%, or at least 90% of the spores from an Alg3Δ fungus have germinated 15 hours after inoculation in CAP medium (such as 80% to 95%, such as 90%), as compared to no more than 60%, no more than 65%, or no more than 75% (such as 55 to 65%, or 60%) for *A. niger* strain 11414KusA. In some examples, increased citric acid production in CAP medium is an increase of at least 10%, at least 20%, at least 30%, at least 40%, at least 50%, at least 60%, at least 65%, or at least 70%, by an Alg3Δ fungus as compared to *A. niger* strain 11414KusA. In some examples, reduced sporulation on complete medium is a reduction of sporulation by at least 20%, at least 30%, at least 40%, at least 50%, or at least 60%, (such as a 40% to 60% reduction) by an Alg34 fungus as compared to *A. niger* strain 11414KusA.

One skilled in the art will appreciate that additional genes can also be inactivated, wherein the additional genes may or may not provide additional enhancement of citric acid production to the fungus. In one example KusA (e.g., GENBANK™ Accession No. EF061656) is also genetically inactivated.

Also provided by the present disclosure are compositions that include isolated Alg3Δ fungi, such as a growth medium. Also provided by the present disclosure are kits that include isolated Alg3Δ fungi, such as a kit that includes a medium for culturing, storing, or growing the fungus. Exemplary mediums include solid medium (such as those containing agar, for example CM, PDA or MM) and liquid media (such as a fermentation broth, such as CM, MM, or CAP medium).

A. Methods of Functionally Deleting Genes

As used herein, an "inactivated" or "functionally deleted" gene means that the gene has been mutated, for example by insertion, deletion, or substitution (or combinations thereof) of one or more nucleotides such that the mutation substantially reduces (and in some cases abolishes) expression or biological activity of the encoded gene product. The mutation can act through affecting transcription or translation of the gene or its mRNA, or the mutation can affect the polypeptide product itself in such a way as to render it substantially inactive.

Genetic inactivation of one or more genes (which in some examples is also referred to as functional deletion) can be performed using any conventional method known in the art. In one example, a strain of *Aspergillus* is transformed with a vector which has the effect of down-regulating or otherwise inactivating an Alg3 gene. This can be done by mutating control elements such as promoters and the like which control gene expression, by mutating the coding region of the gene so that any protein expressed is substantially inactive, or by deleting the Alg3 gene entirely. For example, an Alg3 gene can be functionally deleted by complete or partial deletion mutation (for example by deleting a portion of the coding region of the gene) or by insertional mutation (for example by inserting a sequence of nucleotides into the coding region of the gene, such as a sequence of about 1-5000 nucleotides). Thus, the disclosure in some examples provides transformed fungi that include at least one exogenous nucleic acid molecule which genetically inactivates an Alg3 gene (such as a nucleic acid sequence encoding SEQ ID NO: 2 or 4). In one example, such a transformed cell produces more citric acid, for example relative to a comparable fungus with a native Alg3 sequence.

In particular examples, an insertional mutation includes introduction of a sequence that is in multiples of three bases (e.g., a sequence of 3, 9, 12, or 15 nucleotides) to reduce the possibility that the insertion will be polar on downstream genes. For example, insertion or deletion of even a single nucleotide that causes a frame shift in the open reading frame, which in turn can cause premature termination of the encoded Alg3 polypeptide or expression of a substantially inactive polypeptide. Mutations can also be generated through insertion of foreign gene sequences, for example the insertion of a gene encoding antibiotic resistance (such as hygromycin or bleomycin).

In one example, genetic inactivation is achieved by deletion of a portion of the coding region of the Alg3 gene. For example, some, most (such as at least 50%) or virtually the entire coding region can be deleted. In particular examples, about 5% to about 100% of the gene is deleted, such as at least 20% of the gene, at least 40% of the gene, at least 75% of the gene, or at least 90% of the Alg3 gene.

Deletion mutants can be constructed using any of a number of techniques known in the art. In one example, allelic exchange is employed to genetically inactivate one or more genes in *Aspergillus*. A specific example of such a method is described in Example 2 below.

In one example, a strategy using counterselectable markers can be employed which has been utilized to delete genes. For a review, see Reyrat et al. (*Infec. Immun.* 66:4011-4017, 1998). In this technique, a double selection strategy is employed wherein a plasmid is constructed encoding both a selectable and counterselectable marker, with flanking DNA sequences derived from both sides of the desired deletion. The selectable marker is used to select for fungi in which the plasmid has integrated into the genome in the appropriate location and manner. The counterselecteable marker is used to select for the very small percentage of fungi that have spontaneously eliminated the integrated plasmid. A fraction of these fungi will then contain only the desired deletion with no other foreign DNA present.

In another technique, the cre-lox system is used for site specific recombination of DNA (for example see Steiger et al., *Appl. Environ. Microbiol.* 77(1):114, 2011). The system includes 34 base pair lox sequences that are recognized by the bacterial cre recombinase gene. If the lox sites are present in the DNA in an appropriate orientation, DNA flanked by the lox sites will be excised by the cre recombinase, resulting in the deletion of all sequences except for one remaining copy of the lox sequence. Using standard recombination techniques, the targeted gene of interest (e.g., Alg3) can be deleted in the *Aspergillus* genome and to replace it with a selectable marker (for example a gene coding for kanamycin resistance) that is flanked by the lox sites. Transient expression (by electroporation of a suicide plasmid containing the cre gene under control of a promoter that functions in *Aspergillus*) of the cre recombinase should result in efficient elimination of the lox flanked marker. This process will produce a mutant containing the desired deletion mutation and one copy of the lox sequence.

In another method, an Alg3 gene sequence in the *Aspergillus* genome is replaced with a marker gene, such as green fluorescent protein, β-galactosidase, or luciferase. In this technique, DNA segments flanking a desired deletion are prepared by PCR and cloned into a suicide (non-replicating) vector for *Aspergillus*. An expression cassette, containing a promoter active in *Aspergillus* and the appropriate marker gene, is cloned between the flanking sequences. The plasmid is introduced into wild-type *Aspergillus*. Fungi that incorporate and express the marker gene are isolated and examined for the appropriate recombination event (replacement of the wild type Alg3 gene with the marker gene).

Thus, for example, a fungal cell can be engineered to have a disrupted Alg3 gene using common mutagenesis or knockout technology. (Methods in Yeast Genetics (1997 edition), Adams, Gottschling, Kaiser, and Sterns, Cold Spring Harbor Press, 1998; Datsenko and Wanner, *Proc. Natl. Acad. Sci. USA* 97: 6640-5, 2000; and Dai et al., *Appl. Environ. Microbiol.* 70(4):2474-85, 2004). Alternatively, antisense technology can be used to reduce or eliminate the activity of Alg3. For example, a fungal cell can be engineered to contain a cDNA that encodes an antisense molecule that prevents Alg3 from being translated. The term "antisense molecule" encompasses any nucleic acid molecule or nucleic acid analog (e.g., peptide nucleic acids) that contains a sequence that corresponds to the coding strand of an endogenous Alg3 gene. An antisense molecule also can have flanking sequences (e.g., regulatory sequences). Thus, antisense molecules can be ribozymes or antisense oligonucleotides. A ribozyme can have any general structure including, without limitation, hairpin, hammerhead, or axehead structures, provided the molecule cleaves RNA. Further, gene silencing can be used to reduce the activity of Alg3.

B. Measuring Gene Inactivation

A fungus having an inactivated Alg3 gene can be identified using any method known in the art. For example, PCR and nucleic acid hybridization techniques, such as Northern and Southern analysis, can be used to confirm that a fungus has an inactivated Alg3 gene. Alternatively, real-time reverse transcription PCR (qRT-PCR) can be used for detection and quantification of targeted messenger RNA, such as mRNA of Alg3 gene in the parent and mutant strains as grown at the same culture conditions. Immunohistochemical and biochemical techniques can also be used to determine if a cell expresses Alg3 by detecting the expression of the Alg3 peptide encoded by Alga. For example, an antibody having specificity for Alg3 can be used to determine whether or not a particular fungus contains a functional nucleic acid encoding Alg3 protein. Further, biochemical techniques can be used to determine if a cell contains a particular gene inactivation by detecting a product produced as a result of the expression of the peptide. For example, structural determination of N-glycans excised from glycoproteins can indicate that a fungal cell contains an inactivated Alg3 gene. In addition, measurements of sporulation, germination, secondary metabolite production, and citric acid production can be measured using the methods described herein.

C. Measuring Citric Acid Production

Methods of determining whether a genetic inactivation of Alg3 in *Aspergillus* increases citric acid production, for example relative to the same strain with a native Alg3 sequence (such as a parental strain), are routine in the art. Although particular examples are disclosed herein, the methods are not limiting.

For example, production of citric acid by *Aspergillus* (such as an Alg3Δ strain) can be measured using a spectrophotometric assay. In one example citric acid production can be determined with an endpoint spectrophotometric enzyme assay (for example see, Bergmeyer, H. U. 1985. *Metabolites 2: tri- and dicarboxylic acids, purines, pyrimidines and derivatives, coenzymes, inorganic compounds*, p. 5-10. In Citric acids. VCH Publishers, Weinheim, Germany). Citric acid can also be measured by liquid chromatography (LC) or high-performance liquid chromatography (HPLC) methods.

D. Alg3 Sequences

Alg3 protein and nucleic acid sequences are publicly available and specific examples are provided herein. In addition, Alg3 sequences can be identified using routine molecular biology methods.

Examples of Alg3 nucleic acid sequences shown in SEQ ID NOS: 1 and 3. However, the disclosure also encompasses variants of SEQ ID NOS: 1 and 3 which retain the ability to encode an Alg3 protein. One skilled in the art will understand that variant Alg3 nucleic acid sequences can be inactivated. Variant sequences may contain a single insertion, a single deletion, a single substitution, multiple insertions, multiple deletions, multiple substitutions, or any combination thereof (e.g., single deletion together with multiple insertions). In addition, the degeneracy of the code permits multiple nucleic acid sequences to encode the same protein. For example, FIG. 9 shows an alignment of Alg3 nucleic acid sequences from *A. niger* (nucleotides 1986-2518 of SEQ ID NO: 1) and *A. oryzae* (nucleotides 643-1175 of SEQ ID NO: 3), which permits one to identify nucleotides that can tolerate substitution (e.g., those that are not conserved between species) and those that may not (e.g., those that are conserved between species). Such nucleic acid molecules can share at least 80%, at least 85%, at least 90%, at least 95%, at least 97%, at least 98%, or at least 99% sequence identity to any known Alg3 nucleic acid sequence, such as SEQ ID NO: 1 or 3 or nucleotides 1186-1306, 1393-1916 and 1989-2582 of SEQ ID NO: 1.

Examples of Alg3 protein sequences shown in SEQ ID NOS: 2, 4, 31, 32, 33, 34, 35, and 36. However, the disclosure also encompasses variants SEQ ID NOS: 2, 4, 31, 32, 33, 34, 35, and 36 which retain Alg3 activity. One skilled in the art will understand that variant Alg3 enzyme sequences can be inactivated. Variant sequences may contain a single insertion, a single deletion, a single substitution, multiple insertions, multiple deletions, multiple substitutions, or any combination thereof (e.g., single deletion together with multiple insertions). Such polypeptides share at least 80%, at least 85%, at least 90%, at least 95%, at least 97%, at least 98%, or at least 99% sequence identity to an Alg3 sequence, such as SEQ ID NO: 2, 4, 31, 32, 33, 34, 35, or 36.

Variant sequences can be identified, for example by aligning known Alg3 sequences. For example, FIGS. 10A and 10B show the alignment of seven different Alg3 sequences from different organisms. In addition, FIG. 11 shows a detailed alignment of Alg3 protein sequences from *A. niger* (amino acids 12-411 of SEQ ID NO: 2) and *S. cerevisiae*, indicating amino acids that are identical, conserved (+) or not conserved (space). Based on these alignments, variants of Alg3 sequences can be identified. For example, amino acid residues that are conserved between organisms are ones that should not be substituted (such as amino acids M50, T70, Y81, Q100 and D150 based on the numbering for *A. niger*), while amino acid residues that are not conserved between organisms are ones likely to tolerate substitution (such as amino acids R8, L160, S395 and N405 based on the numbering for *A. niger*). Similarly, amino acid positions in FIGS. 10A and 10B indicated with different amino acids at the same position are ones likely to tolerate substitution, while positions with the same amino acid (*) are not.

In some examples, an Alg3 sequence that is to be genetically inactivated encodes or includes one or more conservative amino acid substitutions. A conservative amino acid substitution is a substitution of one amino acid (such as one found in a native sequence) for another amino acid having similar biochemical properties. Typically, conservative substitutions have little to no impact on the activity of a resulting peptide. In one example, an Alg3 sequence (such as any of SEQ ID NOS: 2, 4, 31, 32, 33, 34, 35, or 36) includes one or more amino acid substitutions (for example at 1, 2, 5 or 10 residues). Examples of amino acids which may be substituted for an original amino acid in a protein and which are regarded as conservative substitutions include: Ser for Ala; Lys for Arg; Gln or His for Asn; Glu for Asp; Ser for Cys; Asn for Gln; Asp for Glu; Pro for Gly; Asn or Gln for His; Leu or Val for Ile; Ile or Val for Leu; Arg or Gln for Lys; Leu or Ile for Met; Met, Leu or Tyr for Phe; Thr for Ser; Ser for Thr; Tyr for Trp; Trp or Phe for Tyr; and Ile or Leu for Val. Further information about conservative substitutions can be found in, among other locations in, Ben-Bassat et al., (*J. Bacteriol.* 169:751-7, 1987), O'Regan et al., (*Gene* 77:237-51, 1989), Sahin-Toth et al., (*Protein Sci.* 3:240-7, 1994), Hochuli et al., (*Bio/Technology* 6:1321-5, 1988), WO 00/67796 (Curd et al.) and in standard textbooks of genetics and molecular biology.

The Alg3 gene inactivated in a fungus, in particular examples, includes a sequence that encodes an Alg3 protein having at least at least 80%, at least 85%, at least 90%, at least 95%, at least 97%, at least 98%, or at least 99% sequence identity to an Alg3 sequence, such as SEQ ID NO: 2, 4, 31, 32, 33, 34, 35, or 36, wherein the protein can catalyze the addition of the first dol-p-man derived mannose in an α-1,3 linkage to Man5GlcNAc2-PP-Dol. In a specific example, the Alg3 gene inactivated in a fungus encodes an Alg3 protein shown in SEQ ID NO: 2, 4, 31, 32, 33, 34, 35, or 36.

The Alg3 gene that is to be inactivated in a fungus, in particular examples, includes a sequence having at least at least 80%, at least 85%, at least 90%, at least 95%, at least 97%, at least 98%, or at least 99% sequence identity to an Alg3 nucleic acid sequence, such as SEQ ID NO: 1 or 3 or nucleotides 1186-1306, 1393-1916 and 1989-2582 of SEQ ID NO: 1, and encode an Alg3 protein that can catalyze the addition of the first dol-p-man derived mannose in an α-1,3 linkage to Man5GlcNAc2-PP-Dol. In a specific example, the Alg3 gene inactivated in a fungus is shown in SEQ ID NO: 2 or 4.

One skilled in the art will appreciate that additional Alg3 sequences can be identified using any method such as those described herein. For example, Alg3 nucleic acid molecules that encode an Alg3 protein can be identified and obtained using common molecular cloning or chemical nucleic acid synthesis procedures and techniques, including PCR. In addition, standard nucleic acid sequencing techniques and software programs that translate nucleic acid sequences into amino acid sequences based on the genetic code can be used to determine whether or not a particular nucleic acid has any sequence homology with known Alg3 sequences. Sequence alignment software such as MEGALIGN (DNASTAR, Madison, Wis., 1997) can be used to compare various sequences.

In addition, nucleic acid hybridization techniques can be used to identify and obtain a nucleic acid molecule that encodes an Alg3 protein. Briefly, any known Alg3 nucleic acid molecule, or fragment thereof, can be used as a probe to identify similar nucleic acid molecules by hybridization under conditions of moderate to high stringency. Such similar nucleic acid molecules then can be isolated, sequenced, and analyzed to determine whether the encoded protein is an Alg3 protein.

Any method can be used to introduce an exogenous nucleic acid molecule into a fungal cell, for example to genetically inactivate Alg3. For example, chemical mediated-protoplast transformation, electroporation, Agrobacterium-mediated transformation, fusion of protoplasts, and biolistic delivery are common methods for introducing nucleic acid into fungal cells. (See, e.g., Ito et al., J. Bacterol. 153:163-8, 1983; Durrens et al., Curr. Genet. 18:7-12, 1990; Sambrook et al., Molecular cloning: A laboratory manual, Cold Spring Harbour Laboratory Press, New York, USA, third edition, 2001; and Becker and Guarente, Methods in Enzymology 194:182-7, 1991. An exogenous nucleic acid molecule contained within a particular cell of the disclosure can be maintained within that cell in any form. For example, exogenous nucleic acid molecules can be integrated into the genome of the cell or maintained in an episomal state. That is, a cell can be a stable or transient transformant.

Fungi with Increased LaeA Expression or Increased LaeA Expression and Alg3 Deletion The present disclosure provides isolated fungi having increased LaeA expression, wherein such increased expression or activity (for example in combination with an Alg3 functional inactivation, Alg3Δ) results in increased citric acid production by the fungi. Such fungi are referred to herein as increased LaeA fungal strains. It is disclosed herein that increased expression of LaeA (for example in combination with genetic inactivation of Alg3, Alg3Δ) results in Aspergillus fungi that can increase citric acid production as compared to Aspergillus having native levels of expression.

Contemplated herein are isolated fungi having increased LaeA activity/expression, for example in combination with a genetic inactivation of Alg3. Any fungus can be used, such as any genus or variety of Aspergillus. In particular examples, the Aspergillus fungus is A. niger, such as Aspergillus niger strain 11414 (American Type Culture Collection (ATCC) No. 11414; NRRL 2270); 1015 (ATCC No. 1015; NRRL 328, CBS 113.46); NRRL 3 (ATCC No. 9029, CBS 120.49, N400); NRRL 3122 (ATCC No. 22343); or 11414KusA-. In other specific examples, the Aspergillus is A. aculeatus, A. awamori, A. carbonarius, A. wentii, A. foetidus, A. fumigatus, A. oryzae, or A. terreus.

The present disclosure also provides isolated A. terreus fungi having increased LaeA expression, wherein such increased expression or activity results in increased itaconic acid production by the fungi. It is disclosed herein that increased expression of LaeA results in A. terreus fungi that can increase itaconic acid production as compared to A. terreus having native levels of LaeA expression. Contemplated herein are isolated A. terreus fungi transformed with a nucleic acid construct comprising an Aspergillus species LaeA gene. The LaeA gene can be from any species of Aspergillus. In some examples, the LaeA gene is an A. niger, A. nidulans, A. aculeatus, A. awamori, A. carbonarius, A. wentii, A. foetidus, A. fumigatus, A. oryzae, or A. terreus LaeA gene.

Any method for genetic enhancement or up-regulation can be used, as long as the expression of the gene and/or gene product is significantly increased, or the function of the expressed protein is significantly increased. In particular examples, LaeA gene expression is up-regulated by transformation of the fungi with one or more copies of a LaeA coding or genomic sequence (which can be a native or non-native LaeA sequence). In some embodiments, up-regulation refers to an increase in gene or protein expression of at least 20%, at least 40%, at least 50%, at least 100%, at least 150%, at least 200%, at least 300%, or at least 500%, for example relative to the parental fungal strain without the additional copies of an LaeA gene. The term "increased" or "up-regulated" as used herein with respect to a cell and a particular gene or protein activity refers to a higher level of activity than that measured in a comparable cell of the same species. For example, a particular fungi having increased or up-regulated LaeA activity has increased LaeA activity if a comparable fungi having native LaeA activity has less detectable LaeA activity (for example as measured by gene or protein expression).

LaeA sequences are disclosed herein and others are publicly available, for example from GENBANK™ or EMBL. In some examples, the LaeA gene upregulated encodes a protein having at least 80%, at least 85%, at least 90%, at least 95%, at least 96%, at least 97%, at least 98% or at least 99% sequence identity to SEQ ID NO: 41 or SEQ ID NO: 59. In some examples, the LaeA gene upregulated comprises at least 80%, at least 85%, at least 90%, at least 95%, at least 96%, at least 97%, at least 98% or at least 99% sequence identity to SEQ ID NO: 40 (e.g., nt 1-236 and 367-1252 of SEQ ID NO: 41) or SEQ ID NO: 58 (e.g., nt 1-230 and 373-1267 of SEQ ID NO: 58).

Increasing LaeA activity (for example in combination with genetic inactivation of Alg3) results in many phenotypes in the fungi. For example, such recombinant fungi exhibit increased citric acid production in CAP medium. Such increases can be relative to a fungi having a native or wild-type level of LaeA (or LaeA and Alg3) gene or protein expression, such as a parental strain (e.g., *A. niger* strain 11414KusA), grown under the same conditions as the fungi with increased LaeA activity (or increased LaeA activity and decreased Alg3 activity). In some examples, increased citric acid production in CAP medium is an increase of at least 20%, at least 30%, at least 50%, at least 60%, at least 65%, or at least 70%, by such a recombinant fungus as compared to *A. niger* strain 11414KusA. In some examples, recombinant fungi with increased LaeA activity (for example in combination with genetic inactivation of Alg3) have increased sporulation relative to *A. niger* Alg3Δ on MM, accumulate red color pigments to *A. niger* strain 11414KusA on complete medium, or both. In other examples, increasing LaeA activity in *A. terreus* fungi results in an increase in itaconic acid production in itaconic acid production media. Such increases can be relative to *A. terreus* fungi having a native or wild-type level of LaeA gene or protein expression, such as a parental strain *A. terreus* strain grown under the same conditions as the fungi with increased LaeA activity. In some examples, increased itaconic acid production is an increase of at least 20%, at least 30%, at least 50%, at least 60%, at least 65%, or at least 70%, as compared to a parental strain.

One skilled in the art will appreciate that additional genes can also be inactivated or upregulated, wherein the additional genes may or may not provide additional enhancement of citric acid production or itaconic acid production to the fungus. In one example KusA (e.g., GENBANK™ Accession No. EF061656) is also genetically inactivated.

Also provided by the present disclosure are compositions that include isolated LaeA up-regulated fungi, such as a growth medium. Also provided by the present disclosure are kits that include isolated LaeA up-regulated fungi, such as a kit that includes a medium for culturing, storing, or growing the fungus. Exemplary mediums include solid medium (such as those containing agar, for example CM, PDA or MM) and liquid media (such as a fermentation broth, such as CM, MM, or CAP medium).

A. Methods of Up-Regulating Gene and/or Protein Expression

As used herein, an "activated" or "up-regulated" gene means that expression of the gene or gene product (e.g., protein) has been up-regulated, for example by introduction of additional copies of the appropriate gene or coding sequence into the fungus (or other common molecular biology methods), such that the introduce nucleic acid sequence is expressed, resulting in increased expression or biological activity of the encoded gene product.

Increasing expression of one or more genes (which in some examples is also referred to as up-regulation) can be performed using any conventional method known in the art. In one example, a strain of *Aspergillus* is transformed with a vector which has the effect of up-regulating or otherwise activating a LaeA gene (such as a native or non-native LaeA gene). This can be done by introducing one or more LaeA coding sequences (such as a gene sequence), whose expression is controlled by elements such as promoters and the like which control gene expression, by introducing a nucleic acid sequence which itself (or its encoded protein) can increase LaeA protein activity in the fungus, or by introducing another molecule (such as a protein or antibody) increases LaeA protein activity in the fungus. For example, a LaeA gene can be up-regulated by introduction of a vector that includes one or more LaeA sequences (such as 1, 2, 3, 4, 5, 6, 7, 8, 9 or 10 LaeA sequences or copies of such sequences) into the desired fungus. In some examples, such LaeA sequences are from different fungal species, can be multiple copies from a single species, or combinations thereof, such as LaeA sequences from at least 2, 3, 4, 5, 6, 7, 8, 9, or 10 different fungal species. In some examples, the LaeA sequence(s) introduced into the fungus is optimized for codon usage. Thus, the disclosure in some examples provides transformed fungi that include at least one exogenous nucleic acid molecule which includes a LaeA gene or coding sequence (such as a nucleic acid sequence encoding SEQ ID NOs: 41 or 59), for example in combination with Alg3Δ. In one example, such transformed cells produce more citric acid, for example relative to a comparable fungus with a native LaeA sequence (or a native LaeA sequence combined with a native Alg3 sequence).

In another technique, the cre-lox system is used for site specific recombination of DNA (for example see Steiger et al., *Appl. Environ. Microbiol.* 77(1):114, 2011). The system includes 34 base pair lox sequences that are recognized by the bacterial cre recombinase gene. If the lox sites are present in the DNA in an appropriate orientation, DNA flanked by the lox sites will be excised by the cre recombinase, resulting in the deletion of all sequences except for one remaining copy of the lox sequence. Using standard recombination techniques, the targeted gene of interest (e.g., LaeA) can be deleted in the *Aspergillus* genome and replaced with one or more copies of a non-native LaeA sequence (for example in *A. niger*, replacing one or both *A. niger* LaeA sequences with one or more, or combination of, LaeA sequences from *A. nidulans, A. flavus, fusarium oxysperorum, penicillium chrysogenum*, which have high secondary metabolite production) flanked by the lox sites. Transient expression (by electroporation of a suicide plasmid containing the cre gene under control of a promoter that functions in *Aspergillus*) of the cre recombinase should result in efficient elimination of the lox flanked marker. This process will produce a fungus containing the desired insertion mutation and one copy of the lox sequence.

In one example, one or more LaeA genes are introduced into fugal cells by chemical mediated proteoplast transformation in combination of yeast-gap repairing method for transgene expression construction.

In one example, a transgene is generated and expressed in the desired fungal cell, such as an Alg3Δ cell, to increase LaeA expression. For example, such a transgene can include a LaeA genomic or cDNA sequence (such as one having at least 80%, at least 85%, at least 90%, at least 95%, at least 97%, at least 98%, or at least 99% sequence identity to any known LaeA sequence, such as SEQ ID NO: 40 or 58), for example operably linked to a promoter, such as a glyceraldehyde 3-phosphate dehydrogenase (gpdA) promoter or other promoter, such as one that has high activity in CAP culture medium, for example a polyubiquitin promoter, Arsa-7, and A-37 from *A. niger*. In one example, the promoter has at least 80%, at least 85%, at least 90%, at least 95%, at least 97%, at least 98%, or at least 99% sequence identity to SEQ ID NO: 37. In one example, the promoter comprises or consists of the sequence shown in SEQ ID NO: 37. In some examples, the transgene further includes pyrG upstream and downstream sequences (for example that are at the 5'- and 3'-end, respectively, of the transgene). The pyrG gene in *A. niger* is mutated and has lost its original functions. Thus, other non-essential gene loci can be used as long as it is not influenced by the native neighbor genes. In one example, the pyrG upstream and downstream sequences have at least 80%, at least 85%, at least 90%, at least 95%, at least 97%, at least 98%, or at least 99% sequence identity to SEQ ID NO: 45 and 48, respectively. In one example, the pyrG upstream and downstream sequences comprise or consist of the sequence shown in SEQ ID NO: 45 or 48, respectively. In some examples, the transgene further includes a trpC transcriptional terminator sequence of *A. nidulans*, for example downstream of the LaeA sequence. As an alternative to trpC, other transcriptional terminators can be used, such as promoters which include a transcriptional terminators (e.g., ArsA7, Arsa-37, polyubiquitin (ubi4)). In one example, the trpC transcriptional terminator has at least 80%, at least 85%, at least 90%, at least 95%, at least 97%, at least 98%, or at least 99% sequence identity to SEQ ID NO: 46. In one example, the trpC transcriptional terminator comprises or consists of the sequence shown in SEQ ID NO: 46. In some examples, the transgene further includes a ptrA sequence, for example downstream of the trpC transcriptional terminator sequence. As an alternative to ptrA, the bleomycin gene or bar gene can be used. In one example, the ptrA sequence has at least 80%, at least 85%, at least 90%, at least 95%, at least 97%, at least 98%, or at least 99% sequence identity to SEQ ID NO: 47. In one example, the ptrA sequence comprises or consists of the sequence shown in SEQ ID NO: 47. In one example, the transgene comprises a sequence having at least 80%, at least 85%, at least 90%, at least 95%, at least 97%, at least 98%, or at least 99% sequence identity to SEQ ID NO: 44 or 57. In one example, the transgene comprises or consists of the sequence shown in SEQ ID NO: 44 or 57.

Thus, for example, a fungal cell can be engineered to have increased copies of LaeA using common recombinant technology methods.

B. Measuring Gene Activation or Up-Regulation

A fungus having an activated or up-regulated LaeA gene can be identified using any method known in the art. For example, PCR and nucleic acid hybridization techniques, such as Northern, RT-PCR, and Southern analysis, can be used to confirm that a fungus has an up-regulated LaeA gene, such as an increase in the LaeA copy number. Immunohistochemical and biochemical techniques can also be used to determine if a cell expresses LaeA by detecting the expression of the LaeA peptide encoded by LaeA. For example, an antibody having specificity for LaeA can be used to determine whether or not a particular fungus has increased LaeA protein expression. Further, biochemical techniques can be used to determine if a cell has increased LaeA expression by detecting a product produced as a result of the expression of the peptide. For example, measurement of secondary metabolites can indicate that a fungal cell contains an up-regulated LaeA gene. In addition, measurements of citric acid production can be measured using the methods described herein.

C. Measuring Citric Acid Production

Methods of determining whether a genetic up-regulation of LaeA (alone or in combination with inactivation of Alg3) in *Aspergillus* increases citric acid production, for example relative to the same strain with a native LaeA sequence, Alg3 sequence, or both (such as a parental strain), are routine in the art. Although particular examples are disclosed herein (see above and in the examples below), the methods are not limiting.

D. Measuring Itaconic Acid Production

Methods of determining whether a genetic up-regulation (e.g. overexpression) of LaeA in *Aspergillus terreus* increases itaconic acid production, for example relative to the same strain that does not overexpress LaeA (such as a parental strain), are routine in the art. Although particular examples are disclosed herein (see Example 14), the methods are not limiting. For example, production of itaconic acid by *A. terreus* can be performed as previously described by Dickman (*Analytical Chem* 24: 1064-1066, 1952), or using the modified method described in Example 14.

E. LaeA Sequences

LaeA protein and nucleic acid sequences are publicly available and specific examples are provided herein. In addition, LaeA sequences can be identified using routine molecular biology methods.

Examples of LaeA nucleic acid sequences shown in SEQ ID NOs: 40 and 58. However, the disclosure also encompasses variants of SEQ ID NOs: 40 and 58 (such as the coding regions nt 1-236 and 367-1252 of SEQ ID NO: 41 and nt 1-230 and 373-1267 of SEQ ID NO: 58) which retain the ability to encode a LaeA protein. One skilled in the art will understand that variant LaeA nucleic acid sequences can be used to increase expression of LaeA. Variant sequences may contain a single insertion, a single deletion, a single substitution, multiple insertions, multiple deletions, multiple substitutions, or any combination thereof (e.g., single deletion together with multiple insertions). In addition, the degeneracy of the code permits multiple nucleic acid sequences to encode the same protein. Thus, in one example, a LaeA sequence having at least 80%, at least 85%, at least 90%, at least 95%, at least 96%, at least 97%, at least 98%, or at least 99% sequence identity to any known LaeA sequence, such as SEQ ID NO: 40 or SEQ ID NO: 58 (such as the coding regions nt 1-236 and 367-1252 of SEQ ID NO: 41 and nt 1-230 and 373-1267 of SEQ ID NO: 58) can be expressed in a fungal cell to increase LaeA expression in the fungal cell.

For example, FIG. 12 shows an alignment of LaeA protein sequences from *A. nidulans* (aa 14-372 of SEQ ID NO: 41) and *A. niger* (aa 14-370 of SEQ ID NO: 59), which permits one to identify amino acids that can tolerate substitution (e.g., those that are not conserved between species) and those that may not (e.g., those that are conserved between species). Based on these alignments, variants of LaeA sequences can be identified. For example, amino acid residues that are conserved between organisms are ones that should not be substituted (such as amino acids S16, M42, and P52 based on the numbering for *A. nidulans*), while amino acid residues that are not conserved between organisms are ones likely to tolerate substitution (such as amino acids T15, S44, and N325 based on the numbering for *A. nidulans*). Similarly, amino acid positions in FIG. 12 indicated with a space are ones likely to tolerate substitution, while positions with the same amino acid are not.

Such protein molecules can share at least 80%, at least 85%, at least 90%, at least 95%, at least 96%, at least 97%, at least 98%, or at least 99% sequence identity to any known LaeA nucleic acid sequence, such as SEQ ID NOs: 41 and 59, and such variants can be used to increase LaeA activity in a fungal cell. One skilled in the art will understand that variant LaeA enzyme sequences can be used to increase LaeA activity in a fungal cell. Variant sequences may contain a single insertion, a single deletion, a single substitution, multiple insertions, multiple deletions, multiple substitutions, or any combination thereof (e.g., single deletion together with multiple insertions).

In some examples, a LaeA sequence whose expression is to be up-regulated encodes or includes one or more conservative amino acid substitutions. A conservative amino acid substitution is a substitution of one amino acid (such as one found in a native sequence) for another amino acid having similar biochemical properties. Typically, conservative substitutions have little to no impact on the activity of a resulting peptide. In one example, a LaeA sequence (such as any of SEQ ID NOs: 41 and 59) includes one or more amino acid substitutions (for example at 1, 2, 5 or 10 residues). Examples of amino acids which may be substituted for an original amino acid in a protein and which are regarded as conservative substitutions include those discussed above for Alg3.

The LaeA gene up-regulated in a fungus, in particular examples, includes a sequence that encodes a LaeA protein having at least at least 80%, at least 85%, at least 90%, at least 95%, at least 96%, at least 97%, at least 98%, or at least 99% sequence identity to an LaeA sequence, such as SEQ ID NO: 41 or SEQ ID NO: 59, wherein the protein can regulate secondary metabolite production in *Aspergillus*. In a specific example, the LaeA gene up-regulated in a fungus encodes a LaeA protein shown in SEQ ID NO: 41 or 59.

The LaeA gene up-regulated in a fungus, in particular examples, includes a sequence having at least at least 80%, at least 85%, at least 90%, at least 95%, at least 96%, at least 97%, at least 98%, or at least 99% sequence identity to a LaeA nucleic acid sequence, such as SEQ ID NO: 40 or SEQ ID NO: 58 (or to the coding regions nt 1-236 and 367-1252 of SEQ ID NO: 41 or nt 1-230 and 373-1267 of SEQ ID NO: 58), and encodes a LaeA protein which can regulate secondary metabolite production in *Aspergillus*. In a specific example, the LaeA gene upregulated in a fungus is shown in SEQ ID NO: 40 or SEQ ID NO: 58 (or includes the coding regions nt 1-236 and 367-1252 of SEQ ID NO: 41 or nt 1-230 and 373-1267 of SEQ ID NO: 58).

One skilled in the art will appreciate that additional LaeA sequences can be identified and obtained using any method such as those described herein. For example, LaeA nucleic acid molecules that encode a LaeA protein can be identified and obtained using common molecular cloning or chemical nucleic acid synthesis procedures and techniques, including PCR. In addition, standard nucleic acid sequencing techniques and software programs that translate nucleic acid sequences into amino acid sequences based on the genetic code can be used to determine whether or not a particular nucleic acid has any sequence homology with known LaeA sequences. Sequence alignment software such as MEGA-LIGN (DNASTAR, Madison, Wis., 1997) can be used to compare various sequences.

In addition, nucleic acid hybridization techniques can be used to identify and obtain a nucleic acid molecule that encodes a LaeA protein. Briefly, any known LaeA nucleic acid molecule, or fragment thereof, can be used as a probe to identify similar nucleic acid molecules by hybridization under conditions of moderate to high stringency. Such similar nucleic acid molecules then can be isolated, sequenced, and analyzed to determine whether the encoded protein is a LaeA protein. The gene specific oligonucleotide pair can also be designed, synthesized and used for real-time RT-PCR to quantify the LaeA gene transcription level.

Any method can be used to introduce an exogenous nucleic acid molecule into a fungal cell, for example to genetically enhance LaeA expression. For example, chemical mediated-protoplast transformation, electroporation, *Agrobacterium*-mediated transformation, fusion of protoplasts, and biolistic delivery are common methods for introducing nucleic acid into fungal cells. (See, e.g., Ito et al., *J. Bacteriol.* 153:163-8, 1983; Durrens et al., *Curr. Genet.* 18:7-12, 1990; Sambrook et al., Molecular cloning: A laboratory manual, Cold Spring Harbour Laboratory Press, New York, USA, second edition, 1989; and Becker and Guarente, *Methods in Enzymology* 194:182-7, 1991). An exogenous nucleic acid molecule contained within a particular cell of the disclosure can be maintained within that cell in any form. For example, exogenous nucleic acid molecules can be integrated into the genome of the cell or maintained in an episomal state. That is, a cell can be a stable or transient transformant.

F. LaeA Deletion and Complementation

Figure 17A:
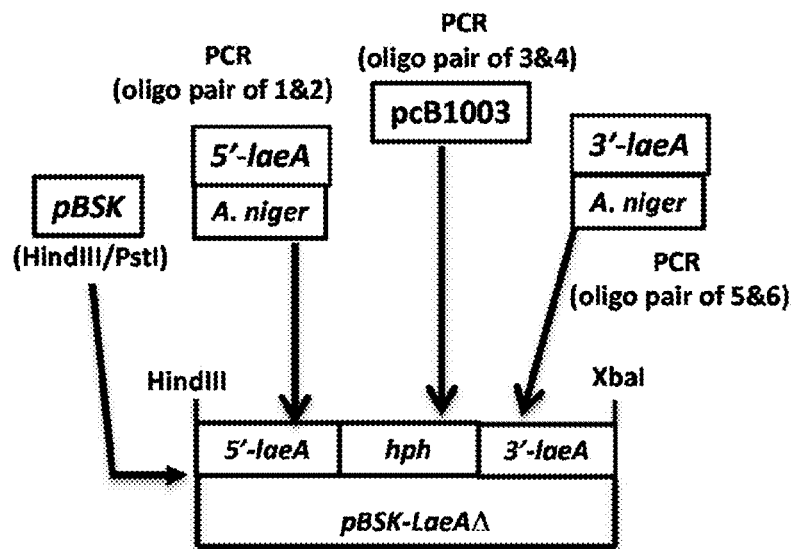
FIG. 17A is a schematic diagram showing the construction of the pBSK-LaeA deletion plasmid vector for *A. niger*. The DNA fragments of the 5' and 3' ends of *A. niger* LaeA (lack of aflR expression) gene and the hph (hygromycin phosphotransferase) expression cassette were isolated from A. niger genomic DNA (LaeA) or pCB1003 plasmid vector DNA by PCR with oligonucleotide pairs 1 and 2; 3 and 4; and 5 and 6. The PCR DNA fragments were assembled together by Gibson assembly cloning kit in pBSK backbone vector prepared by HindIII/PstI double digestion. The plasmid DNA fragment containing the LaeA gene deletion cassette was prepared by restriction enzyme digestion with restriction endonucleases of HindIII and XbaI and used for A. niger transformation.

Disclosed herein is a LaeA deletion cassette for generating a fungus, such an *Aspergillus* species fungus, having a deletion in the LaeA gene. A schematic of the LaeA deletion cassette is shown in FIG. 17A. To generate the deletion cassette, DNA fragments comprising the 5' and 3' ends of the *A. niger* LaeA gene (SEQ ID NOs: 61 and 62, respectively) were isolated from *A. niger* genomic DNA and the hph expression cassette (SEQ ID NO: 63) (hph) was isolated from pCB1003 plasmid vector DNA by PCR. The PCR DNA fragments were assembled in the pBSK backbone vector to produce the LaeA deletion cassette (SEQ ID NO: 65).

Provided herein is a nucleic acid molecule comprising a nucleotide sequence at least 80%, at least 85%, at least 90%, at least 95%, at least 96%, at least 97%, at least 98% or at least 99% identical to SEQ ID NO: 65. In some embodiments, the nucleic acid molecule comprises or consists of the nucleotide sequence of SEQ ID NO: 65. Further provided is an isolated fungus transformed with a nucleic acid molecule comprising a nucleotide sequence at least 80%, at least 85%, at least 90%, at least 95%, at least 96%, at least 97%, at least 98% or at least 99% identical to SEQ ID NO: 65. In some embodiments, the isolated fungus is transformed with a nucleic acid molecule comprising or consisting of the nucleotide sequence of SEQ ID NO: 65. In some embodiments, the fungus is a species of *Aspergillus*, such as *A. niger*.

Further provided herein are isolated fungi (such as filamentous fungi) having a gene inactivation (also referred to as a gene deletion) of a LaeA gene. Any strain of fungi can be used, such as a filamentous fungi, for example *A. niger* or particular strains thereof (for example *A. niger* strain 11414 or 11414KusA). In particular examples, the LaeA gene is genetically inactivated by complete or partial deletion mutation or by insertional mutation. In some examples genetic inactivation need not be 100% genetic inactivation. In some embodiments, genetic inactivation refers to at least 50%, at least 60%, at least 70%, at least 80%, at least 90%, or at least 95% gene or protein inactivation. The term "reduced" or "decreased" as used herein with respect to a cell and a particular gene or protein activity refers to a lower level of activity than that measured in a comparable cell of the same species. For example, a particular fungi lacking LaeA activity has reduced LaeA activity if a comparable fungi not having an LaeA genetic inactivation has detectable LaeA activity. In some embodiments, the isolated fungi having a gene inactivation are generated using the LaeA deletion construct set forth herein as SEQ ID NO: 65.

Figure 17B:
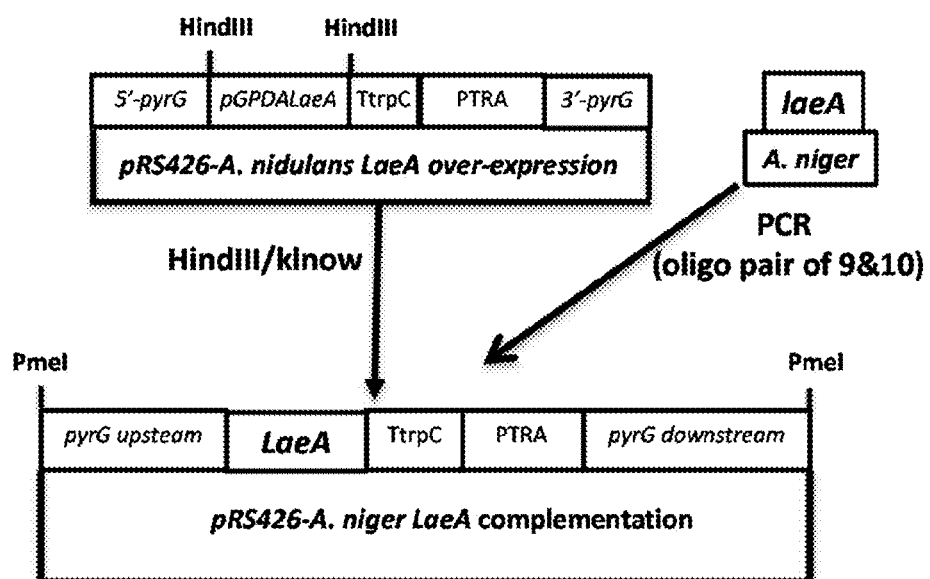
FIG. 17B is a schematic diagram showing the construction of the pRS426-A. niger LaeA complementation plasmid vector for A. niger. The LaeA gene containing both its promoter and transcriptional terminator was isolated by PCR with oligonucleotide pair 9 and 10 from A. niger genomic DNA. The PCR fragment was cloned into the plasmid vector pRSB426-LaeA prepared by restriction endonuclease HindIII digestion and Klenow treatment with blunt-end ligation. The new plasmid DNA vector contains the upstream region of the pyrG gene of A. niger, the entire region of A. niger LaeA gene, the transcriptional terminator of the trpC gene from A. nidulans, the pyrithiamine resistance (ptrA) gene from A. oryzae, and the downstream region of the pyrG gene of A. niger. The unique restriction endonuclease PmeI site was introduced at both ends of the transgene expression fragment.

Also provided herein is a LaeA complementation construct for complementing expression of LaeA in fungi having a deleted LaeA gene. A schematic of the LaeA complementation construct is shown in FIG. 17B. To generate the complementation construct, the LaeA gene containing both its promoter and transcriptional terminator was isolated by PCR from *A. niger* genomic DNA. The PCR fragment was cloned into the plasmid vector pRSB426-LaeA. The new plasmid DNA vector contained the upstream region of the pyrG gene of *A. niger*, the entire region of *A. niger* LaeA gene, the transcriptional terminator of the trpC gene from *A. nidulans*, the pyrithiamine resistance (ptrA) gene from *A. oryzae*, and the downstream region of the pyrG gene of *A. niger* (SEQ ID NO: 66).

Provided herein is a nucleic acid molecule comprising a nucleotide sequence at least 80%, at least 85%, at least 90%, at least 95%, at least 96%, at least 97%, at least 98% or at least 99% identical to SEQ ID NO: 66. In some embodiments, the nucleic acid molecule comprises or consists of the nucleotide sequence of SEQ ID NO: 66. Further provided is an isolated fungus transformed with a nucleic acid molecule comprising a nucleotide sequence at least 80%, at least 85%, at least 90%, at least 95%, at least 96%, at least 97%, at least 98% or at least 99% identical to SEQ ID NO: 66. In some embodiments, the isolated fungus is transformed with a nucleic acid molecule comprising or consisting of the nucleotide sequence of SEQ ID NO: 66. In some embodiments, the fungus is a species of *Aspergillus*, such as *A. niger*.

Further provided herein are isolated fungi (such as filamentous fungi) having a gene inactivation (also referred to as a gene deletion) of a LaeA gene and further transformed by a nucleic acid construct comprising a nucleotide sequence at least 80%, at least 85%, at least 90%, at least 95%, at least 96%, at least 97%, at least 98% or at least 99% identical to SEQ ID NO: 66. In some embodiments, the isolated fungus is transformed with a nucleic acid molecule comprising or consisting of the nucleotide sequence of SEQ ID NO: 66. In some embodiments, the fungus is a species of *Aspergillus*, such as *A. niger*. Any strain of fungi can be used, such as a filamentous fungi, for example *A. niger* or particular strains thereof (for example *A. niger* strain 11414 or 11414KusA).

Production of Citric Acid Using Alg3Δ Mutants, Fungi with Increased LaeA Expression, or Both The fungi provided herein, namely Alg3Δ fungi, up-regulated LaeA fungi, and fungi with both Alg3Δ and up-regulated LaeA, can be used to produce citric acid, as well as derivatives thereof such as hydroxycitric acid (for example for medical applications). Such fungi can be from any species, such as *Aspergillus* or *Rhizopus* cells. For example, the disclosure provides methods of making citric acid, which can include culturing Alg3Δ fungi, up-regulated LaeA fungi, or fungi with both Alg3Δ and up-regulated LaeA, under conditions that permit the fungus to make citric acid, for example in CAP medium.

Citric acid (2-hydroxy-propane-1,2,3-tricarboxylic acid) combines a pleasant taste with low toxicity and palatability and is a ubiquitous food additive. It is also able to complex heavy metal ions, like iron and copper, and is therefore applied in the stabilization of oils and fats or ascorbinic acid during metal ion-catalyzed oxidation reactions. Consequently, it is today one of the bulk products produced by fermentation, most of which occurs with the fungus *Aspergillus niger*, although a small portion is also produced by fermentation with yeast, such as *Candida oleophila* and *Candida lipolytica*.

Citric acid production generally requires a unique combination of several unusual nutrient conditions (e.g., excessive concentrations of carbon source, H$^+$, and dissolved oxygen, or suboptimal concentrations of certain trace metals and phosphate), which synergistically influence the yield of citric acid. Table 1 below shows the environmental parameters that influence citric acid accumulation.

TABLE 1

Parameters that influence citric acid accumulation by *A. niger*

| Parameter | Requirement for citric acid accumulation |
| --- | --- |
| Carbon source concentration | Higher than 50 g/l |
| Carbon source type | Enable rapid catabolism |
| Nitrogen source | Consumption leads to some decrease in pH |
| Phosphate concentration | Suboptimal |
| Aeration | In excess |
| Trace metal ions | Limiting, especially Mn2+ |
| pH | Below pH 3 |

Methods of making citric acid, which can include culturing Alg3Δ fungi, up-regulated LaeA fungi, or fungi with both Alg3Δ and up-regulated LaeA, under conditions that permit the fungus to make citric acid, are provided. In general, the culture media and/or culture conditions can be such that the fungi grow to an adequate density and produce citric acid efficiently. In one example the Alg3Δ fungi, up-regulated LaeA fungi, or fungi with both Alg3Δ and up-regulated LaeA, are cultured or grown in a liquid medium that includes sucrose and/or glucose as the carbon source, for example at a concentration of at least 50 g/liter, such as at least 100 g/l, or at least 140 g/l. Thus, a fungus within the scope of the disclosure in some examples can utilize a variety of carbon sources. In one example the Alg3Δ fungi, up-regulated LaeA fungi, or fungi with both Alg3Δ and up-regulated LaeA, are cultured or grown in a liquid medium that includes a very small amount of manganese, such as less than 100 parts per billion (ppb), less than 50 ppb, less than 20 ppb, less than 15 ppb, for example 5 ppb to 15 ppb or 10 ppb to 15 ppb, such as 5, 10, 13, 15 or 20 ppb. In one example the Alg3Δ fungi, up-regulated LaeA fungi, or fungi with both Alg3Δ and up-regulated LaeA, are cultured or grown in a liquid medium having an initial pH of less than 3, such as less than 2.5, for example about pH 1.8 to 3, 1.8 to 2.5, 1.8 to 2.2, 1.9 to 2.1, for example pH 1.8, 1.9, 2, 2.1, 2.2, 2.3, 2.4, 2.5, 2.6, 2.7, 2.8 or 2.9. In some examples the Alg3Δ fungi, up-regulated LaeA fungi, or fungi with both Alg3Δ and up-regulated LaeA, are cultured or grown in a liquid medium at about 25 to 35° C. (such as 28 to 32° C., or 30° C.) with rotation of 180 to 300 rpm.

In a specific example, the Alg3Δ fungi, up-regulated LaeA fungi, or fungi with both Alg3Δ and up-regulated LaeA, are grown in citric acid production (CAP) medium. In a specific example, the CAP medium includes 140 g of glucose/liter, 3.1 g of NH$_4$NO$_3$/liter, 0.15 g of KH$_2$PO$_4$/liter, 0.15 g of NaCl/liter, 2.2 g of MgSO$_4$ 7H$_2$O/liter, 6.6 mg of ZnSO$_4$ 7H$_2$O/liter, and 0.1 mg of FeCl$_3$/liter adjusted to about pH 2 with 4 M H$_2$SO$_4$. Cations can be removed from the glucose solution by ion exchange on Dowex 50W-X8, 100/200-mesh, H cation exchange resin (Fisher Scientific, Pittsburgh, Pa.) prior to adding the other nutrient components. The manganese concentration in the medium can be adjusted by the addition of appropriate volumes of a stock solution of MnCl$_2$ 4H$_2$O (10 mM). In one example, the manganese concentration is less than 50 ppb, such as less than 20 ppb, for example 5 to 15 ppb, such as 10 ppb.

Methods of culturing *Aspergillus* to enable citric acid production are well known in the art. In one example, the fungi are grown in culture containers (such as baffled flasks, and in some examples are silanized (5% solution of dichlorodimethylsilane in heptane (Sigma, St. Louis, Mo.)). The Alg3Δ fungi, up-regulated LaeA fungi, or fungi with both Alg3Δ and up-regulated LaeA, provided herein can be grown in CAP media containing low amounts of Mn2+(e.g., 10 ppb) at 30° C. with rotation (e.g., 200 to 250 rpm) for at least 3 days (e.g., 3 to 7 days). Each culture container is inoculated with spores (such as at least $10^6$ spores/ml) and incubated for at least 12 or at least 15 hours at 30° C. and 200 to 250 rpm to obtain properly pelleted morphology.

In one example, the Alg3Δ fungi, up-regulated LaeA fungi, or fungi with both Alg3Δ and up-regulated LaeA, produce more citric acid than a corresponding fungus with wild-type Alga. In specific examples, the Alg3Δ fungi, up-regulated LaeA fungi, or fungi with both Alg3Δ and up-regulated LaeA, produce at least 25 g/l of citric acid (for example at least 30 g/l, at least 32 g/l, at least 35 g/l, at least 40 g/l, at least 42 g/l, at least 45 g/l, at least 50 g/l, at least 52 g/l or at least 55 g/l), for example after at least 4 days (such as at least 5 days, at least 6 days, at least 7 days, at least 8 days, or at least 10 days, such as after 4 to 6 days, 8 to 10 days, or 4 to 5 days) when grown in CAP medium at 30° C. with 200 rpm shaking.

In some examples, the method further includes isolating the citric acid made by the Alg3Δ fungi, up-regulated LaeA fungi, or fungi with both Alg3Δ and up-regulated LaeA. Once produced, any method can be used to isolate the citric acid. For example, common separation techniques can be used to remove the fungal biomass from the culture medium, and common isolation procedures (e.g., filtration, distillation, precipitation, electrodialysis, and ion-exchange procedures) can be used to obtain the citric acid from the broth (such as a fungi-free broth). In addition, the citric acid can be isolated from the culture medium after the citric acid production phase has been terminated.

Example 1

Materials and Methods

This example describes methods used in the experiments described in Examples 2-5 below.

Strains and Media.

The *Escherichia coli* strains Top10 and *Saccharomyces cerevisiae* strain YVH10 were used as hosts for routine cloning and gap repair experiments. *A. niger* strain ATCC 11414 (American Type Culture Collection, Rockville, Md.), was grown on potato dextrose agar plates (PDA) and complete medium (CM) agar plates at 30° C. for culture maintenance and spore preparation, respectively. The mutant strain *Aspergillus niger* 11414KusA was generated by the deletion of kusA in *A. niger* strain 11414 by the replacement with *A. fumigatus* pyrG gene, which encodes the ortholog of the ku70 protein that involves in the non-homologous end joining pathway of DNA repair for the integration of a DNA fragment into the genome in other eukaryotes, and was confirmed by Southern blotting analysis. The 11414kusA strain with high rate of homologous replacement was mainly used as a parent strain. The cultures on PDA or complete medium (CM) agar plates were incubated for four days at 30° C. and the spores were harvested by washing with sterile 0.8% Tween 80 (polyoxyethylenesorbitan monooleate). The CM medium contains 20 g of D-glucose/liter, 5 g yeast extract/liter, 2 g trypticase peptone/liter, 1 g casamino acids/liter, 6 g NaNO₃/liter, 0.52 g KCl/liter, 0.52 g MgSO₄·7H₂O/liter, 1.52 g KH₂PO₄/liter, 36.7 mg ZnSO₄·7H₂O/liter, 18.3 mg H₃BO₃/liter, 8.3 mg MnCl₂·4H₂O/liter, 8.3 mg FeSO₄7H₂O, 2.8 mg CoCl₂·6H₂O/liter, 2.7 mg CuSO₄·5H₂O/liter, 2.5 mg Na₂MoO₄·2H₂O/liter, 83.3 mg Na₂EDTA/liter, 1 mg biotin/liter, 1 mg pyridoxin/liter, 1 mg thiamine/liter, 1 mg riboflavin/liter, 1 mg p-aminobenzoic acid/liter and 1 mg nicotinic acid/liter. The PDA medium contains 4 g/liter potato starch and 20 g/liter dextrose. Conidia were enumerated with a hemacytometer. Aliquots of the resulting spore suspension ($1 \times 10^9$ spores/ml) were used to inoculate baffled-flask liquid cultures. The citric acid production (CAP) medium contained 140 g/l of glucose, 3.1 g/l NH₄NO₃, 0.15 g/l KH₂PO₄, 0.15 g/l NaCl, 2.2 g/l MgSO₄·7H₂O, 6.6 mg/l ZnSO₄·7H₂O, and 0.1 mg/l FeCl₃ adjusted to pH 2.1 with 4 M H₂SO₄. Cations were removed from the glucose solution by ion-exchange on Dowex 50W-X8, 100-200 mesh, H cation exchange resin (Fisher Scientific, Pittsburgh, Pa.) prior to adding the other nutrient components.

Culture Methods.

Glass baffled-flasks of 250 ml or 1000 ml were silanized by rinsing in a 5% solution of dichlorodimethylsilane in heptane (Sigma, St. Louis, Mo.) to minimize leaching of metals. For citric acid production tests, $1 \times 10^6$ spores/ml of parent or mutant strains were grown in 80 ml CAP media containing 10 ppb $Mn^{2+}$ in 250 ml baffled flasks or 220 ml CAP media in 1000 ml baffled flasks at 30° C. and 200 rpm. Samples for citric acid analysis were taken at intervals. The biomass of transgenic clones and parent stain were prepared from 2 ml CM station cultures with proper antibiotics and grown in 16×125 mm glass culture-tubes at 30° C. without shaking. The biomass formed on the surface of the culture medium was collected, frozen immediately in liquid nitrogen and dried in the lyophilizer.

Dried Biomass Measurement.

After proper cultivation, the cell mass from citric acid production culture was collected by centrifugation at room temperature and 4500×g for 5 min in Sorvall floor centrifuge with swinging-bucket rotor. The cell mass was then transferred onto the Whatman Grade No 1 filter paper or left in centrifuge tubes for freeze-drying. The biomass was then dried in high temperature oven at 80° C. or freeze-dried in the lyophilizer. Prior to being used, the centrifuge tube or Whatman filter paper was weighted and re-weighted after the biomass was completely dried.

Total Genomic DNA Isolation for PCR and Southern Blotting Analysis.

Total genomic DNA was isolated from *A. niger* according to the SDS extraction method described previously by Dellaporta et al. (*Plant Molecular Biology Reporter* 1(4): 19-21, 1983) with some modifications. Briefly, fungal biomass from 2 ml station cultures was looped and transferred into a 1.5 ml microcentrifuge tube. A needle size hole on the cap was punched with 18 gauge needle. The tube was immediately frozen in liquid N2 for 5 minutes and biomass in the tube was dried in a VirTis benchtop manifold freeze dryer (SP Scientific, Gardiner, N.Y.) overnight. The dried biomass and two 3.5 mm diameter glass beads were transferred into the 2 ml polypropylene microvial, where biomass was pulverized into fine power with Mini-Beadbeater-8 (Bio Spec Products Inc., Bartlesville, Okla.) for one minute. Then, 500 μl of 60° C. extraction buffer and 80 μl of 15% SDS were added into the microcentrifuge tube and incubated at 65° C. for at least 30 minutes with occasionally swirling to mix. Two-hundred microliters of 5M potassium acetate was added, mixed and incubated on ice for 30 minutes. The supernatant was collected by centrifugation at 12,000 g for 10 minutes at 4° C. and transferred into the new microcentrifuge tube. The total nucleic acids were precipitated with 780 μl of 2-propanol for 30 minutes at −20° C. and centrifuged at 12,000 g for 10 minutes. The nucleic acids were re-suspended in 200 μl 50TE buffer containing 2 RNase (10 μg/μl stock solution) and incubated in Eppendorf thermomixer at 50° C. and 500 rpm for 30 minutes. The proteins and cell debris was removed by being added and well mixed 20 µl 3M sodium acetate and equal volume of phenol: chloroform and centrifuged at 15,000 g for 5 minutes. The supernatant was transferred to new DNase-free microcentrifuge tube containing 220 µl of 2-propanol, mixed well and incubated at room temperature for 5 minutes. The genomic DNA was pelleted by centrifugation at 15,000 g for 10 minutes and washed with 500 µl of 70% ethanol. The genomic DNA was re-suspended in 80 µl 10 mM TrisHCl (pH8.0) buffer and determined with Qubit fluorometer (Invitrogen, Carisbad, Calif.). One microgram of total genomic DNA was digested with restriction endonuclease BamH and SacII. The genomic DNA fragments were separated in 1% agarose gel electrophoretically and transferred onto the zeta-probe membrane (BioRad) with alkaline capillary transfer method. A 3.8 kb genomic DNA fragment containing the Alg3 sequence was used for preparation of the biotin-labeled probe. The genomic DNA in Zeta-probe membrane was hybridized with the biotin-labeled probe overnight in 60° C. hybridization oven. The genomic DNA on hybridized membrane was visualized with North2South chemiluminescent detection kit (Pierce Protein Research Products, Rockford, Ill.).

Spore Production and Germination.

The spore production on the PDA or CM agar plates described above was excised with plastic closures of culture tubes in 27 mm diameter and transferred into the 50 ml centrifuge tubes containing 25 ml 0.8% tween 80. The spores were released from the agar surface by scraping with plastic loops and vortexed with vortex mixer at top speed. The spores were diluted properly and enumerated with a hemacytometer. The spore production in a unit area ($cm^2$) was determined. For spore germination, $1 \times 10^5$ spores per well were added into each well of 24 well Schwarz sensoplate and incubated in the microscopic incubator with temperature control at 30° C. The spore germination was automatically imaged hourly for 24 hours through the Olympus inverted system microscope (Olympus America Inc., Center Valley, Pa., USA). The spore germination was visualized with Adobe Photoshop CS5 (San Jose, Calif.) and counted manually.

Citric Acid Measurements.

Citric acid concentrations were determined with an end-point spectrophotometric enzyme assay as described in the instruction from the manufacturer (R-Biopharm AG/Roche, Darmstadt, Germany) with a proper dilution.

Table 2 shows oligonucleotides used in the methods.

TABLE 2

Oligonucleotides

| Name | Sequence | Product size (kb) |
|---|---|---|
| Alg3Δ construction | | |
| Alg3-ForScr | CGGTTTCCCTTCAGTTTCCAGT (SEQ ID NO: 5) | |
| Alg3-1 | GTAACGCCAGGGTTTTCCCAGTCACGACGTCATAACTTCTCTCCCCTCC (SEQ ID NO: 6) | 1.06 |
| Alg3-2 | ATCCACTTAACGTTACTGAAATCTCCAACTTCATGGACACACACAGACC (SEQ ID NO: 7) | |
| Hph-F | GGTCTGTGTGTGTCCATGAAGTTGGAGATTTCAGTAACGTTAAGTGGAT (SEQ ID NO: 8) | 1.49 |
| Hph-R | GCTACTACTGATCCCTCTGCGTCGGAGACAGAAGATGATATTGAAGGAG (SEQ ID NO: 9) | 1.03 |
| Alg3-3 | CTCCTTCAATATCATCTTCTGTCTCCGACGCAGAGGGATCAGTAGTAGC (SEQ ID NO: 10) | |
| Alg3-4 | GCGGATAACAATTTCACACAGGAAACAGCCGTGAGAGGTTTGTAGTACG (SEQ ID NO: 11) | |
| Alg3-RevScr | AAGCTGAGAGCGACATCTTCA (SEQ ID NO: 12) | |
| hyg-RevScr | GTACTTCTACACAGCCATCGGTCCA (SEQ ID NO: 13) | |
| hyg-ForScr | GTACTTCTACACAGCCATCGGTCCA (SEQ ID NO: 14) | |
| Alg3Δ + Alg3 construction | | |
| pryGScr | TCTGCTGTCTTGCATGAGGTCCTT (SEQ ID NO: 15) | |
| pyrGScr | Agcgtaggacaaggtcgtctctgt (SEQ ID NO: 16) | 2.34 |
| 5-pyrG5F | GTAACGCCAGGGTTTTCCCAGTCACGACGtttaaacATGCATCATTCTCCCGCTTTGT (SEQ ID NO: 17) | 1.69 |
| 5-pyrG3R | agaaagagtcaccggtcacGacatcgccaatcacctcaatcac (SEQ ID NO: 18) | 1.47 |
| ble5F | gtgattgaggtgattggcgatgtCgtgaccggtgactctttct (SEQ ID NO: 19) | 1.23 |

TABLE 2-continued

Oligonucleotides

| Name | Sequence | Product size (kb) |
|---|---|---|
| Ble3R | TCCAACCTTGTAGCAACCAAAGCTTCGAGCGTCCCAAAACCT (SEQ ID NO: 20) | |
| Alg3-5F1 | AGGTTTTGGGACGCTCGAAGCTTTGGTTGCTACAAGGTTGGA (SEQ ID NO: 21) | |
| Alg3-3R1 | TCAAGTAGAGCACAGCAAATAGTATCTGA (SEQ ID NO: 22) | |
| Alg3-5F2 | TCAGATACTATTTGCTGTGCTCTACTTGA (SEQ ID NO: 23) | |
| Alg3-3R2 | ttgatccttgtgccacaccaTCCTACGTGGTCATCGATACCA (SEQ ID NO: 24) | |
| 3-pyrG5F | TGGTATCGATGACCACGTAGGAtggtgtggcacaaggatcaa (SEQ ID NO: 25) | |
| 3-pyrG3R | GCGGATAACAATTTCACACAGGAAACAGCgtttaaactgtgccagtcaa ttgtccgaagt (SEQ ID NO: 26) | |
| Alg3Seq-1 | TACAGACGCGTGTACGCATGT (SEQ ID NO: 27) | |
| Alg3seq-2 | TGCTATTGTCCACAGATACCGAGA (SEQ ID NO: 28) | |
| Alg3seq-3 | GAGCTAACCAGACAGTTCATGT (SEQ ID NO: 29) | |
| Alg3seq-4 | Tcgtcgtaccgcattgatcct (SEQ ID NO: 30) | |

Example 2

Genetic Inactivation of Alg3 in *A. niger*

This example describes methods used to genetically clone and then inactivate Alg3 in *A. niger* strain 11414KusA. Based on these teachings, one skilled in the art will appreciate that Alg3 can be similarly inactivated in other strains of *Aspergillus*.

Alg3 has been identified and characterized in *Arabidopsis thaliana*, *Homo sapiens*, *Pichia pastoris*, *Trypanosoma brucei* and *Saccharomyces cerevisiae* (see for example Korner et al., *EMBO J.* 18(23): 6816-6822, 1999; Davidson et al., *Glycobiology* 14(5):399-407, 2004; Manthri et al., *Glycobiology* 18(5): 367-383, 2008; Kajiura et al., *Glycobiology* 20(6):736-751, 2010). A database search based on the amino acid sequence of *S. cerevisiae* Alg3 identified a putative α-1,3-mannosyltransferase gene in JGI (DOE Joint Genome Institute)-*A. niger* genome database (jgi|Aspni5|42720). The *A. niger* Alg3 gene contains two introns and its 1400 bp open reading frame (nt 1186-1306, 1393-1916 and 1989-2582 of SEQ ID NO: 1) encodes a protein consisting of 413 amino acids (SEQ ID NO: 2), which contains one potential N-glycosite at the amino acid position 374. The predicted Alg3 amino acid sequence has 39% sequence identity to the *S. cerevisiae* Alg3.

Figure 1A:
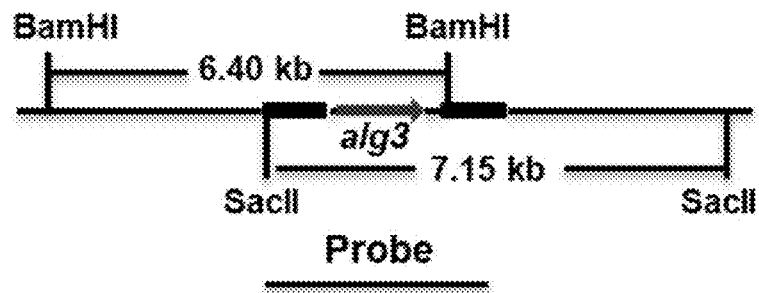
FIG. 1A is a schematic drawing showing a restriction map of the 10.9 kb fragment containing the A. niger Alg3 gene.
Figure 1B:
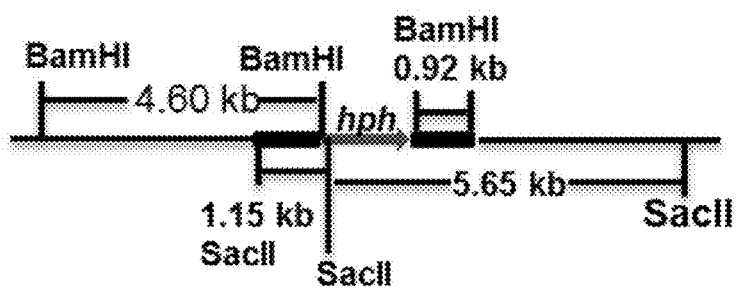
FIG. 1B is a schematic drawing showing the introduction of the hyg-selective marker, which was flanked by the upstream and downstream DNA sequences of Alg3. Integration of the linear molecules by homologous recombination replaces Alg3 with hph in the chromosome.
Figure 1C:
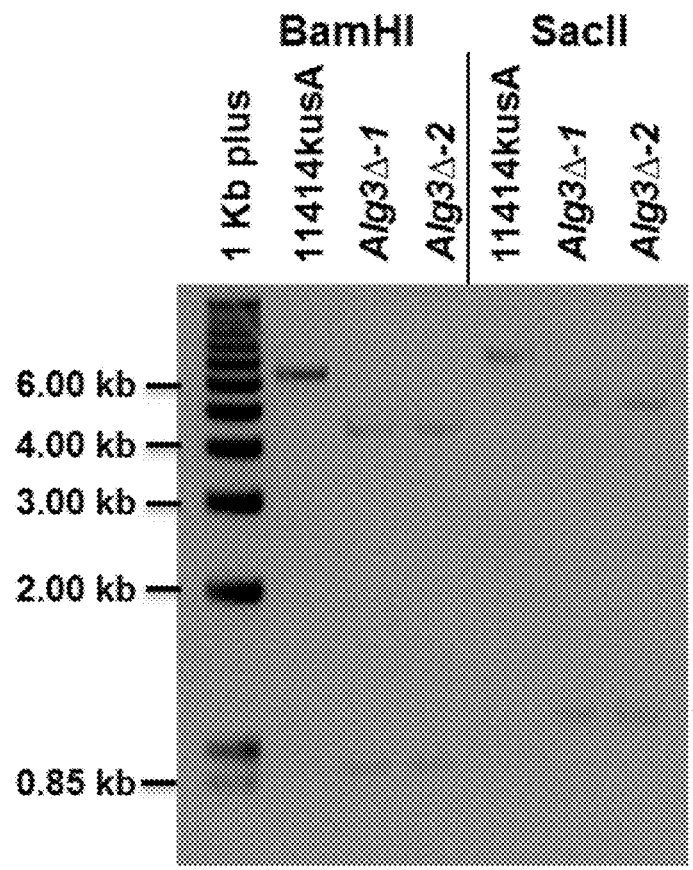
FIG. 1C is a digital image of a Southern blot showing the genomic DNA hybridization of parent and Alg3Δ strains. One parent and two selected Alg3Δ strains are shown, which have the correct enzyme restriction pattern.
Figure 2:
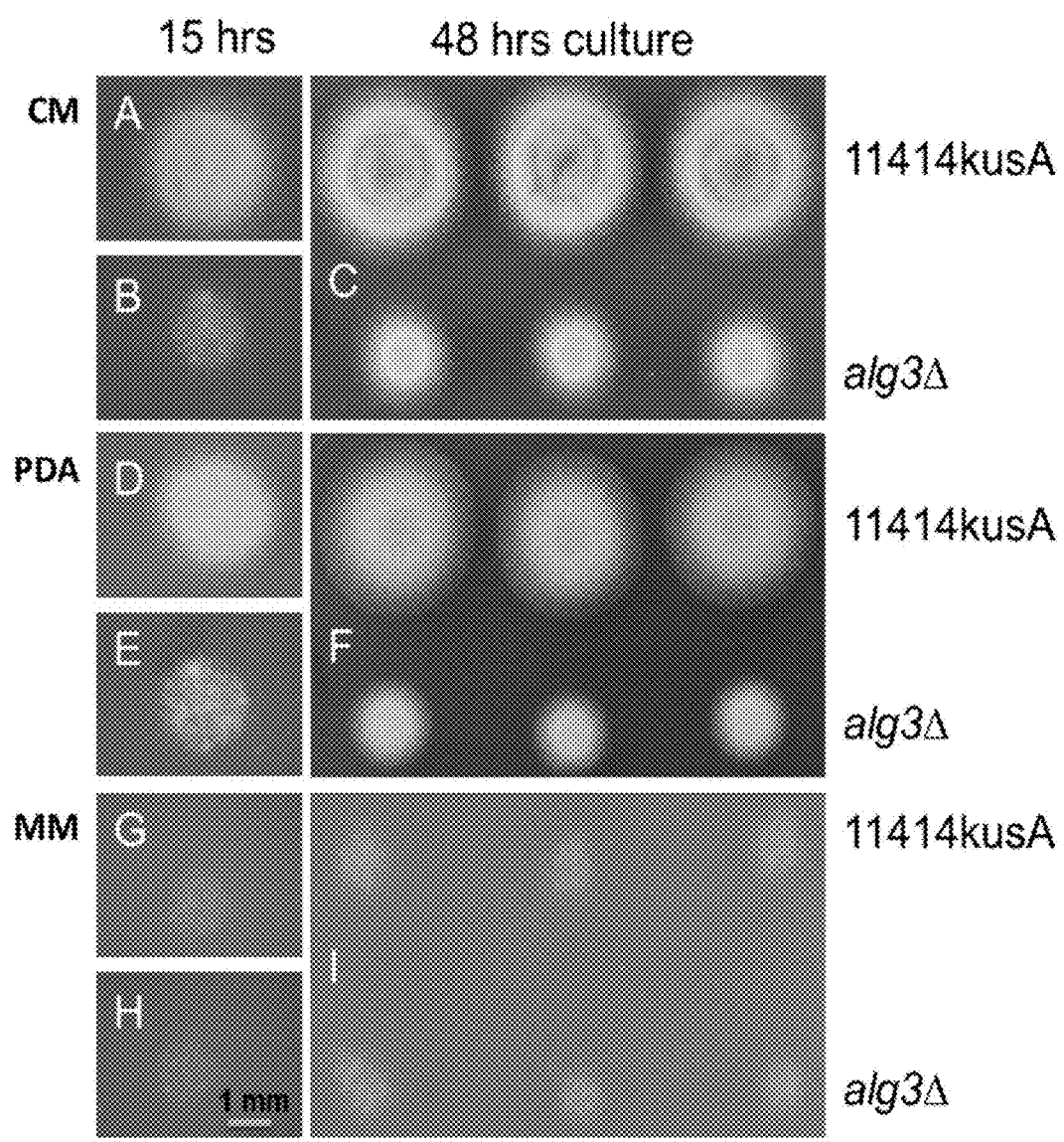
FIG. 2 is a series of digital images showing the Alg3Δ and parent 11414kusA strains grown on agar plates of complete medium (CM), potato dextrose (PDA), and minimal medium (MM) at 30° C. for 15 hours or 48 hours. Parent strain (panel A), Alg3Δ strain (panel B), and both parent and Alg3Δ strains (panel C) grown on complete medium plate. Parent strain (panel D), Alg3Δ strain (panel E), and both parent and Alg3Δ strains (panel F) were grown on PDA agar plates. Parent strain (panel G), Alg3Δ strain (panel H), and both parent and Alg3Δ strains (panel I) were grown on MM agar plates.

Alg3 was functionally inactivated in *A. niger* using a gene deletion vector constructed by yeast gap repairing approach. The 5'- and 3'-end of the hygromycin marker (hph) gene was flanked with about 1 kb upstream and downstream fragments of Alg3 coding region that were isolated by PCR from *A. niger* genomic DNA. The DNA sequence of the upstream and downstream fragments was confirmed by DNA sequencing analysis. The Alg3 in *A. niger* was deleted by homologous replacement with hygromycin marker (hph) gene in the kusA deletion background of *A. niger*, where the kusA gene, encoding the ortholog of the Ku70 protein in other eukaryotes, was deleted for dramatically improved homologous integration efficiency. FIGS. 1A and 1B show the predicted restriction enzyme digestion patterns of genomic DNA of the parent and mutant strains with BamHI and SacII. FIG. 1C shows the Southern blotting analysis of the digested genomic DNA of parent and mutant strains. The results confirm that the Alg3 coding region in *A. niger* was replaced by the hygromycin selection marker gene (hph) in the Alg3Δ strains.

Example 3

Effects of Alg3 Deletion on *A. niger* Growth and Development

This example describes methods used to determine the effect genetically inactivating Alg3 in *A. niger*.

It was previously demonstrated that the deletion of Alg3 in different organisms causes underglycosylation, but no obvious phenotype changes were observed at the selected culture condition in those studies (Aebi et al., *Glycobiology* 6(4):439-444, 1996; Korner et al., *EMBO J.* 18(23): 6816-6822, 1999; Davidson et al., *Glycobiology* 14(5):399-407, 2004; Manthri et al., *Glycobiology* 18(5): 367-383, 2008; Kajiura et al., *Glycobiology* 20(6):736-751, 2010).

Figure 3A:
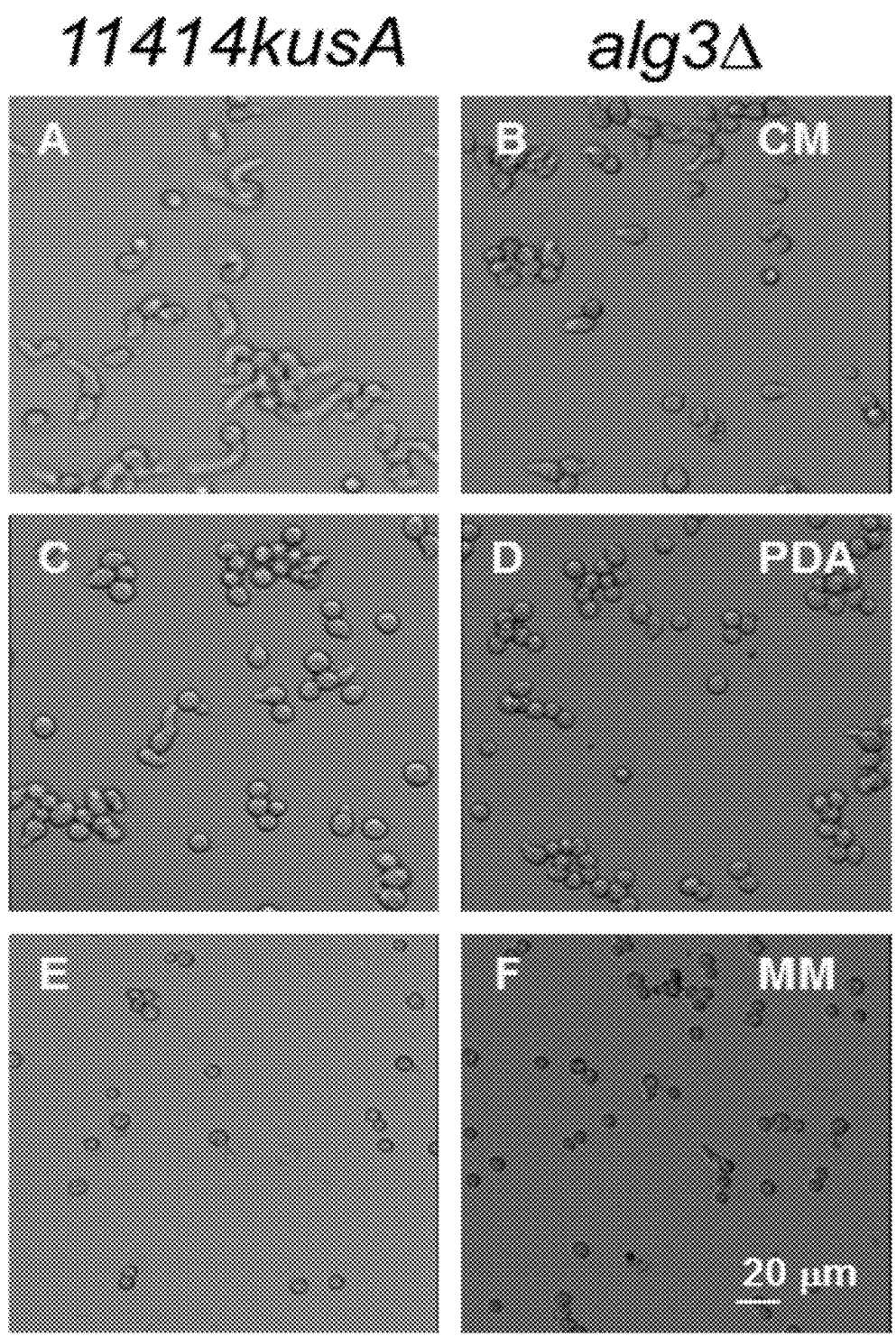
FIG. 3A is a series of digital images showing the spore germination of parent 11414kusA and Alg3Δ strains in liquid cultures of complete medium (CM), potato dextrose medium (PDA), and minimal medium (MM) at 30° C. for 7 hours. Panels A and B are germinated spores in CM liquid culture. Panels C and D are germinated spores in PDA liquid culture. Panels E and F are germinated spores in MM liquid culture. The left panels for the parent 11414kusA strain and the right panels for the Alg3Δ strain.
Figure 3B:
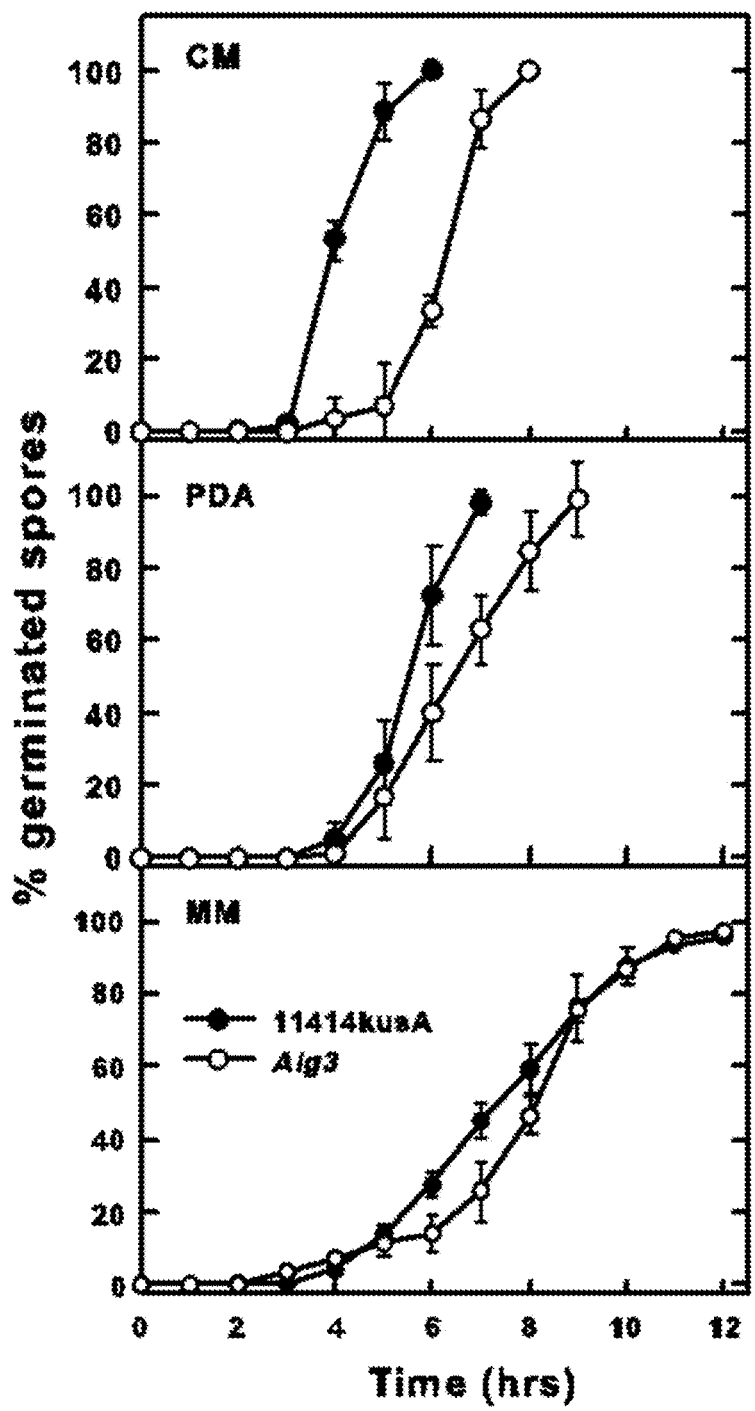
FIG. 3B provides graphs showing the time courses of the percentage of spore germination of parent 11414kusA and Alg3Δ strains grown in the liquid cultures of complete medium (CM; top graph), potato dextrose medium (PDA; middle graph), or minimal medium (MM; bottom graph). The solid filled cycle is the parent 11414kusA strain and open cycle is the Alg3Δ strain.

The effects of the Alg3 deletion were examined on CM, PDA and MM plates. As exhibited in FIGS. 2A-I, the Alg3Δ strain grew much slower than the parent strain when grown on either CM or PDA medium plate, but there was no significant difference between the Alg3Δ mutants and parent strain when grown on the MM medium plate. When both Alg3Δ strain and parent strain were grown in the liquid culture of CM and PDA, the initiation of spore germination of Alg3Δ strain was pronouncedly delayed (FIG. 3A), but the spore germination rate was not affected by the Alg3 deletion (FIG. 3B). These results demonstrate that deletion of Alg3 has significant effects on *A. niger* growth on nutrient rich media.

Figure 4:
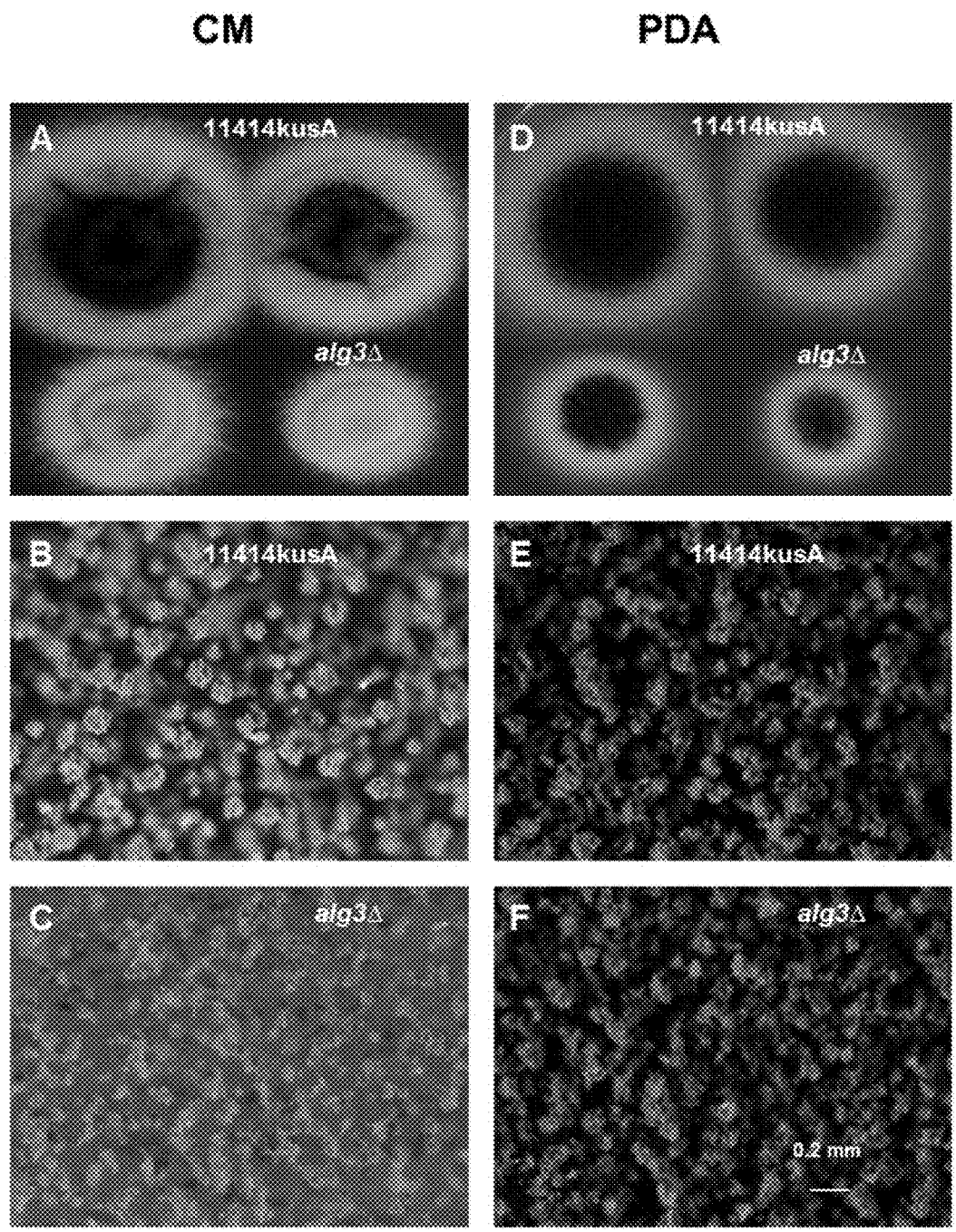
FIG. 4 shows a series of digital images (panels A and D) and stereo microscopy digital images (panels B, C, E and F) of parent and Alg3Δ strains grown on agar plates of complete medium (CM) and potato dextrose (PDA) at 30° C. for 4 days.

The effects of Alg3 deletion on spore production on both CM and PDA plates were also examined. The Alg3 deletion had a substantial reduction of sporulation on CM medium plate, while no obvious difference was exhibited on PDA plate (FIG. 4). The spore production at given area was enumerated with hemocytometer (Table 3). The average spore production of Alg3Δ was $2.64 \times 10^7$ spores/cm², about 40% of parent strain ($6.44 \times 10^7$ spores/cm²) on CM medium plates, while average spore production per a square millimeter was similar between Alg3Δ mutant ($7.72 \times 10^7$ spores/cm²) and parent strains ($7.89 \times 10^7$ spores/cm²) on PDA medium plates.

TABLE 3

Average spore production in PDA and CM media plates ($\times 10^7$ sp/cm^2). This was averaged from four cuts and 3 replicate counting.

| Strain | CM pates | PDA |
| --- | --- | --- |
| 11414-kusA | 6.44 ± 1.24 | 7.72 ± 1.78 |
| Alg3Δ | 2.64 ± 0.49 | 7.89 ± 1.18 |

Example 4

Effects of Alg3 Deletion on Spore Germination, Growth and Citric Acid Production This example describes methods used to measure spore germination, growth, and citric acid production in the Alg3Δ *A. niger* strain generated in Example 1. Based on these teachings, one skilled in the art will appreciate that spore germination, growth, and citric acid production can be similarly measured in other Alg3Δ strains of *Aspergillus*.

*A. niger* strain ATCC11414 is a strain developed for industrial production of citric acid. *A. niger* morphology plays a role in citric acid production. The fungal morphology affect overall molecular regulation in response to the endogenous and exogenous factors, which include the regulations of transcription, post-transcription, translation and post-translation. Therefore, the effects of Alg3 deletion on *A. niger* growth on CAP agar plates at different pHs or in CAP liquid culture conditions was determined.

Figure 5:
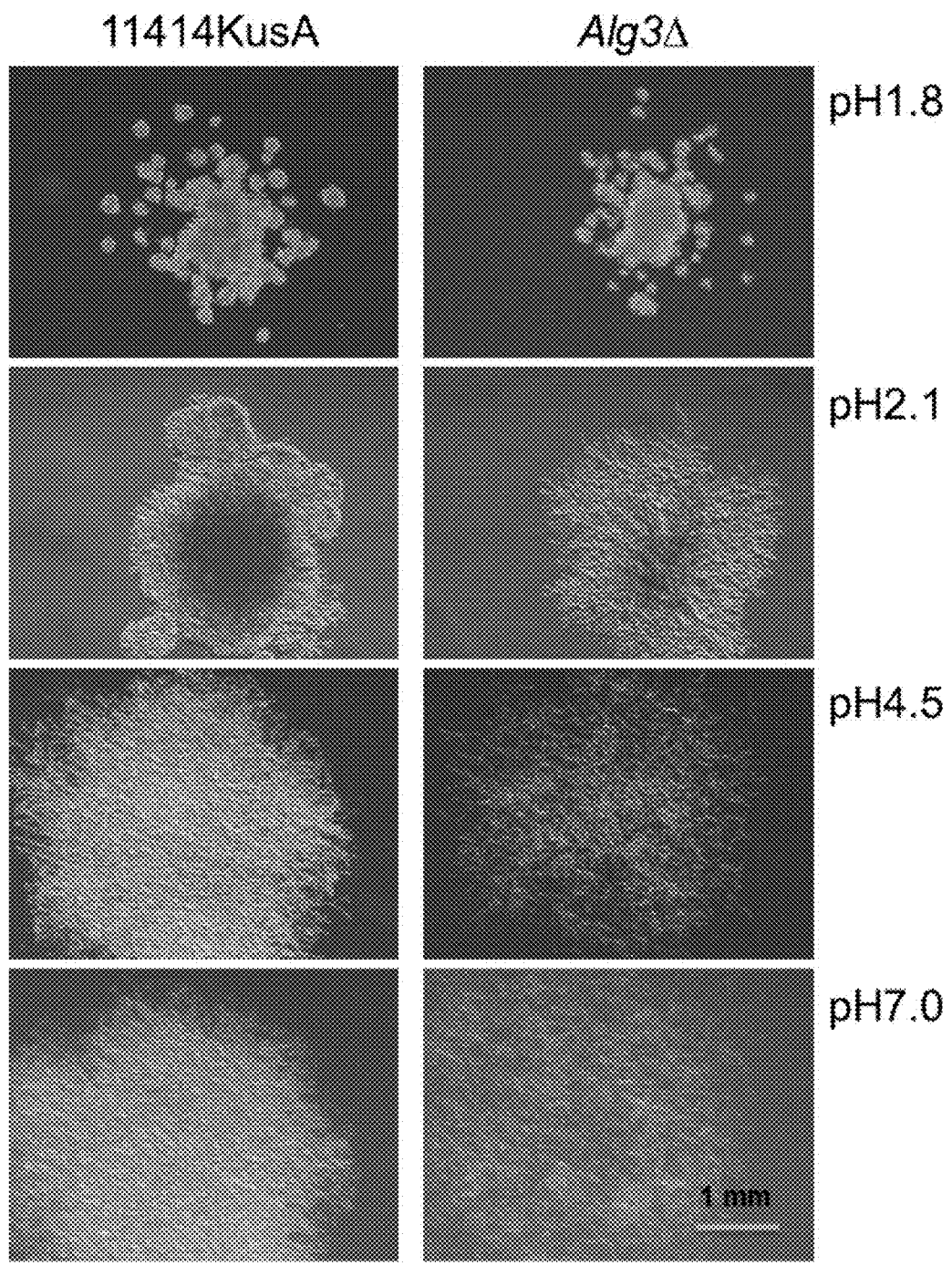
FIG. 5 provides stereo microscopy digital images parent 11414kusA and Alg3Δ strains grown on citric acid production (CAP) medium plates at different pH levels for 27 hours. The left panels for parent strain 11414kusA and right panels for the Alg3Δ strain.

FIG. 5 shows the effects of Alg3 deletion in fungi grown on CAP medium plates at different pH conditions after 28 hours in culture. When the Alg3Δ strain was grown on the CAP medium plates at pH 1.8, its growth was relatively slower than the parent strain, where its colonies were much smaller than the parent strain. At pH 2.1, the Alg3Δ strain formed a less tight pellet than that of parent strain. Growth of the Alg3Δ strain on the CAP medium at pH 4.5 and pH 7.0 was affected more profoundly than that of parent strain, where the Alg3Δ strain formed thinner layer of biomass on the agar plates than that of parent strain. These results show that the Alg3 deletion reduces the normal growth of *A. niger* at different levels on CAP culture medium plates at different pHs.

The spore germination of the Alg3Δ and parent strains in CAP liquid culture medium was also examined by using automated microscopic imaging, enumerating the germination manually in a same visual unit area, and expressing spore germination as a percentage of total spores at the same visual unit area. FIG. 6 shows the different dynamics of spore germination between the Alg3Δ and parent strains. The spore germination of Alg3Δ strain began as early as 3 hours after spore inoculation, while the parent strain was not initiated until 6 hours after spore inoculation. After 8 hours inoculation, more than 32% spores of Alg3Δ mutant germinated, while only 10% of parent strain spores did (FIG. 6A, top panels; and FIG. 6B). After 15 hours growth in CAP liquid medium, more than 90% spores of Alg3Δ strain germinated, while only 50% spores of parent strain did (FIG. 6A, bottom panels; and FIG. 6B). After 24 hours of growth in the liquid culture, about 75% spores of parent strain germinated, while the Alg3Δ strain achieved 94% of germination rate (FIG. 6B). The Alg3 deletion leads to earlier germination and a higher germination rate than parent strain.

Figure 7:
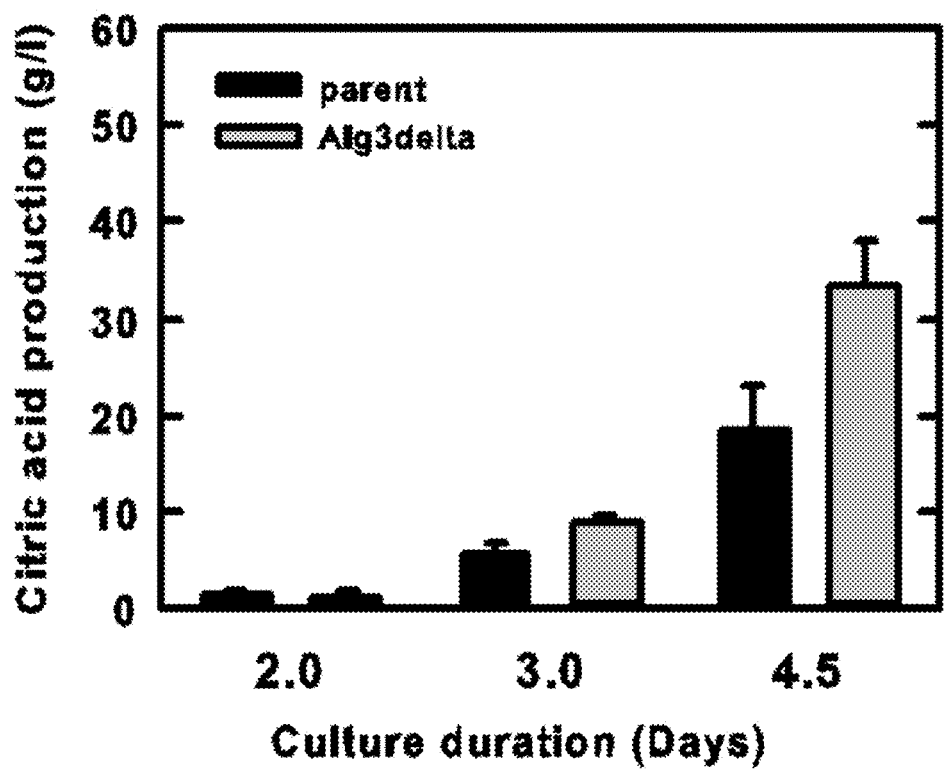
FIG. 7 is a graph showing the time course of citric acid production by parent 11414kusA and Alg3Δ strains in the liquid culture of citric acid production at 30° C. and 200 rmp.

The effect of Alg3 deletion on citric acid production was determined in CAP flask cultures. FIG. 7 shows the time course of citric acid production in CAP liquid medium. The yield of citric acid production was similar between the Alg3Δ mutant and parent strain in 2 days culture. After 3 days culture, the average citric acid production by Alg3Δ mutants was 8.8 g/l citric acid, while the parent strain only produced 5.8 g/l. After 4.5 days of culture, the parent strain accumulated 18.8 g/1 citric acid and the Alg3Δ mutant produced 33.3 g/1 citric acid (more than 70% higher than the parent strain). Thus, the Alg3 deletion substantially improves the citric acid production in *A. niger*.

The effect of Alg3 deletion on citric acid production was also examined by complementation of its original gene into the alg3Δ mutant. FIG. 8B shows the citric acid production in CAP liquid medium after 10 days of culture. The yield of citric acid production was similar between the alg3Δ complemented (cAlg3Δ) mutant and parent strain, but much lower than the alg3Δ mutant in 10 days culture. After 10 days culture, the average citric acid production by Alg3Δ mutants was 46.1 g/1 citric acid, while the parent and calg3Δ strain only produced 34.8 and 29.4 g/l, respectively.

Example 5 pPTRpGPDALaeA Plasmid Vector Construction

This example describes methods used to generate the pPTRpGPDALaeA plasmid vector (FIG. 13). One skilled in the art will appreciate that although gpdA and LaeA sequences were used from *Aspergillus nidulans*, one skilled in the art will appreciate that variants of these sequences can be used in the fungi and methods provided herein, such as gpdA and LaeA sequences from other *Aspergillus* species. In one example, a gpdA sequence having at least 80%, at least 90%, at least 95%, or at least 98% sequence identity to SEQ ID NO: 37 is used in the fungi and methods provided herein.

The *Aspergillus nidulans* glyceraldehyde 3-phosphate dehydrogenase (gpdA) promoter (SEQ ID NO: 37) was isolated from the pAN8-1 plasmid DNA using the primer set gpdA5F/gpdA3R (gpdA5F: CGCAGATCTC AAGCTG-TAAG GATTTCGGCA SEQ ID NO: 38; gpdA3R: CAC-CGGGCCC ATCTCAAACA TTGTGATGTC TGCT-CAAGCG SEQ ID NO: 39) and the LaeA coding sequence of genomic DNA from *A. nidulans* (SEQ ID NO: 40) obtained by PCR using LaeA5F/LaeA3R (LaeA5F: CGCT-TGAGCA GACATCACAA TGTTTGAGAT GGGCCCG-GTG; SEQ ID NO: 42; LaeA3R: CGCAGATCTG AGGAT-TATGA GAAGGGAGC; SEQ ID NO: 43).

The DNA fragment of pGPDA and LaeA was filled together by overlap PCR and a HindIII restriction enzyme site was introduced at both 5'- and 3'-end of the DNA fragment. The DNA fragment (SEQ ID NO: 44) and pPTR1 plasmid DNA were cut with Hind III and ligated together by a quick DNA ligation kit at 25° C. for 30 min. The ligated plasmid DNA was transferred into the Top10 *E. coli* competent cells by lithium acetate mediated transformation. The transformed bacterial colonies were screened for the DNA fragment insertion by PCR with the primers gpdA5F (SEQ ID NO: 38) and LaeA3R (SEQ ID NO: 43). The plasmid DNA for the selected transformed colonies was prepared for restriction enzyme confirmation and further expression vector construction.

Example 6 pRS426-LaeA Vector Construction

Figure 14:
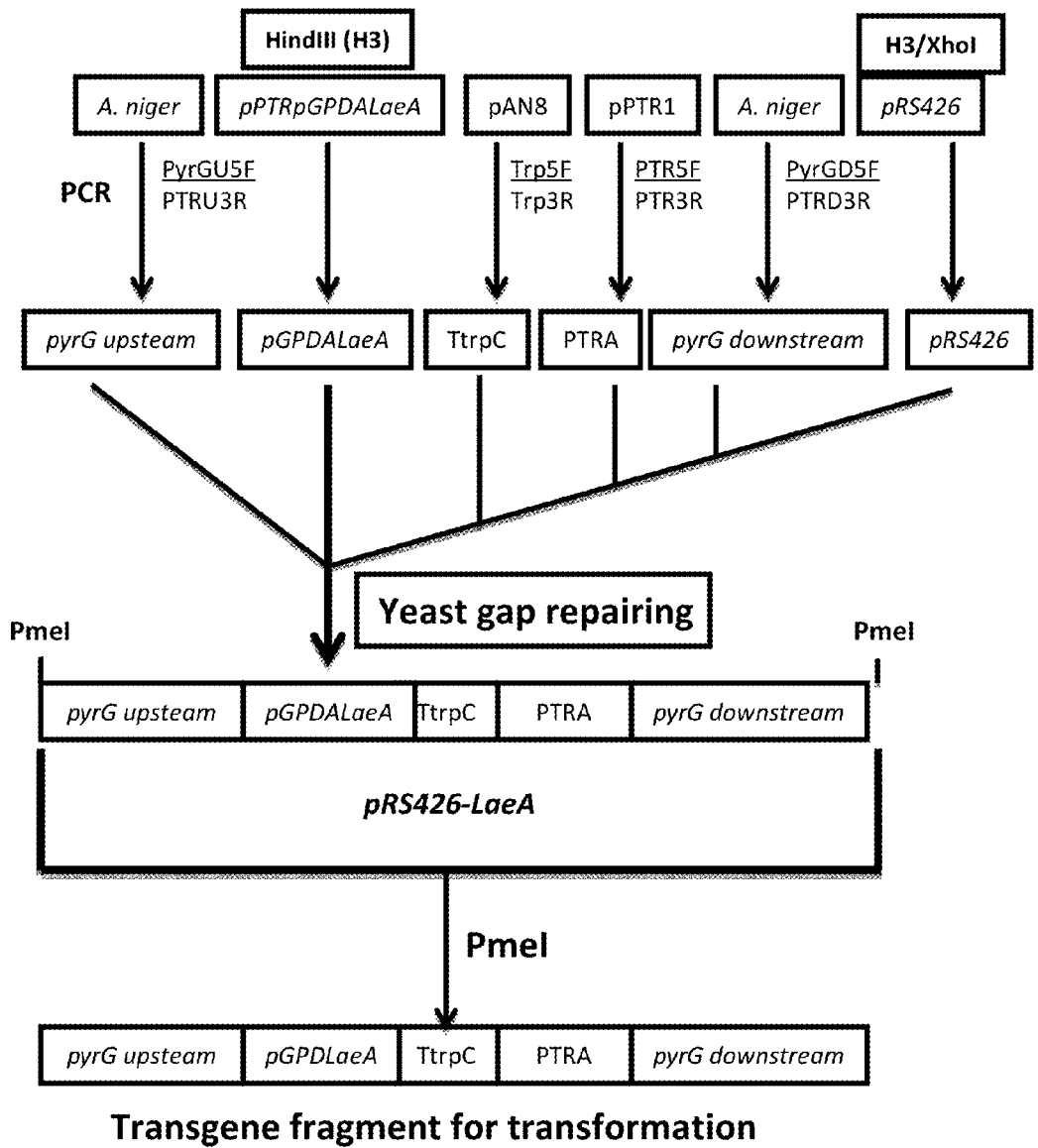
FIG. 14 is a schematic illustrating a plasmid vector pRS426-LaeA, which contains the upstream region of pyrG gene of *A. niger*, the coding region of LaeA gene under the control of gpdA promoter and transcriptional terminator of trpC gene from *A. nidulans*, the pyrithiamine resistance (ptrA) gene from *A. oryzae*, and the downstream region of pyrG gene of *A. niger*. The unique restriction enzyme PmeI site was introduced at the both end of transgene expression fragment.

This example describes methods used to generate a transgene containing *A. niger* LaeA (FIG. 14).

PCR was performed to isolate DNA fragments of *A. niger* pyrG upstream region (SEQ ID NO: 45), trpC transcriptional terminator of *A. nidulans* (SEQ ID NO: 46), pyrithiamine resistance gene (ptrA) of *Aspergillus oryzae* (SEQ ID NO: 47), and *A. niger* pyrG downstream region (SEQ ID NO: 48), using primers pyrGU5F/PTRU3R (pyrGU5F: GTAACGCCAG GGTTTTCCCA GTCACGACGT TTAAACATGC ATCATTCTCC CGCTTTGT, SEQ ID NO: 49; pyrGU3R: TGCCGAAATC CTTACAGCTT GAAGCT-TCAT CGCCAATCAC CTCAATCAC, SEQ ID NO: 50), Trp5F/Trp3R (Trp5F: AGCTCCCTTC TCATAATCCT CAAGCTTGGA CCGATGGCTG TGTAGAAGT, SEQ ID NO: 51; Trp3R: CGTAATCAAT TGCCCGTCTG TCAGA-GAGCG GATTCCTCAG TCTCGT; SEQ ID NO: 52), PTR5F/PTR3R (PTR5F: ACGAGACTGA GGAATCCGCT CTCTGACAGA CGGGCAATTG ATTACG, SEQ ID NO: 53; PTR3R: ACAGCAGTGC TTATCTGCGA TGAC-GAGCCG CTCTTGCATC TTTGT, SEQ ID NO: 54) and PyrGD5F/PTRD3R (pyrGD5F: ACAAAGATGC AAGAGCGGCT CGTCATCGCA GATAAGCACT GCTGT; SEQ ID NO: 55, pyrGD3R: TGAGACGCTG TTTCACCGAG TACATCGCCA ATCACCTCAA TCAC, SEQ ID NO: 56), respectively.

As shown in FIG. 14, the DNA fragment of pGDPALaeA (SEQ ID NO: 44) was isolated from pPTRpGDPALaeA (FIG. 13) by HindIII digestion. The yeast gap repairing vector pRS426 was double digested with restriction enzyme HindIII and XhoI. Hundred nanograms of each DNA fragment generated from PCR (i.e., SEQ ID NOs: 45-56) or restriction enzyme digestions were used for *S. cerevisiae* transformation. The gap repairing plasmid DNA in the total *S. cerevisiae* genomic DNA was isolated by transferred into the Top10 *E. coli* cells.

The transformed plasmid DNA was confirmed by PCR and digested with PmeI. The PmeI DNA fragment (SEQ ID NO: 57) was used for *A. niger* transformation.

One skilled in the art will appreciate that although the pyrG upstream and downstream sequences, trpC transcriptional terminator sequence, and ptrA sequence used were from particular organisms, one skilled in the art will appreciate that variants of these sequences can be used in the fungi and methods provided herein, such as those from other *Aspergillus* species. In one example, pyrG upstream and downstream sequences having at least 80%, at least 90%, at least 95%, or at least 98% sequence identity to SEQ ID NO: 45 and 48 are used in the fungi and methods provided herein. In one example, a trpC transcriptional terminator sequence having at least 80%, at least 90%, at least 95%, or at least 98% sequence identity to SEQ ID NO: 46 is used in the fungi and methods provided herein. In one example, a ptrA sequence having at least 80%, at least 90%, at least 95%, or at least 98% sequence identity to SEQ ID NO: 47 is used in the fungi and methods provided herein.

Example 7

Expression of pGDPALaeA-Containing Transgene in *A. niger* Alg3Δ

This example describes methods used to introduce pGP-DALaeA (SEQ ID NO: 57) into *A. niger*.

The originally transformed *A. niger* colonies were picked from the minimal medium plates with 0.1 µg/ml pyrithiamine hydrobromide selection on minimal medium agar plates without thiamine supplementation. The single spore colonies were picked for spore production after the initial transformant spores were grown on the same selection medium plates. The biomass was harvested from the single spore colony isolates grown in minimal medium with pyrithiamine selection and dried in the VirTis bench top freeze dryer. The genomic DNA was prepared for PCR confirmation of pGDPALaeA insertion in transgenic *A. niger*. As shown in FIG. 15A, the primer set of PTR5F (SEQ ID NO: 53) and PTR3R (SEQ ID NO: 54) was used to confirm the presence of *A. oryzae* pyrithiamine resistance gene (ptrA) in transgenic *A. niger* with the expected size of 2 kb PCR DNA fragment. As shown in FIG. 15B, the primer set LaeA5F (SEQ ID NO: 42) and TRP3R (SEQ ID NO: 52) was used to demonstrate that the transgene *A. nidulans* LaeA was under the control of gdpA promoter and trpC transcriptional terminator of *A. nidulans* with the expected 3.4 kb PCR fragment size. The genomic DNA of parent strain and the plasmid DNA of transgene vector carrying the pGDPA-LaeA fragment were used for negative and positive references.

Example 8

Increased Production of Citric Acid

This example describes methods used to demonstrate that citric acid production was increased in the presence of increased expression of LaeA, alone or in combination with deletion of Alg3.

Citric acid was produced as described in Example 1.

Figure 16:
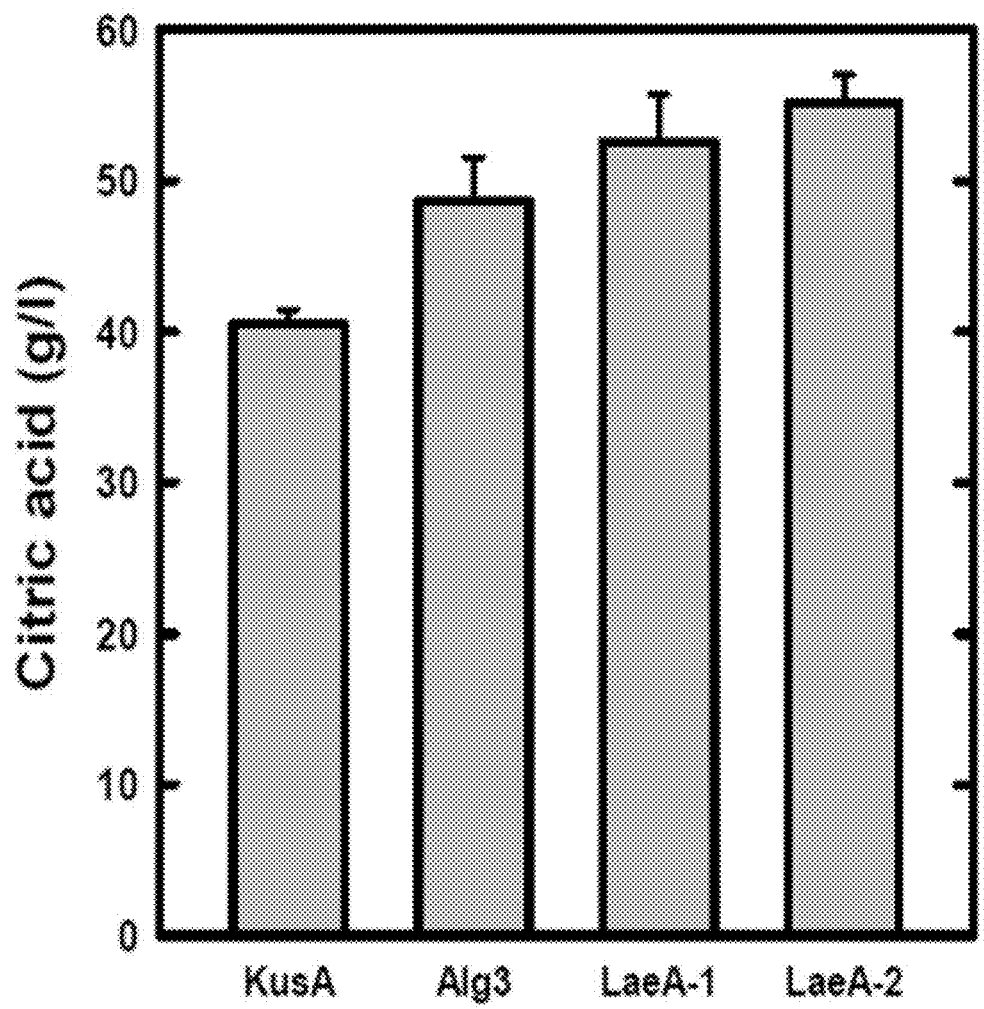
FIG. 16 is a bar graph showing the results of citric acid production after 10 days in culture of parent strain (kusA), alg3Δ mutant (Alg3), and over-expression of LaeA gene in alg3Δ (LaeA-1 and LaeA-2) mutants. The data for each strain is the average of three replicates.

As shown in FIG. 16, of citric acid production was increased in the Alg3Δ mutant (Alg3), and in the mutants over-expressing LaeA in Alg3Δ (LaeA-1 and LaeA-2), as compared to the parent strain (kusA).

Example 9 pBSK-LaeA a Plasmid Vector Construction

This example describes methods used to generate the pBSK-LaeAΔ plasmid vector (FIG. 17A). The 5' (SEQ ID NO: 61) and 3' (SEQ ID NO: 62) ends of the *Aspergillus niger* LaeA gene were isolated from *A. niger* genomic DNA by PCR using oligonucleotide sets D1 & D2, and D5 & D6 (see Table 4 below). The hph expression cassette was isolated from plasmid vector DNA of pCB1003 (SEQ ID NO: 63) by PCR using the oligonucleotide sets D3 & D4. The DNA fragments were assembled together into the backbone plasmid vector of pBSK linearized with restriction endonucleases of both HindIII and PstI using the Gibson assembly cloning kit. The assembled plasmid DNA was transferred into the Top10 *E. coli* competent cells by lithium acetate mediated transformation. The transformed bacterial colonies were screened for the DNA fragment insertion by restriction endonuclease digestion of PvuII and XhoI. The plasmid DNA for the transformed colonies was prepared and digested with endonucleases of HindIII and XbaI for further LaeA deletion in *A. niger*.

TABLE 4

Oligonucleotide Primers for *A. niger* LaeA Deletion

| Name | Sequence | SEQ ID NO: |
|---|---|---|
| D1 | gtcgacggtatcgataAGCTTCAAGACAGCGGCTGCAA | 67 |
| D2 | gccgaccgTGGTAGAGATACAGGGGTTC | 68 |
| D3 | ctctaccaCGGTCGGCATCTACTCTATTC | 69 |
| D4 | gcgactgaGCTGGAGCTAGTGGAGGT | 70 |
| D5 | gctccagcTCAGTCGCATCTTTCACTG | 71 |
| D6 | atcccccgggctgcaTGGTAGGCTGTCTCAAGG | 72 |
| SC7 | ACTCGCAGCAGAGATGCCATCT | 73 |
| SC8 | CGTTATGTTTATCGGCACTTTGCAT | 74 |

Example 10 pRS426-*A. niger* LaeA Complementation Plasmid Vector Construction

This example describes methods used to generate the pBSK-LaeAΔ plasmid vector (FIG. 17B). The entire LaeA gene (2.34 kb; SEQ ID NO: 64) containing 740 bp of promoter region and 330 bp of transcriptional terminator region was isolated from *A. niger* genomic DNA by PCR using oligonucleotide set CP9 & CP10 (see Table 5 below). The DNA fragment was ligated into the plasmid DNA of pRS426-*A. nidulans* LaeA over-expression vector at a HindIII restriction endonuclease site after the pGPDALaeA fragment in the vector was removed by agarose gel separation. The assembled plasmid DNA was transferred into the Top10 *E. coli* competent cells by lithium acetate mediated transformation. The transformed bacterial colonies were screened for the DNA fragment insertion by restriction endonuclease digestion of BamHI and XhoI. The plasmid DNA for the transformed colonies was prepared and digested with PmeI restriction endonuclease for *A. niger* LaeA expression at pyrG locus to complement the LaeA deletion in *A. niger* LaeAΔ mutants.

TABLE 5

Oligonucleotide Primers for *A. niger* LaeA Complementation

| Name | Sequence | SEQ ID NO: |
|---|---|---|
| CP9 | aggtgattggcgatgaTGCCGTTCAGCTGTCTGC | 75 |
| CP10 | acagccatcggtccaTCTCTCCTCGTAACGCCTG | 76 |
| SC11 | ggatagaatcgggtgccgctgatct | 77 |
| SC12 | gagaaccatggcaccgaaggt | 78 |

Example 11

Deletion of *A. niger* LaeA Gene in *A. niger*

This example describes methods used to introduce the HindIII/XbaI DNA fragment contain the LaeA deletion cassette (SEQ ID NO: 65) into *A. niger*.

Figure 18:
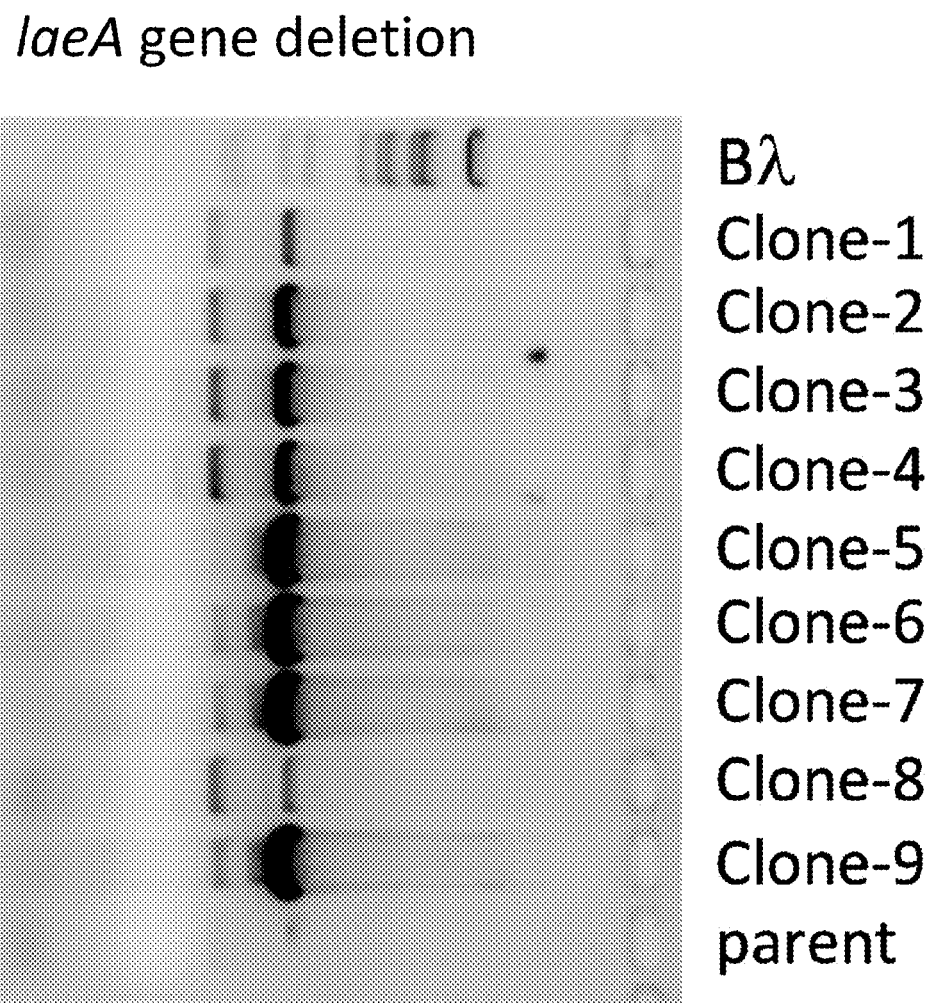
FIG. 18 shows a digital image of the results of PCR analysis of the LaeA gene deletion in the transgenic A. niger genome by homologous recombination at the pyrG locus. The PCR products corresponding to the 5' end of the A. niger LaeA gene and part of the hph expression cassette were amplified with oligonucleotide pair 7 and 8, and were detected in selected single spore colony isolate (SCI) of LaeA gene deletion transgenic mutants.

The originally transformed *A. niger* colonies were picked from the minimal medium plates with 100 μg/ml Hygromycin B selection on minimal medium agar plates. The single spore colonies were picked for spore production after the initial transformant spores were grown on the same selection medium plates. The biomass was harvested from the single spore colony isolates grown in complete medium with Hygromycin B selection and dried in the VirTis bench top freeze dryer. The genomic DNA was prepared for PCR confirmation of the replacement of LaeA gene coding region in transgenic *A. niger*. As shown in FIG. 18, the primer set SC7 and SC8 (see Table 4) was used to confirm the hph replacement of the LaeA gene in transgenic *A. niger* with the expected 2 kb PCR DNA fragment. The genomic DNA of parent strain was used for negative and positive references.

Example 12

Expression of pGDPALaeA-Containing Transgene in *A. niger*

This example describes methods used to introduce the *A. niger* LaeA gene into the pyrG locus in the *A. niger* LaeAΔ mutant to complement the loss of LaeA function with PmeI DNA fragment (SEQ ID NO: 66).

Figure 19:
FIG. 19 shows a digital image of the results of PCR analysis of the LaeA gene complementation (cLaeA) in the genetic background of LaeA deletion mutant or A. nidulans LaeA over-expression (LaeA) in the genetic background of 11414kusA of those transgenic A. niger genome by homologous recombination. PCR products of A. oryzae ptrA gene detected in selected single spore colony isolate (SCI) of LaeA gene transgenic mutants and parent kusA (negative) and plasmid DNA of pRS426-laeA (positive) represent control DNA.

The originally transformed *A. niger* colonies were picked from the minimal medium plates with 0.1 μg/ml pyrithiamine hydrobromide selection on minimal medium agar plates without thiamine supplementation. The single spore colonies were picked for spore production after the initial transformant spores were grown on the same selection medium plates. The biomass was harvested from the single spore colony isolates grown in minimal medium with pyrithiamine selection and dried in the VirTis bench top freeze dryer. The genomic DNA was prepared for PCR confirmation of LaeA gene insertion in transgenic *A. niger*. As shown in FIG. 19, the primer set of PTR5F (SEQ ID NO: 53) and PTR3R (SEQ ID NO: 54) was used to confirm the presence of *A. oryzae* pyrithiamine resistance gene (ptrA) in transgenic *A. niger* with the expected size of 2 kb PCR DNA fragment. The genomic DNA of the parent strain and the plasmid DNA of the transgene vector carrying the *A. oryzae* pyrithiamine resistance gene (ptrA) fragment were used for negative and positive references.

Example 13

Figure 20:
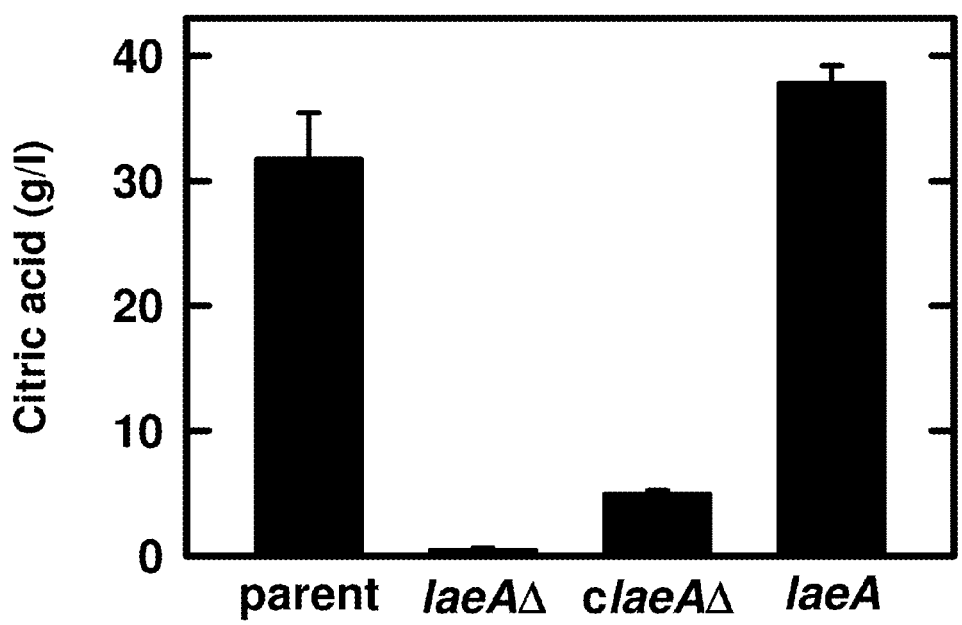
FIG. 20 is a bar graph showing the results of citric acid production after 5 days in culture of the parent strain (kusA), the LaeAΔ mutant, A. niger LaeA gene complementation in the LaeAΔ mutant (cLaeAΔ), and over-expression of A. nidulans LaeA gene in the parent (KusA) strain. The data for each strain is the average of at least three biological replicates.

The Effects of LaeA Gene Deletion and Complementation and Over-Expression of *A. nidulans* LaeA Gene on Citric Acid Production This example describes methods used to demonstrate that citric acid production in *A. niger* mutant strains was significantly influenced by perturbing the LaeA gene expression in *A. niger*. At least three individual clones per mutant strain were selected for spore production on complete medium plates at 30° C. for 4 days. The spores were counted with a hemocytometer. Citric acid production culture was initiated by inoculation with a $1\times10^6$ spore/ml of 75 ml citric acid production culture medium in a 250 ml baffled Erlenmeyer glass flask siliconized with a 5% solution of dichlorodimethylsilane in hexane solvent. The culture was maintained at 30° C. and 220 rpm in shaker incubator for 5 days. One microliter of culture was harvested and briefly spun down in a microcentrifuge at full speed. The supernatants of cultures were diluted 200-fold with $dH_2O$ prior to citric acid measurement. The citric acid in the supernatant was quantified with the citric acid assay kit from R-Biopharm AG. The detailed procedure for the citric acid assay was performed essentially according to the manufacturer's description. The results in FIG. 20 show that deletion of the LaeA gene in *A. niger* (LaeAΔ) led to loss of citric acid production in citric acid production culture. When the original *A. niger* LaeA gene was used for complementation in the LaeAΔ mutant (cLaeAΔ) at the pyrG locus, the citric acid production was partially recovered, which indicates the importance of chromosome location of LaeA gene. When *A. nidulans* LaeA was over-expressed in the *A. niger* parent strain (LaeA), the citric acid production was higher than the parent strain. This indicates that the LaeA is involved in citric acid production in *A. niger*.

Example 14

Enhancement of Itaconic Production by LaeA Complementation *A. terreus* Growth Conditions All strains were maintained on potato dextrose agar (PDA), which is composed of 39 g/L of Difco Potato Dextrose Agar (BD, USA). Spore inocula were grown on PDA and harvested after 5 days. The transformant was selected for either hygromycin or bleomycin resistance on minimum media (MM, 50 ml 20× nitrate salts, 1 ml 1000× trace elements, 1 ml 1000× vitamin stock, 10 g glucose, pH 6.5, 100 μg/ml hygromycin or 250 μg/ml bleomycin). The 20×$NO_3$ salts contains in one liter $H_2O$: $Na_2NO_3$, 120 g; KCL, 10.4 g; $MgSO_4 \cdot 7H_2O$, 10.4 g; $KH_2PO_4$, 30.4 g. The 1000× vitamin solution (yellow) contains in 100 ml $H_2O$: biotin, 0.01 g; pyridoxine-HCl, 0.01 g; thiamine-HCl, 0.01 g; riboflavin, 0.01 g; para-amino benzoic acid, 0.01 g; and nicotinic acid (or niacin), 0.01 g, filtered and stored at 4° C. The 1000× trace elements contains per 100 ml $H_2O$: $ZnSO_4 \cdot 7H_2O$, 2.2 g; $H_3BO_3$, 1.1 g; $MnCl_2 \cdot 4H_2O$, 0.5 g; $FeSO_4 \cdot 7H_2O$, 0.5 g; $CoCl_2 \cdot 6H_2O$, 0.17 g; $CuSO_4 \cdot 5H_2O$, 0.16 g; $Na_2MoO_4 \cdot 2H_2O$, 0.15 g; $Na_2EDTA$, 5 g, which is added in the order, boil and cool to room temperature and adjusted the pH to 6.5 with KOH. For pyrithiamine marker selection, the thiamine-HCl was eliminated from minimum media.

About 1×$10^6$ spores/ml were used to inoculate 50 ml of itaconic acid production media in 250 ml glass flask. The itaconic acid production medium essentially followed the description of Riscaldati et al. (*J Biotechnol* 83:219-230, 2000). Itaconic acid production medium contains in grams per liter (g/l): glucose, 100; ammonium sulfate, 2.36; potassium phosphate dibase, 0.11; magnesium sulfate heptahydrate, 2.08; calcium chloride dihydrate, 0.13; sodium chloride, 0.074; copper sulfate pentahydrate 2×$10^{-4}$; ferrous sulfate heptahydrate, 5.5×$10^{-3}$; manganese chloride tetrahydrate, 7×$10^{-4}$; and zinc sulfate heptahydrate, 1.3×$10^{-3}$. The flask cultures were shaken at 30° C. and 150 rpm. At least three biological replicates for each strain were used for each experiment.

Itaconic Acid Measurement

The itaconic acid method followed the previous description by Dickman (*Analytical Chem* 24: 1064-1066, 1952) with some modification. The reaction volume was scaled down to 1.4 ml for each reaction. Ten to 250 μl of culture supernatant or itaconic acid standard dissolved in $dH_2O$ were used. The proper amount of culture supernatant or itaconic acid standard was added into 690 to 930 μl $dH_2O$ in 1.5 ml microcentrifuge tube. Then, 60 μl of freshly prepared metaphosphoric acid (0.425 g/ml) was added into the tube, mixed well, and incubated at 4° C. for 10 minutes. Next, 400 μl of freshly prepared potassium permanganate (5 mM) from stock solution (100 mM) was added, mixed well and incubated in the dark at room temperature for 10 minutes. Finally, the absorbency of the reaction mixture was determined at 530 nm spectrophotometrically.

LaeA Deletion Construct

Figure 21A:
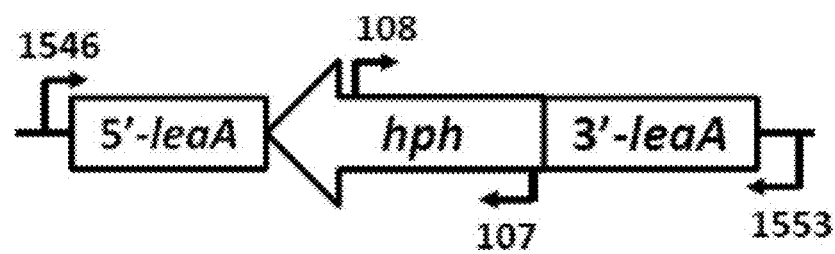
FIG. 21A is a diagram illustrating the LaeA deletion construct in which the LaeA coding region was replaced by the bacterial hygromycin B phosphotransferase (hph) gene. Oligonucleotides 1546, 108, 107 and 1553 (see Table 6) were used for LaeA gene deletion confirmation in A. terreus.
Figure 21B:
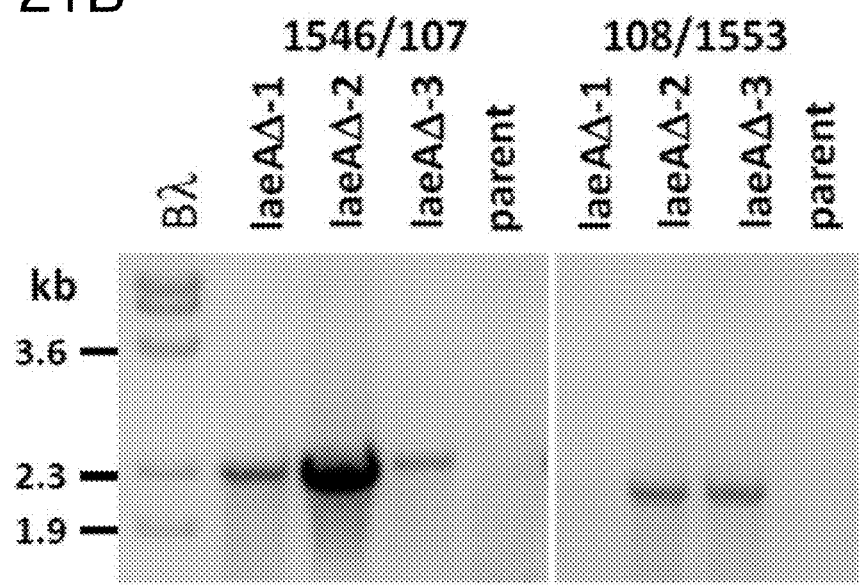
FIG. 21B shows the genomic PCR confirmation of selected LaeA deletion mutants with oligonucleotide pair 1546/107 or 108/1553.

The DNA fragments corresponding to the upstream and downstream regions of the LaeA gene in *A. terreus* and hph were isolated with oligonucleotide pairs 1546/1548, 1551/1553 and 1549/1550, respectively (see Table 6 for oligonucleotide sequences). These three DNA fragments (SEQ ID NOs: 89-91) were fused together by double-joint PCR (Yu, et al., *Fungal Genetics and Biology* 41: 973-981, 2004). The whole LaeA deletion fragment was isolated by PCR with oligonucleotide pair 1547/1552 (see Table 6 and SEQ ID NO: 104). FIG. 21A depicts the LaeA deletion construct. FIG. 21B shows genomic PCR confirmation of selected LaeA deletion mutants with oligonucleotide pair 1546/107 or 108/1553.

LaeA Complementation Construct

Figure 22A:
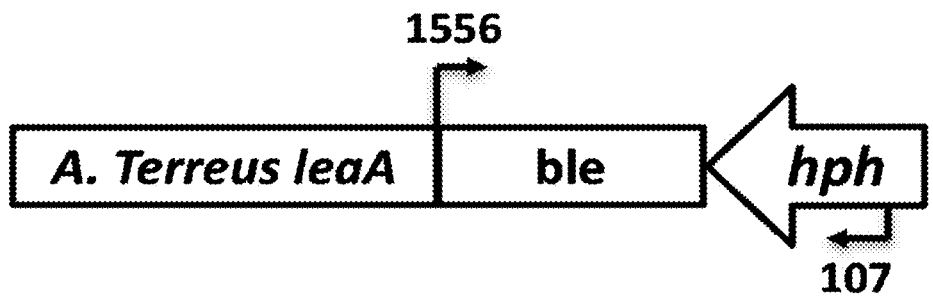
FIG. 22A is a diagram illustrating LaeA complementation in A. terreus LaeA deletion mutants. The complementation transgene fragment was targeted upstream of the LaeA gene and the bacterial bleomycin resistance gene (ble) was used for transgenic strain selection. The insertion of LaeA complementation was confirmed by oligonucleotide pair 1556/107.
Figure 22B:
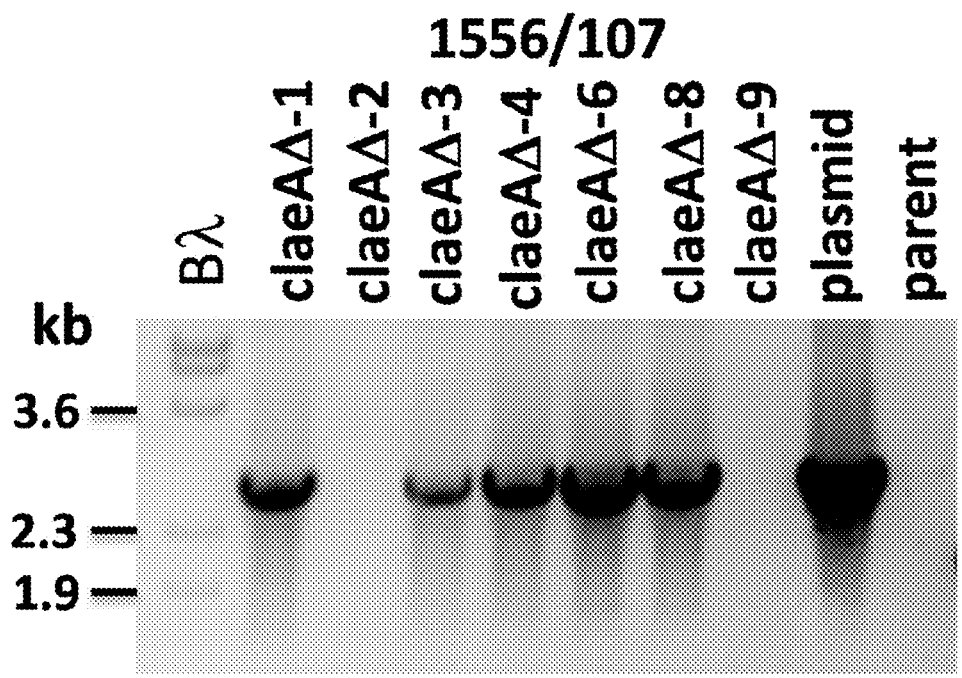
FIG. 22B shows gel electrophoresis of genomic PCR product corresponding to ble and part of hph.

The LaeA complementation construct was prepared for targeting upstream of the LaeA locus in *A. terreus* using the Gibson Assembly method. The DNA fragments of the whole LaeA gene, ble selection marker gene, and hph gene used for gene deletion were isolated by PCR with oligonucleotide pairs 1554/1555, 1556/15557, and 1558/1559, respectively (see Table 6). In order to isolate the whole transgene cassette, an XbaI restriction endonuclease site was introduced into the upstream fragment of 1554/1555. The three DNA fragments (SEQ ID NOs: 107-109) were then assembled into the cloning vector of pBluescript SK(-). FIG. 22A is a diagram illustrating the LaeA complementation constructs. The insertion of LaeA complementation was confirmed by oligonucleotide pair 1556/107. FIG. 22B shows gel electrophoresis of genomic PCR products corresponding to ble and part of hph.

LaeA Over-Expression Construct

Figure 24A:
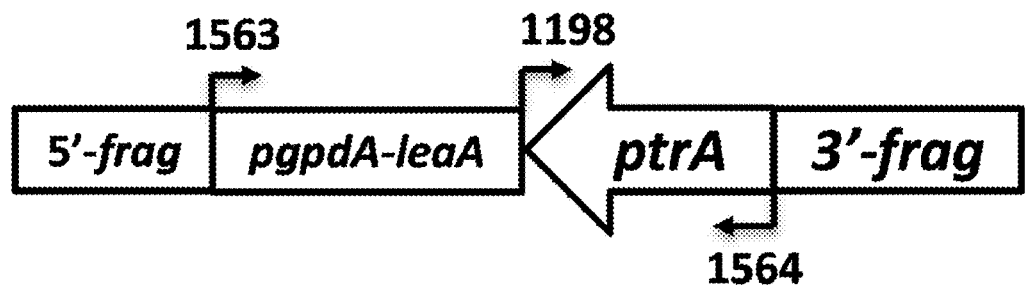
FIG. 24A shows a diagram of the transgene over-expression cassette of the A. nidulans LaeA gene under the control of the A. nidulans gpdA promoter and TrpC terminator with a locus target of 2.5 kb of the A. terreus LaeA gene. The pyrithiamine resistance gene (ptrA) of A. oryzae was used for transgene expression selection. Oligonucleotides 1563, 1198 and 1564 (see Table 6) were used for genomic PCR to confirm the gene insertion.
Figure 24B:
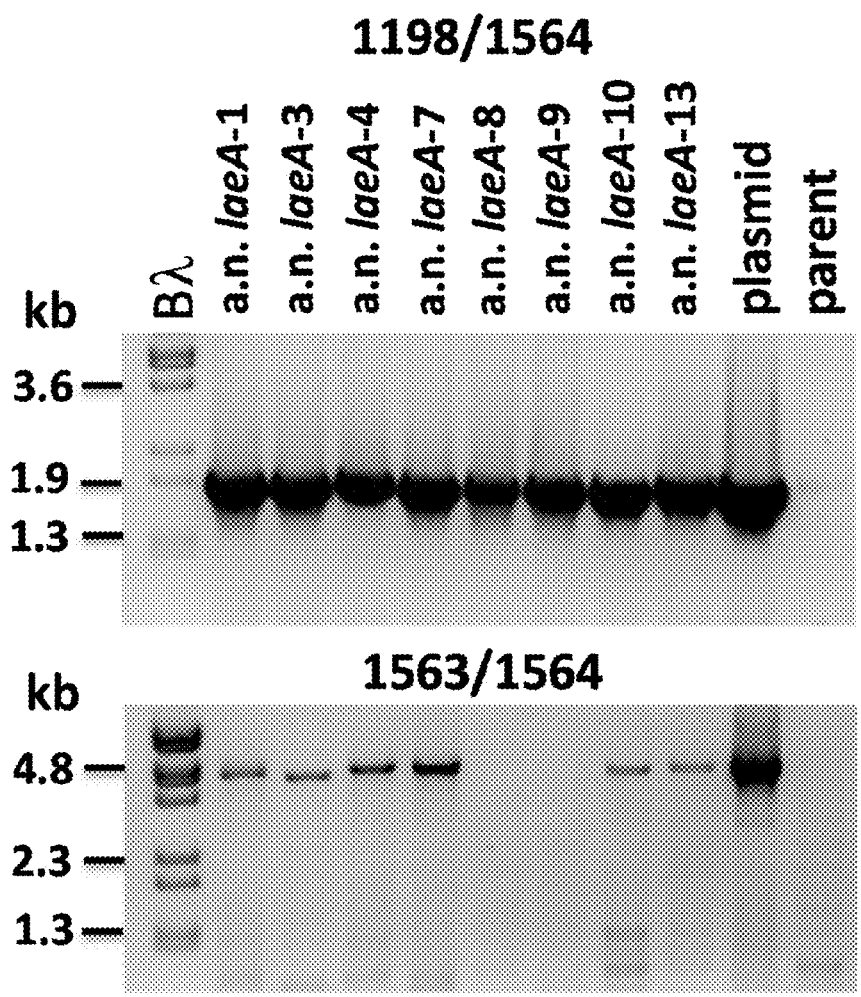
FIG. 24B shows gel electrophoresis of PCR products corresponding to the oligonucleotide pairs 1198/1564 and 1563/1564 in selected transgenic strains.

The *Aspergillus nidulans* LaeA gene under the control of *A. nidulans* gpdA promoter and TrpC transcription terminator, and the selection marker gene of pyrithiamine resistance gene (ptrA) of *Aspergillus oryzae*, were isolated from the transgene expression construct used for *A. niger* transformation (as described in Example 6) with oligonucleotide pair 1563 and 1564 (Table 6). Due to the extremely high homologous replacement rate in *A. terreus*, the laeA over-expression transgene cassette was designed to replace the 127 bp genomic DNA fragment of the non-gene region located at 1571 bp upstream in *A. terreus* laeA coding gene sequence. The corresponding DNA fragments franked to the both ends of LaeA expression cassette for homologous replacement were isolated by PCR with oligonucleotide pairs 1561/1562 and 1565/1566 (Table 6). The three DNA fragments (SEQ ID NOs: 96-98) were fused together in pBluescript SK(-) by Gibson Assembly. The restriction endonuclease site for PmeI was introduced into the 5' end of the upstream region fragment of 1561/1562 (SEQ ID NO: 96) and the 3' end of the downstream region fragment of 1565/1566 (SEQ ID NO: 110), which enables the isolation of whole transgene expression construct. FIG. 24A is a diagram of the transgene over-expression cassette of the *A.* nidulans LaeA gene. Oligonucleotides 1563, 1198 and 1564 (see Table 6) were used for genomic PCR to confirm the gene insertion. FIG. 24B shows gel electrophoresis of PCR products corresponding to the oligonucleotide pairs 1198/1564 and 1563/1564 in selected transgenic strains.

A. terreus Protoplast Isolation and Transformation

A. terreus ($10^6$ conidia/ml) was inoculated into 100 ml of complete media containing in g/l: D-glucose, 10; peptone, 2; yeast extract, 1; casamino acids, 1; 20× nitrate salts, 50 ml; trace elements, 1 ml; vitamin solution, 1 ml (pH6.5) or MM without thiamine-HCl. The inoculated culture was shaken at 150 rpm and 30° C. for 16-22 hours. The mycelia were harvested by filtering the culture through Miracloth and rinsed well with sterile $dH_2O$. The mycelia (mass of approximately several bean sizes) were digested with 20 ml of 20 mg/ml lysing enzyme (L1412, Sigma) that was dissolved in osmotic washing buffer (0.5 M KCl, 10 mM sodium phosphate, pH 5.8) for approximately 2-3 hours at 80 rpm and 30° C. Protoplasts were filtered through sterile miracloth into a 50 ml sterile centrifuge tube and centrifuged for 10 minutes at 1000×g and 4° C. Protoplasts were washed twice with 20 ml washing solution (0.6M KCl, 0.1 M Tris-HCl, pH 7.0) and once in 10 ml conditioning solution (0.6M KCl, 50 mM $CaCl_2$, 10 mM Tris-HCl, pH 7.5).

For transformation, 1-2 μg DNA was added to $2×10^7$ protoplasts in 0.1 ml conditioning solution. After addition of 25 μl PEG solution, the protoplasts were incubated on ice for 20 minutes. An additional 500 μl PEG solution was carefully added, mixed and incubated on ice for additional 5 minutes. Finally, 1 ml cold conditioning solution was added and mixed by inverting the tube several times. About 300-500 μl of transformed protoplasts were pipetted into 12 ml melted MM agar (MM+0.6M KCl+1.5% agar+antibiotics) tubes at 50° C. The transformed protoplasts were mixed well by inverting the tubes 3-4 times and poured directly onto the 100 mm petri dishes. The petri dishes were incubated overnight at 30° C. An additional 8 ml of regular MM agar with proper antibiotics was overlaid and further incubated at 30° C. for approximately 3-4 days. The transformed colonies were picked and further grown on 2 ml MM agar gel for spore production.

TABLE 6

| Oligonucleotides | | |
|---|---|---|
| Oligo | DNA sequence | SEQ ID NO: |
| 107 | GTACTTCTACACAGCCATCGGTCCA | 79 |
| 108 | CGTTATGTTTATCGGCACTTTGCAT | 80 |
| 1546 | ACAGGTACTTCCATCTTGTACTGGT | 81 |
| 1547 | TCtcctccaacgtccgatct | 82 |
| 1548 | acctccactagctccagcaagccgaacaga ggtaaagacga | 83 |
| 1549 | tcgtctttacctctgttcggcttgctggag ctagtggaggtca | 84 |
| 1550 | taccaacgtgcgaccatttTCTcggtcggc atctactctattcct | 85 |
| 1551 | aggaatagagtagatgccgaccgAGAaaat ggtcgcacgttggta | 86 |
| 1552 | AAGCGTCTCTTTCCTGGGTCTT | 87 |
| 1553 | TGCCAGTTCTGTTGGACATCTCT | 88 |
| 1554 | tcgaggtcgacggtatcgatatctagaACA GGTACTTCCATCTTGTAC | 89 |
| 1555 | ggtcactgtTCCTGGCAGCTGACATTG | 90 |
| 1556 | ctgccaggaACAGTGACCGGTGACTCT | 91 |
| 1557 | aagcagcagatACGACCGTTGATCTGCTTG | 92 |
| 1558 | acggtcgtATCTGCTGCTTGGTGCAC | 93 |
| 1559 | actagtggatccccgggctgcagCGGTCG GCATCTACTCTATTC | 94 |
| 1561 | cgaggtcgacggtatcgataGTTTAAACCT CCCAGGTACCGACTAAC | 95 |
| 1562 | ctcaatcacaGATCATGTTTGGGTGGGTTC | 96 |
| 1563 | aaacatgatcTGTGATTGAGGTGATTGGCG | 97 |
| 1564 | ctctgtgcctACAGCAGTGCTTATCTGC GATG | 98 |
| 1565 | gcactgctgtAGGCACAGAGTAACAGGTAG GTAGACAG | 99 |
| 1566 | agtggatccccgggctgcaGTTTAAACTC CGCACCACGAAAGCAACT | 100 |

Results

Figure 23:
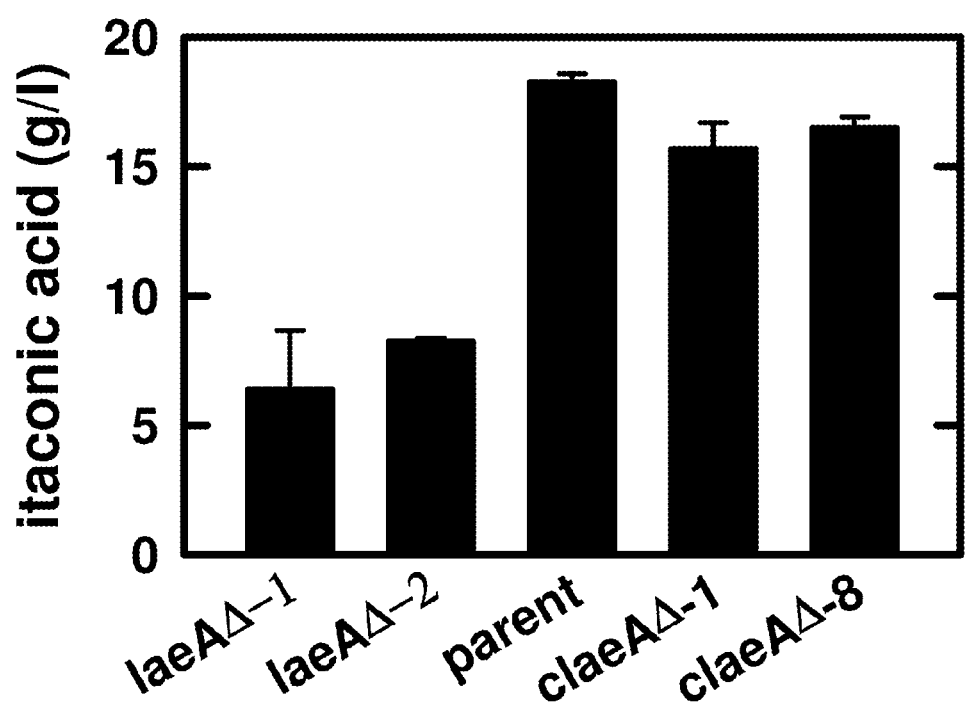
FIG. 23 is a graph showing itaconic acid production in selected strains of parent, LaeA deletion (LaeAΔ) and LaeA complementation (cLaeAΔ) mutants after 4 days of culture in itaconic acid production medium.

Itaconic acid production in selected LaeA deletion (LaeAΔ) and LaeA complementation (cLaeAΔ) mutants of A. terreus was tested after four days of culture in itaconic acid production medium. The parental A. terreus strain was also tested as a control. As shown in FIG. 23, deletion of LaeA significantly decreased the production of itaconic acid. However, complementation of the LaeA gene in A. terreus enabled itaconic acid production to similar levels observed in the A. terreus parent.

Figure 25:
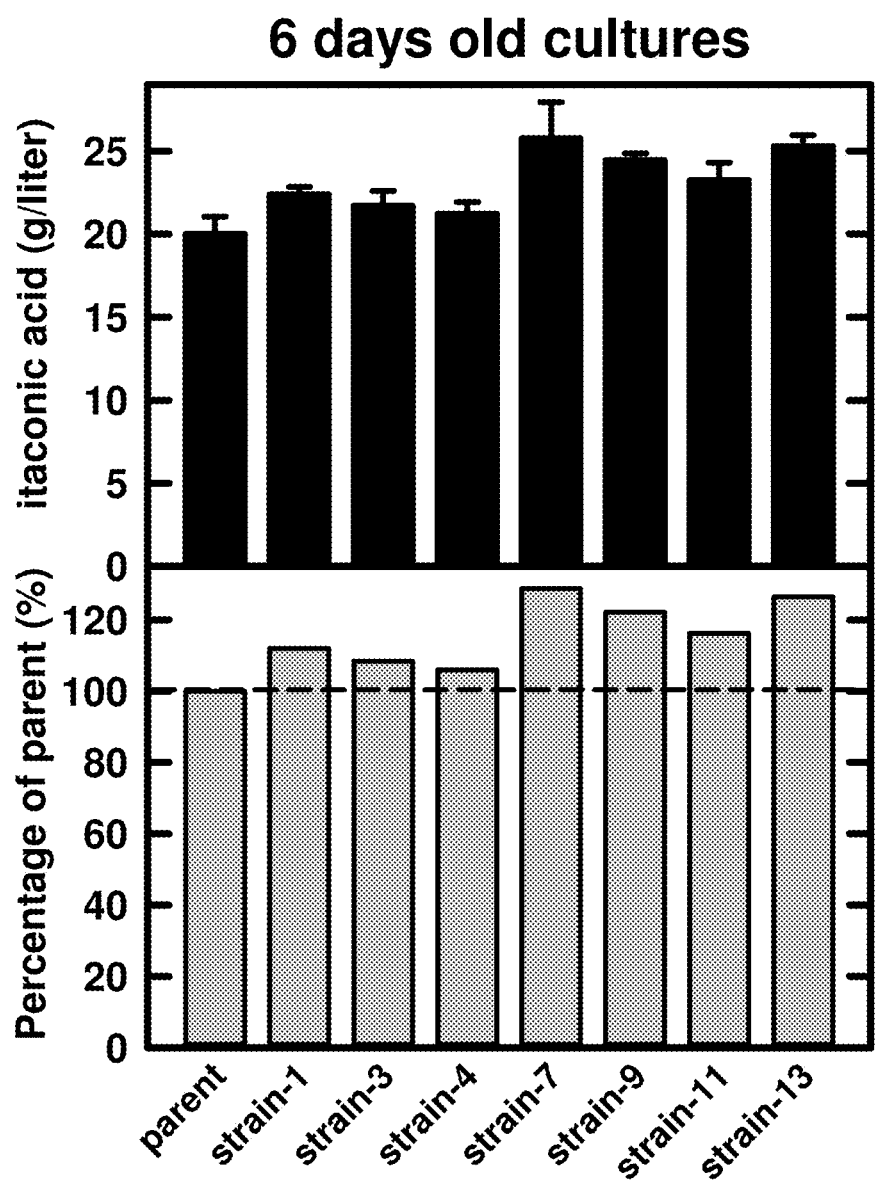
FIG. 25 is a bar graph showing itaconic acid production in selected A. terreus transgenic strains with the A. nidulans LaeA over-expression transgene after 5 days of culture in itaconic acid production medium.

An additional study was performed to test the effect of overexpression of the LaeA gene in A. terreus. FIG. 25 is a graph showing itaconic acid production in selected A. terreus transgenic strains having the A. nidulans LaeA overexpression transgene following five days of culture in itaconic acid production medium. Also shown in FIG. 25 is the percentage of itaconic acid production relative to the parent strain. The results demonstrated that overexpression of LaeA in A. terreus led to a significant increase in itaconic acid production relative to itaconic acid production in the parental strain.

In view of the many possible embodiments to which the principles of the disclosed invention may be applied, it should be recognized that the illustrated embodiments are only examples of the disclosure and should not be taken as limiting the scope of the invention. Rather, the scope of the invention is defined by the following claims. We therefore claim as our invention all that comes within the scope and spirit of these claims.

The invention claimed is:

1. An isolated *Aspergillus terreus* fungus transformed with a heterologous nucleic acid construct comprising an *Aspergillus* species LaeA (loss of aflR expression A) gene, wherein the LaeA gene encodes a LaeA protein comprising an amino acid sequence which is at least 80% identical to the amino acid sequence of SEQ ID NO: 41 or SEQ ID NO: 59 and the heterologous nucleic acid construct is inserted upstream of the coding region of the endogenous LaeA gene, and wherein expression of the *Aspergillus* species LaeA gene is increased in the transformed fungus compared to an *A. terreus* fungus that is not transformed with the heterologous nucleic acid construct.

2. The isolated *A. terreus* fungus of claim 1, wherein the heterologous nucleic acid construct further comprises a heterologous promoter, a heterologous transcription terminator, a heterologous selective marker gene, or any combination thereof.

3. The isolated *A. terreus* fungus of claim 1, wherein the *Aspergillus* species LaeA gene encodes a protein comprising the amino acid sequence of SEQ ID NO: 41.

4. The isolated *A. terreus* fungus of claim 1, wherein the *Aspergillus* species LaeA gene encodes a protein comprising the amino acid sequence of SEQ ID NO: 59.

5. The isolated *A. terreus* fungus of claim 1, wherein the heterologous nucleic acid construct comprises a promoter operably linked to the *Aspergillus* species LaeA gene, a transcription terminator and a selective marker gene.

6. The isolated *A. terreus* fungus of claim 5, wherein:
the promoter comprises the *A. nidulans* gpdA promoter;
the *Aspergillus* species LaeA gene is an *A. nidulans* LaeA gene;
the transcription terminator comprises the *A. nidulans* TrpC transcription terminator; or
the selective marker gene comprises the *A. oryzae* pyrithiamine resistance (ptrA) gene.

7. The isolated *A. terreus* fungus of claim 6, wherein the heterologous nucleic acid construct comprises the nucleotide sequence of SEQ ID NO: 109.

8. A method of making itaconic acid, comprising culturing the isolated *A. terreus* fungus of claim 1 under conditions that permit the fungus to make itaconic acid, thereby making itaconic acid.

9. The method of claim 8, wherein the fungus is cultured in itaconic acid production media.

10. The method of claim 8, wherein the heterologous nucleic acid construct further comprises a heterologous promoter, a heterologous transcription terminator, a heterologous selective maker gene, or any combination thereof.

11. The method of claim 10, wherein the *Aspergillus* species LaeA gene in the heterologous nucleic acid construct is an *A. nidulans* or an *A. niger* LaeA gene.

12. The method of claim 9, wherein the *Aspergillus* species LaeA gene encodes a protein having an amino acid sequence at least 80% identical to the amino acid sequence of SEQ ID NO: 41 or SEQ ID NO: 59.

13. The method of claim 12, wherein the *Aspergillus* species LaeA gene encodes a protein having the amino acid sequence of SEQ ID NO: 41 or the amino acid sequence of SEQ ID NO: 59.

14. The method of claim 8, wherein the heterologous nucleic acid construct comprises a promoter operably linked to the *Aspergillus* species LaeA gene, a transcription terminator and a selective marker gene.

15. The method of claim 14, wherein:
the promoter comprises the *A. nidulans* gpdA promoter;
the *Aspergillus* species LaeA gene is an *A. nidulans* or an *A. niger* LaeA gene;
the transcription terminator comprises the *A. nidulans* TrpC transcription terminator; or
the selective marker gene comprises the *A. oryzae* pyrithiamine resistance (ptrA) gene.

16. The method of claim 15, wherein the heterologous nucleic acid construct comprises the nucleotide sequence of SEQ ID NO: 109.

* * * * *

SEQUENCE LISTING

<160> NUMBER OF SEQ ID NOS: 110

<210> SEQ ID NO 1
<211> LENGTH: 3888
<212> TYPE: DNA
<213> ORGANISM: Aspergillus niger
<220> FEATURE:
<221> NAME/KEY: CDS
<222> LOCATION: (1186)..(1306)
<220> FEATURE:
<221> NAME/KEY: Intron
<222> LOCATION: (1307)..(1392)
<220> FEATURE:
<221> NAME/KEY: CDS
<222> LOCATION: (1393)..(1916)
<220> FEATURE:
<221> NAME/KEY: Intron
<222> LOCATION: (1917)..(1988)
<220> FEATURE:
<221> NAME/KEY: CDS
<222> LOCATION: (1989)..(2582)

<400> SEQUENCE: 1

```
tctgacattg aactacagtc ataacttctc tcccctcccc ggcttcccg gtcgtccttc      60 tatcgccgcc ccccccgcta tccattggtg aggccatgct atgattgggg cgtcctacct     120
tgcctgtcat taagttttg tgctttggtt gctacaagt tggactattc ctttcttttg     180
cattgttctt ttacaccgaa actaacgcat gcccgcggcc tagtgaacgc atcgtcgtta     240
ccgtcaccct ccgctccgca taaatcttct ccttaattgc tcacatccac atttcaacat     300
gccgccgcat ctacatcccc ggtcacggtc aacgtcctcc ctcttcgccg ggacgctcct     360
ggcttccttg gtcgtcgtcg gcctaccaca tgtcttcccc tgtcccgccc cgcgtcgcac     420
attcgccgat tctgagatga taatgtcggc agatgggcaa cctatccaga gaatccgcag     480
acgacgtcgg aaagacgaag aactccttgg ccaggatggc aatccgctcg gccagacgca     540
gcctgcagcc gatgaagagg tgtctacgtt cctacaattg gaagaagaag cacagagatt     600
ggccaaggca ggccacgagt gtcctgttcc caagcctcga gggattctgg gcgaattgct     660
gggttttacg agtagtggag gtatttcgac atcaacgacg acacaggcac aacaggttgg     720
agagggtcgg taaccgacaa ttggaaagca aggaggactc aatcaaggct aaaataggct     780
ttgagcatgt acagcgtgaa ggaactgtgg attatatcac gaaataagcc atgaggcagt     840
cgtgttggct tcgacggagg ttggcttcgg aaattttcgg ccgggcacca aatccgaccc     900
atggcagcaa tacccatc tttgtatcga tagtgtactt acaaaaactg tctactatat     960
gattatgcat atgcgattaa atacaactct caattgatgc acaattcgcc tcaacttcta    1020
tggtaacgaa cccacctgtt ctgcagacat gcggccgcgc ggtctgtgtg tgtccatgaa    1080
cgctaatccc aaacgggaca gctctcattg gctctccggc acgaagaggc caccccgacat    1140 ctacagctgt agaagaaagt agctggttca acaaccgcat gcaag atg gac tgg atg   1197
                                                 Met Asp Trp Met
                                                  1 cgc cta att cgc gat ttg tgt ttc aat ccc cga cac aca aaa tgg atg   1245
Arg Leu Ile Arg Asp Leu Cys Phe Asn Pro Arg His Thr Lys Trp Met
 5               10                  15                  20 gct ccg ctc ctg gtc ctg ggt gac gct ttc ctc tgc gcg ctg atc atc   1293
Ala Pro Leu Leu Val Leu Gly Asp Ala Phe Leu Cys Ala Leu Ile Ile
             25                  30                  35 tgg aaa gtg ccc t gtaaggctac agctaagctc cgttcacacc cttttgcgac      1346
Trp Lys Val Pro
         40
```

```
aagtgaagca atgccactaa cctagccccg ttgctattgt ccacag at  acc gag              1400
                                                    Tyr Thr Glu att gac tgg gcc acg tac atg caa caa ata tcg ctt tat ttg tca gga             1448
Ile Asp Trp Ala Thr Tyr Met Gln Gln Ile Ser Leu Tyr Leu Ser Gly
 45              50                  55 gaa cgc gat tat act ctc atc aga gga tca acc ggt ccc ctt gtc tac             1496
Glu Arg Asp Tyr Thr Leu Ile Arg Gly Ser Thr Gly Pro Leu Val Tyr
 60              65                  70                  75 ccg gcc gcc cat gta tac agt tat acg gcc ctc tac cat ctc acc gat             1544
Pro Ala Ala His Val Tyr Ser Tyr Thr Ala Leu Tyr His Leu Thr Asp
                 80                  85                  90 gag ggg cgc gat att ttc ttc ggt cag ata cta ttt gct gtg ctc tac             1592
Glu Gly Arg Asp Ile Phe Phe Gly Gln Ile Leu Phe Ala Val Leu Tyr
             95                 100                 105 ttg atc acg ctg gtg gtt gtg ctg tgc tgt tat aga cag tcg ggt gct             1640
Leu Ile Thr Leu Val Val Val Leu Cys Cys Tyr Arg Gln Ser Gly Ala
         110                 115                 120 ccg ccg tac ttg ctt ccg ctg ctg gtc ctt tcc aag aga ctt cac agc             1688
Pro Pro Tyr Leu Leu Pro Leu Leu Val Leu Ser Lys Arg Leu His Ser
     125                 130                 135 gtt tat gtc ctg cgt ctg ttc aat gat ggc ttg gcg gcg ctg gcg atg             1736
Val Tyr Val Leu Arg Leu Phe Asn Asp Gly Leu Ala Ala Leu Ala Met
140                 145                 150                 155 tgg gtt gcc att ctg tta ttc atg aat cgg aag tgg acg gct gcg gtc             1784
Trp Val Ala Ile Leu Leu Phe Met Asn Arg Lys Trp Thr Ala Ala Val
                160                 165                 170 gca gtg tgg tct act ggt gtt gcg att aag atg aca ctg ttg ctg ctg             1832
Ala Val Trp Ser Thr Gly Val Ala Ile Lys Met Thr Leu Leu Leu Leu
            175                 180                 185 gcc ccg gct att gct gtg gtc acg gtg ctt agt ctg tcg ctt ggt cct             1880
Ala Pro Ala Ile Ala Val Val Thr Val Leu Ser Leu Ser Leu Gly Pro
        190                 195                 200 agc gtg ggg ctg ggg gtt ctg gcg gtg ctt gtc cag gtaggttccc                  1926
Ser Val Gly Leu Gly Val Leu Ala Val Leu Val Gln
    205                 210                 215 atgaggctgt agggttggcc aaaggcaatt tgtgtgaaga cttgtctgac attgaactac           1986 ag gtt tta ctc gcg ata ccg ttc cta caa aac aac ccg gcg ggg tat              2033
   Val Leu Leu Ala Ile Pro Phe Leu Gln Asn Asn Pro Ala Gly Tyr
                   220                 225                 230 ctc tcg cgg gcg ttc gag cta acc aga cag ttc atg ttt aaa tgg aca             2081
Leu Ser Arg Ala Phe Glu Leu Thr Arg Gln Phe Met Phe Lys Trp Thr
                235                 240                 245 gtc aat tgg aga ttt gtt ggc gaa gaa gta ttc tta tct aag agc ttt             2129
Val Asn Trp Arg Phe Val Gly Glu Glu Val Phe Leu Ser Lys Ser Phe
            250                 255                 260 tcc ctg gca ttg ctg gcc gtc cac att gtg ctg cta ggc gct ttt gcc             2177
Ser Leu Ala Leu Leu Ala Val His Ile Val Leu Leu Gly Ala Phe Ala
        265                 270                 275 gtc act ggt tgg ctg aga tac tcc agg tct agc ttg cct gcg ttc att             2225
Val Thr Gly Trp Leu Arg Tyr Ser Arg Ser Ser Leu Pro Ala Phe Ile
    280                 285                 290 cgg aat ctg cta gcg ggt cga cat cgc aca gtg tcc ctc ccc aaa ccc             2273
Arg Asn Leu Leu Ala Gly Arg His Arg Thr Val Ser Leu Pro Lys Pro
295                 300                 305                 310 tac atc atg agc gtg atg ctc tcg tct ctg aca gtt ggc ttg ttg tgc             2321
Tyr Ile Met Ser Val Met Leu Ser Ser Leu Thr Val Gly Leu Leu Cys
                315                 320                 325 gca agg tcc ctt cat tac caa ttc ttc gcc tac ctc tcc tgg gcg aca             2369
Ala Arg Ser Leu His Tyr Gln Phe Phe Ala Tyr Leu Ser Trp Ala Thr
```

```
                    330                 335                 340
ccc ttc ctc ctc tgg cgc gca ggg ttt cat cca atc ttg ctg tac ctt      2417
Pro Phe Leu Leu Trp Arg Ala Gly Phe His Pro Ile Leu Leu Tyr Leu
        345                 350                 355 atc tgg gct atg caa gag tgg gct tgg aac aca ttc ccc agc acc aac      2465
Ile Trp Ala Met Gln Glu Trp Ala Trp Asn Thr Phe Pro Ser Thr Asn
360                 365                 370 ctc agt tcc atc att gtt gtc ctc tca ctt gct acc cag agt ttc ggc      2513
Leu Ser Ser Ile Ile Val Val Leu Ser Leu Ala Thr Gln Ser Phe Gly
375                 380                 385                 390 gtc ctt gcg aat agt gcc agc gcc ttt tat acc atg cgt tcg aac cct      2561
Val Leu Ala Asn Ser Ala Ser Ala Phe Tyr Thr Met Arg Ser Asn Pro
                395                 400                 405 agc ggt aaa gag cat aac caa tagaagtgac acccggccag tatcgagatc         2612
Ser Gly Lys Glu His Asn Gln
            410 gggctgtgac aggtgcatcg ataatcgcaa tcagtcttgt acccatgaga atccctgaaa    2672
aagtaagact gctctgtcag gtagtccatt gcccatgcga taggttcgga cgcctaaagg    2732
atcaatcaag atgccaatca agcatccgac tcatcggaag aaggcatctt gccgacattg    2792
gactcatcct cttcgtccga gtcgtcggcg acaacagcag cttgcttagc gaactccttt    2852
ggcctgcaga gggatcagta gtagcccag gcaccgcgat tgagggatcc actcaccaaa     2912
acggggcttt cgccacgct ttctcatcac gaacgatgtt gactatttct cccttgagct     2972
tgttgtcgcg ccctcaaga gcattggtat cgatgaccac gtaggaaccc cgcttgatcc     3032
agatggtcga tcggaagcgg gcagggagct ccaccaaaac cgactccttc gagggaagtt    3092
ccaccgagta gatgttgttt ccggtcgcct tgatagcccg ggcaattaga tggccctgag    3152
acagctcatc cggcgggaac atggtctctt ccgccgtagc gagaaccttg cgcctagggg    3212
gacccatttc taacgtatac gcaagtggtt cagcgggaag tagtgtcgat ctaaattggg    3272
atgaacacca aagagactga agaaagagtg agcaaaatgc gagaaaccgt cgactgcgga    3332
gagttttact cgaatgaaga aattcgggcg gcagaaaatc cccggtgggg agtgtgggtc    3392
ccccatccgc ttctttgcca atctcgctct ctctcttctc tcatctccgc catctacgga    3452
gtagagctcc agtactacta tctacttacg gccgtgctca tatccattgg ttgtgaggaa    3512
tgtggcatct tagttggcta cacagtgcac tacacaatcc atcgaatcaa ggtcttcctg    3572
gcgagtcagt tcccctgcac aatgtttggc ctaaggcgga catctagacc acttgacctc    3632
gtgttttttgg gcccttctgc cggcatttgg agtggatgta tcatatcgtg aaacttgcat   3692
gtgtctgatt ggcttccggc ttttatctct ttgaacttcg ctcactggtg gggttcgcgg    3752
agtgatattc cgctcaagct aattcacctc catggatatt aataatgacc ccgacacgtt    3812
ggggatcccc aaacctccgt aaaagaatcg tttatcctgg ggtctcggac agatttcgta    3872
ctacaaacct ctcacg                                                    3888

<210> SEQ ID NO 2
<211> LENGTH: 413
<212> TYPE: PRT
<213> ORGANISM: Aspergillus niger

<400> SEQUENCE: 2

Met Asp Trp Met Arg Leu Ile Arg Asp Leu Cys Phe Asn Pro Arg His
1               5                   10                  15

Thr Lys Trp Met Ala Pro Leu Leu Val Leu Gly Asp Ala Phe Leu Cys
            20                  25                  30
```

Ala Leu Ile Ile Trp Lys Val Pro Tyr Thr Glu Ile Asp Trp Ala Thr
         35                  40                  45

Tyr Met Gln Gln Ile Ser Leu Tyr Leu Ser Gly Glu Arg Asp Tyr Thr
     50                  55                  60

Leu Ile Arg Gly Ser Thr Gly Pro Leu Val Tyr Pro Ala Ala His Val
 65                  70                  75                  80

Tyr Ser Tyr Thr Ala Leu Tyr His Leu Thr Asp Glu Gly Arg Asp Ile
                 85                  90                  95

Phe Phe Gly Gln Ile Leu Phe Ala Val Leu Tyr Leu Ile Thr Leu Val
            100                 105                 110

Val Val Leu Cys Cys Tyr Arg Gln Ser Gly Ala Pro Pro Tyr Leu Leu
        115                 120                 125

Pro Leu Leu Val Leu Ser Lys Arg Leu His Ser Val Tyr Val Leu Arg
    130                 135                 140

Leu Phe Asn Asp Gly Leu Ala Ala Leu Ala Met Trp Val Ala Ile Leu
145                 150                 155                 160

Leu Phe Met Asn Arg Lys Trp Thr Ala Ala Val Ala Val Trp Ser Thr
                165                 170                 175

Gly Val Ala Ile Lys Met Thr Leu Leu Leu Ala Pro Ala Ile Ala
            180                 185                 190

Val Val Thr Val Leu Ser Leu Ser Leu Gly Pro Ser Val Gly Leu Gly
        195                 200                 205

Val Leu Ala Val Leu Val Gln Val Leu Leu Ala Ile Pro Phe Leu Gln
    210                 215                 220

Asn Asn Pro Ala Gly Tyr Leu Ser Arg Ala Phe Glu Leu Thr Arg Gln
225                 230                 235                 240

Phe Met Phe Lys Trp Thr Val Asn Trp Arg Phe Val Gly Glu Glu Val
                245                 250                 255

Phe Leu Ser Lys Ser Phe Ser Leu Ala Leu Leu Ala Val His Ile Val
            260                 265                 270

Leu Leu Gly Ala Phe Ala Val Thr Gly Trp Leu Arg Tyr Ser Arg Ser
        275                 280                 285

Ser Leu Pro Ala Phe Ile Arg Asn Leu Leu Ala Gly Arg His Arg Thr
    290                 295                 300

Val Ser Leu Pro Lys Pro Tyr Ile Met Ser Val Met Leu Ser Ser Leu
305                 310                 315                 320

Thr Val Gly Leu Leu Cys Ala Arg Ser Leu His Tyr Gln Phe Phe Ala
                325                 330                 335

Tyr Leu Ser Trp Ala Thr Pro Phe Leu Leu Trp Arg Ala Gly Phe His
            340                 345                 350

Pro Ile Leu Leu Tyr Leu Ile Trp Ala Met Gln Glu Trp Ala Trp Asn
        355                 360                 365

Thr Phe Pro Ser Thr Asn Leu Ser Ser Ile Ile Val Val Leu Ser Leu
    370                 375                 380

Ala Thr Gln Ser Phe Gly Val Leu Ala Asn Ser Ala Ser Ala Phe Tyr
385                 390                 395                 400

Thr Met Arg Ser Asn Pro Ser Gly Lys Glu His Asn Gln
                405                 410

<210> SEQ ID NO 3
<211> LENGTH: 1923
<212> TYPE: DNA
<213> ORGANISM: Aspergillus oryzae
<220> FEATURE:

```
<221> NAME/KEY: CDS
<222> LOCATION: (1)..(1242)

<400> SEQUENCE: 3 atg gag ttg aag cac ttc atc cac gaa ctc tgc cta aac ccc aga cat      48
Met Glu Leu Lys His Phe Ile His Glu Leu Cys Leu Asn Pro Arg His
1               5                   10                  15 aca aaa tgg att gca ccg ctt ctt gtc ata ggc gat gcc ttc cta tgt      96
Thr Lys Trp Ile Ala Pro Leu Leu Val Ile Gly Asp Ala Phe Leu Cys
            20                  25                  30 gct ctt atc atc tgg aag atc cca tat act gag atc gac tgg acg acg     144
Ala Leu Ile Ile Trp Lys Ile Pro Tyr Thr Glu Ile Asp Trp Thr Thr
        35                  40                  45 tac atg cag cag ata gcg ctt tac atc tct ggc gaa cgt gac tat acc     192
Tyr Met Gln Gln Ile Ala Leu Tyr Ile Ser Gly Glu Arg Asp Tyr Thr
    50                  55                  60 ctg atc aag ggg tcc act gga ccc ctt gta tac ccg gcc gcc cac gta     240
Leu Ile Lys Gly Ser Thr Gly Pro Leu Val Tyr Pro Ala Ala His Val
65                  70                  75                  80 tat agc tac atg gca ctc tat cac cta aca gat gaa ggc cga gat att     288
Tyr Ser Tyr Met Ala Leu Tyr His Leu Thr Asp Glu Gly Arg Asp Ile
                85                  90                  95 ctt ttc ggg cag ata tta ttt gct gtc ctt tac ctt gtc acg cta gca     336
Leu Phe Gly Gln Ile Leu Phe Ala Val Leu Tyr Leu Val Thr Leu Ala
            100                 105                 110 gtt gtg atg gtt tgc tac agg cag tca ggt gcc cct ccg tac ctg ttt     384
Val Val Met Val Cys Tyr Arg Gln Ser Gly Ala Pro Pro Tyr Leu Phe
        115                 120                 125 cct ctt ctt gtc ctt tcc aag cgg ctc cac agt gtc ttt gtt ttg cgc     432
Pro Leu Leu Val Leu Ser Lys Arg Leu His Ser Val Phe Val Leu Arg
    130                 135                 140 ctt ttc aat gat ggc ctc gcg gtc tgt gcc atg tgg ata gcg att ctg     480
Leu Phe Asn Asp Gly Leu Ala Val Cys Ala Met Trp Ile Ala Ile Leu
145                 150                 155                 160 ctc ttc cag aat aag aaa tgg acg gct ggt gtt acg gcc tgg act gtt     528
Leu Phe Gln Asn Lys Lys Trp Thr Ala Gly Val Thr Ala Trp Thr Val
                165                 170                 175 ggg gtt ggc att aag atg acg tta ctg ctc ctt gcg cca gcc att gcg     576
Gly Val Gly Ile Lys Met Thr Leu Leu Leu Leu Ala Pro Ala Ile Ala
            180                 185                 190 gtg gta act gtg ctc agc ctt tcc ctc gtg cct agt att cga ctt gga     624
Val Val Thr Val Leu Ser Leu Ser Leu Val Pro Ser Ile Arg Leu Gly
        195                 200                 205 att cta gca ttg ctc att cag gtt cta cta gcg att ccc ttc cta cag     672
Ile Leu Ala Leu Leu Ile Gln Val Leu Leu Ala Ile Pro Phe Leu Gln
    210                 215                 220 ggt aac ccc ata gga tac gtc gcg cgg gcc ttt gag ttg act aga cag     720
Gly Asn Pro Ile Gly Tyr Val Ala Arg Ala Phe Glu Leu Thr Arg Gln
225                 230                 235                 240 ttt atg ttc aaa tgg act gtc aat tgg agg ttt gtg ggt gaa gac ttg     768
Phe Met Phe Lys Trp Thr Val Asn Trp Arg Phe Val Gly Glu Asp Leu
                245                 250                 255 ttc cta tcc aaa cag ttt tct cta gcc tta cta ggt tgc att att ttt     816
Phe Leu Ser Lys Gln Phe Ser Leu Ala Leu Leu Gly Leu His Ile Phe
            260                 265                 270 ctg ctg gga tta ttt gtt acc aca ggc tgg tta cgg ccg tca gga tct     864
Leu Leu Gly Leu Phe Val Thr Thr Gly Trp Leu Arg Pro Ser Gly Ser
        275                 280                 285 aac gtc cct gac ttc ctc cgg agc cta ctc caa gga cgc caa cgc acc     912
Asn Val Pro Asp Phe Leu Arg Ser Leu Leu Gln Gly Arg Gln Arg Thr
```

```
          290                 295                 300
gtg gtg ctt tct aag tct ttc ata atg acc gtg atg ttg aca tcg ctg         960
Val Val Leu Ser Lys Ser Phe Ile Met Thr Val Met Leu Thr Ser Leu
305                 310                 315                 320 gcg atc ggg ttg ttg tgc gca agg tcc ctt cat tac caa ttc ttt gcc        1008
Ala Ile Gly Leu Leu Cys Ala Arg Ser Leu His Tyr Gln Phe Phe Ala
                325                 330                 335 tat ctc tcc tgg gct acg cct tgc ctt ctc tgg cgg gct cgg ctc cat        1056
Tyr Leu Ser Trp Ala Thr Pro Cys Leu Leu Trp Arg Ala Arg Leu His
            340                 345                 350 ccg atc ctt ata tat gcg atc tgg gca cta cag gag tgg gct tgg aat        1104
Pro Ile Leu Ile Tyr Ala Ile Trp Ala Leu Gln Glu Trp Ala Trp Asn
        355                 360                 365 gtc tac cca agc acc aat gcc agt tct tcg gtc gtt gtc ttc tca ctt        1152
Val Tyr Pro Ser Thr Asn Ala Ser Ser Ser Val Val Val Phe Ser Leu
    370                 375                 380 gct gtt cag gtt ttc ggt gtc ctc ctc aat agc aga aac gca ctg agc        1200
Ala Val Gln Val Phe Gly Val Leu Leu Asn Ser Arg Asn Ala Leu Ser
385                 390                 395                 400 gat gcg cct ccg aga cgc aaa gga aag gag cac atc cag tga                1242
Asp Ala Pro Pro Arg Arg Lys Gly Lys Glu His Ile Gln
                405                 410 taatgagcca ctcataggct ccaaatttat cgttcccttc attgttttca tcacttggtc      1302
ctcgtggttc acattaaatg tagacgcacg tgcattggat acagcgatca ccatacgtcg      1362
attagttcaa gcatcagagt cgtccgaggg aggcatcttg cccacatttg actcttcctc      1422
atcctctgaa tccgaagcaa caaccgtaga ttgcttgacg aattccttcg gcctaatgga      1482
gccttgcgcc aaactttctc atcccgaacg atattaatga tttccccagc aagcttattg      1542
tcccggtcct caagagcgtt ggtatcgacc acgacgtagg agttgcgttt catccagatt      1602
cttgaacgga agcgggaagg tagttcgacc aaaaccgtgt cttttgatgg cagttcgacc      1662
acatataaat tgttccccgt tgccttgatg actcgcgcga tttgctgtcc ctgttgaagc      1722
tcatctggag gggtcatagt ttcttccgct gttgcgagta ccttgcgccg tggtggtgcc      1782
atgatggtat attgcaattg ggatctcttt tcttggaacc taaattgtcg caatctctta      1842
gatgctgtct tgtatgaagc aattgctgat cagataagct gtggtgaggg gtagtcttat      1902
tgtgtttgat agcggagggg t                                                1923

<210> SEQ ID NO 4
<211> LENGTH: 413
<212> TYPE: PRT
<213> ORGANISM: Aspergillus oryzae

<400> SEQUENCE: 4

Met Glu Leu Lys His Phe Ile His Glu Leu Cys Leu Asn Pro Arg His
1               5                   10                  15

Thr Lys Trp Ile Ala Pro Leu Leu Val Ile Gly Asp Ala Phe Leu Cys
            20                  25                  30

Ala Leu Ile Ile Trp Lys Ile Pro Tyr Thr Glu Ile Asp Trp Thr Thr
        35                  40                  45

Tyr Met Gln Gln Ile Ala Leu Tyr Ile Ser Gly Glu Arg Asp Tyr Thr
    50                  55                  60

Leu Ile Lys Gly Ser Thr Gly Pro Leu Val Tyr Pro Ala Ala His Val
65                  70                  75                  80

Tyr Ser Tyr Met Ala Leu Tyr His Leu Thr Asp Glu Gly Arg Asp Ile
                85                  90                  95
```

Leu Phe Gly Gln Ile Leu Phe Ala Val Leu Tyr Leu Val Thr Leu Ala
            100                 105                 110

Val Val Met Val Cys Tyr Arg Gln Ser Gly Ala Pro Pro Tyr Leu Phe
        115                 120                 125

Pro Leu Leu Val Leu Ser Lys Arg Leu His Ser Val Phe Val Leu Arg
    130                 135                 140

Leu Phe Asn Asp Gly Leu Ala Val Cys Ala Met Trp Ile Ala Ile Leu
145                 150                 155                 160

Leu Phe Gln Asn Lys Lys Trp Thr Ala Gly Val Thr Ala Trp Thr Val
                165                 170                 175

Gly Val Gly Ile Lys Met Thr Leu Leu Leu Ala Pro Ala Ile Ala
                180                 185                 190

Val Val Thr Val Leu Ser Leu Ser Leu Val Pro Ser Ile Arg Leu Gly
                195                 200                 205

Ile Leu Ala Leu Leu Ile Gln Val Leu Ala Ile Pro Phe Leu Gln
    210                 215                 220

Gly Asn Pro Ile Gly Tyr Val Ala Arg Ala Phe Glu Leu Thr Arg Gln
225                 230                 235                 240

Phe Met Phe Lys Trp Thr Val Asn Trp Arg Phe Val Gly Glu Asp Leu
                245                 250                 255

Phe Leu Ser Lys Gln Phe Ser Leu Ala Leu Leu Gly Leu His Ile Phe
                260                 265                 270

Leu Leu Gly Leu Phe Val Thr Thr Gly Trp Leu Arg Pro Ser Gly Ser
                275                 280                 285

Asn Val Pro Asp Phe Leu Arg Ser Leu Leu Gln Gly Arg Gln Arg Thr
                290                 295                 300

Val Val Leu Ser Lys Ser Phe Ile Met Thr Val Met Leu Thr Ser Leu
305                 310                 315                 320

Ala Ile Gly Leu Leu Cys Ala Arg Ser Leu His Tyr Gln Phe Phe Ala
                325                 330                 335

Tyr Leu Ser Trp Ala Thr Pro Cys Leu Leu Trp Arg Ala Arg Leu His
                340                 345                 350

Pro Ile Leu Ile Tyr Ala Ile Trp Ala Leu Gln Glu Trp Ala Trp Asn
                355                 360                 365

Val Tyr Pro Ser Thr Asn Ala Ser Ser Val Val Phe Ser Leu
    370                 375                 380

Ala Val Gln Val Phe Gly Val Leu Leu Asn Ser Arg Asn Ala Leu Ser
385                 390                 395                 400

Asp Ala Pro Pro Arg Arg Lys Gly Lys Glu His Ile Gln
                405                 410

<210> SEQ ID NO 5
<211> LENGTH: 22
<212> TYPE: DNA
<213> ORGANISM: Artificial Sequence
<220> FEATURE:
<223> OTHER INFORMATION: Alg3-ForScr primer

<400> SEQUENCE: 5
cggtttccct tcagtttcca gt                                           22

<210> SEQ ID NO 6
<211> LENGTH: 49
<212> TYPE: DNA
<213> ORGANISM: Artificial Sequence
<220> FEATURE:

<223> OTHER INFORMATION: Alg3-1 primer

<400> SEQUENCE: 6
gtaacgccag ggttttccca gtcacgacgt cataacttct ctcccctcc                49

<210> SEQ ID NO 7
<211> LENGTH: 49
<212> TYPE: DNA
<213> ORGANISM: Artificial Sequence
<220> FEATURE:
<223> OTHER INFORMATION: Alg3-2 primer

<400> SEQUENCE: 7
atccacttaa cgttactgaa atctccaact tcatggacac acacagacc                49

<210> SEQ ID NO 8
<211> LENGTH: 49
<212> TYPE: DNA
<213> ORGANISM: Artificial Sequence
<220> FEATURE:
<223> OTHER INFORMATION: Hph-F primer

<400> SEQUENCE: 8
ggtctgtgtg tgtccatgaa gttggagatt tcagtaacgt taagtggat                49

<210> SEQ ID NO 9
<211> LENGTH: 49
<212> TYPE: DNA
<213> ORGANISM: Artificial Sequence
<220> FEATURE:
<223> OTHER INFORMATION: Hph-R primer

<400> SEQUENCE: 9
gctactactg atccctctgc gtcggagaca gaagatgata ttgaaggag                49

<210> SEQ ID NO 10
<211> LENGTH: 49
<212> TYPE: DNA
<213> ORGANISM: Artificial Sequence
<220> FEATURE:
<223> OTHER INFORMATION: Alg3-3 primer

<400> SEQUENCE: 10
ctccttcaat atcatcttct gtctccgacg cagagggatc agtagtagc                49

<210> SEQ ID NO 11
<211> LENGTH: 49
<212> TYPE: DNA
<213> ORGANISM: Artificial Sequence
<220> FEATURE:
<223> OTHER INFORMATION: Alg3-4 primer

<400> SEQUENCE: 11
gcggataaca atttcacaca ggaaacagcc gtgagaggtt tgtagtacg                49

<210> SEQ ID NO 12
<211> LENGTH: 21
<212> TYPE: DNA
<213> ORGANISM: Artificial Sequence
<220> FEATURE:
<223> OTHER INFORMATION: Alg3-RevScr primer

<400> SEQUENCE: 12
aagctgagag cgacatcttc a                                              21

```
<210> SEQ ID NO 13
<211> LENGTH: 25
<212> TYPE: DNA
<213> ORGANISM: Artificial Sequence
<220> FEATURE:
<223> OTHER INFORMATION: hyg-RevScr primer

<400> SEQUENCE: 13
gtacttctac acagccatcg gtcca                                              25

<210> SEQ ID NO 14
<211> LENGTH: 25
<212> TYPE: DNA
<213> ORGANISM: Artificial Sequence
<220> FEATURE:
<223> OTHER INFORMATION: hyg-ForScr primer

<400> SEQUENCE: 14
gtacttctac acagccatcg gtcca                                              25

<210> SEQ ID NO 15
<211> LENGTH: 24
<212> TYPE: DNA
<213> ORGANISM: Artificial Sequence
<220> FEATURE:
<223> OTHER INFORMATION: pryGScr primer

<400> SEQUENCE: 15
tctgctgtct tgcatgaggt cctt                                               24

<210> SEQ ID NO 16
<211> LENGTH: 24
<212> TYPE: DNA
<213> ORGANISM: Artificial Sequence
<220> FEATURE:
<223> OTHER INFORMATION: primer

<400> SEQUENCE: 16
agcgtaggac aaggtcgtct ctgt                                               24

<210> SEQ ID NO 17
<211> LENGTH: 58
<212> TYPE: DNA
<213> ORGANISM: Artificial Sequence
<220> FEATURE:
<223> OTHER INFORMATION: 5-pyrG5F primer

<400> SEQUENCE: 17
gtaacgccag ggttttccca gtcacgacgt ttaaacatgc atcattctcc cgctttgt          58

<210> SEQ ID NO 18
<211> LENGTH: 43
<212> TYPE: DNA
<213> ORGANISM: Artificial Sequence
<220> FEATURE:
<223> OTHER INFORMATION: 5-pyrG3R primer

<400> SEQUENCE: 18
agaaagagtc accggtcacg acatcgccaa tcacctcaat cac                          43

<210> SEQ ID NO 19
<211> LENGTH: 43
<212> TYPE: DNA
<213> ORGANISM: Artificial Sequence
<220> FEATURE:
<223> OTHER INFORMATION: ble5F primer
```

<400> SEQUENCE: 19
gtgattgagg tgattggcga tgtcgtgacc ggtgactctt tct                          43

<210> SEQ ID NO 20
<211> LENGTH: 42
<212> TYPE: DNA
<213> ORGANISM: Artificial Sequence
<220> FEATURE:
<223> OTHER INFORMATION: Ble3R primer

<400> SEQUENCE: 20
tccaaccttg tagcaaccaa agcttcgagc gtcccaaaac ct                           42

<210> SEQ ID NO 21
<211> LENGTH: 42
<212> TYPE: DNA
<213> ORGANISM: Artificial Sequence
<220> FEATURE:
<223> OTHER INFORMATION: Alg3-5F1 primer

<400> SEQUENCE: 21
aggttttggg acgctcgaag ctttggttgc tacaaggttg ga                           42

<210> SEQ ID NO 22
<211> LENGTH: 29
<212> TYPE: DNA
<213> ORGANISM: Artificial Sequence
<220> FEATURE:
<223> OTHER INFORMATION: Alg3-3R1 primer

<400> SEQUENCE: 22
tcaagtagag cacagcaaat agtatctga                                          29

<210> SEQ ID NO 23
<211> LENGTH: 29
<212> TYPE: DNA
<213> ORGANISM: Artificial Sequence
<220> FEATURE:
<223> OTHER INFORMATION: Alg3-5F2 primer

<400> SEQUENCE: 23
tcagatacta tttgctgtgc tctacttga                                          29

<210> SEQ ID NO 24
<211> LENGTH: 42
<212> TYPE: DNA
<213> ORGANISM: Artificial Sequence
<220> FEATURE:
<223> OTHER INFORMATION: Alg3-3R2 primer

<400> SEQUENCE: 24
ttgatccttg tgccacacca tcctacgtgg tcatcgatac ca                           42

<210> SEQ ID NO 25
<211> LENGTH: 42
<212> TYPE: DNA
<213> ORGANISM: Artificial Sequence
<220> FEATURE:
<223> OTHER INFORMATION: 3-pyrG5F primer

<400> SEQUENCE: 25
tggtatcgat gaccacgtag gatggtgtgg cacaaggatc aa                           42

<210> SEQ ID NO 26
<211> LENGTH: 60

```
<212> TYPE: DNA
<213> ORGANISM: Artificial Sequence
<220> FEATURE:
<223> OTHER INFORMATION: 3=pyrG3R primer

<400> SEQUENCE: 26
gcggataaca atttcacaca ggaaacagcg tttaaactgt gccagtcaat tgtccgaagt    60

<210> SEQ ID NO 27
<211> LENGTH: 21
<212> TYPE: DNA
<213> ORGANISM: Artificial Sequence
<220> FEATURE:
<223> OTHER INFORMATION: Alg3seq-1 primer

<400> SEQUENCE: 27
tacagacgcg tgtacgcatg t                                              21

<210> SEQ ID NO 28
<211> LENGTH: 24
<212> TYPE: DNA
<213> ORGANISM: Artificial Sequence
<220> FEATURE:
<223> OTHER INFORMATION: Alg3seq-2 primer

<400> SEQUENCE: 28
tgctattgtc cacagatacc gaga                                           24

<210> SEQ ID NO 29
<211> LENGTH: 22
<212> TYPE: DNA
<213> ORGANISM: Artificial Sequence
<220> FEATURE:
<223> OTHER INFORMATION: Alg3seq-3 primer

<400> SEQUENCE: 29
gagctaacca gacagttcat gt                                             22

<210> SEQ ID NO 30
<211> LENGTH: 21
<212> TYPE: DNA
<213> ORGANISM: Artificial Sequence
<220> FEATURE:
<223> OTHER INFORMATION: Alg3seq-4 primer

<400> SEQUENCE: 30
tcgtcgtacc gcattgatcc t                                              21

<210> SEQ ID NO 31
<211> LENGTH: 413
<212> TYPE: PRT
<213> ORGANISM: Aspergillus nidulans

<400> SEQUENCE: 31

Met Ala Leu Thr Asp Leu Val Ser Gly Leu Cys Ser Asn Pro Lys His
1               5                   10                  15

Thr Lys Trp Ile Ala Pro Ile Leu Asn Ile Ala Asp Gly Leu Leu Cys
            20                  25                  30

Ala Phe Ile Ile Trp Lys Val Pro Tyr Thr Glu Ile Asp Trp Thr Thr
        35                  40                  45

Tyr Met Gln Gln Val Lys Leu Tyr Leu Ser Gly Glu Arg Asp Tyr Thr
    50                  55                  60

Leu Ile Lys Gly Ser Thr Gly Pro Leu Val Tyr Pro Ala Ala His Val
65                  70                  75                  80
```

Tyr Ser Tyr Ser Leu Phe His His Leu Thr Asp Glu Gly Arg Asp Ile
            85                  90                  95

Val Phe Gly Gln Ile Ile Phe Ala Phe Leu Tyr Leu Ile Cys Leu Thr
            100                 105                 110

Val Val Met Ala Cys Tyr Arg Arg Val Gly Ala Pro Pro Tyr Leu Phe
            115                 120                 125

Pro Leu Val Leu Ser Lys Arg Leu His Ser Val Tyr Met Leu Arg
        130                 135                 140

Leu Phe Asn Asp Gly Leu Ala Ala Leu Ala Met Trp Gly Ser Ile Trp
145                 150                 155                 160

Leu Phe Ile Asn Arg Lys Trp Thr Pro Ala Val Val Leu Trp Ser Leu
            165                 170                 175

Gly Leu Gly Val Lys Met Thr Leu Ile Leu Leu Val Pro Ala Val Met
            180                 185                 190

Val Val Leu Ala Leu Ser Leu Asp Ile Gly Arg Cys Ile Arg Leu Ala
            195                 200                 205

Gly Leu Ala Leu Gly Ile Gln Ile Leu Leu Ala Ile Pro Phe Leu Lys
            210                 215                 220

Thr Asn Pro Ser Gly Tyr Phe Glu Arg Ala Phe Glu Phe Gly Arg Gln
225                 230                 235                 240

Phe Met Phe Lys Trp Thr Val Asn Trp Arg Phe Val Gly Glu Asp Ile
            245                 250                 255

Phe Leu Ser Lys Gly Phe Trp Ala Gly Leu Ile Val Leu His Leu Leu
            260                 265                 270

Ile Leu Val Val Leu Gly Phe Thr Cys Phe Leu Asn Pro Ser Gly Thr
            275                 280                 285

Ser Leu Pro Asp Phe Ala Gly Arg Phe Leu Thr Gly Gln His Arg Gly
            290                 295                 300

Ile Ala Leu His Pro Ser Phe Ile Met Ser Ala Leu Leu Thr Ser Leu
305                 310                 315                 320

Ser Val Gly Leu Leu Cys Ala Arg Ser Leu His Tyr Gln Phe Phe Ala
            325                 330                 335

Tyr Leu Ser Trp Ala Thr Pro Phe Leu Leu Trp Gln Ala Gly Tyr His
            340                 345                 350

Pro Ile Leu Val Tyr Ala Leu Trp Leu Val Gln Glu Trp Ala Trp Asn
            355                 360                 365

Val Tyr Pro Ser Thr Asn Leu Ser Ser Ala Ala Val Val Leu Leu Leu
            370                 375                 380

Gly Ala Gln Val Leu Gly Val Leu Val Asn Arg Asp Arg Ala Phe Pro
385                 390                 395                 400

Ser Ser Pro Pro Thr Pro Lys Ala Lys Gln His Val Gln
            405                 410

<210> SEQ ID NO 32
<211> LENGTH: 434
<212> TYPE: PRT
<213> ORGANISM: Fusarium oxysporum

<400> SEQUENCE: 32

Met Pro Glu Ser Ala Ser Gly Thr Leu Ser Gln Gly Val Arg Phe Leu
1               5                   10                  15

Arg Asn Val Leu Asn Gly Arg His Ala Leu Ser Lys Leu Ile Pro Ile
            20                  25                  30

Ala Leu Trp Leu Val Asp Ala Leu Gly Cys Gly Leu Ile Ile Trp Lys

```
            35                  40                  45
Ile Pro Tyr Thr Glu Ile Asp Trp Val Ala Tyr Met Gln Gln Ile Ser
 50                  55                  60

Gln Phe Val Ser Gly Glu Arg Asp Tyr Thr Lys Met Glu Gly Asp Thr
 65                  70                  75                  80

Gly Pro Leu Val Tyr Pro Ala Ala His Val Tyr Thr Tyr Thr Gly Leu
                     85                  90                  95

Tyr Tyr Ile Thr Asp Lys Gly Thr Asn Ile Leu Leu Ala Gln Gln Ile
                    100                 105                 110

Phe Ala Val Leu Tyr Met Ala Thr Leu Ala Val Val Met Leu Cys Tyr
                115                 120                 125

Trp Lys Ala Lys Val Pro Pro Tyr Met Phe Ile Phe Leu Ile Ala Ser
            130                 135                 140

Lys Arg Leu His Ser Leu Phe Val Leu Arg Cys Phe Asn Asp Cys Phe
145                 150                 155                 160

Ala Val Phe Phe Leu Trp Leu Thr Ile Phe Leu Phe Gln Arg Arg Gln
                    165                 170                 175

Trp Thr Val Gly Ser Leu Val Tyr Ser Trp Gly Leu Gly Ile Lys Met
                180                 185                 190

Ser Leu Leu Leu Val Leu Pro Ala Ile Gly Val Ile Leu Phe Leu Gly
            195                 200                 205

Arg Gly Leu Trp Pro Ser Leu Arg Leu Ala Trp Leu Met Ala Gln Ile
210                 215                 220

Gln Phe Ala Ile Gly Leu Pro Phe Ile Thr Lys Asn Pro Arg Gly Tyr
225                 230                 235                 240

Ala Ala Arg Ala Phe Glu Leu Ser Arg Gln Phe Gln Phe Lys Trp Thr
                    245                 250                 255

Val Asn Trp Arg Met Leu Gly Glu Val Phe Leu Ser Lys Tyr Phe
                260                 265                 270

Ala Leu Ser Leu Leu Ala Cys His Ile Leu Val Leu Leu Ile Phe Ile
            275                 280                 285

Ser Lys Arg Trp Ile Gln Pro Thr Gly Arg Ser Leu Tyr Asp Leu Ile
290                 295                 300

Pro Ser Phe Leu Arg Leu Lys Ser Pro Phe Thr Met Gln Glu Gln Leu
305                 310                 315                 320

Arg Ile Ser His Tyr Val Thr Pro Glu Tyr Ala Met Thr Thr Met Leu
                325                 330                 335

Thr Ala Asn Leu Ile Gly Leu Leu Phe Ala Arg Ser Leu His Tyr Gln
                340                 345                 350

Phe Tyr Ala Tyr Leu Ala Trp Ala Thr Pro Tyr Leu Leu Trp Arg Ala
            355                 360                 365

Thr Glu Asp Pro Val Ile Val Ala Ile Ile Trp Ala Ala Gln Glu Trp
            370                 375                 380

Ala Trp Asn Val Tyr Pro Ser Thr Asp Leu Ser Ser Thr Ile Ala Val
385                 390                 395                 400

Asn Thr Met Leu Ala Thr Val Leu Val Tyr Leu Gly Thr Ala Arg
                405                 410                 415

Arg Ala Val Pro Ala Pro Ala Ala Gln Val Gly Asn Val Asp Asp Lys
                420                 425                 430

Asn Lys

<210> SEQ ID NO 33
<211> LENGTH: 502
```

```
<212> TYPE: PRT
<213> ORGANISM: Neurospora crassa

<400> SEQUENCE: 33
```

Met Ala Ala Pro Ser Ser Arg Pro Glu Ser Asn Pro Pro Leu Tyr Lys
1               5                   10                  15

Gln Ala Leu Asp Phe Ala Leu Asp Val Ala Asn Gly Arg His Ala Leu
            20                  25                  30

Ser Lys Leu Ile Pro Pro Ala Leu Phe Leu Val Asp Ala Leu Leu Cys
        35                  40                  45

Gly Leu Ile Ile Trp Lys Val Pro Tyr Thr Glu Ile Asp Trp Ala Ala
50                  55                  60

Tyr Met Glu Gln Val Ser Gln Ile Leu Ser Gly Glu Arg Asp Tyr Thr
65                  70                  75                  80

Lys Val Arg Gly Gly Thr Gly Pro Leu Val Tyr Pro Ala Ala His Val
                85                  90                  95

Tyr Ile Tyr Thr Gly Leu Tyr His Leu Thr Asp Glu Gly Arg Asn Ile
            100                 105                 110

Leu Leu Ala Gln Gln Leu Phe Ala Gly Leu Tyr Met Val Thr Leu Ala
        115                 120                 125

Val Val Met Gly Cys Tyr Trp Gln Ala Lys Ala Pro Pro Tyr Leu Phe
130                 135                 140

Pro Leu Leu Thr Leu Ser Lys Arg Leu His Ser Ile Phe Val Leu Arg
145                 150                 155                 160

Cys Phe Asn Asp Cys Phe Ala Val Leu Phe Leu Trp Leu Ala Ile Phe
                165                 170                 175

Phe Phe Gln Arg Arg Asn Trp Gln Ala Gly Ala Leu Leu Tyr Thr Leu
            180                 185                 190

Gly Leu Gly Val Lys Met Thr Leu Leu Ser Leu Pro Ala Val Gly Gly
        195                 200                 205

Ile Val Leu Phe Leu Gly Ser Gly Ser Phe Val Thr Thr Leu Gln Leu
210                 215                 220

Val Ala Thr Met Gly Leu Val Gln Ile Ala Ile Gly Leu Pro Phe Ile
225                 230                 235                 240

Thr Lys Asn Pro Arg Gly Tyr Ala Ala Arg Ala Phe Glu Leu Ser Arg
                245                 250                 255

Gln Phe Gln Phe Lys Trp Thr Val Asn Trp Arg Met Leu Gly Glu Glu
            260                 265                 270

Val Phe Leu Ser Lys Tyr Phe Ala Leu Ser Leu Leu Ala Cys His Ile
        275                 280                 285

Leu Val Leu Leu Ile Leu Ile Gly Val Pro Phe Leu Ala His Tyr Pro
290                 295                 300

Thr Glu Tyr Leu Ser Arg Ala Phe Glu Leu Ser Arg Gln Phe Phe Phe
305                 310                 315                 320

Lys Trp Thr Val Asn Trp Arg Phe Val Gly Glu Glu Ile Phe Leu Ser
                325                 330                 335

Lys Gly Phe Ala Leu Thr Leu Ala Leu His Val Leu Val Leu Gly
            340                 345                 350

Ile Phe Ile Thr Thr Arg Trp Ile Lys Pro Ala Arg Lys Ser Leu Val
        355                 360                 365

Gln Leu Ile Ser Pro Val Leu Leu Ala Gly Lys Pro Pro Leu Thr Val
370                 375                 380

Pro Glu His Arg Ala Ala Ala Arg Asp Val Thr Pro Arg Tyr Ile Met
385                 390                 395                 400

```
Thr Thr Ile Leu Ser Ala Asn Ala Val Gly Leu Leu Phe Ala Arg Ser
                405                 410                 415

Leu His Tyr Gln Phe Tyr Ala Tyr Val Ala Trp Ser Thr Pro Phe Leu
                420                 425                 430

Leu Trp Arg Ala Gly Leu His Pro Val Leu Val Tyr Leu Leu Trp Ala
                435                 440                 445

Val His Glu Trp Ala Trp Asn Val Phe Pro Ser Thr Pro Ala Ser Ser
450                 455                 460

Ala Val Val Gly Val Leu Gly Val Thr Val Ala Gly Val Trp Phe
465                 470                 475                 480

Gly Ala Arg Glu Glu Trp Glu Pro Gly Met Lys Ser Ser Lys Lys
                485                 490                 495

Glu Glu Ala Ala Met Arg
                500

<210> SEQ ID NO 34
<211> LENGTH: 434
<212> TYPE: PRT
<213> ORGANISM: Saccharomyces cerevisiae

<400> SEQUENCE: 34

Met Ala Gly Gly Lys Lys Ser Ser Thr Ala Pro Ser Arg Phe Gln
1               5                   10                  15

Lys Thr Leu Ser Ser Ile Trp Gln Asp Lys His Thr Val Leu Phe Lys
                20                  25                  30

Pro Glu Tyr Thr Leu Leu Val Thr Ala Val Leu Trp Phe Leu Glu Ile
                35                  40                  45

Ala Ile Asn Ile Trp Val Ile Gln Lys Val Ser Tyr Thr Glu Ile Asp
50                  55                  60

Trp Lys Ala Tyr Met Asp Glu Val Glu Gly Val Ile Asn Gly Thr Tyr
65                  70                  75                  80

Asp Tyr Thr Gln Leu Lys Gly Asp Thr Gly Pro Leu Val Tyr Pro Ala
                85                  90                  95

Gly Phe Val Tyr Ile Phe Thr Gly Leu Tyr Tyr Leu Thr Asp His Gly
                100                 105                 110

His Asn Ile Arg Leu Gly Gln Tyr Val Phe Ala Val Ser Tyr Leu Ile
                115                 120                 125

Asn Leu Leu Leu Val Met Arg Ile Tyr His Arg Thr Lys Lys Val Pro
                130                 135                 140

Pro Tyr Val Phe Phe Phe Ile Cys Cys Ala Ser Tyr Arg Ile His Ser
145                 150                 155                 160

Ile Phe Ile Leu Arg Leu Phe Asn Asp Pro Val Ala Met Met Leu Cys
                165                 170                 175

Phe Gly Ala Ile Asn Leu Phe Leu Asp Gly Arg Trp Thr Leu Gly Cys
                180                 185                 190

Ala Leu Tyr Ser Leu Ala Val Ser Val Lys Met Asn Val Leu Leu Phe
                195                 200                 205

Ala Pro Gly Leu Leu Phe Leu Leu Cys Glu Phe Gly Leu Trp Lys
                210                 215                 220

Thr Leu Pro Arg Leu Ala Leu Cys Ala Val Ile Gln Leu Leu Val Gly
225                 230                 235                 240

Leu Pro Phe Leu Ile Thr Tyr Pro Val Ser Tyr Ile Ala Asn Ala Phe
                245                 250                 255

Asp Leu Gly Arg Val Phe Ile His Phe Trp Ser Val Asn Phe Lys Phe
```

```
            260                 265                 270
Val Pro Glu Arg Val Phe Val Ser Lys Glu Phe Ala Val Cys Leu Leu
        275                 280                 285

Ile Ala His Leu Phe Leu Leu Val Ala Phe Ala Leu Lys Arg Trp Lys
        290                 295                 300

Arg Ser Gly Ser Ser Ile Trp Thr Ile Leu Lys Asp Pro Ser Glu Arg
305                 310                 315                 320

Lys Glu Thr Ala His Lys Val Asn Ala Asp Gln Met Val Leu Ile Leu
                325                 330                 335

Phe Thr Ser Asn Phe Ile Gly Met Cys Phe Ser Arg Ser Leu His Tyr
                340                 345                 350

Gln Phe Tyr Val Trp Tyr Phe His Thr Leu Pro Tyr Leu Leu Trp Ser
        355                 360                 365

Gly Gly Val Lys Lys Leu Ala Arg Leu Leu Arg Val Leu Ile Leu Gly
        370                 375                 380

Leu Ile Glu Leu Ser Trp Asn Thr Tyr Pro Ser Thr Asn Tyr Ser Ser
385                 390                 395                 400

Leu Ser Leu His Val Cys His Leu Ile Ile Leu Leu Cys Leu Trp Leu
                405                 410                 415

Asn Pro Asn Pro Ala Ser Pro Ser His Arg Ser Glu Asn Lys Ala Lys
                420                 425                 430

Ser His
```

<210> SEQ ID NO 35
<211> LENGTH: 437
<212> TYPE: PRT
<213> ORGANISM: Arabidopsis thaliana

<400> SEQUENCE: 35

```
Met Ala Gly Ala Ser Ser Pro Ala Ser Leu Arg Ala Ser Arg Ser Arg
1               5                   10                  15

Arg Leu Gly Lys Glu Thr Asn Arg Ser Asp Leu Phe Lys Lys Pro Ala
                20                  25                  30

Val Pro Phe Ala Phe Ala Leu Ile Leu Ala Asp Ala Ile Leu Val Ala
            35                  40                  45

Leu Ile Ile Ala Tyr Val Pro Tyr Thr Lys Ile Asp Trp Asp Ala Tyr
    50                  55                  60

Met Ser Gln Val Ser Gly Phe Leu Gly Gly Glu Arg Asp Tyr Gly Asn
65                  70                  75                  80

Leu Lys Gly Asp Thr Gly Pro Leu Val Tyr Pro Ala Gly Phe Leu Tyr
                85                  90                  95

Val Tyr Ser Ala Val Gln Asn Leu Thr Gly Gly Glu Val Tyr Pro Ala
            100                 105                 110

Gln Ile Leu Phe Gly Val Leu Tyr Ile Val Asn Leu Gly Ile Val Leu
        115                 120                 125

Ile Ile Tyr Val Lys Thr Asp Val Pro Trp Trp Ala Leu Ser Leu Leu
    130                 135                 140

Cys Leu Ser Lys Arg Ile His Ser Ile Phe Val Leu Arg Leu Phe Asn
145                 150                 155                 160

Asp Cys Phe Ala Met Thr Leu Leu His Ala Ser Met Ala Leu Phe Leu
                165                 170                 175

Tyr Arg Lys Trp His Leu Gly Met Leu Val Phe Ser Gly Ala Val Ser
                180                 185                 190

Val Lys Met Asn Val Leu Leu Tyr Ala Pro Thr Leu Leu Leu Leu Leu
```

```
                195                 200                 205
Leu Lys Ala Met Asn Ile Ile Gly Val Val Ser Ala Leu Ala Gly Ala
210                 215                 220

Ala Leu Val Gln Ile Leu Val Gly Leu Pro Phe Leu Ile Thr Tyr Pro
225                 230                 235                 240

Val Ser Tyr Ile Ala Asn Ala Phe Asp Leu Gly Arg Val Phe Ile His
                245                 250                 255

Phe Trp Ser Val Asn Phe Lys Phe Val Pro Glu Arg Val Phe Val Ser
            260                 265                 270

Lys Glu Phe Ala Val Cys Leu Leu Ile Ala His Leu Phe Leu Leu Val
        275                 280                 285

Ala Phe Ala Asn Tyr Lys Trp Cys Lys His Glu Gly Ile Ile Gly
290                 295                 300

Phe Met Arg Ser Arg His Phe Phe Leu Thr Leu Pro Ser Ser Leu Ser
305                 310                 315                 320

Phe Ser Asp Val Ser Ala Ser Arg Ile Ile Thr Lys Glu His Val Val
                325                 330                 335

Thr Ala Met Phe Val Gly Asn Phe Ile Gly Ile Val Phe Ala Arg Ser
            340                 345                 350

Leu His Tyr Gln Phe Tyr Ser Trp Tyr Phe Tyr Ser Leu Pro Tyr Leu
        355                 360                 365

Leu Trp Arg Thr Pro Phe Pro Thr Trp Leu Arg Leu Ile Met Phe Leu
370                 375                 380

Gly Ile Glu Leu Cys Trp Asn Val Tyr Pro Ser Thr Pro Ser Ser Ser
385                 390                 395                 400

Gly Leu Leu Leu Cys Leu His Leu Ile Ile Leu Val Gly Leu Trp Leu
                405                 410                 415

Ala Pro Ser Val Asp Pro Tyr Gln Leu Lys Glu His Pro Lys Ser Gln
            420                 425                 430

Ile His Lys Lys Ala
        435

<210> SEQ ID NO 36
<211> LENGTH: 433
<212> TYPE: PRT
<213> ORGANISM: Homo sapiens

<400> SEQUENCE: 36

Arg Lys Arg Gly Arg Ser Gly Ser Ala Ala Gln Ala Glu Gly Leu Cys
1               5                   10                  15

Lys Gln Trp Leu Gln Arg Ala Trp Gln Glu Arg Arg Leu Leu Leu Arg
            20                  25                  30

Glu Pro Arg Tyr Thr Leu Leu Val Ala Ala Cys Leu Cys Leu Ala Glu
        35                  40                  45

Val Gly Ile Thr Phe Trp Val Ile His Arg Val Ala Tyr Thr Glu Ile
50                  55                  60

Asp Trp Lys Ala Tyr Met Ala Glu Val Glu Gly Val Ile Asn Gly Thr
65                  70                  75                  80

Tyr Asp Tyr Thr Gln Leu Gln Gly Asp Thr Gly Pro Leu Val Tyr Pro
                85                  90                  95

Ala Gly Phe Val Tyr Ile Phe Met Gly Leu Tyr Tyr Ala Thr Ser Arg
            100                 105                 110

Gly Thr Asp Ile Arg Met Ala Gln Asn Ile Phe Ala Val Leu Tyr Leu
        115                 120                 125
```

Ala Thr Leu Leu Leu Val Phe Leu Ile Tyr His Gln Thr Cys Lys Val
130                 135                 140

Pro Pro Phe Val Phe Phe Met Cys Cys Ala Ser Tyr Arg Val His
145                 150                 155                 160

Ser Ile Phe Val Leu Arg Leu Phe Asn Asp Pro Val Ala Met Val Leu
                165                 170                 175

Leu Phe Leu Ser Ile Asn Leu Leu Leu Ala Gln Arg Trp Gly Trp Gly
                180                 185                 190

Cys Cys Phe Phe Ser Leu Ala Val Ser Val Lys Met Asn Val Leu Leu
                195                 200                 205

Phe Ala Pro Gly Leu Leu Phe Leu Leu Thr Gln Phe Gly Phe Arg
210                 215                 220

Gly Ala Leu Pro Lys Leu Gly Ile Cys Ala Gly Leu Gln Val Val Leu
225                 230                 235                 240

Gly Leu Pro Phe Leu Leu Glu Asn Pro Ser Gly Tyr Leu Ser Arg Ser
                245                 250                 255

Phe Asp Leu Gly Arg Gln Phe Leu Phe His Trp Thr Val Asn Trp Arg
                260                 265                 270

Phe Leu Pro Glu Ala Leu Phe Leu His Arg Ala Phe His Leu Ala Leu
                275                 280                 285

Leu Thr Ala His Leu Thr Leu Leu Leu Phe Ala Leu Cys Arg Trp
290                 295                 300

His Arg Thr Gly Glu Ser Ile Leu Ser Leu Leu Arg Asp Pro Ser Lys
305                 310                 315                 320

Arg Lys Val Pro Pro Gln Pro Leu Thr Pro Asn Gln Ile Val Ser Thr
                325                 330                 335

Leu Phe Thr Ser Asn Phe Ile Gly Ile Cys Phe Ser Arg Ser Leu His
                340                 345                 350

Tyr Gln Phe Tyr Val Trp Tyr Phe His Thr Leu Pro Tyr Leu Leu Trp
                355                 360                 365

Ala Met Pro Ala Arg Trp Leu Thr His Leu Leu Arg Leu Leu Val Leu
370                 375                 380

Gly Leu Ile Glu Leu Ser Trp Asn Thr Tyr Pro Ser Thr Ser Cys Ser
385                 390                 395                 400

Ser Ala Ala Leu His Ile Cys His Ala Val Ile Leu Leu Gln Leu Trp
                405                 410                 415

Leu Gly Pro Gln Pro Phe Pro Lys Ser Thr Gln His Ser Lys Lys Ala
                420                 425                 430

His

<210> SEQ ID NO 37
<211> LENGTH: 1291
<212> TYPE: DNA
<213> ORGANISM: Aspergillus nidulans

<400> SEQUENCE: 37
aagcttcaag ctgtaaggat ttcggcacgg ctacggaaga cggagaagcc caccttcagt    60
ggactcgagt accatttaat tctatttgtg tttgatcgag acctaataca gccectacaa   120 cgaccatcaa agtcgtatag ctaccagtga ggaagtggac tcaaatcgac ttcagcaaca   180
tctcctggat aaactttaag cctaaactat acagaataag atggtggaga cttataccg    240 agctcccaaa tctgtccaga tcatggttga ccggtgcctg gatcttccta tagaatcatc   300
cttattcgtt gacctagctg attctggagt gacccagagg gtcatgactt gagcctaaaa   360

-continued

```
tccgccgcct ccaccatttg tagaaaaatg tgacgaactc gtgagctctg tacagtgacc    420
ggtgactctt tctggcatgc ggagagacgg acggacgcag agagaagggc tgagtaataa    480
gcgccactgc gccagacagc tctggcggct ctgaggtgca gtggatgatt attaatccgg    540
gaccggccgc ccctccgccc cgaagtggaa aggctggtgt gccctcgtt gaccaagaat    600 ctattgcatc atcggagaat atggagcttc atcgaatcac cggcagtaag cgaaggagaa    660
tgtgaagcca gggtgtata gccgtcggcg aaatagcatg ccattaaccct aggtacagaa    720 gtccaattgc ttccgatctg gtaaaagatt cacgagatag taccttctcc gaagtaggta    780
gagcgagtac ccggcgcgta agctccctaa ttggcccatc cggcatctgt agggcgtcca    840
aatatcgtgc ctctcctgct ttgcccggtg tatgaaaccg gaaaggccgc tcaggagctg    900
gccagcggcg cagaccggga acacaagctg gcagtcgacc catccggtgc tctgcactcg    960
acctgctgag gtccctcagt ccctggtagg cagctttgcc ccgtctgtcc gcccggtgtg   1020
tcggcggggt tgacaaggtc gttgcgtcag tccaacattt gttgccatat tttcctgctc   1080
tccccaccag ctgctctttt cttttctctt tcttttccca tcttcagtat attcatcttc   1140
ccatccaaga acctttattt cccctaagta agtactttgc tacatccata ctccatcctt   1200
cccatccctt attcctttga acctttcagt tcgagctttc ccacttcatc gcagcttgac   1260
taacagctac cccgcttgag cagacatcac a                                  1291
```

<210> SEQ ID NO 38
<211> LENGTH: 30
<212> TYPE: DNA
<213> ORGANISM: Artificial Sequence
<220> FEATURE:
<223> OTHER INFORMATION: gpdA5F primer

<400> SEQUENCE: 38

```
cgcagatctc aagctgtaag gatttcggca                                       30
```

<210> SEQ ID NO 39
<211> LENGTH: 40
<212> TYPE: DNA
<213> ORGANISM: Artificial Sequence
<220> FEATURE:
<223> OTHER INFORMATION: gpdA3R primer

<400> SEQUENCE: 39

```
caccgggccc atctcaaaca ttgtgatgtc tgctcaagcg                             40
```

<210> SEQ ID NO 40
<211> LENGTH: 1255
<212> TYPE: DNA
<213> ORGANISM: Aspergillus nidulans
<220> FEATURE:
<221> NAME/KEY: CDS
<222> LOCATION: (1)..(236)
<220> FEATURE:
<221> NAME/KEY: Intron
<222> LOCATION: (237)..(366)
<220> FEATURE:
<221> NAME/KEY: CDS
<222> LOCATION: (367)..(1252)

<400> SEQUENCE: 40

```
atg ttt gag atg ggc ccg gtg gga act cgt ctc ccc gcc atg acc tct    48
Met Phe Glu Met Gly Pro Val Gly Thr Arg Leu Pro Ala Met Thr Ser
1               5                   10                  15 cca gcg cac aac cac tac agc tac cac tct ccc acc tcc agc gac aga    96
Pro Ala His Asn His Tyr Ser Tyr His Ser Pro Thr Ser Ser Asp Arg
```

```
                   20                  25                  30
ggc cgg tca agg cag aac tcg gat gcc atg gac atc cag tcc atc act      144
Gly Arg Ser Arg Gln Asn Ser Asp Ala Met Asp Ile Gln Ser Ile Thr
        35                  40                  45 gaa cga gag ccg gcg acc aga tac gcg gtt gcg ggc ggc cct gcg ccc      192
Glu Arg Glu Pro Ala Thr Arg Tyr Ala Val Ala Gly Gly Pro Ala Pro
 50                  55                  60 tgg aat cgc aac ggg tct ccg agc atg agc cct atg tat agc aa          236
Trp Asn Arg Asn Gly Ser Pro Ser Met Ser Pro Met Tyr Ser Asn
 65                  70                  75 gtacatctct cttaccccct cgtttctttc tgcttttcta ccaccccatc cctctttcca    296
gtctgagtcc aggcttgttc cgcttgaagt ggctaatgtg atcctcgtct tctctctttc    356
tgtgttttag c aat tcc gag cga aac cag ttt cat gaa gag aac gga cgc    406
            Asn Ser Glu Arg Asn Gln Phe His Glu Glu Asn Gly Arg
                     80                  85                  90 acc tac cat ggc ttt cgc agg gga atg tat ttt ctt ccg tgc gat gag     454
Thr Tyr His Gly Phe Arg Arg Gly Met Tyr Phe Leu Pro Cys Asp Glu
             95                  100                 105 caa gaa cag gat cgc ctc gac atc ttc cat aag cta ttc acg gta gcg     502
Gln Glu Gln Asp Arg Leu Asp Ile Phe His Lys Leu Phe Thr Val Ala
 110                 115                 120 cgg gta tcg gag agt ctg atc tac gcg ccc cat cca acc aac ggc cgg     550
Arg Val Ser Glu Ser Leu Ile Tyr Ala Pro His Pro Thr Asn Gly Arg
125                 130                 135                 140 ttt ctg gac cta gga tgt gga act ggt atc tgg gcg atc gag gta gcg     598
Phe Leu Asp Leu Gly Cys Gly Thr Gly Ile Trp Ala Ile Glu Val Ala
             145                 150                 155 aac aag tac cct gat gcg ttt gtc gct ggt gtg gat ttg gct cct att     646
Asn Lys Tyr Pro Asp Ala Phe Val Ala Gly Val Asp Leu Ala Pro Ile
             160                 165                 170 cag cct ccg aac cac ccg aag aac tgc gag ttc tac gcg ccc ttc gac     694
Gln Pro Pro Asn His Pro Lys Asn Cys Glu Phe Tyr Ala Pro Phe Asp
             175                 180                 185 ttc gaa gcg cca tgg gcc atg ggg gag gat tcc tgg gat cta atc cat     742
Phe Glu Ala Pro Trp Ala Met Gly Glu Asp Ser Trp Asp Leu Ile His
 190                 195                 200 ctg cag atg ggt tgc ggt agt gtc atg ggc tgg cca aac ttg tat cga     790
Leu Gln Met Gly Cys Gly Ser Val Met Gly Trp Pro Asn Leu Tyr Arg
205                 210                 215                 220 agg ata ttc gca cat ctc cgt ccc ggt gcc tgg ttt gag cag gtt gag     838
Arg Ile Phe Ala His Leu Arg Pro Gly Ala Trp Phe Glu Gln Val Glu
             225                 230                 235 atc gat ttc gag cct cga tgt gat gat cgg tca cta gat gga acg gca     886
Ile Asp Phe Glu Pro Arg Cys Asp Asp Arg Ser Leu Asp Gly Thr Ala
             240                 245                 250 ttg cgg cat tgg tac gat tgt ctt aaa cag gcg aca gca gag acc atg     934
Leu Arg His Trp Tyr Asp Cys Leu Lys Gln Ala Thr Ala Glu Thr Met
             255                 260                 265 cgg cca atc gcc cat agc tcc cgc gat aca ata aaa gac ctg cag gac     982
Arg Pro Ile Ala His Ser Ser Arg Asp Thr Ile Lys Asp Leu Gln Asp
 270                 275                 280 gct ggg ttc acg gag atc gac cat caa ata gtg gga ctc ccg ctc aac     1030
Ala Gly Phe Thr Glu Ile Asp His Gln Ile Val Gly Leu Pro Leu Asn
285                 290                 295                 300 ccg tgg cat cag gac gaa cac gag cgg aag gtg gca cgt tgg tat aac     1078
Pro Trp His Gln Asp Glu His Glu Arg Lys Val Ala Arg Trp Tyr Asn
             305                 310                 315 ctg gcc gtc tca gag agc atc gaa aac ctc agt ctg gct ccc ttc agt     1126
```

```
Leu Ala Val Ser Glu Ser Ile Glu Asn Leu Ser Leu Ala Pro Phe Ser
            320                 325                 330 cgt gtc tat cgc tgg ccc ctg gag aga atc cag caa ctc gcc gca gat    1174
Arg Val Tyr Arg Trp Pro Leu Glu Arg Ile Gln Gln Leu Ala Ala Asp
            335                 340                 345 gtg aag tcc gaa gca ttc aac aaa gag atc cat gcc tac aat ata ctg    1222
Val Lys Ser Glu Ala Phe Asn Lys Glu Ile His Ala Tyr Asn Ile Leu
    350                 355                 360 cac ata tac cag gct agg aaa cca tta aga taa                        1255
His Ile Tyr Gln Ala Arg Lys Pro Leu Arg
365                 370

<210> SEQ ID NO 41
<211> LENGTH: 374
<212> TYPE: PRT
<213> ORGANISM: Aspergillus nidulans

<400> SEQUENCE: 41

Met Phe Glu Met Gly Pro Val Gly Thr Arg Leu Pro Ala Met Thr Ser
1               5                   10                  15

Pro Ala His Asn His Tyr Ser Tyr His Ser Pro Thr Ser Ser Asp Arg
                20                  25                  30

Gly Arg Ser Arg Gln Asn Ser Asp Ala Met Asp Ile Gln Ser Ile Thr
            35                  40                  45

Glu Arg Glu Pro Ala Thr Arg Tyr Ala Val Ala Gly Pro Ala Pro
    50                  55                  60

Trp Asn Arg Asn Gly Ser Pro Ser Met Ser Pro Met Tyr Ser Asn Asn
65                  70                  75                  80

Ser Glu Arg Asn Gln Phe His Glu Glu Asn Gly Arg Thr Tyr His Gly
                85                  90                  95

Phe Arg Arg Gly Met Tyr Phe Leu Pro Cys Asp Glu Gln Glu Gln Asp
            100                 105                 110

Arg Leu Asp Ile Phe His Lys Leu Phe Thr Val Ala Arg Val Ser Glu
        115                 120                 125

Ser Leu Ile Tyr Ala Pro His Pro Thr Asn Gly Arg Phe Leu Asp Leu
    130                 135                 140

Gly Cys Gly Thr Gly Ile Trp Ala Ile Glu Val Ala Asn Lys Tyr Pro
145                 150                 155                 160

Asp Ala Phe Val Ala Gly Val Asp Leu Ala Pro Ile Gln Pro Pro Asn
                165                 170                 175

His Pro Lys Asn Cys Glu Phe Tyr Ala Pro Phe Asp Phe Glu Ala Pro
            180                 185                 190

Trp Ala Met Gly Glu Asp Ser Trp Asp Leu Ile His Leu Gln Met Gly
        195                 200                 205

Cys Gly Ser Val Met Gly Trp Pro Asn Leu Tyr Arg Arg Ile Phe Ala
    210                 215                 220

His Leu Arg Pro Gly Ala Trp Phe Glu Gln Val Glu Ile Asp Phe Glu
225                 230                 235                 240

Pro Arg Cys Asp Asp Arg Ser Leu Asp Gly Thr Ala Leu Arg His Trp
                245                 250                 255

Tyr Asp Cys Leu Lys Gln Ala Thr Ala Glu Thr Met Arg Pro Ile Ala
            260                 265                 270

His Ser Ser Arg Asp Thr Ile Lys Asp Leu Gln Asp Ala Gly Phe Thr
        275                 280                 285

Glu Ile Asp His Gln Ile Val Gly Leu Pro Leu Asn Pro Trp His Gln
    290                 295                 300
```

Asp Glu His Glu Arg Lys Val Ala Arg Trp Tyr Asn Leu Ala Val Ser
305                 310                 315                 320

Glu Ser Ile Glu Asn Leu Ser Leu Ala Pro Phe Ser Arg Val Tyr Arg
            325                 330                 335

Trp Pro Leu Glu Arg Ile Gln Gln Leu Ala Ala Asp Val Lys Ser Glu
        340                 345                 350

Ala Phe Asn Lys Glu Ile His Ala Tyr Asn Ile Leu His Ile Tyr Gln
    355                 360                 365

Ala Arg Lys Pro Leu Arg
    370

<210> SEQ ID NO 42
<211> LENGTH: 40
<212> TYPE: DNA
<213> ORGANISM: Artificial Sequence
<220> FEATURE:
<223> OTHER INFORMATION: LaeA5F primer

<400> SEQUENCE: 42
cgcttgagca gacatcacaa tgtttgagat gggcccggtg                    40

<210> SEQ ID NO 43
<211> LENGTH: 29
<212> TYPE: DNA
<213> ORGANISM: Artificial Sequence
<220> FEATURE:
<223> OTHER INFORMATION: LaeA3R primer

<400> SEQUENCE: 43
cgcagatctg aggattatga agggagc                                  29

<210> SEQ ID NO 44
<211> LENGTH: 2866
<212> TYPE: DNA
<213> ORGANISM: Artificial Sequence
<220> FEATURE:
<223> OTHER INFORMATION: pGPDA promoter LeaA fragment

<400> SEQUENCE: 44
aagcttcaag ctgtaaggat tcggcacgg ctacggaaga cggagaagcc caccttcagt   60
ggactcgagt accatttaat tctatttgtg tttgatcgag acctaataca gcccctacaa  120
cgaccatcaa agtcgtatag ctaccagtga ggaagtggac tcaaatcgac ttcagcaaca  180
tctcctggat aaactttaag cctaaactat acagaataag atggtggaga gcttataccg  240
agctcccaaa tctgtccaga tcatggttga ccggtgcctg gatcttccta tagaatcatc  300
cttattcgtt gacctagctg attctggagt gacccagagg gtcatgactt gagcctaaaa  360
tccgccgcct ccaccatttg tagaaaaatg tgacgaactc gtgagctctg tacagtgacc  420
ggtgactctt tctggcatgc ggagagacgg acgacgcag agagaagggc tgagtaataa   480
gcgccactgc gccagacagc tctggcggct ctgaggtgca gtggatgatt attaatccgg  540
gaccggccgc ccctccgccc gaagtggaa aggctggtgt gcccctcgtt gaccaagaat  600
ctattgcatc atcggagaat atggagcttc atcgaatcac cggcagtaag cgaaggagaa  660
tgtgaagcca ggggtgtata gccgtcggcg aaatagcatg ccattaacct aggtacagaa  720
gtccaattgc ttccgatctg gtaaaagatt cacgagatag taccttctcc gaagtaggta  780
gagcgagtac ccggcgcgta agctccctaa ttggcccatc cggcatctgt agggcgtcca  840
aatatcgtgc ctctcctgct tgcccggtg tatgaaaccg gaaaggccgc tcaggagctg  900

```
gccagcggcg cagaccggga acacaagctg gcagtcgacc catccggtgc tctgcactcg      960
acctgctgag gtccctcagt ccctggtagg cagctttgcc ccgtctgtcc gcccggtgtg     1020
tcggcggggt tgacaaggtc gttgcgtcag tccaacattt gttgccatat tttcctgctc     1080
tccccaccag ctgctctttt cttttctctt tcttttccca tcttcagtat attcatcttc     1140
ccatccaaga acctttattt cccctaagta agtactttgc tacatccata ctccatcctt     1200
cccatccctt attcctttga acctttcagt tcgagctttc ccacttcatc gcagcttgac     1260
taacagctac cccgcttgag cagacatcac aatgtttgag atgggcccgg tgggaactcg     1320
tctccccgcc atgacctctc cagcgcacaa ccactacagc taccactctc ccacctccag     1380
cgacagaggc cggtcaaggc agaactcgga tgccatggac atccagtcca tcactgaacg     1440
agagccggcg accagatacg cggttgcggg cggccctgcg ccctggaatc gcaacgggtc     1500
tccgagcatg agccctatgt atagcaagta catctctctt accccctccgt ttctttctgc     1560 ttttctacca ccccatccct ctttccagtc tgagtccagg cttgttccgc ttgaagtggc     1620
taatgtgatc ctcgtcttct ctctttctgt gttttagcaa ttccgagcga aaccagtttc     1680
atgaagagaa cggacgcacc taccatggct ttcgcagggg aatgtatttt cttccgtgcg     1740
atgagcaaga acaggatcgc ctcgacatct tccataagct attcacggta gcgcgggtat     1800
cggagagtct gatctacgcg ccccatccaa ccaacggccg gtttctggac ctaggatgtg     1860
gaactggtat ctgggcgatc gaggtagcga acaagtaccc tgatgcgttt gtcgctggtg     1920
tggatttggc tcctattcag cctccgaacc acccgaagaa ctgcgagttc tacgcgccct     1980
tcgacttcga agcgccatgg gccatggggg aggattcctg ggatctaatc catctgcaga     2040
tgggttgcgg tagtgtcatg ggctggccaa acttgtatcg aaggatattc gcacatctcc     2100
gtcccggtgc ctggtttgag caggttgaga tcgatttcga gcctcgatgt gatgatcggt     2160
cactagatgg aacggcattg cggcattggt acgattgtct taaacaggcg acagcagaga     2220
ccatgcggcc aatcgcccat agctcccgcg atacaataaa agacctgcag gacgctgggt     2280
tcacggagat cgaccatcaa atagtgggac tcccgctcaa cccgtggcat caggacgaac     2340
acgagcggaa ggtggcacgt tggtataacc tggccgtctc agagagcatc gaaaacctca     2400
gtctggctcc cttcagtcgt gtctatcgct ggcccctgga gagaatccag caactcgccg     2460
cagatgtgaa gtccgaagca ttcaacaaag agatccatgc ctacaatata ctgcacatat     2520
accaggctag gaaaccatta agataagagc aaaaggcgac cacatccagg aacgcaaaac     2580
gaaaaggagg aaaactgcta gcgcaagttt atgtcacgct ggcacacgcc cagccatcag     2640
aaatctcaac agcgaaagtt atgaaccgca tcaaccgagt atgaacgaca attcgtccat     2700
cacacaccct tcggttcctc tcgcaggccc agcatggcgc cctatcaacc tgctttacga     2760
cgtcgtatat actggcgaag tatcctctct atctactctg gcgctctaga taccgtgaag     2820
atgcagacaa aattggccga gctcccttct cataatcctc aagctt                    2866
```

<210> SEQ ID NO 45
<211> LENGTH: 1279
<212> TYPE: DNA
<213> ORGANISM: Aspergillus niger

<400> SEQUENCE: 45

```
atgcatcatt ctcccgcttt gttttgggc ccaaactaac cgagtaggtg tggcatttgc        60
gggcatgatg tttcaactac cgctgatcat tatcaccgcc ccattagaga agatccaaga      120
```

| | |
|---|---|
| ccctactggg aaggtgatag gcaattccat tttctgggtt agttttgtc ttgtcggcca | 180 |
| gcctttggga gctttgctgt acttctttgc ctggcaagcg aagtatggca gtgtgagccg | 240 |
| aatgtgaatg taaaagcacg cacgtgtccg ctgtttgtca tagatgtaaa taaatgccaa | 300 |
| caacttcagc cattttttga aaagcaaagc aaccgaagta aacgatcctg taccatcagc | 360 |
| gctcctcaca atggaatctt ttagatgttt ctgttccatt catcttgctt actgcaatgt | 420 |
| tcttttcgcg tttgactaat tctccggatg ttgaatggca acgctgtcgg cgtcgggtct | 480 |
| tcagggatcc gccaaggatg ctctggatcc gcatccggcc gctcttgcgc cccatcaatc | 540 |
| gcccgactat aaatcgaact actttcggca tcttctagac ttcctaatac cgcctagtca | 600 |
| tagcagattc aagctgagaa caccacaagt aaatatcacc catcatgctt accctgaccg | 660 |
| tccctgaaaa ctacgggtat gtgccaattc tacaattcct tgcagacaat gccattctcc | 720 |
| ccatgaagtc tgatgctaac tatcctgcag ctctgtcatt gccgtcgctc tgggtgccat | 780 |
| ccccgtcctg agcttcgtcc atggcgccgt cgtgtctcgt ctccgcaagg aagctgattg | 840 |
| cccctaccct cactgctatg cgaccgtaga gcagtgcaag accaacgtaa gccaacctca | 900 |
| cacaaacagg attcctcgag ctaacataca ttccgaaccg tgcagcccaa ggccgagcag | 960 |
| ttcaactgcg ctcagcgcgc tcatgccaac ttccttgaga actccagcca aactatgctc | 1020 |
| ttcctcctgg tagctggact gaagtacccc cagttggcga ctggcctcgg aagcatctgg | 1080 |
| gtcctcggtc gctcactgtt cctttacgga tatgtgtact ccggcaagcc gcggggtcgc | 1140 |
| ggtcgtttgt acggcagctt ctacttgctt gcacagggag ctctctgggg cttgacgtct | 1200 |
| tttggagttg cgagggagtt gatttcctac ttctaagttt ggactgaatc cgtggtgtga | 1260 |
| ttgaggtgat tggcgatgt | 1279 |

<210> SEQ ID NO 46
<211> LENGTH: 472
<212> TYPE: DNA
<213> ORGANISM: Aspergillus nidulans
<220> FEATURE:
<221> NAME/KEY: misc_feature
<222> LOCATION: (361)..(361)
<223> OTHER INFORMATION: n is a, c, g, or t

<400> SEQUENCE: 46

| | |
|---|---|
| ggaccgatgg ctgtgtagaa gtactcgccg atagtggaaa ccgacgcccc agcactcgtc | 60 |
| cgagggcaaa ggaatagagt agatgccgac cgcgggatcc acttaacgtt actgaaatca | 120 |
| tcaaacagct tgacgaatct ggatataaga tcgttggtgt cgatgtcagc tccgagttg | 180 |
| agacaaatgg tgttcaggat ctcgataaga tacgttcatt tgtccaagca gcaaagagtg | 240 |
| ccttctagtg atttaatagc tccatgtcaa caagaataaa acgcgttttc gggtttacct | 300 |
| cttccagata cagctcatct gcaatgcatt aatgcattga ctgcaaccta gtaacgcctt | 360 |
| ncaggctccg gcgaagagaa gaatagctta gcagagctat tttcattttc gggagacgag | 420 |
| atcaagcaga tcaacggtcg tcaagagacc tacgagactg aggaatccgc tc | 472 |

<210> SEQ ID NO 47
<211> LENGTH: 2005
<212> TYPE: DNA
<213> ORGANISM: Aspergillus oryzae

<400> SEQUENCE: 47

| | |
|---|---|
| tctgacagac gggcaattga ttacgggatc ccattggtaa cgaaatgtaa aagctaggag | 60 |
| atcgtccgcc gatgtcagga tgatttcact tgtttcttgt ccggctcacc ggtcaaagct | 120 |

```
aaagaggagc aaaaggaacg gatagaatcg ggtgccgctg atctatacgg tatagtgccc      180
ttatcacgtt gactcaaccc atgctattta actcaacccc tccttctgaa ccccaccatc      240
ttcttccttt tcctctcatc ccacacaatt ctctatctca gatttgaatt ccaaaagtcc      300
tcggacgaaa ctgaacaagt cttcctccct tcgataaacc tttggtgatt ggaataactg      360
accatcttct atagttccca aaccaaccga caatgtaaat acactcctcg attagccctc      420
tagagggcat acgatggaag tcatggaata cttttggctg gactctcaca atgatcaagg      480
tatcttaggt aacgtctttg gcgtgggccg gtgttcgttc ccagtcatcg atgcattcac      540
atgccctccc taagctgggc cctagactct aggatcctag tctagaagga catggcatcg      600
atggactggg ttcgttctga gattatacgg ctaaaacttg atctggataa taccagcgaa      660
aagggtcatg ccttctctcg ttcttcctgt tgatggaatg gctaacagat gatagtcatt      720
gcaacttgaa acatgtctcc tccagctgcc atctacgaac ccactgtggc cgctaccggc      780
ctcaagggta aggtcgtggt ttctgagacc gtccccgttg agggagcttc tcagaccaag      840
ctgttggacc atttcggtgg caagtgggac gagttcaagt tcgcccctat ccgcgaaagc      900
caggtctctc gtgccatgac cagacgttac tttgaggacc tggacaagta cgctgaaagt      960
gacgttgtca ttgttggtgc tggttcctgc ggtctgagca ctgcgtacgt cttggccaag     1020
gctcgtccgg acctgaagat tgctatcgtc gaggccagcg tctctcctgg tcagtagtcc     1080
atgatggatt gccttgcact cagctttccg gaactaacgt gcaataggtg gcggtgcctg     1140
gttgggtggc caactctttt ctgctatggt catgcgccgt cccgcggaag tcttcctgaa     1200
cgagctgggt gttccttacg aagaggacgc aaaccccaac tacgttgtcg tcaagcacgc     1260
ctccctgttt acctcgacac tcatgtcgaa ggttctctcc ttccccaatg tcaagctctt     1320
caatgctacc gctgttgagg acttgatcac ccgtccgacc gagaacggca accccccagat     1380 tgctggtgtt gtcgtcaact ggacgctggt caccccttcac cacgatgatc actcctgcat     1440
ggaccccaac actatcaacg ctcctgtcat catcagtacc actggtcacg atgggccatt     1500
cggcgccttc tgtgcgaagc gcttggtgtc catgggcagc gtcgacaagc taggtggcat     1560
gcgtggtctc gacatgaact cggccgagga tgccatcgtc aagaacaccc gcgaggttac     1620
taagggcttg ataatcggcg gtatggagct gtctgaaatt gatggctttta accgcatggg     1680 ccctaccttc ggtgccatgg ttctcagtgg tgtcaaggct gccgaggagg cattgaaggt     1740
gttcgacgag cgtcagcgcg agtgtgctga gtaaatgact cactacccga atgggttcag     1800
tgcatgaacc ggatttgtct tacggtcttt gacgataggg gaatgatgat tatgtgatag     1860
ttctgagatt tgaatgaact cgttagctcg taatccacat gcatatgtaa atggctgtgt     1920
cccgtatgta acgtggggc attctagaat aattatgtgt aacaagaaag acagtataat     1980
acaaacaaag atgcaagagc ggctc                                           2005

<210> SEQ ID NO 48
<211> LENGTH: 1052
<212> TYPE: DNA
<213> ORGANISM: Aspergillus niger

<400> SEQUENCE: 48
gtcatcgcag ataagcactg ctgtcttgca tccaagtcag cgtcagcaga aatacgggac       60
ttccgaaagt atatggcaaa attaaagaac ttgactctcc agcaatgttt tgccctgacc      120
gtcgctaaaa cgttactacc cctatacccg tctgtttgtc ccagcccgag gcattaggtc      180
```

| | |
|---|---|
| tgactgacag cacggcgcca tgcgggcttg ggacgccatg tccgtcgcgt gataagggtt | 240 |
| gatccatgca gctactatcc ttccatcgtt ccattcccat ccttgtccta tctccatcct | 300 |
| tgaaacttta ctagtttagt tggatgctcg agcttgctct cggctactcc gtccaatgga | 360 |
| taagaccccg atgccggtcc tcattggtct ccagctggta tcgccccaac cttcgtgtga | 420 |
| tcgcctctct gcttcccctc atcatcatta ctaactagta catccaaaag ccatcccagt | 480 |
| gcttcccctc acccttgccc aagacattcc aagtgggcct tcggctggaa acatggacc | 540 |
| cattggttcc atcgataagc tagctcctcg tccgttaccc cagattgata ccagataaca | 600 |
| ttgaccagcg gcttatcacc gaggtctgcg ggtgagaccc cccctgcgac aagttagata | 660 |
| aaagaaactc gcctcattgt gcttccgatg gggtcggatg acgagccttc ggaaagagct | 720 |
| ggcgcctctt taaggggac agctgtcgcc aagttgtgaa attctccgat aactactaac | 780 |
| aatctctccc ttccttcccg ctactgtggt caccaaatca actctctttt ctcggccaag | 840 |
| atctaacatg gcggatgaga agactgaaaa gtctcccca ccgatgacgg tggatgagga | 900 |
| gactggcaca acagaggaaa ttgacccgac aatggcaaag catacgaagg atgcagacga | 960 |
| ggcactggcg gtcttcgaag acctccatgg tgaagtcatc acacttgatg aggagacaaa | 1020 |
| caaaaggata cttcggacaa ttgactggca ca | 1052 |

<210> SEQ ID NO 49
<211> LENGTH: 58
<212> TYPE: DNA
<213> ORGANISM: Artificial Sequence
<220> FEATURE:
<223> OTHER INFORMATION: pyrGU5F primer

<400> SEQUENCE: 49
gtaacgccag ggttttccca gtcacgacgt ttaaacatgc atcattctcc cgctttgt    58

<210> SEQ ID NO 50
<211> LENGTH: 49
<212> TYPE: DNA
<213> ORGANISM: Artificial Sequence
<220> FEATURE:
<223> OTHER INFORMATION: pyrGU3R primer

<400> SEQUENCE: 50
tgccgaaatc cttacagctt gaagcttcat cgccaatcac ctcaatcac    49

<210> SEQ ID NO 51
<211> LENGTH: 49
<212> TYPE: DNA
<213> ORGANISM: Artificial Sequence
<220> FEATURE:
<223> OTHER INFORMATION: Trp5F primer

<400> SEQUENCE: 51
agctcccttc tcataatcct caagcttgga ccgatggctg tgtagaagt    49

<210> SEQ ID NO 52
<211> LENGTH: 46
<212> TYPE: DNA
<213> ORGANISM: Artificial Sequence
<220> FEATURE:
<223> OTHER INFORMATION: Trp3R primer

<400> SEQUENCE: 52
cgtaatcaat tgcccgtctg tcagagagcg gattcctcag tctcgt    46

<210> SEQ ID NO 53
<211> LENGTH: 46
<212> TYPE: DNA
<213> ORGANISM: Artificial Sequence
<220> FEATURE:
<223> OTHER INFORMATION: PTR5F primer

<400> SEQUENCE: 53
acgagactga ggaatccgct ctctgacaga cgggcaattg attacg          46

<210> SEQ ID NO 54
<211> LENGTH: 45
<212> TYPE: DNA
<213> ORGANISM: Artificial Sequence
<220> FEATURE:
<223> OTHER INFORMATION: PTR3R primer

<400> SEQUENCE: 54
acagcagtgc ttatctgcga tgacgagccg ctcttgcatc tttgt           45

<210> SEQ ID NO 55
<211> LENGTH: 45
<212> TYPE: DNA
<213> ORGANISM: Artificial Sequence
<220> FEATURE:
<223> OTHER INFORMATION: PyrGD5F primer

<400> SEQUENCE: 55
acaaagatgc aagagcggct cgtcatcgca gataagcact gctgt           45

<210> SEQ ID NO 56
<211> LENGTH: 44
<212> TYPE: DNA
<213> ORGANISM: Artificial Sequence
<220> FEATURE:
<223> OTHER INFORMATION: PyrGD3R primer

<400> SEQUENCE: 56
tgagacgctg tttcaccgag tacatcgcca atcacctcaa tcac            44

<210> SEQ ID NO 57
<211> LENGTH: 7689
<212> TYPE: DNA
<213> ORGANISM: Artificial Sequence
<220> FEATURE:
<223> OTHER INFORMATION: transgene
<220> FEATURE:
<221> NAME/KEY: misc_feature
<222> LOCATION: (4513)..(4513)
<223> OTHER INFORMATION: n is a, c, g, or t

<400> SEQUENCE: 57
gtttaaacat gcatcattct cccgctttgt ttttgggccc aaactaaccg agtaggtgtg    60
gcatttgcgg gcatgatgtt tcaactaccg ctgatcatta tcaccgcccc attagagaag   120
atccaagacc ctactgggaa ggtgataggc aattccattt tctgggttag tttttgtctt   180
gtcggccagc ctttgggagc tttgctgtac ttctttgcct ggcaagcgaa gtatggcagt   240
gtgagccgaa tgtgaatgta aaagcacgca cgtgtccgct gtttgtcata gatgtaaata   300
aatgccaaca acttcagcca ttttttgaaa agcaaagcaa ccgaagtaaa cgatcctgta   360
ccatcagcgc tcctcacaat ggaatctttt agatgtttct gttccattca tcttgcttac   420
tgcaatgttc ttttcgcgtt tgactaattc tccggatgtt gaatggcaac gctgtcggcg   480
tcgggtcttc agggatccgc caaggatgct ctggatccgc atccggccgc tcttgcgccc   540

```
catcaatcgc ccgactataa atcgaactac tttcggcatc ttctagactt cctaataccg   600
cctagtcata gcagattcaa gctgagaaca ccacaagtaa atatcaccca tcatgcttac   660
cctgaccgtc cctgaaaact acgggtatgt gccaattcta caattccttg cagacaatgc   720
cattctcccc atgaagtctg atgctaacta tcctgcagct ctgtcattgc cgtcgctctg   780
ggtgccatcc ccgtcctgag cttcgtccat ggcgccgtcg tgtctcgtct ccgcaaggaa   840
gctgattgcc cctaccctca ctgctatgcg accgtagagc agtgcaagac caacgtaagc   900
caacctcaca caaacaggat tcctcgagct aacatacatt ccgaaccgtg cagcccaagg   960
ccgagcagtt caactgcgct cagcgcgctc atgccaactt ccttgagaac tccagccaaa  1020
ctatgctctt cctcctggta gctggactga agtaccccca gttggcgact ggcctcggaa  1080
gcatctgggt cctcggtcgc tcactgttcc tttacggata tgtgtactcc ggcaagccgc  1140
ggggtcgcgg tcgtttgtac ggcagcttct acttgcttgc acaggagct ctctggggct  1200
tgacgtcttt tggagttgcg agggagttga tttcctactt ctaagtttgg actgaatccg  1260
tggtgtgatt gaggtgattg gcgatgaagc ttcaagctgt aaggatttcg gcacggctac  1320
ggaagacgga gaagcccacc ttcagtggac tcgagtacca tttaattcta tttgtgtttg  1380
atcgagacct aatacagccc ctacaacgac catcaaagtc gtatagctac cagtgaggaa  1440
gtggactcaa atcgacttca gcaacatctc ctggataaac tttaagccta aactatacag  1500
aataagatgg tggagagctt ataccgagct cccaaatctg tccagatcat ggttgaccgg  1560
tgcctggatc ttcctataga atcatcctta ttcgttgacc tagctgattc tggagtgacc  1620
cagagggtca tgacttgagc ctaaaatccg ccgcctccac catttgtaga aaatgtgac   1680
gaactcgtga gctctgtaca gtgaccggtg actcttcctg gcatgcggag agacggacgg  1740
acgcagagag aagggctgag taataagcgc cactgcgcca gacagctctg gcggctctga  1800
ggtgcagtgg atgattatta atccgggacc ggccgcccct ccgccccgaa gtggaaaggc  1860
tggtgtgccc ctcgttgacc aagaatctat tgcatcatcg gagaatatgg agcttcatcg  1920
aatcaccggc agtaagcgaa ggagaatgtg aagccagggg tgtatagccg tcggcgaaat  1980
agcatgccat taacctaggt acagaagtcc aattgcttcc gatctggtaa aagattcacg  2040
agatagtacc ttctccgaag taggtagagc gagtacccgg cgcgtaagct ccctaattgg  2100
cccatccggc atctgtaggg cgtccaaata tcgtgcctct cctgctttgc ccggtgtatg  2160
aaaccggaaa ggccgctcag gagctggcca gcggcgcaga ccgggaacac aagctggcag  2220
tcgacccatc cggtgctctg cactcgacct gctgaggtcc ctcagtccct ggtaggcagc  2280
tttgccccgt ctgtccgccc ggtgtgtcgg cggggttgac aaggtcgttg cgtcagtcca  2340
acatttgttg ccatattttc ctgctctccc caccagctgc tcttttcttt tctctttctt  2400
ttcccatctt cagtatattc atcttcccat ccaagaacct ttatttcccc taagtaagta  2460
ctttgctaca tccatactcc atccttccca tcccttattc ctttgaacct ttcagttcga  2520
gctttcccac ttcatcgcag cttgactaac agctaccccg cttgagcaga catcacaatg  2580
tttgagatgg gcccggtggg aactcgtctc cccgccatga cctctccagc gcacaaccac  2640
tacagctacc actctcccac ctccagcgac agaggccggt caaggcagaa tcggatgcc   2700
atggacatcc agtccatcac tgaacgagag ccggcgacca gatacgcggt tgcgggcggc  2760
cctgcgccct ggaatcgcaa cgggtctccg agcatgagcc ctatgtatag caagtacatc  2820
tctcttaccc ctccgtttct ttctgctttt ctaccacccc atccctcttt ccagtctgag  2880
tccaggcttg ttccgcttga agtggctaat gtgatcctcg tcttctctct ttctgtgttt  2940
```

```
tagcaattcc gagcgaaacc agtttcatga agagaacgga cgcacctacc atggctttcg   3000 cagggaatg tattttcttc cgtgcgatga gcaagaacag gatcgcctcg acatcttcca    3060
taagctattc acggtagcgc gggtatcgga gagtctgatc tacgcgcccc atccaaccaa   3120
cggccggttt ctggacctag gatgtggaac tggtatctgg gcgatcgagg tagcgaacaa   3180
gtaccctgat gcgtttgtcg ctggtgtgga tttggctcct attcagcctc cgaaccaccc   3240
gaagaactgc gagttctacg cgcccttcga cttcgaagcg ccatgggcca tggggagga    3300 ttcctgggat ctaatccatc tgcagatggg ttgcggtagt gtcatgggct ggccaaactt   3360
gtatcgaagg atattcgcac atctccgtcc cggtgcctgg tttgagcagg ttgagatcga   3420
tttcgagcct cgatgtgatg atcggtcact agatggaacg gcattgcggc attggtacga   3480
ttgtcttaaa caggcgacag cagagaccat gcggccaatc gcccatagct cccgcgatac   3540
aataaaagac ctgcaggacg ctgggttcac ggagatcgac catcaaatag tgggactccc   3600
gctcaacccg tggcatcagg acgaacacga gcggaaggtg gcacgttggt ataacctggc   3660
cgtctcagag agcatcgaaa acctcagtct ggctcccttc agtcgtgtct atcgctggcc   3720
cctggagaga atccagcaac tcgccgcaga tgtgaagtcc gaagcattca acaaagagat   3780
ccatgcctac aatatactgc acatatacca ggctaggaaa ccattaagat aagagcaaaa   3840
ggcgaccaca tccaggaacg caaaacgaaa aggaggaaaa ctgctagcgc aagtttatgt   3900
cacgctggca cacgcccagc catcagaaat ctcaacagcg aaagttatga accgcatcaa   3960
ccgagtatga acgacaattc gtccatcaca caccccttcgg ttcctctcgc aggcccagca   4020
tggcgcccta tcaacctgct ttacgacgtc gtatatactg gcgaagtatc ctctctatct   4080
actctggcgc tctagatacc gtgaagatgc agacaaaatt ggccgagctc ccttctcata   4140
atcctcaagc ttggaccgat ggctgtgtag aagtactcgc cgatagtgga aaccgacgcc   4200
ccagcactcg tccgagggca aaggaataga gtagatgccg accgcgggat ccacttaacg   4260
ttactgaaat catcaaacag cttgacgaat ctggatataa gatcgttggt gtcgatgtca   4320
gctccggagt tgagacaaat ggtgttcagg atctcgataa gatacgttca tttgtccaag   4380
cagcaaagag tgccttctag tgatttaata gctccatgtc aacaagaata aaacgcgttt   4440
tcgggtttac ctcttccaga tacagctcat ctgcaatgca ttaatgcatt gactgcaacc   4500
tagtaacgcc ttncaggctc cggcgaagag aagaatagct tagcagagct attttcattt   4560
tcgggagacg agatcaagca gatcaacggt cgtcaagaga cctacgagac tgaggaatcc   4620
gctctctgac agacgggcaa ttgattacgg gatcccattg gtaacgaaat gtaaaagcta   4680
ggagatcgtc cgccgatgtc aggatgattt cacttgtttc ttgtccggct caccggtcaa   4740
agctaaagag gagcaaaagg aacggataga atcgggtgcc gctgatctat acggtatagt   4800
gcccttatca cgttgactca acccatgcta tttaactcaa cccctccttc tgaaccccac   4860
catcttcttc cttttcctct catcccacac aattctctat ctcagatttg aattccaaaa   4920
gtcctcggac gaaactgaac aagtcttcct cccttcgata aacctttggt gattggaata   4980
actgaccatc ttctatagtt cccaaaccaa ccgacaatgt aaatacactc ctcgattagc   5040
cctctagagg gcatacgatg gaagtcatgg aatacttttg gctggactct cacaatgatc   5100
aaggtatctt aggtaacgtc tttggcgtgg gccggtgttc gttcccagtc atcgatgcat   5160
tcacatgccc tccctaagct gggccctaga ctctaggatc ctagtctaga aggacatggc   5220
atcgatggac tgggttcgtt ctgagattat acggctaaaa cttgatctgg ataataccag   5280
```

```
cgaaaagggt catgccttct ctcgttcttc ctgttgatgg aatggctaac agatgatagt      5340
cattgcaact tgaaacatgt ctcctccagc tgccatctac gaacccactg tggccgctac      5400
cggcctcaag ggtaaggtcg tggtttctga gaccgtcccc gttgagggag cttctcagac      5460
caagctgttg gaccatttcg gtggcaagtg ggacgagttc aagttcgccc ctatccgcga      5520
aagccaggtc tctcgtgcca tgaccagacg ttactttgag gacctggaca agtacgctga      5580
aagtgacgtt gtcattgttg gtgctggttc ctgcggtctg agcactgcgt acgtcttggc      5640
caaggctcgt ccggacctga agattgctat cgtcgaggcc agcgtctctc ctggtcagta      5700
gtccatgatg gattgccttg cactcagctt tccggaacta acgtgcaata ggtggcggtg      5760
cctggttggg tggccaactc ttttctgcta tggtcatgcg ccgtcccgcg gaagtcttcc      5820
tgaacgagct gggtgttcct tacgaagagg acgcaaaccc caactacgtt gtcgtcaagc      5880
acgcctccct gtttacctcg acactcatgt cgaaggttct ctccttcccc aatgtcaagc      5940
tcttcaatgc taccgctgtt gaggacttga tcacccgtcc gaccgagaac ggcaaccccc      6000
agattgctgg tgttgtcgtc aactggacgc tggtcaccct tcaccacgat gatcactcct      6060
gcatggaccc caacactatc aacgctcctg tcatcatcag taccactggt cacgatgggc      6120
cattcggcgc cttctgtgcg aagcgcttgg tgtccatggg cagcgtcgac aagctaggtg      6180
gcatgcgtgg tctcgacatg aactcggccg aggatgccat cgtcaagaac acccgcgagg      6240
ttactaaggg cttgataatc ggcggtatgg agctgtctga aattgatggc tttaaccgca      6300
tgggccctac cttcggtgcc atggttctca gtggtgtcaa ggctgccgag gaggcattga      6360
aggtgttcga cgagcgtcag cgcgagtgtg ctgagtaaat gactcactac ccgaatgggt      6420
tcagtgcatg aaccggattt gtcttacggt ctttgacgat aggggaatga tgattatgtg      6480
atagttctga gatttgaatg aactcgttag ctcgtaatcc acatgcatat gtaaatggct      6540
gtgtcccgta tgtaacggtg gggcattcta gaataattat gtgtaacaag aaagacagta      6600
taatacaaac aaagatgcaa gagcggctcg tcatcgcaga taagcactgc tgtcttgcat      6660
ccaagtcagc gtcagcagaa atacgggact tccgaaagta tatggcaaaa ttaaagaact      6720
tgactctcca gcaatgtttt gccctgaccg tcgctaaaac gttactaccc ctatacccgt      6780
ctgtttgtcc cagcccgagg cattaggtct gactgacagc acggcgccat gcgggcttgg      6840
gacgccatgt ccgtcgcgtg ataagggttg atccatgcag ctactatcct tccatcgttc      6900
cattcccatc cttgtcctat ctccatcctt gaaactttac tagtttagtt ggatgctcga      6960
gcttgctctc ggctactccg tccaatggat aagaccccga tgccggtcct cattggtctc      7020
cagctggtat cgccccaacc ttcgtgtgat cgcctctctg cttcccctca tcatcattac      7080
taactagtac atccaaaagc catcccagtg cttcccctca cccttgccca agacattcca      7140
agtgggcctt cggctggaaa acatggaccc attggttcca tcgataagct agctcctcgt      7200
ccgttacccc agattgatac cagataacat tgaccagcgg cttatcaccg aggtctgcgg      7260
gtgagacccc ccctgcgaca agttagataa aagaaactcg cctcattgtg cttccgatgg      7320
ggtcggatga cgagccttcg gaaagagctg gcgcctcttt aaaggggaca gctgtcgcca      7380
agttgtgaaa ttctccgata actactaaca atctctccct tccttcccgc tactgtggtc      7440
accaaatcaa ctctctttc tcggccaaga tctaacatgg cggatgagaa gactgaaaag      7500
tctcccccac cgatgacggt ggatgaggag actggcacaa cagaggaaat tgacccgaca      7560
atggcaaagc atacgaagga tgcagacgag gcactggcgg tcttcgaaga cctccatggt      7620
gaagtcatca cacttgatga ggagacaaac aaaaggatac ttcggacaat tgactggcac      7680
```

-continued agtttaaac                                                                 7689

<210> SEQ ID NO 58
<211> LENGTH: 1270
<212> TYPE: DNA
<213> ORGANISM: Aspergillus niger
<220> FEATURE:
<221> NAME/KEY: CDS
<222> LOCATION: (1)..(230)
<220> FEATURE:
<221> NAME/KEY: Intron
<222> LOCATION: (231)..(372)
<220> FEATURE:
<221> NAME/KEY: CDS
<222> LOCATION: (373)..(1267)

<400> SEQUENCE: 58

```
atg ttt gaa atc agc cga ctt ttg cat cag cca att act atg gct tcg        48
Met Phe Glu Ile Ser Arg Leu Leu His Gln Pro Ile Thr Met Ala Ser
1               5                   10                  15 ccg aat cgc aat aac tac agc tac caa ggg ata gaa tcc tat gat tcc        96
Pro Asn Arg Asn Asn Tyr Ser Tyr Gln Gly Ile Glu Ser Tyr Asp Ser
            20                  25                  30 ggc cgt tcc agg caa aac tcg gat gct atg gac att cac gtc att acg       144
Gly Arg Ser Arg Gln Asn Ser Asp Ala Met Asp Ile His Val Ile Thr
        35                  40                  45 gcc caa gaa cct cct cga gaa ccc ccg gac aac aac gat cct tat gat       192
Ala Gln Glu Pro Pro Arg Glu Pro Pro Asp Asn Asn Asp Pro Tyr Asp
    50                  55                  60 ggc cat ggg ggt cca gct ggg act agc cat tat agc aa  gtacttctcc        240
Gly His Gly Gly Pro Ala Gly Thr Ser His Tyr Ser Lys
65                  70                  75 cttctcatac tctgcacccc acgtaccccg caaaatccct ttttctcatg ccgtgcaaat      300
atcacactta tttctacaac taccgggcga ctaattcagg gaactttctt ttccgttgtt      360
cgtttaatct ag g cct cca aac aga tgg ctc ttc tat gaa gaa aat ggg       409
              Pro Pro Asn Arg Trp Leu Phe Tyr Glu Glu Asn Gly
                            80                  85 cga aca tat cat gga tat cgc aga gga gtt tac ccg ctg cca tgc gat       457
Arg Thr Tyr His Gly Tyr Arg Arg Gly Val Tyr Pro Leu Pro Cys Asp
90                  95                  100                 105 gaa cag gaa cag gac cgt ctc gat atc ttc cat aaa ctg ttc aca gta       505
Glu Gln Glu Gln Asp Arg Leu Asp Ile Phe His Lys Leu Phe Thr Val
                110                 115                 120 gca cgg atg tcc gag agc tta atc tac gca cct cac ccc cca aat ggt       553
Ala Arg Met Ser Glu Ser Leu Ile Tyr Ala Pro His Pro Pro Asn Gly
            125                 130                 135 cga ttc cta gat ctg ggg tgc ggc act ggg atc tgg gcc att gat gta       601
Arg Phe Leu Asp Leu Gly Cys Gly Thr Gly Ile Trp Ala Ile Asp Val
        140                 145                 150 gcc cac aag tat ccc aat gct ttc gtt gct gga gta gat cta gca cct       649
Ala His Lys Tyr Pro Asn Ala Phe Val Ala Gly Val Asp Leu Ala Pro
    155                 160                 165 ata cag cct ccc aac cac ccc gat aac tgc gag ttc tat gca cct ttt       697
Ile Gln Pro Pro Asn His Pro Asp Asn Cys Glu Phe Tyr Ala Pro Phe
170                 175                 180                 185 gac ttt gag gcg cca tgg acg ctt ggg gaa aat tct tgg gat ctc att       745
Asp Phe Glu Ala Pro Trp Thr Leu Gly Glu Asn Ser Trp Asp Leu Ile
                190                 195                 200 cat cta cag atg ggt tgc ggc agt gtt ctg ggc tgg cag aat ctc tac       793
His Leu Gln Met Gly Cys Gly Ser Val Leu Gly Trp Gln Asn Leu Tyr
            205                 210                 215
```

```
aag cga atc tta agg cat ctt cag cct ggg gca tgg ttt gaa cag gtg      841
Lys Arg Ile Leu Arg His Leu Gln Pro Gly Ala Trp Phe Glu Gln Val
        220                 225                 230 gaa ata gat ttc gaa ccc cgc tgc gat gat cgc tcc ctg aat gga ctg      889
Glu Ile Asp Phe Glu Pro Arg Cys Asp Asp Arg Ser Leu Asn Gly Leu
235                 240                 245 gca ctc cgg gag tgg tac cag tac ctg aag cag gcg aca caa gat aca      937
Ala Leu Arg Glu Trp Tyr Gln Tyr Leu Lys Gln Ala Thr Gln Asp Thr
250                 255                 260                 265 atg cga ccc ata gcg cac agc tcg cgg gat acc atc aga cac ctt gag      985
Met Arg Pro Ile Ala His Ser Ser Arg Asp Thr Ile Arg His Leu Glu
                270                 275                 280 gag gca ggc ttt acc cag atc gac cat cag atg gtg ggg ctg cct ctc     1033
Glu Ala Gly Phe Thr Gln Ile Asp His Gln Met Val Gly Leu Pro Leu
        285                 290                 295 aac cct tgg cac cgt gat gaa cat gag cag aag gta gcc cgt tgg tat     1081
Asn Pro Trp His Arg Asp Glu His Glu Gln Lys Val Ala Arg Trp Tyr
300                 305                 310 aac ctc gca atc tct gag agt atc gag acg ctc agc ctc gcc cct ttc     1129
Asn Leu Ala Ile Ser Glu Ser Ile Glu Thr Leu Ser Leu Ala Pro Phe
315                 320                 325 agt cgc atc ttt cac tgg gat ctg gat agg atc aga cag atc aca gcg     1177
Ser Arg Ile Phe His Trp Asp Leu Asp Arg Ile Arg Gln Ile Thr Ala
330                 335                 340                 345 gag gtc aag tca caa gcc ttc aac aag gaa atc cac gct tac aat atc     1225
Glu Val Lys Ser Gln Ala Phe Asn Lys Glu Ile His Ala Tyr Asn Ile
                350                 355                 360 tta cat ata tac cag gca cgg aag ccg ggc ggc cca tca ctt tga         1270
Leu His Ile Tyr Gln Ala Arg Lys Pro Gly Gly Pro Ser Leu
        365                 370                 375

<210> SEQ ID NO 59
<211> LENGTH: 375
<212> TYPE: PRT
<213> ORGANISM: Aspergillus niger

<400> SEQUENCE: 59

Met Phe Glu Ile Ser Arg Leu Leu His Gln Pro Ile Thr Met Ala Ser
1               5                   10                  15

Pro Asn Arg Asn Asn Tyr Ser Tyr Gln Gly Ile Glu Ser Tyr Asp Ser
            20                  25                  30

Gly Arg Ser Arg Gln Asn Ser Asp Ala Met Asp Ile His Val Ile Thr
        35                  40                  45

Ala Gln Glu Pro Pro Arg Glu Pro Pro Asp Asn Asn Asp Pro Tyr Asp
    50                  55                  60

Gly His Gly Pro Ala Gly Thr Ser His Tyr Ser Lys Pro Pro Asn
65                  70                  75                  80

Arg Trp Leu Phe Tyr Glu Glu Asn Gly Arg Thr Tyr His Gly Tyr Arg
                85                  90                  95

Arg Gly Val Tyr Pro Leu Pro Cys Asp Glu Gln Glu Gln Asp Arg Leu
            100                 105                 110

Asp Ile Phe His Lys Leu Phe Thr Val Ala Arg Met Ser Glu Ser Leu
        115                 120                 125

Ile Tyr Ala Pro His Pro Pro Asn Gly Arg Phe Leu Asp Leu Gly Cys
    130                 135                 140

Gly Thr Gly Ile Trp Ala Ile Asp Val Ala His Lys Tyr Pro Asn Ala
145                 150                 155                 160
```

```
Phe Val Ala Gly Val Asp Leu Ala Pro Ile Gln Pro Pro Asn His Pro
                165                 170                 175

Asp Asn Cys Glu Phe Tyr Ala Pro Phe Asp Phe Glu Ala Pro Trp Thr
            180                 185                 190

Leu Gly Glu Asn Ser Trp Asp Leu Ile His Leu Gln Met Gly Cys Gly
        195                 200                 205

Ser Val Leu Gly Trp Gln Asn Leu Tyr Lys Arg Ile Leu Arg His Leu
    210                 215                 220

Gln Pro Gly Ala Trp Phe Glu Gln Val Glu Ile Asp Phe Glu Pro Arg
225                 230                 235                 240

Cys Asp Asp Arg Ser Leu Asn Gly Leu Ala Leu Arg Glu Trp Tyr Gln
                245                 250                 255

Tyr Leu Lys Gln Ala Thr Gln Asp Thr Met Arg Pro Ile Ala His Ser
            260                 265                 270

Ser Arg Asp Thr Ile Arg His Leu Glu Glu Ala Gly Phe Thr Gln Ile
        275                 280                 285

Asp His Gln Met Val Gly Leu Pro Leu Asn Pro Trp His Arg Asp Glu
    290                 295                 300

His Glu Gln Lys Val Ala Arg Trp Tyr Asn Leu Ala Ile Ser Glu Ser
305                 310                 315                 320

Ile Glu Thr Leu Ser Leu Ala Pro Phe Ser Arg Ile Phe His Trp Asp
                325                 330                 335

Leu Asp Arg Ile Arg Gln Ile Thr Ala Glu Val Lys Ser Gln Ala Phe
            340                 345                 350

Asn Lys Glu Ile His Ala Tyr Asn Ile Leu His Ile Tyr Gln Ala Arg
        355                 360                 365

Lys Pro Gly Gly Pro Ser Leu
    370                 375

<210> SEQ ID NO 60
<211> LENGTH: 6411
<212> TYPE: DNA
<213> ORGANISM: Artificial Sequence
<220> FEATURE:
<223> OTHER INFORMATION: transgene to complement alg3delta mutant

<400> SEQUENCE: 60
gtttaaacat gcatcattct cccgctttgt ttttgggccc aaactaaccg agtaggtgtg     60
gcatttgcgg gcatgatgtt tcaactaccg ctgatcatta tcaccgcccc attagagaag    120
atccaagacc ctactgggaa ggtgataggc aattccattt tctgggttag ttttttgtctt   180 gtcggccagc ctttgggagc tttgctgtac ttctttgcct ggcaagcgaa gtatggcagt    240
gtgagccgaa tgtgaatgta aaagcacgca cgtgtccgct gtttgtcata gatgtaaata    300
aatgccaaca acttcagcca ttttttgaaa agcaaagcaa ccgaagtaaa cgatcctgta    360
ccatcagcgc tcctcacaat ggaatctttt agatgtttct gttccattca tcttgcttac    420
tgcaatgttc ttttcgcgtt tgactaattc tccggatgtt gaatgcaac gctgtcggcg     480 tcgggtcttc agggatccgc caaggatgct ctggatccgc atccggccgc tcttgcgccc    540
catcaatcgc ccgactataa atcgaactac tttcggcatc ttctagactt cctaataccg    600
cctagtcata gcagattcaa gctgagaaca ccacaagtaa atatcaccca tcatgcttac    660
cctgaccgtc cctgaaaact acgggtatgt gccaattcta caattccttg cagacaatgc    720
cattctcccc atgaagtctg atgctaacta tcctgcagct ctgtcattgc cgtcgctctg    780
ggtgccatcc ccgtcctgag cttcgtccat ggcgccgtcg tgtctcgtct ccgcaaggaa    840
```

```
gctgattgcc cctaccctca ctgctatgcg accgtagagc agtgcaagac caacgtaagc    900
caacctcaca caaacaggat tcctcgagct aacatacatt ccgaaccgtg cagcccaagg    960
ccgagcagtt caactgcgct cagcgcgctc atgccaactt ccttgagaac tccagccaaa   1020
ctatgctctt cctcctggta gctggactga agtaccccca gttggcgact ggcctcggaa   1080
gcatctgggt cctcggtcgc tcactgttcc tttacggata tgtgtactcc ggcaagccgc   1140
ggggtcgcgg tcgtttgtac ggcagcttct acttgcttgc acaggagct ctctggggct    1200
tgacgtcttt tggagttgcg agggagttga tttcctactt ctaagtttgg actgaatccg   1260
tggtgtgatt gaggtgattg gcgatgtcgt gaccggtgac tctttctggc atgcggagag   1320
acggacggac gcagagagaa gggctgagta ataagccact ggccagacag ctctggcggc   1380
tctgaggtgc agtggatgat tattaatccg ggaccggccg cccctccgcc cgaagtgga    1440
aaggctggtg tgcccctcgt tgaccaagaa tctattgcat catcggagaa tatggagctt   1500
catcgaatca ccggcagtaa gcgaaggaga atgtgaagcc aggggtgtat agccgtcggc   1560
gaaatagcat gccattaacc taggtacaga agtccaattg cttccgatct ggtaaaagat   1620
tcacgagata gtaccttctc cgaagtaggt agagcgagta cccggcgcgt aagctcccta   1680
attggcccat ccggcatctg tagggcgtcc aaatatcgtg cctctcctgc tttgcccggt   1740
gtatgaaacc ggaaaggccg ctcaggagct ggccagcggc gcagaccggg aacacaagct   1800
ggcagtcgac ccatccggtg ctctgcactc gacctgctga ggtccctcag tccctggtag   1860
gcagctttgc cccgtctgtc cgcccggtgt gtcggcgggg ttgacaaggt cgttgcgtca   1920
gtccaacatt tgttgccata ttttcctgct ctccccacca gctgctcttt tcttttctct   1980
ttcttttccc atcttcagta tattcatctt cccatccaag aacctttatt tcccctaagt   2040
aagtactttg ctacatccat actccatcct tcccatccct tattcctttg aacctttcag   2100
ttcgagcttt cccacttcat cgcagcttga ctaacagcta ccccgcttga gcagacatca   2160
ccatggccaa gttgaccagt gccgttccgg tgctcaccgc gcgcgacgtc gccggagcgg   2220
tcgagttctg gaccgaccgg ctcgggttct cccgggactt cgtggaggac gacttcgccg   2280
gtgtggtccg ggacgacgtg accctgttca tcagcgcggt ccaggaccag gtggtgccgg   2340
acaacaccct ggcctgggtg tgggtgcgcg gcctggacga gctgtacgcc gagtggtcgg   2400
aggtcgtgtc cacgaacttc cgggacgcct ccgggccggc catgaccgag atcggcgagc   2460
agccgtgggg gcgggagttc gccctgcgcg accggccgg caactgcgtg cacttcgtgg   2520
ccgaggagca ggactgaccg acgccgacca acaccgccgg tccgacggcg cccacgggt    2580
cccaggagct tgagatccag gagcaggact gaccgacgcc gaccaacacc gccggtccga   2640
cgcggcccga cgggtccgag gcctcggaga tccgtcccc ttttcctttg tcgatatcat    2700
gtaattagtt atgtcacgct tacattcacg ccctcccccc acatccgctc taaccgaaaa   2760
ggaaggagtt agacaacctg aagtctaggt ccctatttat tttttttatag ttatgttagt  2820
attaagaacg ttatttatat ttcaaatttt tctttttttt ctgtacagac gcgtgtacgc   2880
atgtaacatt atactgaaaa ccttgcttga gaaggttttg gacgctcga agccgatgaa    2940
gaggtgtcta cgttcctaca attggaagaa gaagcacaga gattggccaa ggcaggccac   3000
gagtgtcctg ttcccaagcc tcgagggatt ctgggcgaat tgctgggttt tacgagtagt   3060
ggaggtatt cgacatcaac gacgacacag gcacaacagg ttggagaggg tcggtaaccg    3120
acaattggaa agcaaggagg actcaatcaa ggctaaaata ggctttgagc atgtacagcg   3180
```

-continued

```
tgaaggaact gtggattata tcacgaaata agccatgagg cagtcgtgtt ggcttcgacg    3240
gaggttggct tcggaaattt tcggccgggc accaaatccg acccatggca gcaatatacc    3300
catctttgta tcgatagtgt acttacaaaa actgtctact atatgattat gcatatgcga    3360
ttaaatacaa ctctcaattg atgcacaatt cgcctcaact tctatggtaa cgaacccacc    3420
tgttctgcag acatgcggcc gcgcggtctg tgtgtgtcca tgaacgctaa tcccaaacgg    3480
gacagctctc attggctctc cggcacgaag aggccacccg acatctacag ctgtagaaga    3540
aagtagctgg ttcaacaacc gcatgcaaga tggactggat gcgcctaatt cgcgatttgt    3600
gtttcaatcc ccgacacaca aaatggatgg ctccgctcct ggtcctgggt gacgcttttcc   3660 tctgcgcgct gatcatctgg aaagtgccct gtaaggctac agctaagctc cgttcacacc    3720
cttttgcgac aagtgaagca atgccactaa cctagccccg ttgctattgt ccacagatac    3780
cgagattgac tgggccacgt acatgcaaca aatatcgctt tatttgtcag gagaacgcga    3840
ttatactctc atcagaggat caaccggtcc ccttgtctac ccggccgccc atgtatacag    3900
ttatacggcc ctctaccatc tcaccgatga ggggcgcgat atttt cttcg gtcagatact    3960 atttgctgtg ctctacttga tcacgctggt ggttgtgctg tgctgttata gacagtcggg    4020
tgctccgccg tacttgcttc cgctgctggt cctttccaag agacttcaca gcgtttatgt    4080
cctgcgtctg ttcaatgatg gcttggcggc gctggcgatg tgggttgcca ttctgttatt    4140
catgaatcgg aagtggacgg ctgccggtcgc agtgtggtct actggtgttg cgattaagat    4200
gacactgttg ctgctggccc cggctattgc tgtggtcacg gtgcttagtc tgtcgcttgg    4260
tcctagcgtg gggctggggg ttctggccggt gcttgtccag gtaggttccc atgaggctgt    4320
agggttggcc aaaggcaatt tgtgtgaaga cttgtctgac attgaactac aggttttact    4380 cgcgatacog ttcctacaaa acaacccggc ggggtatctc tcgcgggcgt tcgagctaac    4440
cagacagttc atgtttaaat ggacagtcaa ttggagattt gttggcgaag aagtattctt    4500
atctaagagc ttttccctgg cattgctggc cgtccacatt gtgctgctag cgcttttgc     4560 cgtcactggt tggctgagat actccaggtc tagcttgcct gcgttcattc ggaatctgct    4620
agcgggtcga catcgcacag tgtccctccc caaacccctac atcatgagcg tgatgctctc    4680
gtctctgaca gttggcttgt tgtgcgcaag gtcccttcat taccaattct tcgcctacct    4740
ctcctgggcg acaccttcc tcctctggcg cgcagggttt catccaatct tgctgtacct    4800
tatctgggct atgcaagagt gggcttggaa cacattcccc agcaccaacc tcagttccat    4860
cattgttgtc ctctcacttg ctacccgagt tttcggcgtc cttgcgaata gtgccagcgc    4920 ctttatacc atgcgttcga accctagcgg taaagagcat aaccaataga agtgacaccc    4980
ggccagtatc gagatcgggc tgtgacaggt gcatcgataa tcgcaatcag tcttgtaccc    5040
atgagaatcc ctgaaaaagt aagactgctc tgtcaggtag tccattgccc atgcgatagg    5100
ttcggacgcc taaaggatca atcaagatgc caatcaagca tccgactcat cggaagaagg    5160
catcttgccg acattggact catcctcttc gtccgagtcg tcggcgacaa cagcagcttg    5220
cttagcgatg gtgtggcaca aggatcaatg cggtacgacg atttgatgca gataagcagg    5280
ctgcgaagta gtaactcttg cgtagagaaa atgcgacgg gtggctgata agggcggtga     5340
taagcttaat tgtcatcgca gataagcact gctgtcttgc atccaagtca gcgtcagcag    5400
aaatacggga cttccgaaag tatatggcaa aattaaagaa cttgactctc cagcaatgtt    5460
ttgccctgac cgtcgctaaa acgttactac ccctataccc gtctgtttgt cccagcccga    5520
ggcattaggt ctgactgaca gcacggcgcc atgcgggctt gggacgccat gtccgtcgcg    5580
```

```
tgataagggt tgatccatgc agctactatc cttccatcgt tccattccca tccttgtcct    5640
atctccatcc ttgaaacttt actagtttag ttggatgctc gagcttgctc tcggctactc    5700
cgtccaatgg ataagacccc gatgccggtc ctcattggtc tccagctggt atcgccccaa    5760
ccttcgtgtg atcgcctctc tgcttcccct catcatcatt actaactagt acatccaaaa    5820
gccatcccag tgcttcccct caccccttgcc caagacattc caagtgggcc ttcggctgga    5880
aaacatggac ccattggttc catcgataag ctagctcctc gtccgttacc ccagattgat    5940
accagataac attgaccagc ggcttatcac cgaggtctgc gggtgagacc ccccctgcga    6000
caagttagat aaaagaaact cgcctcattg tgcttccgat ggggtcggat gacgagcctt    6060
cggaaagagc tggcgcctct ttaaagggga cagctgtcgc caagttgtga aattctccga    6120
taactactaa caatctctcc cttccttccc gctactgtgg tcaccaaatc aactctcttt    6180
tctcggccaa gatctaacat ggcggatgag aagactgaaa agtctccccc accgatgacg    6240
gtggatgagg agactggcac aacagaggaa attgacccga caatggcaaa gcatacgaag    6300
gatgcagacg aggcactggc ggtcttcgaa gacctccatg gtgaagtcat cacacttgat    6360
gaggagacaa acaaaaggat acttcggaca attgactggc acagtttaaa c             6411

<210> SEQ ID NO 61
<211> LENGTH: 899
<212> TYPE: DNA
<213> ORGANISM: Aspergillus niger

<400> SEQUENCE: 61
tcaagacagc ggctgcaaca accttaaagg cagggttgct ttgcttttg ccttctttcc      60 tctgccctct attccacccc ccctctctct tcccccctct ccgctgtccg aatggacttg    120
cacttccggg atcggatttt ccctttctga tccgatgatc cagtccaatt gacctaactc    180
tcgatcgtcc tcccccgatc catggttgtt ctttagtcgc ctctctcctc gtaacgcctg    240
acacctgctg ctgttatcga taccctattt attatttatt atttatttt tttccctatt     300 ttcctatgcc gctgccgtga ccgctacttt tctcttttgt tctctccccc ccgacgggtt    360
cctgtccttg cggggaggag acttttttcc ccctacctat ttagtatcct cattcctcct    420
tgtgcctcgg ccgagatttg gagatactct tctccaccgt gtgtgactgt gggtgtgcgc    480
atgcacgggt gtgcgtgcct ctttgctctc atacaactct cctgggttgg ggcaaattta    540
caccattgtg gactttggat cattcttact tactatcctt ggcttttgc tctccggctt     600 tccactctcc tccttcttcc aatccttta ccccttctcg gccactgatt cattccgcgg      660 aggataccccc cagttagtag ttttgtggtt gccgtctttt cgtctgatca gctttttcaat 720 ccaatcattg gctcaattg cggcgccgaa ctccaacttc ctctatgtgc cacctgactt     780
acgattcccc gatatcacct gcagcctgca tacaccctgt tggctaacat ggcgttttta    840
cgttaccgtc acgaagaacg ccggtctctt tgattgaacg aacccctgta tctctacca    899

<210> SEQ ID NO 62
<211> LENGTH: 1012
<212> TYPE: DNA
<213> ORGANISM: Aspergillus niger

<400> SEQUENCE: 62
tcagtcgcat ctttcactgg gatctggata ggatcagaca gatcacagcg gaggtcaagt     60
cacaagcctt caacaaggaa atccacgctt acaatatctt acatatatac caggcacgga    120
```

| | |
|---|---|
| agccgggcgg cccatcactt tgaaagtaca gagaaaatta cggcagtgcc ggctgtaatg | 180 |
| cagatttcat tccggatacc catatgcagc cttttgtggg agggccatcc tacctgttct | 240 |
| cttcttttg ttcattccat ttttttctcg atgaggatta gtgacgacca attccatctc | 300 |
| cttgacggga tcatactgaa atgcttatac accaaagcga gcaaagccca caaaaccatc | 360 |
| actggacttg aactcgtacc aacactgcta gtttgacgca agaatgccag gaacgcagac | 420 |
| aggcttatct tcattgtgtt attgcctact ttagtgcaga cagctgaacg gcacaaaggg | 480 |
| acgcgaagta tattatcaat cacaccatgt ggattgttac cgtcgcaaaa gatactgctc | 540 |
| gaggttttaa ataatagaag cacttcaaga agatgaggtg ccgttgtcgg gactcgaaga | 600 |
| agtggccgac gactataaag taccagattt gccaggatcc aaaagaagct accaatctca | 660 |
| tgttgcattt ttggaaagcc ctgtaattca ggccggctga actgcggaga tcccagaatc | 720 |
| atggcagttg actgagtact tgtcgtgacg ggccctaaac atcagccatt ccatccgaac | 780 |
| tcaaaactct ctgatgaccg tggcggctct gtggcacagc caccgataat tttttttgtt | 840 |
| ggcacttatt aatgaattag atgagaaaga agcgaagaac cgagggcttg aacaaacgca | 900 |
| aagccctcca aatggttact attgaacttt ttgctctccc accgaaactc ccactgatca | 960 |
| tgtaccgtaa gtatatcgaa aaatatgcca tgtcccttga cacagcctac ca | 1012 |

<210> SEQ ID NO 63
<211> LENGTH: 1360
<212> TYPE: DNA
<213> ORGANISM: Artificial Sequence
<220> FEATURE:
<223> OTHER INFORMATION: Synthetic polynucleotide (hph expression cassette)

<400> SEQUENCE: 63

| | |
|---|---|
| gctggagcta gtggaggtca acacatcaat gctattttgg tttagtcgtc caggcggatc | 60 |
| acaaatttg tgtcgtttga caagatggtt catttaggca actggtcaga tcagcccact | 120 |
| tgtaagcagt agcggcggcg ctcgaagtgt gactcttatt agcagacagg aacgaggaca | 180 |
| ttattatcat ctgctgcttg gtgcacgata acttgtgcgt ttgtcaagca aggtaagtga | 240 |
| acgacccggt cataccttct taagttcgcc cttcctccct ttatttcaga ttcaatctga | 300 |
| cttacctatt ctacccaagc atccaaatgc ctgaactcac cgcgacgtct gtcgagaagt | 360 |
| ttctgatcga aaagttcgac agcgtctccg acctgatgca gctctcggag ggcgaagaat | 420 |
| ctcgtgcttt cagcttcgat gtaggagggc gtggatatgt cctgcgggta aatagctgcg | 480 |
| ccgatggttt ctacaaagat cgttatgttt atcggcactt tgcatcggcc gcgctcccga | 540 |
| ttccggaagt gcttgacatt ggggagttca gcgagagcct gacctattgc atctcccgcc | 600 |
| gtgcacaggg tgtcacgttg caagacctgc ctgaaaccga actgcccgct gttctggagc | 660 |
| cggtcgcgga ggccatggat gcgatcgctg cggccgatct tagccagacg agcgggttcg | 720 |
| gcccattcgg accgcaagga atcggtcaat acactacatg gcgtgatttc atatgcgcga | 780 |
| ttgctgatcc ccatgtgtat cactggcaaa ctgtgatgga cgacaccgtc agtgcgtccg | 840 |
| tcgcgcaggc tctcgatgag ctgatgcttt gggccgagga ctgccccgaa gtccggcacc | 900 |
| tcgtgcacgc ggatttcggc tccaacaatg tcctgacgga caatggccgc ataacagcgg | 960 |
| tcattgactg agcgaggcg atgttcgggg attcccaata cgaggtcgcc aacatcttct | 1020 |
| tctggaggcc gtggttggct tgtatggagc agcagacgcg ctacttcgag cggaggcatc | 1080 |
| cggagcttgc aggatcgccg cgcctccggg cgtatatgct ccgcattggt cttgaccaac | 1140 |

```
tctatcagag cttggttgac ggcaatttcg atgatgcagc ttgggcgcag ggtcgatgcg   1200
acgcaatcgt ccgatccgga gccgggactg tcgggcgtac acaaatcgcc cgcagaagcg   1260
cggccgtctg gaccgatggc tgtgtagaag tactcgccga tagtggaaac cgacgcccca   1320
gcactcgtcc gagggcaaag gaatagagta gatgccgacc                         1360
```

<210> SEQ ID NO 64
<211> LENGTH: 2340
<212> TYPE: DNA
<213> ORGANISM: Aspergillus niger

<400> SEQUENCE: 64

```
tctctcctcg taacgcctga cacctgctgc tgttatcgat accctatttta ttatttatta   60 tttattttt ttccctattt tcctatgccg ctgccgtgac cgctactttt ctcttttgtt    120 ctctccccccc cgacgggttc ctgtccttgc ggggaggaga cttttttccc cctacctatt  180
tagtatcctc attcctcctt gtgcctcggc cgagatttgg agatactctt ctccaccgtg   240
tgtgactgtg ggtgtgcgca tgcacgggtg tgcgtgcctc tttgctctca tacaactctc   300
ctgggttggg gcaaatttac accattgtgg actttggatc attcttactt actatccttg   360 gcttttgct ctccggcttt ccactctcct ccttcttcca atccttttac cccttctcgg    420
ccactgattc attccgcgga ggatacccccc agttagtagt tttgtggttg ccgtcttttc  480
gtctgatcag cttttcaatc caatcattgg ctcaatttgc ggcgccgaac tccaacttcc   540
tctatgtgcc acctgactta cgattccccg atatcacctg cagcctgcat acaccctgtt   600
ggctaacatt ggcgttttac gttaccgtca cgaagaacgc cggtctcttt gattgaacga   660 accctgtat ctctaccata ccttgagcag gaaaagtcga atctcttccc agcgaaccga    720
tccttggact tcagggttcc atgtttgaaa tcagccgact tttgcatcag ccaattacta   780
tggcttcgcc gaatcgcaat aactacagct accaagggat agaatcctat gattccggcc   840
gttccaggca aaactcggat gctatggaca ttcacgtcat tacggcccaa gaacctcctc   900
gagaaccccc ggacaacaac gatccttatg atggccatgg gggtccagct gggactagcc   960
attatagcaa gtacttctcc cttctcatac tctgcacccc acgtacccccg caaaatccct  1020 ttttctcatg ccgtgcaaat atcacactta tttctacaac taccgggcga ctaattcagg   1080
gaactttctt ttccgttgtt cgtttaatct aggcctccaa acagatggct cttctatgaa   1140
gaaaatgggc gaacatatca tggatatcgc agaggagttt acccgctgcc atgcgatgaa   1200
caggaacagg accgtctcga tatcttccat aaactgttca cagtagcacg gatgtccgag   1260
agcttaatct acgcacctca cccccccaaat ggtcgattcc tagatctggg gtgcggcact   1320
gggatctggg ccattgatgt agcccacaag tatcccaatg ctttcgttgc tggagtagat   1380
ctagcaccta tacagcctcc caaccacccc gataactgcg agttctatgc acctttttgac 1440 tttgaggcgc catggacgct tggggaaaat tcttgggatc tcattcatct acagatgggt   1500
tgcggcagtg ttctgggctg gcagaatctc tacaagcgaa tcttaaggca tcttcagcct   1560
ggggcatggt ttgaacaggt ggaaatagat ttcgaacccc gctgcgatga tcgctccctg   1620
aatggactgg cactccggga gtggtaccag tacctgaagc aggcgacaca agatacaatg   1680
cgacccatag cgcacagctc gcgggatacc atcagacacc ttgaggaggc aggctttacc   1740
cagatcgacc atcagatggt ggggctgcct ctcaacccctt ggcaccgtga tgaacatgag   1800
cagaaggtag cccgttggta taacctcgca atctctgaga gtatcgagac gctcagcctc   1860 gccccttttca gtcgcatctt tcactgggat ctggataggga tcagacagat cacagcggag  1920
```

```
gtcaagtcac aagccttcaa caaggaaatc cacgcttaca atatcttaca tatataccag    1980
gcacggaagc cgggcggccc atcactttga aagtacagag aaaattacgg cagtgccggc    2040
tgtaatgcag atttcattcc ggatacccat atgcagcctt tgtgggagg gccatcctac     2100 ctgttctctt cttttgttc attccatttt tttctcgatg aggattagtg acgaccaatt     2160
ccatctcctt gacgggatca tactgaaatg cttatacacc aaagcgagca agcccacaa     2220 aaccatcact ggacttgaac tcgtaccaac actgctagtt tgacgcaaga atgccaggaa    2280
cgcagacagg cttatcttca ttgtgttatt gcctacttta gtgcagacag ctgaacggca    2340
```

<210> SEQ ID NO 65
<211> LENGTH: 3306
<212> TYPE: DNA
<213> ORGANISM: Artificial Sequence
<220> FEATURE:
<223> OTHER INFORMATION: Synthetic polynucleotide (laeA deletion cassette)

<400> SEQUENCE: 65

```
aagcttcaag acagcggctg caacaacctt aaaggcaggg ttgctttgct ttttgccttc      60
tttcctctgc cctctattcc accccccctc tctcttcccc cctctccgct gtccgaatgg     120
acttgcactt ccgggatcgg attttccctt tctgatccga tgatccagtc caattgacct    180
aactctcgat cgtcctcccc cgatccatgg ttgttcttta gtcgcctctc tcctcgtaac    240
gcctgacacc tgctgctgtt atcgataccc tatttattat ttattattta ttttttttcc    300 ctatttcct atgccgctgc cgtgaccgct acttttctct tttgttctct cccccccgac     360
gggttcctgt ccttgcgggg aggagacttt tttccccta cctatttagt atcctcattc     420
ctccttgtgc ctcggccgag atttggagat actcttctcc accgtgtgtg actgtgggtg    480
tgcgcatgca cgggtgtgcg tgcctctttg ctctcataca actctcctgg gttggggcaa    540
atttacacca ttgtggactt tggatcattc ttacttacta tccttggctt tttgctctcc    600
ggctttccac tctcctcctt cttccaatcc ttttaccct tctcggccac tgattcattc     660
cgcggaggat accccagtt agtagttttg tggttgccgt cttttcgtct gatcagcttt     720
tcaatccaat cattggctca atttgcggcg ccgaactcca acttcctcta tgtgccacct    780
gacttacgat tccccgatat cacctgcagc ctgcatacac cctgttggct aacattggcg    840
ttttacgtta ccgtcacgaa gaacgccggt ctctttgatt gaacgaaccc ctgtatctct    900
accacggtcg gcatctactc tattcctttg ccctcggacg agtgctgggg cgtcggtttc    960
cactatcggc gagtacttct acacagccat cggtccagac ggccgcgctt ctgcgggcga   1020
tttgtgtacg cccgacagtc ccggctccgg atcggacgat tgcgtcgcat cgaccctgcg   1080
cccaagctgc atcatcgaaa ttgccgtcaa ccaagctctg atagagttgg tcaagaccaa   1140
tgcggagcat atacgcccgg aggcgcggcg atcctgcaag ctccggatgc ctccgctcga   1200
agtagcgcgt ctgctgctcc atacaagcca accacgcct ccagaagaag atgttggcga    1260
cctcgtattg ggaatccccg aacatcgcct cgctccagtc aatgaccgct gttatgcggc   1320
cattgtccgt caggacattg ttggagccga atccgcgtg cacgaggtgc cggacttcgg    1380
ggcagtcctc ggcccaaagc atcagctcat cgagagcctg cgcgacggac gcactgacgg   1440
tgtcgtccat cacagtttgc cagtgataca catgggatc agcaatcgcg catatgaaat    1500
cacgccatgt agtgtattga ccgattcctt gcggtccgaa tgggccgaac ccgctcgtct   1560
ggctaagatc ggccgcagcg atcgcatcca tggcctccgc gaccggctcc agaacagcgg   1620
```

```
gcagttcggt tcaggcagg tcttgcaacg tgacaccctg tgcacggcgg gagatgcaat    1680
aggtcaggct ctcgctgaac tccccaatgt caagcacttc cggaatcggg agcgcggccg    1740
atgcaaagtg ccgataaaca taacgatctt tgtagaaacc atcggcgcag ctatttaccc    1800
gcaggacata tccacgccct cctacatcga agctgaaagc acgagattct tcgccctccg    1860
agagctgcat caggtcggag acgctgtcga acttttcgat cagaaacttc tcgacagacg    1920
tcgcggtgag ttcaggcatt tggatgcttg ggtagaatag gtaagtcaga ttgaatctga    1980
aataaaggga ggaagggcga acttaagaag gtatgaccgg gtcgttcact taccttgctt    2040
gacaaacgca caagttatcg tgcaccaagc agcagatgat aataatgtcc tcgttcctgt    2100
ctgctaataa gagtcacact tcgagcgccg ccgctactgc ttacaagtgg gctgatctga    2160
ccagttgcct aaatgaacca tcttgtcaaa cgacacaaat tttgtgatcc gcctggacga    2220
ctaaaccaaa atagcattga tgtgttgacc tccactagct ccagctcagt cgcatctttc    2280
actgggatct ggataggatc agacagatca cagcggaggc caagtcacaa gccttcaaca    2340
aggaaatcca cgcttacaat atcttacata tataccaggc acggaagccg ggcggcccat    2400
cactttgaaa gtacagagaa aattacggca gtgccggctg taatgcagat ttcattccgg    2460 atcccatat gcagccttt gtgggagggc catcctacct gttctcttct ttttgttcat    2520
tccatttttt tctcgatgag gattagtgac gaccaattcc atctccttga cgggatcata    2580
ctgaaatgct tatacaccaa agcgagcaaa gcccacaaaa ccatcactgg acttgaactc    2640
gtaccaacac tgctagtttg acgcaagaat gccaggaacg cagacaggct tatcttcatt    2700
gtgttattgc ctactttagt gcagacagct gaacggcaca aagggacgcg aagtatatta    2760
tcaatcacac catgtggatt gttaccgtcg caaaagatac tgctcgaggt tttaaataat    2820
agaagcactt caagaagatg aggtgccgtt gtcgggactc gaagaagtgg ccgacgacta    2880
taaagtacca gatttgccag gatccaaaag aagctaccaa tctcatgttg cattttgga    2940 aagccctgta attcaggccg gctgaactgc ggagatccca gaatcatggc agttgactga    3000
gtacttgtcg tgacgggccc taaacatcag ccattccatc cgaactcaaa actctctgat    3060
gaccgtggcg gctctgtggc acagccaccg ataatttttt ttgttggcac ttattaatga    3120
attagatgag aaagaagcga agaaccgagg gcttgaacaa acgcaaagcc ctccaaatgg    3180
ttactattga acttttgct ctcccaccga aactcccact gatcatgtac cgtaagtata    3240
tcgaaaaata tgccatgtcc cttgagacag cctaccatgc agcccggggg atccactagt    3300
tctaga                                                                 3306
```

<210> SEQ ID NO 66
<211> LENGTH: 7163
<212> TYPE: DNA
<213> ORGANISM: Artificial Sequence
<220> FEATURE:
<223> OTHER INFORMATION: Synthetic polynucleotide (LaeA complementation
      construct)

<400> SEQUENCE: 66

```
gtttaaacat gcatcattct cccgctttgt ttttgggccc aaactaaccg agtaggtgtg      60
gcatttgcgg gcatgatgtt tcaactaccg ctgatcatta tcaccgcccc attagagaag     120
atccaagacc ctactgggaa ggtgataggc aattccattt tctgggttag ttttttgtctt    180 gtcggccagc ctttgggagc tttgctgtac ttctttgcct ggcaagcgaa gtatggcagt    240
gtgagccgaa tgtgaatgta aaagcacgca cgtgtccgct gtttgtcata gatgtaaata    300
```

```
aatgccaaca acttcagcca tttttttgaaa agcaaagcaa ccgaagtaaa cgatcctgta    360
ccatcagcgc tcctcacaat ggaatctttt agatgtttct gttccattca tcttgcttac    420
tgcaatgttc ttttcgcgtt tgactaattc tccggatgtt gaatggcaac gctgtcggcg    480
tcgggtcttc agggatccgc caaggatgct ctggatccgc atccggccgc tcttgcgccc    540
catcaatcgc ccgactataa atcgaactac tttcggcatc ttctagactt cctaataccg    600
cctagtcata gcagattcaa gctgagaaca ccacaagtaa atatcaccca tcatgcttac    660
cctgaccgtc cctgaaaact acgggtatgt gccaattcta caattccttg cagacaatgc    720
cattctcccc atgaagtctg atgctaacta tcctgcagct ctgtcattgc cgtcgctctg    780
ggtgccatcc ccgtcctgag cttcgtccat ggcgccgtcg tgtctcgtct ccgcaaggaa    840
gctgattgcc cctaccctca ctgctatgcg accgtagagc agtgcaagac caacgtaagc    900
caacctcaca caaacaggat tcctcgagct aacatacatt ccgaaccgtg cagcccaagg    960
ccgagcagtt caactgcgct cagcgcgctc atgccaactt ccttgagaac tccagccaaa    1020
ctatgctctt cctcctggta gctggactga agtaccccca gttggcgact ggcctcggaa    1080
gcatctgggt cctcggtcgc tcactgttcc tttacggata tgtgtactcc ggcaagccgc    1140
ggggtcgcgg tcgtttgtac ggcagcttct acttgcttgc acagggagct ctctggggct    1200
tgacgtcttt tggagttgcg agggagttga tttcctactt ctaagtttgg actgaatccg    1260
tggtgtgatt gaggtgattg gcgatgatgc cgttcagctg tctgcactaa agtaggcaat    1320
aacacaatga agataagcct gtctgcgttc ctggcattct tgcgtcaaac tagcagtgtt    1380
ggtacgagtt caagtccagt gatggttttg tgggctttgc tcgctttggt gtataagcat    1440
ttcagtatga tcccgtcaag gagatggaat tggtcgtcac taatcctcat cgagaaaaaa    1500
atggaatgaa caaaaagaag agaacaggta ggatggccct cccacaaaag gctgcatatg    1560
ggtatccgga atgaaatctg cattacagcc ggcactgccg taattttctc tgtactttca    1620
aagtgatggg ccgcccggct tccgtgcctg gtatatatgt aagatattgt aagcgtggat    1680
ttccttgttg aaggcttgtg acttgacctc cgctgtgatc tgtctgatcc tatccagatc    1740
ccagtgaaag atgcgactga aaggggcgag gctgagcgtc tcgatactct cagagattgc    1800
gaggttatac caacgggcta ccttctgctc atgttcatca cggtgccaag ggttgagagg    1860
cagccccacc atctgatggt cgatctgggt aaagcctgcc tcctcaaggt gtctgatggt    1920
atcccgcgag ctgtgcgcta tgggtcgcat tgtatcttgt gtcgcctgct tcaggtactg    1980
gtaccactcc cggagtgcca gtccattcag ggagcgatca tcgcagcggg gttcgaaatc    2040
tatttccacc tgttcaaacc atgccccagg ctgaagatgc cttaagattc gcttgtagag    2100
attctgccag cccagaacac tgccgcaacc catctgtaga tgaatgagat cccaagaatt    2160
ttccccaagc gtccatggcg cctcaaagtc aaaaggtgca tagaactcgc agttatcggg    2220
gtggttggga ggctgtatag gtgctagatc tactccagca acgaaagcat gggatactt    2280 gtgggctaca tcaatggccc agatcccagt gccgcacccc agatctagga atcgaccatt    2340 tgggggggtga ggtgcgtaga ttaagctctc ggacatccgt gctactgtga acagtttatg    2400
gaagatatcg agacggtcct gttcctgttc atcgcatggc agcgggtaaa ctcctctgcg    2460
atatccatga tatgttcgcc catttcttc atagaagagc catctgtttg gaggcctaga    2520
ttaaacgaac aacggaaaag aaagttccct gaattagtcg cccggtagtt gtagaaataa    2580
gtgtgatatt tgcacggcat gagaaaaagg gattttgcgg ggtacgtggg gtgcagagta    2640
```

```
tgagaaggga gaagtacttg ctataatggc tagtcccagc tggacccca  tggccatcat  2700
aaggatcgtt gttgtccggg ggttctcgag gaggttcttg gccgtaatg  acgtgaatgt  2760
ccatagcatc cgagttttgc ctggaacggc cggaatcata ggattctatc ccttggtagc  2820
tgtagttatt gcgattcggc gaagccatag taattggctg atgcaaaagt cggctgattt  2880
caaacatgga accctgaagt ccaaggatcg gttcgctggg aagagattcg acttttcctg  2940
ctcaaggtat ggtagagata caggggttcg ttcaatcaaa gagaccggcg ttcttcgtga  3000
cggtaacgta aaacgccaat gttagccaac agggtgtatg caggctgcag gtgatatcgg  3060
ggaatcgtaa gtcaggtggc acatagagga agttggagtt cggcgccgca aattgagcca  3120
atgattggat tgaaaagctg atcagacgaa aagacggcaa ccacaaaact actaactggg  3180
ggtatcctcc gcggaatgaa tcagtggccg agaaggggta aaaggattgg aagaaggagg  3240
agagtggaaa gccggagagc aaaaagccaa ggatagtaag taagaatgat ccaaagtcca  3300
caatggtgta aatttgcccc aacccaggag agttgtatga gagcaaagag gcacgcacac  3360
ccgtgcatgc gcacacccac agtcacacac ggtggagaag agtatctcca aatctcggcc  3420
gaggcacaag gaggaatgag gatactaaat aggtaggggg aaaaaagtct cctccccgca  3480
aggacaggaa cccgtcgggg gggagagaac aaaagagaaa agtagcggtc acggcagcgg  3540
cataggaaaa tagggaaaaa aaataaataa taaataataa atagggtatc gataacagca  3600
gcaggtgtca ggcgttacga ggagagatgg accgatggct gtgtagaagt actcgccgat  3660
agtggaaacc gacgcccag  cactcgtccg agggcaaagg aatagagtag atgccgaccg  3720
cgggatccac ttaacgttac tgaaatcatc aaacagcttg acgaatctgg atataagatc  3780
gttggtgtcg atgtcagctc cggagttgag acaaatggtg ttcaggatct cgataagata  3840
cgttcatttg tccaagcagc aaagagtgcc ttcagtgat  ttaatagctc catgtcaaca  3900
agaataaaac gcgttttcgg gtttacctct tccagataca gctcatctgc aatgcattaa  3960
tgcattgact gcaacctagt aacgccttca ggctccggcg aagagaagaa tagcttagca  4020
gagctatttt cattttcggg agacgagatc aagcagatca acggtcgtca agagacctac  4080
gagactgagg aatccgctct ctgacagacg ggcaattgat tacgggatcc cattggtaac  4140
gaaatgtaaa agctaggaga tcgtccgccg atgtcaggat gatttcactt gtttcttgtc  4200
cggctcaccg gtcaaagcta aagaggagca aaaggaacgg atagaatcgg gtgccgctga  4260
tctatacggt atagtgccct tatcacgttg actcaaccca tgctatttaa ctcaacccct  4320
ccttctgaac cccaccatct tcttcctttt cctctcatcc cacacaattc tctatctcag  4380
atttgaattc caaaagtcct cggacgaaac tgaacaagtc ttcctcccct cgataaacct  4440
ttggtgattg gaataactga ccatcttcta tagttcccaa accaaccgac aatgtaaata  4500
cactcctcga ttagccctct agagggcata cgatggaagt catggaatac ttttggctgg  4560
actctcacaa tgatcaaggt atcttaggta acgtctttgg cgtgggccgg tgttcgttcc  4620
cagtcatcga tgcattcaca tgccctccct aagctgggcc ctagactcta ggatcctagt  4680
ctagaaggac atggcatcga tggactgggt tcgttctgag attatacggc taaaacttga  4740
tctggataat accagcgaaa aggtcatgc  cttctctcgt tcttcctgtt gatggaatgg  4800
ctaacagatg atagtcattg caacttgaaa catgtctcct ccagctgcca tctacgaacc  4860
cactgtggcc gctaccggcc tcaagggtaa ggtcgtggtt tctgagaccg tcccgttga   4920
gggagcttct cagaccaagc tgttggacca tttcggtggc aagtgggacg agttcaagtt  4980
cgcccctatc cgcgaaagcc aggtctctcg tgccatgacc agacgttact ttgaggacct  5040
```

```
ggacaagtac gctgaaagtg acgttgtcat tgttggtgct ggttcctgcg gtctgagcac    5100
tgcgtacgtc ttggccaagg ctcgtccgga cctgaagatt gctatcgtcg aggccagcgt    5160
ctctcctggt cagtagtcca tgatggattg ccttgcactc agctttccgg aactaacgtg    5220
caataggtgg cggtgcctgg ttgggtggcc aactcttttc tgctatggtc atgcgccgtc    5280
ccgcggaagt cttcctgaac gagctgggtg ttccttacga agaggacgca aaccccaact    5340
acgttgtcgt caagcacgcc tccctgttta cctcgacact catgtcgaag gttctctcct    5400
tccccaatgt caagctcttc aatgctaccg ctgttgagga cttgatcacc cgtccgaccg    5460
agaacggcaa ccccccagatt gctggtgttg tcgtcaactg gacgctggtc acccttcacc    5520
acgatgatca ctcctgcatg gaccccaaca ctatcaacgc tcctgtcatc atcagtacca    5580
ctggtcacga tgggccattc ggcgccttct gtgcgaagcg cttggtgtcc atgggcagcg    5640
tcgacaagct aggtggcatg cgtggtctcg acatgaactc ggccgaggat gccatcgtca    5700
agaacacccg cgaggttact aagggcttga taatcggcgg tatggagctg tctgaaattg    5760
atggctttaa ccgcatgggc cctaccttcg gtgccatggt tctcagtggt gtcaaggctg    5820
ccgaggaggc attgaaggtg ttcgacgagc gtcagcgcga gtgtgctgag taaatgactc    5880
actacccgaa tgggttcagt gcatgaaccg gatttgtctt acggtctttg acgatagggg    5940
aatgatgatt atgtgatagt tctgagattt gaatgaactc gttagctcgt aatccacatg    6000
catatgtaaa tggctgtgtc ccgtatgtaa cggtggggca ttctagaata attatgtgta    6060
acaagaaaga cagtataata caaacaaaga tgcaagagcg gctcgtcatc gcagataagc    6120
actgctgtct tgcatccaag tcagcgtcag cagaaatacg ggacttccga agtatatgg     6180
caaaattaaa gaacttgact ctccagcaat gttttgccct gaccgtcgct aaaacgttac    6240
taccccctata cccgtctgtt tgtcccagcc cgaggcatta ggtctgactg acagcacggc    6300
gccatgcggg cttgggacgc catgtccgtc gcgtgataag ggttgatcca tgcagctact    6360
atccttccat cgttccattc ccatccttgt cctatctcca tccttgaaac tttactagtt    6420
tagttggatg ctcgagcttg ctctcggcta ctccgtccaa tggataagac cccgatgccg    6480
gtcctcattg gtctccagct ggtatcgccc caaccttcgt gtgatcgcct ctctgcttcc    6540
cctcatcatc attactaact agtacatcca aaagccatcc cagtgcttcc cctcacccc    6600
gcccaagaca ttccaagtgg gccttcggct ggaaaacatg gacccattgg ttccatcgat    6660
aagctagctc ctcgtccgtt accccagatt gataccagat aacattgacc agcggcttat    6720
caccgaggtc tgcgggtgag accccccctg cgacaagtta gataaagaa actgcctca     6780
ttgtgcttcc gatggggtcg gatgacgagc cttcggaaag agctggcgcc tctttaaagg    6840
ggacagctgt cgccaagttg tgaaattctc cgataactac taacaatctc tcccttcctt    6900
cccgctactg tggtcaccaa atcaactctc ttttctcggc caagatctaa catggcggat    6960
gagaagactg aaaagtctcc cccaccgatg acggtggatg aggagactgg cacaacagag    7020
gaaattgacc cgacaatggc aaagcatacg aaggatgcag acgaggcact ggcggtcttc    7080
gaagacctcc atggtgaagt catcacactt gatgaggaga caaacaaaag gatacttcgg    7140
acaattgact ggcacagttt aac                                             7163
```

<210> SEQ ID NO 67
<211> LENGTH: 38
<212> TYPE: DNA
<213> ORGANISM: Artificial Sequence
<220> FEATURE:

<223> OTHER INFORMATION: Synthetic oligonucleotide

<400> SEQUENCE: 67
gtcgacggta tcgataagct tcaagacagc ggctgcaa                                    38

<210> SEQ ID NO 68
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 68
gccgaccgtg gtagagatac agggggttc                                              28

<210> SEQ ID NO 69
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 69
ctctaccacg gtcggcatct actctattc                                              29

<210> SEQ ID NO 70
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 70
gcgactgagc tggagctagt ggaggt                                                 26

<210> SEQ ID NO 71
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 71
gctccagctc agtcgcatct ttcactg                                                27

<210> SEQ ID NO 72
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 72
atcccccggg ctgcatggta ggctgtctca agg                                         33

<210> SEQ ID NO 73
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 73
actcgcagca gagatgccat ct                                                     22

```
<210> SEQ ID NO 74
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 74
cgttatgttt atcggcactt tgcat                                          25

<210> SEQ ID NO 75
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 75
aggtgattgg cgatgatgcc gttcagctgt ctgc                                34

<210> SEQ ID NO 76
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 76
acagccatcg gtccatctct cctcgtaacg cctg                                34

<210> SEQ ID NO 77
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 77
ggatagaatc gggtgccgct gatct                                          25

<210> SEQ ID NO 78
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 78
gagaaccatg gcaccgaagg t                                              21

<210> SEQ ID NO 79
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 79
gtacttctac acagccatcg gtcca                                          25

<210> SEQ ID NO 80
<211> LENGTH: 25
<212> TYPE: DNA
<213> ORGANISM: Artificial Sequence
<220> FEATURE:
<223> OTHER INFORMATION: Synthetic oligonucleotide
```

<400> SEQUENCE: 80
cgttatgttt atcggcactt tgcat                                           25

<210> SEQ ID NO 81
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 81
acaggtactt ccatcttgta ctggt                                           25

<210> SEQ ID NO 82
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 82
tctcctccaa cgtccgatct                                                 20

<210> SEQ ID NO 83
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 83
acctccacta gctccagcaa gccgaacaga ggtaaagacg a                         41

<210> SEQ ID NO 84
<211> LENGTH: 43
<212> TYPE: DNA
<213> ORGANISM: Artificial Sequence
<220> FEATURE:
<223> OTHER INFORMATION: Synthetic oligonucleotide

<400> SEQUENCE: 84
tcgtctttac ctctgttcgg cttgctggag ctagtggagg tca                       43

<210> SEQ ID NO 85
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 85
taccaacgtg cgaccatttt ctcggtcggc atctactcta ttcct                     45

<210> SEQ ID NO 86
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 86
aggaatagag tagatgccga ccgagaaaat ggtcgcacgt tggta                     45

<210> SEQ ID NO 87
<211> LENGTH: 22

```
<212> TYPE: DNA
<213> ORGANISM: Artificial Sequence
<220> FEATURE:
<223> OTHER INFORMATION: Synthetic oligonucleotide

<400> SEQUENCE: 87
aagcgtctct ttcctgggtc tt                                              22

<210> SEQ ID NO 88
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 88
tgccagttct gttggacatc tct                                             23

<210> SEQ ID NO 89
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 89
tcgaggtcga cggtatcgat atctagaaca ggtacttcca tcttgtac                  48

<210> SEQ ID NO 90
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 90
ggtcactgtt cctggcagct gacattg                                         27

<210> SEQ ID NO 91
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 91
ctgccaggaa cagtgaccgg tgactct                                         27

<210> SEQ ID NO 92
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 92
aagcagcaga tacgaccgtt gatctgcttg                                      30

<210> SEQ ID NO 93
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 93
```

```
acggtcgtat ctgctgcttg gtgcac                                          26

<210> SEQ ID NO 94
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 94
actagtggat ccccggggct gcagcggtcg gcatctactc tattc                    45

<210> SEQ ID NO 95
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 95
cgaggtcgac ggtatcgata gtttaaacct cccaggtacc gactaac                  47

<210> SEQ ID NO 96
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 96
ctcaatcaca gatcatgttt gggtgggttc                                      30

<210> SEQ ID NO 97
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 97
aaacatgatc tgtgattgag gtgattggcg                                      30

<210> SEQ ID NO 98
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 98
ctctgtgcct acagcagtgc ttatctgcga tg                                   32

<210> SEQ ID NO 99
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 99
gcactgctgt aggcacagag taacaggtag gtagacag                             38

<210> SEQ ID NO 100
<211> LENGTH: 48
<212> TYPE: DNA
<213> ORGANISM: Artificial Sequence
```

-continued

```
<220> FEATURE:
<223> OTHER INFORMATION: Synthetic oligonucleotide

<400> SEQUENCE: 100
agtggatccc ccgggctgca gtttaaactc ccacgcacga aagcaact                    48

<210> SEQ ID NO 101
<211> LENGTH: 1102
<212> TYPE: DNA
<213> ORGANISM: Artificial Sequence
<220> FEATURE:
<223> OTHER INFORMATION: Synthetic polynucleotide (1546/1548 fragment)

<400> SEQUENCE: 101
acaggtactt ccatcttgta ctggtaagtc ccgtccgtac tttaaataca ggggacctcc       60
cgtacgtcag gtacctatgt catgattctt cttctccccg gcattaagat ttgtttcttc      120
ttattaatta tcatcactat tattcctgca gcaggaacgc cccctatcct ctcctccaac      180
gtccgatcta tcgtgtgttt cgagtcgtgc tgttcacaca cacgcacgca cacacacact      240
ctcaaacata tctgcccccct cttgcccctc catccctcca gaacccgagt tcacggtgcc     300
aactctcttt tccttgtgtc tcctatcccg ttaaaaaaaa aagaggtacg cagaaccgaa      360
cccaatcgac ctccgccgac taattaagtg ggattctctg gcccccaggg atcggcttct      420
tccttccatc ctgcggctcg aaaccagacg tcccaatcac cggagctgac cctggatcgg      480
cctctgatcc atggctagtt tgccctgaca tttgtcgccc gttaaagccg tgggacctgc      540
gcccagtaca taaaccgcct gcgtcgtgac accgcctctt tggccgcgct tcccgtctac      600
tttcttcgac gcctccgtta ttttcatcgc ggcgctcatc gcggcgccca tcccattgcg      660
ccgcagttgc tttcgtgcgt gggattttgg tttccgtttc ttgtcttttt ctcttgggcg      720
ttcgtctcat cccgacctgc tccacggctt gattgattta tttgatttttc aattttgtct    780 aaagtcgcct gcatcagacc gtcctccaac tccgaattcg tcttgtcgga acacctccag      840
ctgcctcgcc cgtcccccgc ctcaccatcc gagcaatttc gcatgaggcg cagtcagcct      900
gatatttgat tgaacgcctt gctttcgtcc attgccaggc cctcagactt gtctgtggcc      960
gcctgttatc caggacggcc cttcggtctc tgatctatat cctgatctcc tggtgttct      1020 cattatcgac agctctcccc ggttcggtct cggcttgtct ccggcattcg aactgctttc     1080
gtctttacct ctgttcggct tg                                             1102

<210> SEQ ID NO 102
<211> LENGTH: 1361
<212> TYPE: DNA
<213> ORGANISM: Artificial Sequence
<220> FEATURE:
<223> OTHER INFORMATION: Synthetic polynucleotide (1549/1550 fragment)

<400> SEQUENCE: 102
gctggagcta gtggaggtca acacatcaat gctattttgg tttagtcgtc caggcggatc       60
acaaaatttg tgtcgtttga caagatggtt catttaggca actggtcaga tcagcccact      120
tgtaagcagt agcggcggcg ctcgaagtgt gactcttatt agcagacagg aacgaggaca      180
ttattatcat ctgctgcttg gtgcacgata acttgtgcgt ttgtcaagca aggtaagtga      240
acgacccggt catacctttct taagttcgcc cttcctccct ttatttcaga ttcaatctga     300
cttacctatt ctacccaagc atccaaatgc ctgaactcac cgcgacgtct gtcgagaagt      360
ttctgatcga aaagttcgac agcgtctccg acctgatgca gctctcggag ggcgaagaat      420
```

| | |
|---|---|
| ctcgtgctttcagcttcgatgtaggagggcgtggatatgtcctgcgggtaaatagctgcg | 480 |
| ccgatggtttctacaaagatcgttatgtttatcggcacttgcatcggccgcgctcccga | 540 |
| ttccggaagtgcttgacattggggagttcagcgagagcctgacctattgcatctcccgcc | 600 |
| gtgcacagggtgtcacgttgcaagacctgcctgaaaccgaactgcccgctgttctggagc | 660 |
| cggtcgcggaggccatggatgcgatcgctgcggccgatcttagccagacgagcgggttcg | 720 |
| gcccattcggaccgcaaggaatcggtcaatacactacatgcgtgatttcatatgcgcga | 780 |
| ttgctgatcccatgtgtatcactggcaaactgtgatggacgacaccgtcagtgcgtccg | 840 |
| tcgcgcaggctctcgatgagctgatgctttgggccgaggactgccccgaagtccggcacc | 900 |
| tcgtgcacgcggatttcggctccaacaatgtcctgacggacaatggccgcataacagcgg | 960 |
| tcattgactggagcgaggcgatgttcggggattcccaatacgaggtcgccaacatcttct | 1020 |
| tctggaggccgtggttggctgtatggagcagcagacgcgctacttcgagcggaggcatc | 1080 |
| cggagcttgcaggatcgccgcgcctccgggcgtatatgctccgcattggtcttgaccaac | 1140 |
| tctatcagagcttggttgacggcaatttcgatgatgcagcttgggcgcaggtcgatgcg | 1200 |
| acgcaatcgtccgatccggaccgggactgtcgggcgtacacaaatcgccgcagaagcg | 1260 |
| cggccgtctgaccgatggctgtgtagaagtactcgccgatagtggaaaacgacgccca | 1320 |
| gcactcgtccgagggcaaaggaatagagtagatgccgaccg | 1361 |

<210> SEQ ID NO 103
<211> LENGTH: 1300
<212> TYPE: DNA
<213> ORGANISM: Artificial Sequence
<220> FEATURE:
<223> OTHER INFORMATION: Synthetic polynucleotide (1551/1553 fragment)

<400> SEQUENCE: 103

| | |
|---|---|
| aaatggtcgcacgttggtaccatctcgccattacggagagtatcgaaaccctcagtctgg | 60 |
| ccccgtttagccgggttttcggttgggatagggaaaaaatccggcgtatcgcgtctgagg | 120 |
| tcaggtcggaggctttcaacaaggacatccatgcctataacattttacatatctaccaag | 180 |
| ctcggaagcctcctgtcaactgacaaccagcgatcaactagcgcgagaccgagaacatca | 240 |
| aagtcgcgctaggatttcttgtccaagagtggataatggagtccctgttttcgctcctctc | 300 |
| ttcccttggctccacgagcgactgcgatcagggtaactctccgtagtacctgtgctatc | 360 |
| gcggcctcatactggccttgaccccagcaatgctgatgcattctggtagccgaaccgtg | 420 |
| caacgcactgctgcgacgtccagatattcacgacgtctcgcgggagcttctcactttgc | 480 |
| gtatatgggtctaaagtgagtgtctgcccgctgtgttcaatcacgctgcaatgtcagctg | 540 |
| ccaggatgaaagactatacaaacaagctctgctcaacttataccaattcttcgctttca | 600 |
| cgaaaggattaagagcgagccgcggaattcccatgggtggttgaccctgcgtcagaga | 660 |
| gcggttaattgagattgacctgtcttgaatctctccgctctcgtaccttcaaaacatgtc | 720 |
| cctcaacttcccttgcacatgcggctgtagttgagacgcatctgcctctcacccgacgg | 780 |
| ctctgggcttattttgattgcccatatttaacggacccgtgaaacactcgtactgtgtc | 840 |
| gccacgagttggaacccgagatacctagacactacatctactgatgaaggaaaaataa | 900 |
| atcgaatcaactaaaacaagctgaatctcccttgtcctatccttctattgggccgacgg | 960 |
| agactattccggctatacaattgatacttcataagatgcgtgtctacatacgcgagtaag | 1020 |
| atacagaaacacaaacaccaaccacccccaaagcccaccgaaacgccgacaaagacccag | 1080 |
| gaaagagacgctttcgaacatcgcataataatagcgggatgcaccggggtccccaaaact | 1140 |

```
catcgccggc gacccttctg acgagacgtg ttattcttgc cactcgccgt atcttcataa    1200
tcccgaccag cgccgggact gcgccttcgc atggtccccg ggcctaccgc gacaatatcc    1260
tcttcactct cactatcaga gatgtccaac agaactggca                          1300
```

<210> SEQ ID NO 104
<211> LENGTH: 3389
<212> TYPE: DNA
<213> ORGANISM: Artificial Sequence
<220> FEATURE:
<223> OTHER INFORMATION: Synthetic polynucleotide (1547/1552 fragment)

<400> SEQUENCE: 104

```
tctcctccaa cgtccgatct atcgtgtgtt tcgagtcgtg ctgttcacac acacgcacgc      60
acacacacac tctcaaacat atctgccccc tcttgccccct ccatccctcc agaacccgag    120
ttcacggtgc caactctctt ttccttgtgt ctcctatccc gtttaaaaaa aaagaggtac    180
gcagaaccga acccaatcga cctccgccga ctaattaagt gggattctct ggccccagg     240 gatcggcttc ttccttccat cctgcggctc gaaaccagac gtcccaatca ccggagctga    300
ccctggatcg gcctctgatc catggctagt ttgccctgac atttgtcgcc cgttaaagcc    360
gtgggacctg cgcccagtac ataaaccgcc tgcgtcgtga caccgcctct ttggccgcgc    420
ttcccgtcta cttttcttcga cgcctccgtt attttcatcg cggcgctcat cgcggcgccc    480
atcccattgc gccgcagttg ctttcgtgcg tgggattttg gtttccgttt cttgtctttt    540
tctcttgggc gttcgtctca tcccgacctg ctccacggct tgattgattt atttgatttt    600
caattttgtc taaagtcgcc tgcatcagac cgtcctccaa ctccgaattc gtcttgtcgg    660
aacacctcca gctgcctcgc ccgtcccccg cctcaccatc cgagcaattt cgcatgaggc    720
gcagtcagcc tgatatttga ttgaacgcct tgctttcgtc cattgccagg ccctcagact    780
tgtctgtggc cgcctgttat ccaggacggc ccttcggtct ctgatctata tcctgatctc    840
ctggtgttct tcattatcga cagctctccc cggttcggtc tcggcttgtc tccggcattc    900
gaactgcttt cgtctttacc tctgttcggc ttgctggagc tagtggaggt caacacatca    960
atgctatttt ggtttagtcg tccaggcgga tcacaaaatt tgtgtcgttt gacaagatgg    1020
ttcatttagg caactggtca gatcagccca cttgtaagca gtagcggcgg cgctcgaagt    1080
gtgactctta ttagcagaca ggaacgagga cattattatc atctgctgct tggtgcacga    1140
taacttgtgc gtttgtcaag caaggtaagt gaacgacccg gtcataccct cttaagttcg    1200
ccctccctcc ctttatttca gattcaatct gacttaccta ttctacccaa gcatccaaat    1260
gcctgaactc accgcgacgt ctgtcgagaa gtttctgatc gaaaagttcg acagcgtctc    1320
cgacctgatg cagctctcgg agggcgaaga atctcgtgct ttcagcttcg atgtaggagg    1380
gcgtggatat gtcctgcggg taaatagctg cgccgatggt ttctacaaag atcgttatgt    1440
ttatcggcac tttgcatcgg ccgcgctccc gattccggaa gtgcttgaca ttggggagtt    1500
cagcgagagc ctgacctatt gcatctcccg ccgtgcacag ggtgtcacgt tgcaagacct    1560
gcctgaaacc gaactgcccg ctgttctgga gccggtcgcg gaggccatgg atgcgatcgc    1620
tgcggccgat cttagccaga cgagcgggtt cggcccattc ggaccgcaag gaatcggtca    1680
atacactaca tggcgtgatt tcatatgcgc gattgctgat ccccatgtgt atcactggca    1740
aactgtgatg gacgacaccg tcagtgcgtc cgtcgcgcag gctctcgatg agctgatgct    1800
ttgggccgag gactgccccg aagtccggca cctcgtgcac gcggatttcg ctccaacaa    1860
```

```
tgtcctgacg acaatggcc gcataacagc ggtcattgac tggagcgagg cgatgttcgg      1920
ggattcccaa tacgaggtcg ccaacatctt cttctggagg ccgtggttgg cttgtatgga      1980
gcagcagacg cgctacttcg agcggaggca tccggagctt gcaggatcgc cgcgcctccg      2040
ggcgtatatg ctccgcattg gtcttgacca actctatcag agcttggttg acggcaattt      2100
cgatgatgca gcttgggcgc agggtcgatg cgacgcaatc gtccgatccg agccgggac      2160 tgtcgggcgt acacaaatcg cccgcagaag cgcggccgtc tggaccgatg gctgtgtaga      2220
agtactcgcc gatagtggaa accgacgccc cagcactcgt ccgagggcaa aggaatagag      2280
tagatgccga ccgagaaaat ggtcgcacgt tggtaccatc tcgccattac ggagagtatc      2340
gaaaccctca gtctggcccc gtttagccgg gttttcggtt gggataggga aaaaatccgg      2400
cgtatcgcgt ctgaggtcag gtcggaggct ttcaacaagg acatccatgc ctataacatt      2460
ttacatatct accaagctcg gaagcctcct gtcaactgac aaccagcgat caactagcgc      2520
gagaccgaga acatcaaagt cgcgctagga tttcttgtcc aagagtggat aatggagtcc      2580
ctgtttcgct cctctcttcc cttggctcca cgagcgactg cgatcgaggg taactctccg      2640
tagtacctgt gctatcgcgg cctcatactg gccttggacc ccagcaatgc tgatgcattc      2700
tggtagccga accgtgcaac gcactggctg cgacgtccag atattcacga cgtctcgcgg      2760
gagcttctca ctttgcgtat atgggtctaa agtgagtgtc tgcccgctgt gttcaatcac      2820
gctgcaatgt cagctgccag gatgaaagac tatacaaaca agctctgctc aacttatacc      2880
aattctttcg ctttcacgaa aggattaaga gcgagcccgc ggaatttccc atgggtggtt      2940
gaccctgcgt cagagagcgg ttaattgaga ttgacctgtc ttgaatctct ccgctctcgt      3000
accttcaaaa catgtccctc aacttccctt gcacatgcgg ctgtagttga gacgcatctg      3060
cctctccacc cgacggctct gggcttattt tgattgccca tatttaacgg acccgttgaa      3120
acactcgtac tgtgtcgcca cgagtttgga acccgagata ccctagacac tacatctact      3180
gatgaaggaa aaataaatcg aatcaactaa aacaagctga atctcccttg tcctattcct      3240
tctattgggc cgacggagac tattccggct atacaattga tacttcataa gatgcgtgtc      3300
tacatacgcg agtaagatac agaaacacaa acaccaacca cccccaaagc ccaccgaaac      3360
gccgacaaag acccaggaaa gagacgctt                                        3389
```

<210> SEQ ID NO 105
<211> LENGTH: 2678
<212> TYPE: DNA
<213> ORGANISM: Artificial Sequence
<220> FEATURE:
<223> OTHER INFORMATION: Synthetic polynucleotide (1554/1555 fragment)

<400> SEQUENCE: 105

```
acaggtactt ccatcttgta ctggtaagtc ccgtccgtac tttaaataca ggggacctcc        60
cgtacgtcag gtacctatgt catgattctt cttctccccg gcattaagat ttgtttcttc       120
ttattaatta tcatcactat tattcctgca gcaggaacgc cccctatcct ctcctccaac       180
gtccgatcta tcgtgtgttt cgagtcgtgc tgttcacaca cacgcacgca cacacacact       240
ctcaaacata tctgccccct cttgcccctc catccctcca gaacccgagt tcacggtgcc       300
aactctcttt tccttgtgtc tcctatcccg tttaaaaaaa agaggtacg cagaaccgaa        360 cccaatcgac ctccgccgac taattaagtg ggattctctg gccccagggg atcggcttct       420
tccttccatc ctgcggctcg aaaccagacg tcccaatcac cggagctgac cctggatcgg       480
cctctgatcc atggctagtt tgccctgaca tttgtcgccc gttaaagccg tgggacctgc       540
```

```
gcccagtaca taaaccgcct gcgtcgtgac accgcctctt tggccgcgct tcccgtctac    600
tttcttcgac gcctccgtta ttttcatcgc ggcgctcatc gcggcgccca tcccattgcg    660
ccgcagttgc tttcgtgcgt gggattttgg tttccgtttc ttgtcttttt ctcttgggcg    720
ttcgtctcat cccgacctgc tccacggctt gattgattta tttgattttc aattttgtct    780
aaagtcgcct gcatcagacc gtcctccaac tccgaattcg tcttgtcgga cacctccag    840 ctgcctcgcc cgtcccccgc ctcaccatcc gagcaatttc gcatgaggcg cagtcagcct    900
gatatttgat tgaacgcctt gctttcgtcc attgccaggc cctcagactt gtctgtggcc    960
gcctgttatc caggacggcc cttcggtctc tgatctatat cctgatctcc tggtgttctt   1020
cattatcgac agctctcccc ggttcggtct cggcttgtct ccggcattcg aactgctttc   1080
gtctttacct ctgttcggct tgttgcctgg gagggctccg cattgactcg gaggcctcat   1140
gtttgggaac ggacacggcc cgggacaacc tatcaccatg accccctccgt cttacaataa   1200 gtttggctcc cagtcgtcgg cttctggccg ctcgagaacc aattccgatg ctatggacat   1260
ccacgtcata acggatcggg acttggatgc acgagaacat aatcctggct acagcaattg   1320
gacgaacaat ggttccccat cgatatacac caagtaattc accccgccc cttttttc     1380 ccattctatg tggattgttc tacccagttc acttttcctg ttgggtgatt aatcttgtat   1440
cccaggagtc cagaaaagca gtactatgaa gaaatggac ggctgtacca tgcgtatcga   1500
aaaggagtct atatgctacc atgcgatgac gaggagcagg atcgcctcga tcttttccac   1560
aagttgttca ccgaggcgag ggtatctgat ggtctgattt acgcacctca cccgagaaac   1620
ggtcgattct tggatttggg atgtgggaca gggatctggg caattgacgt ggccaacaaa   1680
taccccgatg ctttcgttgt cggggtagat cttgctccga tccagccccc aaaccacccc   1740
aagaactgcg aattttacgc tcctttcgat tacgaaagcc cctgggcgat gggtgaagac   1800
tcctgggact tgatccacct ccaaatgggc tgcggaagcg tgttaggatg gccaaacctc   1860
taccgaagga tcttcgccca ccttcgaccg ggtgcttggt ttgagcaagt ggagatcgat   1920
ttcgaacccc gttgtgacga ccgatccttg ggacggactg gcgcttcgcg aatggtacca   1980
atacttgaaa cgagcaaccc aggagaccat gcgaccaatc gcccacaact cccgggaaac   2040
catcaaagat ttgcaggacg ccggcttcac tgagatcgat catcagatgg ttggattgcc   2100
cttgaatcct tggcaccagg acgagcacga gaaaatggtc gcacgttggt accatctcgc   2160
cattacggag agtatcgaaa ccctcagtct ggccccgttt agccgggttt tcggttggga   2220
tagggaaaaa atccggcgta tcgcgtctga ggtcaggtcg gaggctttca acaaggacat   2280
ccatgcctat aacattttac atatctacca agctcggaag cctcctgtca actgacaacc   2340
agcgatcaac tagcgcgaga ccgagaacat caaagtcgcg ctaggatttc ttgtccaaga   2400
gtggataatg gagtccctgt ttcgctcctc tcttcccttg gctccacgag cgactgcgat   2460
cgagggtaac tctccgtagt acctgtgcta tcgcggcctc atactggcct tggacccccag   2520 caatgctgat gcattctggt agccgaaccg tgcaacgcac tggctgcgac gtccagatat   2580
tcacgacgtc tcgcgggagc ttctcacttt gcgtatatgg gtctaaagtg agtgtctgcc   2640
cgctgtgttc aatcacgctg caatgtcagc tgccagga                           2678
```

<210> SEQ ID NO 106
<211> LENGTH: 1651
<212> TYPE: DNA
<213> ORGANISM: Artificial Sequence
<220> FEATURE:

<223> OTHER INFORMATION: Synthetic polynucleotide (1556/1557 fragment)

<400> SEQUENCE: 106

```
acagtgaccg gtgactcttt ctggcatgcg gagagacgga cggacgcaga gagaagggct      60
gagtaataag ccactggcca gacagctctg gcggctctga ggtgcagtgg atgattatta     120
atccgggacc ggccgcccct ccgccccgaa gtggaaaggc tggtgtgccc ctcgttgacc     180
aagaatctat tgcatcatcg gagaaatatg agcttcatcg aatcaccggc agtaagcgaa     240
ggagaatgtg aagccagggg tgtatagccg tcggcgaaat agcatgccat taacctaggt     300
acagaagtcc aattgcttcc gatctggtaa aagattcacg agatagtacc ttctccgaag     360
taggtagagc gagtacccgg cgcgtaagct ccctaattgg cccatccggc atctgtaggg     420
cgtccaaata tcgtgcctct cctgctttgc ccggtgtatg aaaccggaaa ggccgctcag     480
gagctggcca gcggcgcaga ccgggaacac aagctggcag tcgacccatc cggtgctctg     540
cactcgacct gctgaggtcc ctcagtccct ggtaggcagc tttgcccgt ctgtccgccc      600
ggtgtgtcgg cggggttgac aaggtcgttg cgtcagtcca acatttgttg ccatattttc     660
ctgctctccc caccagctgc tcttttcttt tctctttctt ttcccatctt cagtatattc     720
atcttcccat ccaagaacct ttatttcccc taagtaagta ctttgctaca tccatactcc     780
atccttccca tcccttattc ctttgaacct ttcagttcga gctttcccac ttcatcgcag     840
cttgactaac agctaccccg cttgagcaga catcaccatg ccaagttga ccagtgccgt      900
tccggtgctc accgcgcgcg acgtcgccgg agcggtcgag ttctggaccg accggctcgg     960
gttctcccgg gacttcgtgg aggacgactt cgccggtgtg gtccgggacg acgtgaccct    1020
gttcatcagc gcggtccagg accaggtggt gccggacaac accctggcct gggtgtgggt    1080
gcgcggcctg gacgagctgt acgccgagtg gtcggaggtc gtgtccacga acttccggga    1140
cgcctccggg ccggccatga ccgagatcgg cgagcagccg tgggggcggg agttcgccct    1200
gcgcgacccg gccggcaact gcgtgcactt cgtggccgag gagcaggact gaccgacgcc    1260
gaccaacacc gccggtccga cggcggccca cgggtcccag gagcttgaga tccacttaac    1320
gttactgaaa tcatcaaaca gcttgacgaa tctggatata agatcgttgg tgtcgatgtc    1380
agctccggag ttgagacaaa tggtgttcag gatctcgata agatacgttc atttgtccaa    1440
gcagcaaaga gtgccttcta gtgatttaat agctccatgt caacaagaat aaaacgcgtt    1500
ttcgggttta cctcttccag atacagctca tctgcaatgc attaatgcat tgactgcaac    1560
ctagtaacgc cttacaggct ccggcgaaga gaagaatagc ttagcagagc tattttcatt    1620
ttcgggagac gagatcaagc agatcaacgg t                                   1651
```

<210> SEQ ID NO 107
<211> LENGTH: 1362
<212> TYPE: DNA
<213> ORGANISM: Artificial Sequence
<220> FEATURE:
<223> OTHER INFORMATION: Synthetic polynucleotide (1558/1559 fragment)

<400> SEQUENCE: 107

```
tgctggagct agtggaggtc aacacatcaa tgctattttg gtttagtcgt ccaggcggat      60
cacaaaattt gtgtcgtttg acaagatggt tcatttaggc aactggtcag atcagcccac     120
ttgtaagcag tagcggcggc gctcgaagtg tgactcttat tagcagacag gaacgaggac     180
attattatca tctgctgctt ggtgcacgat aacttgtgcg tttgtcaagc aaggtaagtg     240
aacgacccgg tcataccttc ttaagttcgc ccttcctccc tttatttcag attcaatctg     300
```

```
acttacctat tctacccaag catccaaatg cctgaactca ccgcgacgtc tgtcgagaag      360
tttctgatcg aaaagttcga cagcgtctcc gacctgatgc agctctcgga gggcgaagaa      420
tctcgtgctt tcagcttcga tgtaggaggg cgtggatatg tcctgcgggt aaatagctgc      480
gccgatggtt tctacaaaga tcgttatgtt tatcggcact ttgcatcggc cgcgctcccg      540
attccggaag tgcttgacat tggggagttc agcgagagcc tgacctattg catctcccgc      600
cgtgcacagg tgtcacgtt gcaagacctg cctgaaaccg aactgcccgc tgttctggag       660
ccggtcgcgg aggccatgga tgcgatcgct gcggccgatc ttagccagac gagcgggttc      720
ggcccattcg gaccgcaagg aatcggtcaa tacactacat ggcgtgattt catatgcgcg      780
attgctgatc cccatgtgta tcactggcaa actgtgatgg acgacaccgt cagtgcgtcc      840
gtcgcgcagg ctctcgatga gctgatgctt tgggccgagg actgccccga agtccggcac      900
ctcgtgcacg cggatttcgg ctccaacaat gtcctgacgg acaatggccg cataacagcg      960
gtcattgact ggagcgaggc gatgttcggg gattcccaat acgaggtcgc caacatcttc     1020
ttctggaggc cgtggttggc ttgtatggag cagcagacgc gctacttcga gcggaggcat     1080
ccggagcttg caggatcgcc gcgcctccgg gcgtatatgc tccgcattgg tcttgaccaa     1140
ctctatcaga gcttggttga cggcaatttc gatgatgcag cttgggcgca gggtcgatgc     1200
gacgcaatcg tccgatccgg agccgggact gtcgggcgta cacaaatcgc ccgcagaagc     1260
gcggccgtct ggaccgatgg ctgtgtagaa gtactcgccg atagtggaaa ccgacgcccc     1320
agcactcgtc cgagggcaaa ggaatagagt agatgccgac cg                       1362
```

<210> SEQ ID NO 108
<211> LENGTH: 1017
<212> TYPE: DNA
<213> ORGANISM: Artificial Sequence
<220> FEATURE:
<223> OTHER INFORMATION: Synthetic polynucleotide (1561/1562 fragment)

<400> SEQUENCE: 108

```
acctcccagg taccgactaa ctagatctag tagcacctgt actaccttac taaggttcct       60
agaatgtgct ccgtaacatt cgtcccaaac taaggtacgt gtgggaggcg ggccgtcacc      120
acccggaagt cactttcatc gtcagcaaca gtggatcatt tcctagaaag cgtttggcat      180
gttttctttt ttccttttcca tttttttta ccaacaaaac cctcctactg gccggagtcc       240
cgtcgtgccg agaatgagcg gcagttaccg agaagagtaa tcgcacggag tcctatcagc      300
aacgaggaga ttgttggacc catctgattg aacgttaact tctatggagt acaggtactg      360
ttggcttagg agtctcccct acgctcccga atctcttctg actccagagt gcttgttaac      420
atgatatgtt ctcctgttca ctctcccatt ctgcaggacg gaatgatttt ccgcatgcgg      480
gcgcgctatt cacacgagtt gattagtttt aatctatcgg acgaaaggtt atcgttcatg      540
ttggtctggg ttaagttccg tcaaatagtt tcccgccact tggttctggg cgacagtgat      600
tgacgccagg cccgagcact tgggtagtcc gttagggaaa aaggggggga gaaataaata     660
tagaaaaaga aaagagaaaa agaaattaaa aaaaaaggg ccggtgacag atagataaat      720
gtcaccgaag gagcggatgt acggacgacg tacaggtacc cgacatgcat acccttata       780 catgaatgga atgtactccg tacatatacc tagcgatatc tcgcctaccg attactccgt      840
aatctatata ggaatggtga gacacaagaa tagaacaact tcgtccacca agatccatcc      900
atggctggga tcgcccccgc aaccaatgac tctggctccg aagcgcccta ccttgtcggg      960
```

```
gagatggcgg ttctccaggg acctttcggt ttcggacgaa cccacccaaa catgatc      1017
```

<210> SEQ ID NO 109
<211> LENGTH: 5390
<212> TYPE: DNA
<213> ORGANISM: Artificial Sequence
<220> FEATURE:
<223> OTHER INFORMATION: Synthetic polynucleotide (1563/1564 fragment)

<400> SEQUENCE: 109

```
tgtgattgag gtgattggcg atgaagcttc aagctgtaag gatttcggca cggctacgga    60
agacggagaa gcccaccttc agtggactcg agtaccattt aattctattt gtgtttgatc   120
gagacctaat acagcccta caacgaccat caaagtcgta tagctaccag tgaggaagtg    180
gactcaaatc gacttcagca acatctcctg gataaacttt aagcctaaac tatacagaat   240
aagatggtgg agagcttata ccgagctccc aaatctgtcc agatcatggt tgaccggtgc   300
ctggatcttc ctatagaatc atccttattc gttgacctag ctgattctgg agtgacccag   360
agggtcatga cttgagccta aaatccgccg cctccaccat ttgtagaaaa atgtgacgaa   420
ctcgtgagct ctgtacagtg accggtgact cttcctggca tgcggagaga cggacggacg   480
cagagagaag ggctgagtaa taagcgccac tgcgccagac agctctggcg gctctgaggt   540
gcagtggatg attattaatc cgggaccggc cgcccctccg ccccgaagtg gaaaggctgg   600
tgtgcccctc gttgaccaag aatctattgc atcatcggga aatatggagc ttcatcgaat   660
caccggcagt aagcgaagga gaatgtgaag ccaggggtgt atagccgtcg gcgaaatagc   720
atgccattaa cctaggtaca gaagtccaat tgcttccgat ctggtaaaag attcacgaga   780
tagtaccttc tccgaagtag gtagagcgag tacccggcgc gtaagctccc taattggccc   840
atccggcatc tgtagggcgt ccaaatatcg tgcctctcct gctttgcccg gtgtatgaaa   900
ccggaaaggc cgctcaggag ctggccagcg gcgcagaccg ggaacacaag ctggcagtcg   960
acccatccgg tgctctgcac tcgacctgct gaggtccctc agtccctggt aggcagcttt  1020
gccccgtctg tccgcccggt gtgtcggcgg ggttgacaag gtcgttgcgt cagtccaaca  1080
tttgttgcca tattttcctg ctctcccac cagctgctct tttcttttct ctttcttttc   1140
ccatcttcag tatattcatc ttcccatcca agaaccttta tttcccctaa gtaagtactt  1200
tgctacatcc atactccatc cttcccatcc cttattcctt tgaacctttc agttcgagct  1260
ttcccacttc atcgcagctt gactaacagc taccccgctt gagcagacat cacaatgttt  1320
gagatgggcc cggtgggaac tcgtctcccc gccatgacct ctccagcgca caaccactac  1380
agctaccact ctcccacctc cagcgacaga ggccggtcaa ggcagaactc ggatgccatg  1440
gacatccagt ccatcactga acgagagccg gcgaccagat acgcggttgc gggcggccct  1500
gcgccctgga atcgcaacgg gtctccgagc atgagcccta tgtatagcaa gtacatctct  1560
cttacccctc cgtttctttc tgcttttcta ccaccccatc cctctttcca gtctgagtcc  1620
aggcttgttc cgcttgaagt ggctaatgtg atcctcgtct tctctctttc tgtgttttag  1680
caattccgag cgaaaccagt ttcatgaaga gaacggacgc acctaccatg gctttcgcag  1740
gggaatgtat tttcttccgt gcgatgagca agaacaggat cgcctcgaca tcttccataa  1800
gctattcacg gtagcgcggg tatcggagag tctgatctac gcgcccatc caaccaacgg   1860
ccggtttctg gacctaggat gtggaactgg tatctgggcg atcgaggtag cgaacaagta  1920
ccctgatgcg tttgtcgctg gtgtggattt ggctcctatt cagcctccga accacccgaa  1980
gaactgcgag ttctacgcgc ccttcgactt cgaagcgcca tgggccatgg gggaggattc  2040
```

```
ctgggatcta atccatctgc agatgggttg cggtagtgtc atgggctggc caaacttgta    2100
tcgaaggata ttcgcacatc tccgtcccgg tgcctggttt gagcaggttg agatcgattt    2160
cgagcctcga tgtgatgatc ggtcactaga tggaacggca ttgcggcatt ggtacgattg    2220
tcttaaacag gcgacagcag agaccatgcg gccaatcgcc catagctccc gcgatacaat    2280
aaaagacctg caggacgctg ggttcacgga gatcgaccat caaatagtgg gactcccgct    2340
caacccgtgg catcaggacg aacacgagcg aaggtggca cgttggtata acctggccgt     2400
ctcagagagc atcgaaaacc tcagtctggc tcccttcagt cgtgtctatc gctggcccct    2460
ggagagaatc cagcaactcg ccgcagatgt gaagtccgaa gcattcaaca aagagatcca    2520
tgcctacaat atactgcaca tataccaggc taggaaacca ttaagataag agcaaaaggc    2580
gaccacatcc aggaacgcaa aacgaaaagg aggaaaactg ctagcgcaag tttatgtcac    2640
gctggcacac gcccagccat cagaaatctc aacagcgaaa gttatgaacc gcatcaaccg    2700
agtatgaacg acaattcgtc catcacacac ccttcggttc ctctcgcagg cccagcatgg    2760
cgccctatca acctgcttta cgacgtcgta tatactggcg aagtatcctc tctatctact    2820
ctggcgctct agataccgtg aagatgcaga caaaattggc cgagctccct tctcataatc    2880
ctcaagcttg gaccgatggc tgtgtagaag tactcgccga tagtggaaac cgacgcccca    2940
gcactcgtcc gagggcaaag gaatagagta gatgccgacc gcgggatcca cttaacgtta    3000
ctgaaatcat caaacagctt gacgaatctg gatataagat cgttggtgtc gatgtcagct    3060
ccggagttga gacaaatggt gttcaggatc tcgataagat acgttcattt gtccaagcag    3120
caaagagtgc cttctagtga tttaatagct ccatgtcaac aagaataaaa cgcgttttcg    3180
ggtttacctc ttccagatac agctcatctg caatgcatta atgcattgac tgcaacctag    3240
taacgcctta caggctccgg cgaagagaag aatagcttag cagagctatt ttcattttcg    3300
ggagacgaga tcaagcagat caacggtcgt caagagacct acgagactga ggaatccgct    3360
ctctgacaga cgggcaattg attacgggat cccattggta acgaaatgta aaagctagga    3420
gatcgtccgc cgatgtcagg atgatttcac ttgtttcttg tccggctcac cggtcaaagc    3480
taaagaggag caaaaggaac ggatagaatc gggtgccgct gatctatacg gtatagtgcc    3540
cttatcacgt tgactcaacc catgctattt aactcaaccc ctccttctga accccaccat    3600
cttcttcctt ttcctctcat cccacacaat tctctatctc agatttgaat tccaaaagtc    3660
ctcggacgaa actgaacaag tcttcctccc ttcgataaac ctttggtgat tggaataact    3720
gaccatcttc tatagttccc aaaccaaccg acaatgtaaa tacactcctc gattagccct    3780
ctagagggca tacgatggaa gtcatggaat acttttggct ggactctcac aatgatcaag    3840
gtatcttagg taacgtcttt ggcgtgggcc ggtgttcgtt cccagtcatc gatgcattca    3900
catgccctcc ctaagctggg ccctagactc taggatccta gtctagaagg acatggcatc    3960
gatggactgg gttcgttctg agattatacg gctaaaactt gatctggata ataccagcga    4020
aaagggtcat gccttctctc gttcttcctg ttgatggaat ggctaacaga tgatagtcat    4080
tgcaacttga acatgtctc ctccagctgc catctacgaa cccactgtgg ccgctaccgg     4140
cctcaagggt aaggtcgtgg tttctgagac cgtccccgtt gagggagctt ctcagaccaa    4200
gctgttggac catttcggtg gcaagtggga cgagttcaag ttcgccccta tccgcgaaag    4260
ccaggtctct cgtgccatga ccagacgtta ctttggaggac ctggacaagt acgctgaaag   4320
tgacgttgtc attgttggtg ctggttcctg cggtctgagc actgcgtacg tcttggccaa    4380
```

```
ggctcgtccg gacctgaaga ttgctatcgt cgaggccagc gtctctcctg gtcagtagtc    4440
catgatggat tgccttgcac tcagctttcc ggaactaacg tgcaataggt ggcggtgcct    4500
ggttgggtgg ccaactcttt tctgctatgg tcatgcgccg tcccgcggaa gtcttcctga    4560
acgagctggg tgttccttac gaagaggacg caaaccccaa ctacgttgtc gtcaagcacg    4620
cctccctgtt tacctcgaca ctcatgtcga aggttctctc cttccccaat gtcaagctct    4680
tcaatgctac cgctgttgag gacttgatca cccgtccgac cgagaacggc aaccccaga    4740 ttgctggtgt tgtcgtcaac tggacgctgg tcacccttca ccacgatgat cactcctgca    4800
tggaccccaa cactatcaac gctcctgtca tcatcagtac cactggtcac gatgggccat    4860
tcggcgcctt ctgtgcgaag cgcttggtgt ccatgggcag cgtcgacaag ctaggtggca    4920
tgcgtggtct cgacatgaac tcggccgagg atgccatcgt caagaacacc cgcgaggtta    4980
ctaagggctt gataatcggc ggtatggagc tgtctgaaat tgatggcttt aaccgcatgg    5040
gccctacctt cggtgccatg gttctcagtg gtgtcaaggc tgccgaggag gcattgaagg    5100
tgttcgacga gcgtcagcgc gagtgtgctg agtaaatgac tcactaccccg aatgggttca    5160 gtgcatgaac cggatttgtc ttacggtctt tgacgatagg ggaatgatga ttatgtgata    5220
gttctgagat ttgaatgaac tcgttagctc gtaatccaca tgcatatgta aatggctgtg    5280
tcccgtatgt aacggtgggg cattctagaa taattatgtg taacaagaaa gacagtataa    5340
tacaaacaaa gatgcaagag cggctcgtca tcgcagataa gcactgctgt                5390

<210> SEQ ID NO 110
<211> LENGTH: 1078
<212> TYPE: DNA
<213> ORGANISM: Artificial Sequence
<220> FEATURE:
<223> OTHER INFORMATION: Synthetic polynucleotide (1565/1566 fragment)

<400> SEQUENCE: 110
aggcacagag taacaggtag gtagacagtc gattgattgt aaatatcgtt attctacagt      60
tctcagaaat cgccccgctg cttcctgggc ttcattctc tctctctctc tcttttttt      120 tttttttttt ttccctgttt ttctaattt tttttctgg tccaatttct cccacccat      180 ttgtttcccg gcccgtggaa cccaacgggg agcaagaaag actagactac tagactaggt     240
aactacctgt agctgggtgc taataataat attcacggcg gcaagacagc catggcctta     300
taaactttcc tgtcatccct accgttgacc tagtattatt attattatat gtggtgaggt     360
cgtacctagg tacctgggag cttaaagaga tactacaggt acttccatct tgtactggta     420
agtcccgtcc gtactttaaa tacaggggac ctcccgtacg tcaggtacct atgtcatgat     480
tcttcttctc cccggcatta agatttgttt cttcttatta attatcatca ctattattcc     540
tgcagcagga acgcccccta tcctctcctc caacgtccga tctatcgtgt gtttcgagtc     600
gtgctgttca cacacacgca cgcacacaca cactctcaaa catatctgcc cctcttgcc     660 cctccatccc tccagaaccc gagttcacgg tgccaactct cttttccttg tgtctcctat     720
cccgtttaaa aaaaagagg tacgcagaac cgaacccaat cgacctccgc cgactaatta     780
agtgggattc tctggccccc agggatcggc ttcttcctc catcctgcgg ctcgaaacca     840
gacgtcccaa tcaccggagc tgaccctgga tcggcctctg atccatggct agtttgccct     900
gacatttgtc gcccgttaaa gccgtgggac ctgcgcccag tacataaacc gcctgcgtcg     960
```

```
tgacaccgcc tctttggccg cgcttcccgt ctactttctt cgacgcctcc gttattttca    1020
tcgcggcgct catcgcggcg cccatcccat tgcgccgcag ttgctttcgt gcgtggga      1078
```